United States Patent
Scherz et al.

(10) Patent No.: US 9,957,293 B2
(45) Date of Patent: May 1, 2018

(54) CONJUGATES OF RGD PEPTIDES AND PORPHYRIN OR (BACTERIO)CHLOROPHYLL PHOTOSYNTHESIZERS AND THEIR USES

(75) Inventors: Avigdor Scherz, Rehovot (IL); Yoram Salomon, Rehovot (IL); Efrat Rubinstein, Rehovot (IL); Alexander Brandis, Rehovot (IL); Doron Eren, Rehovot (IL); Karin Neimann, Rehovot (IL)

(73) Assignee: YEDA RESEARCH AND DEVELOPMENT COMPANY LTD., Rehovot (IL)

( * ) Notice: Subject to any disclaimer, the term of this patent is extended or adjusted under 35 U.S.C. 154(b) by 0 days. days.

(21) Appl. No.: 13/447,825

(22) Filed: Apr. 16, 2012

(65) Prior Publication Data
US 2012/0294801 A1 Nov. 22, 2012

Related U.S. Application Data

(63) Continuation-in-part of application No. 11/843,996, filed on Aug. 23, 2007, now abandoned.

(60) Provisional application No. 60/839,409, filed on Aug. 23, 2006.

(51) Int. Cl.
| | |
|---|---|
| C07K 5/12 | (2006.01) |
| C07K 5/09 | (2006.01) |
| C07K 5/10 | (2006.01) |
| C07K 7/06 | (2006.01) |
| C07K 7/64 | (2006.01) |
| A61K 41/00 | (2006.01) |
| A61K 51/08 | (2006.01) |
| G01N 33/574 | (2006.01) |
| A61K 47/64 | (2017.01) |
| A61K 51/00 | (2006.01) |
| A61M 36/14 | (2006.01) |

(52) U.S. Cl.
CPC ......... *C07K 5/123* (2013.01); *A61K 41/0071* (2013.01); *A61K 47/64* (2017.08); *A61K 51/082* (2013.01); *A61K 51/088* (2013.01); *C07K 5/0817* (2013.01); *C07K 5/10* (2013.01); *C07K 5/126* (2013.01); *C07K 7/06* (2013.01); *C07K 7/64* (2013.01); *G01N 33/57426* (2013.01); *A61K 41/00* (2013.01); *G01N 2333/96411* (2013.01)

(58) Field of Classification Search
USPC ....................................................... 424/1.69
See application file for complete search history.

(56) References Cited

U.S. PATENT DOCUMENTS

| | | | |
|---|---|---|---|
| 5,352,667 A | 10/1994 | Lider | |
| 5,650,292 A | 7/1997 | Scherz et al. | |
| 2003/0023081 A1 | 1/2003 | Nifantiev et al. | |
| 2006/0223750 A1* | 10/2006 | Burke et al. | ............... 514/12 |

FOREIGN PATENT DOCUMENTS

| | | |
|---|---|---|
| WO | 1998/10795 A2 | 3/1998 |
| WO | 01/97860 A2 | 12/2001 |

OTHER PUBLICATIONS

Mazor et al. Photochemistry and Photobiology, 81(2):342-351.*
Temming, Kai, et al., "RGD-based strategies for selective delivery of therapeutics and imaging agents to the tumour vascalature," Drug Resistance Updates, 2005, vol. 8, No. 6. p. 381-402.
Koudinova, Natalia, et al., "Photodynamic Therapy with Pd-Bacteriopheophorbide (Tookad): Successful in Vivo Treatment of Human Prostatic Small Cell Carcinoma Xenografts," Int. J. Cancer, 2003, vol. 104, No. 6, p. 782-789.
Janssen, Marcel, et al., "Tumor Targeting with Radiolabeled αvβ3 Integrin Binding Peptides in a Nude Mouse Model," Cancer Research, 2002, vol. 62, p. 6146-6151.
Janssen, Marcel, et al., "Comparison of a Monomeric and Dimeric Radiolabeled RGD-Peptide for Tumor Targeting," Cancer Biotherapy & Radiopharmaceuticals, 2002, vol. 17, No. 6, p. 641-646.
Haubner, Roland, et al. "Noninvasive Imaging of αvβ3 Integrin Expression Using 18F-labeled RGD-containing Glycopeptide and Positron Emission Tomography," Advances in Brief, 2001, vol. 61, p. 1781-1785.
Ellerby, H.M., et al., "Anti-cancer activity of targeted pro-apoptotic peptides," Nature Medicine, 1999, vol. 5, No. 9, p. 1032-1038.
Chaleix, Vincent, et al., "RGD-Porphyrin Conjugates: Synthesis and Potential Application in Photodynamic Therapy," Eur. J. Org. Chem., 2003, p. 1486-1493.
Brandis, Alexander, et al., "Novel Water-soluble Bacteriochlorophyll Derivatives for Vascular-targeted Photodynamic Therapy: Synthesis, Solubility, Phototoxicity and the Effect of Serum Proteins," Photochemistry and Photobiology, 2005, vol. 81, p. 983-993.
Arap, Wadih, et al. "Cancer Treatment by Targeted Drug Delivery to Tumor Vascalature in a Mouse Model," Science, 1998, vol. 279, p. 377-380.
Arap, Wadih, et al. "Targeting the prostate for destruction through a vascular address," Proceedings of the National Academy of Sciences, 2002, vol. 99, No. 3, p. 1527-1531.
Chaleix, V. et al, "RGD-Porphyrin Conjugates: Synthesis and Potential Application in Photodynamic Therapy", Eur. J. Org. Chern., 8:1486-1493 (2003).
Chaleix, V. et al, "Efficient Synthesis of RGD-Containing Cyclic Peptide-Porphyrin Conjugates by Ring-Closing Metathesis on Solid Support", Tetrahedron Lett., 45:5295-5299 (2004).

(Continued)

*Primary Examiner* — Michael G Hartley
*Assistant Examiner* — Melissa J Perreira
(74) *Attorney, Agent, or Firm* — Browdy and Neimark, PLLC

(57) ABSTRACT

Conjugates of porphyrin, chlorophyll and bacteriochlorophyll photosensitizers with RGD-containing peptides or RGD peptidomimetics are provided that are useful for photodynamic therapy (PDT), particularly vascular-targeted PDT (VTP), of tumors and nonneoplastic vascular diseases such as age-related macular degeneration, and for diagnosis of tumors by different techniques.

13 Claims, 40 Drawing Sheets
(23 of 40 Drawing Sheet(s) Filed in Color)

(56) References Cited

OTHER PUBLICATIONS

Frochot, C. et al, "Interest of RGD-Containing Linear or Cyclic Peptide Targeted Tetraphenylchlorin as Novel Photosensitizers for Selective Photodynamic Acivity", Bioorg. Chem., 35:205-220 (2007).

Sol, V. et al, "Amino Porphyrins as Photoinhibitors of Gram-positive and -negative Bacteria", Bioorg. Medicinal Chem. Letters, 14:4207-4211 (2004).

Sternberg, E. et aL, "Porphyrin-based Photosensitizers for Use in Photodynamic Therapy", Tetrahedron, 54:4151-4202 (1998).

Goldshaid et al., "Novel design principles enable specific targeting of imaging and therapeutic agents to necrotic domains in breast tumors" Breast Cancer Research 12:R29, pp. 1-18 (2010).

Haubner et al., "Glycosylated RGD-Containing Peptides: Tracer for Tumor Targeting and Angiogenesis Imaging with Improved Biokinetics," J Nucl Med 42:326-336 (2001).

Temming et al., "RGD-based strategies for selective delivery of therapeutics and imaging agents to the tumour vasculature," Drug Resistance Updates 8:381-402 (2005).

Fridlender et al., "Polarization of Tumor-Associated Neutrophil Phenotype by TGF-b: "N1" versus "N2" TAN" Cancer Cell 16:183-194 (2009).

Gabrilovich et al., "Myeloid-derived suppressor cells as regulators of the immune system" Nature 9:162-174 (2009).

Greish "Chapter 3: Enhanced Permeability and Retention (EPR) Effect for Anticancer Nanomedicine Drug Targeting" in "Cancer Nanotechnology," Grobmyer and Moudgil (eds), Methods in Molecular Biology 624:25-37 (2010).

Gross et al., "Monitoring photodynamic therapy of solid tumors online by BOLD-contrast MRI" Nature Medicine 9(10):1327-1331 (2003).

Iyer et al., "Exploiting the enhanced permeability and retention effect for tumor targeting" Drug Discovery Today 11 (17/18):812-818 (2006).

Maeda et al., "Polymeric drugs for efficient tumor-targeted drug delivery based on EPR-effect" European Journal of Pharmaceutics and Biopharmaceutics 71:409-419 (2009).

Movahedi et al., "Identification of discrete tumor-induced myeloid-derived suppressor cell subpopulations with distinct T cell-suppressive activity" Blood. 111:4233-4244 (2008).

Murdoch et al., "The role of myeloid cells in the promotion of tumour angiogenesis" Nature 8:618-631.

Rader et al., "Integrin alphavBeta3-targeted therapy for Kaposi's sarcoma with an in vitro-evolved antibody" The FASEB Journal, express article 10.1096/fj.02-0281fje, published online Oct. 18, 2002.

Sugahara et al., "Coadministration of a Tumor-Penetrating Peptide Enhances the Efficacy of Cancer Drugs" Science 328:1031-1036 (2010).

Tanaka et al., Tumor targeting based on the effect of enhanced permeability and retention (EPR) and the mechanism of receptor-mediated endocytosis (RME) International Journal of Pharmaceutics 277:39-61 (2004).

Wang et al., "Integrin targeted drug and gene delivery" Expert Opin. Drug Deliv. 7(2):159-171 (2010).

Morales et al., "Small molecule fluorophore and copolymer RGD peptide conjugates for ex vivo two-photon fluorescence tumor vasculature imaging" Biomaterials, 33(33): 8477-8485 (2012).

Line et al., "Targeting Tumor Angiogenesis: Comparison of Peptide and Polymer-Peptide Conjugates" J Nucl Med, 46:1552-1560 (2005).

\* cited by examiner

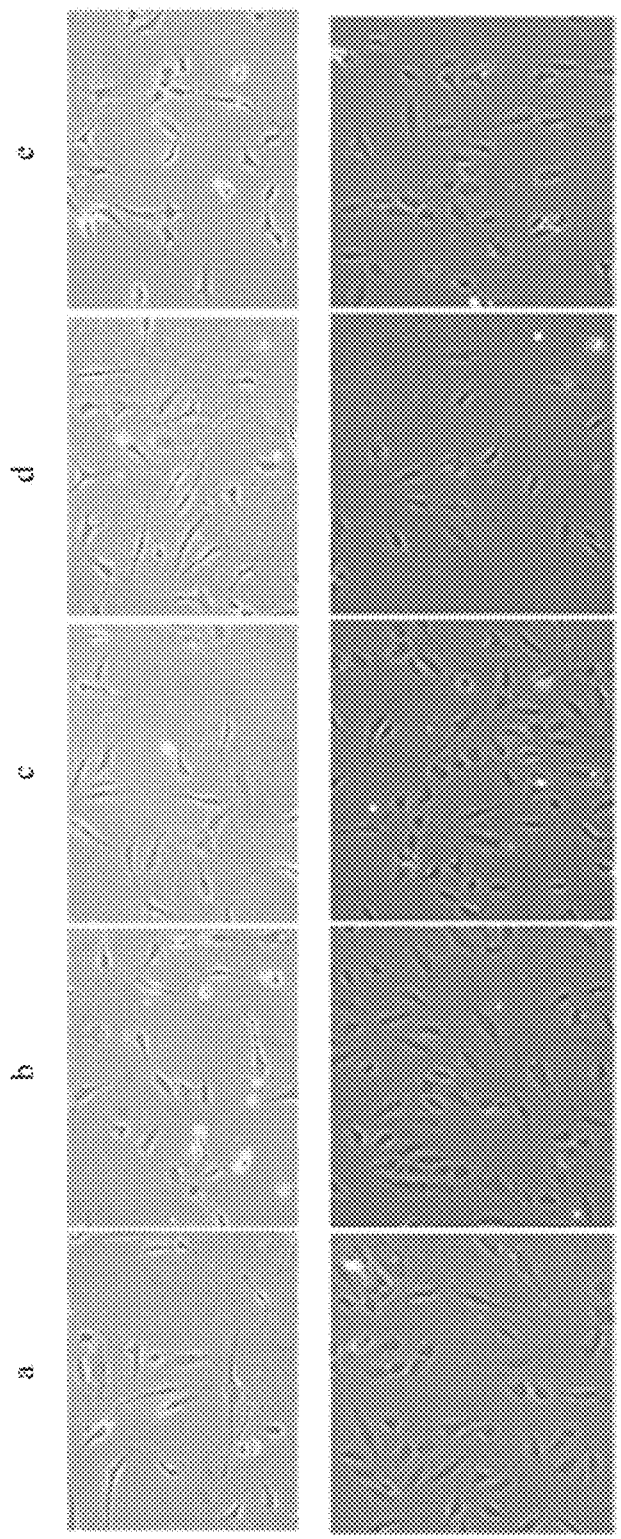

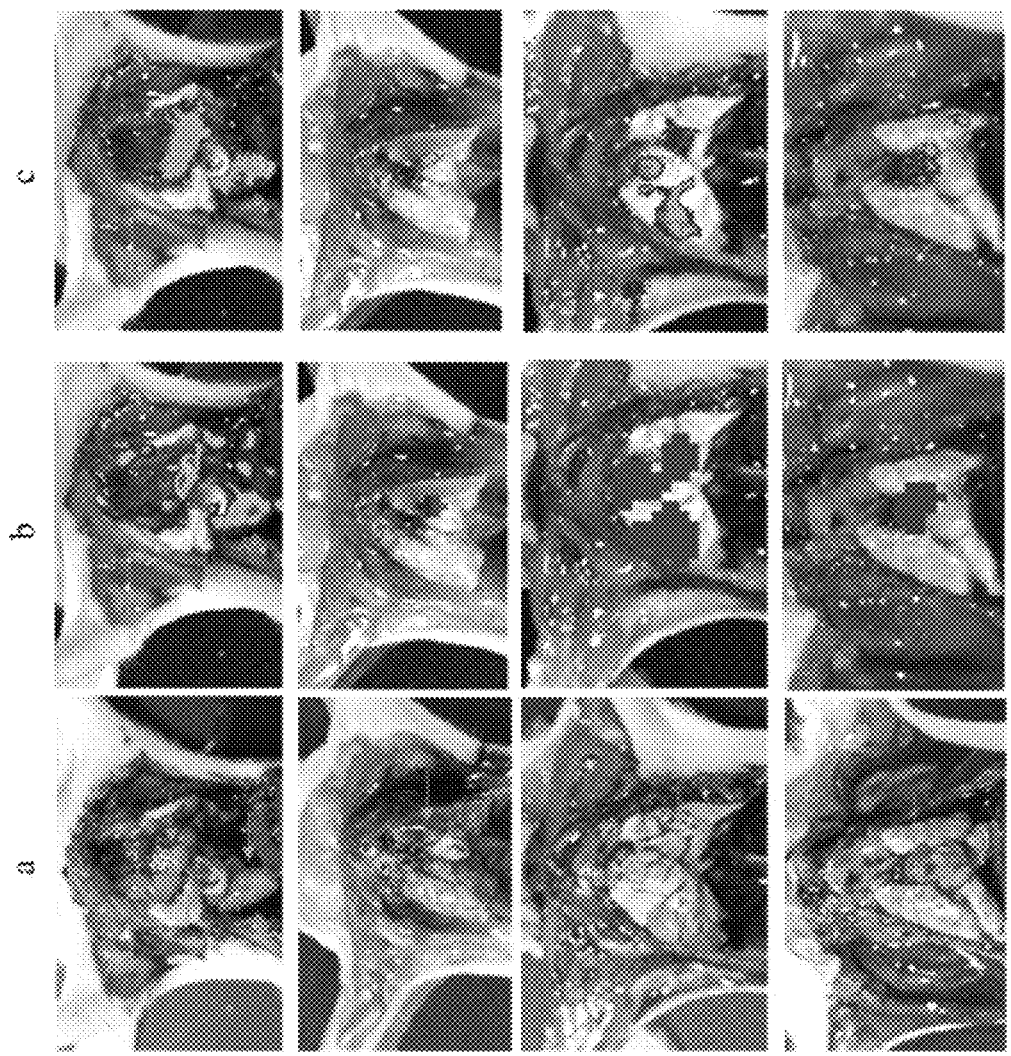

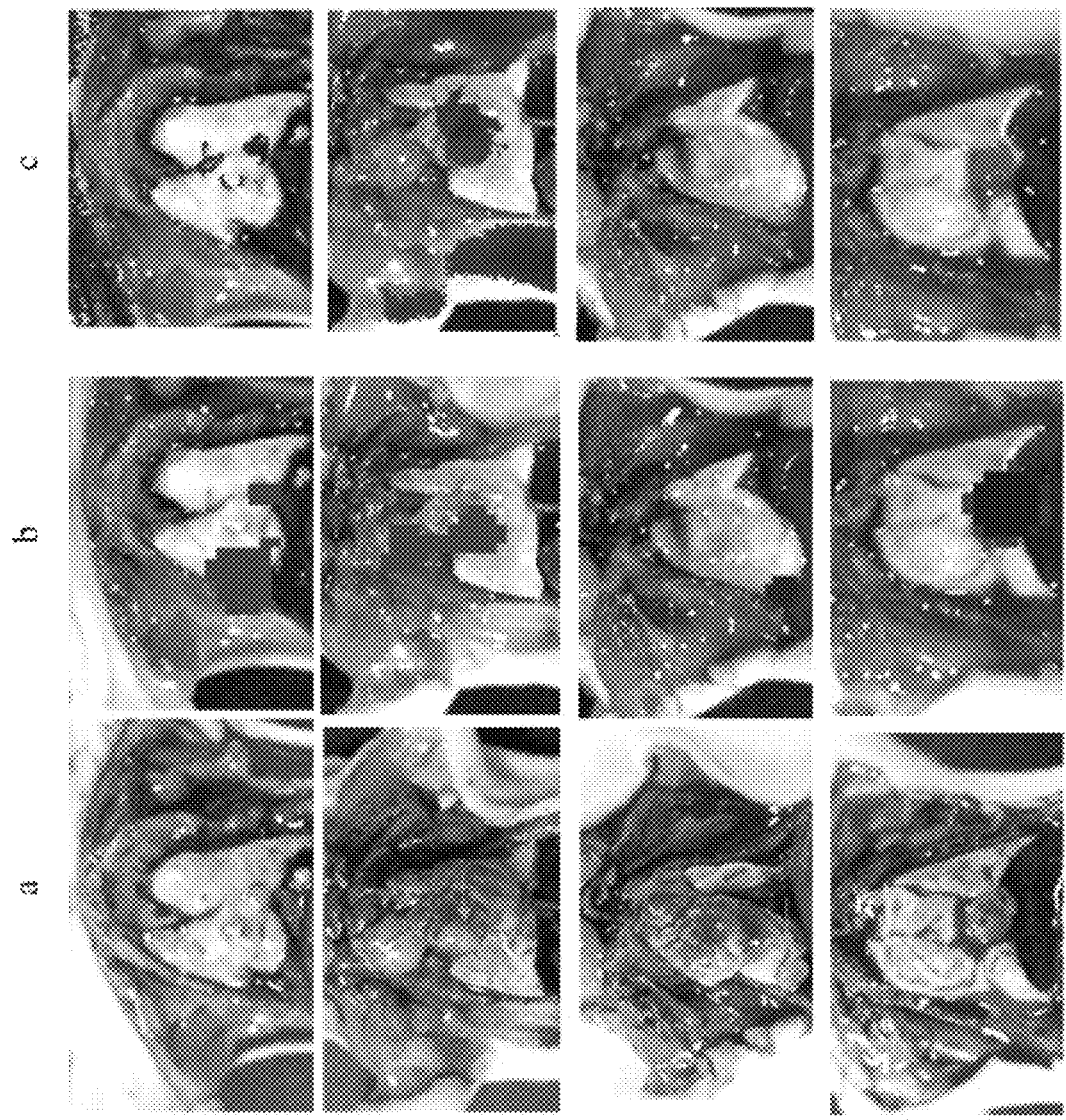

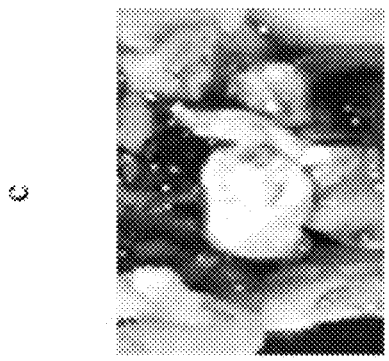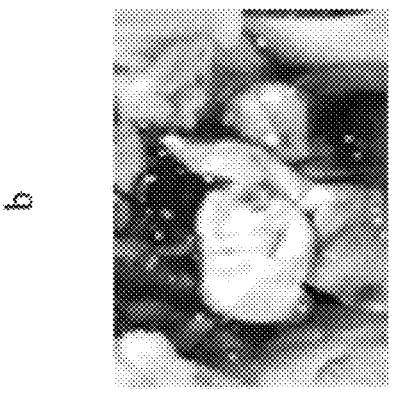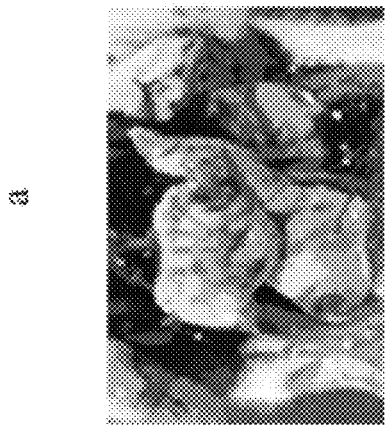
Fig. 23I

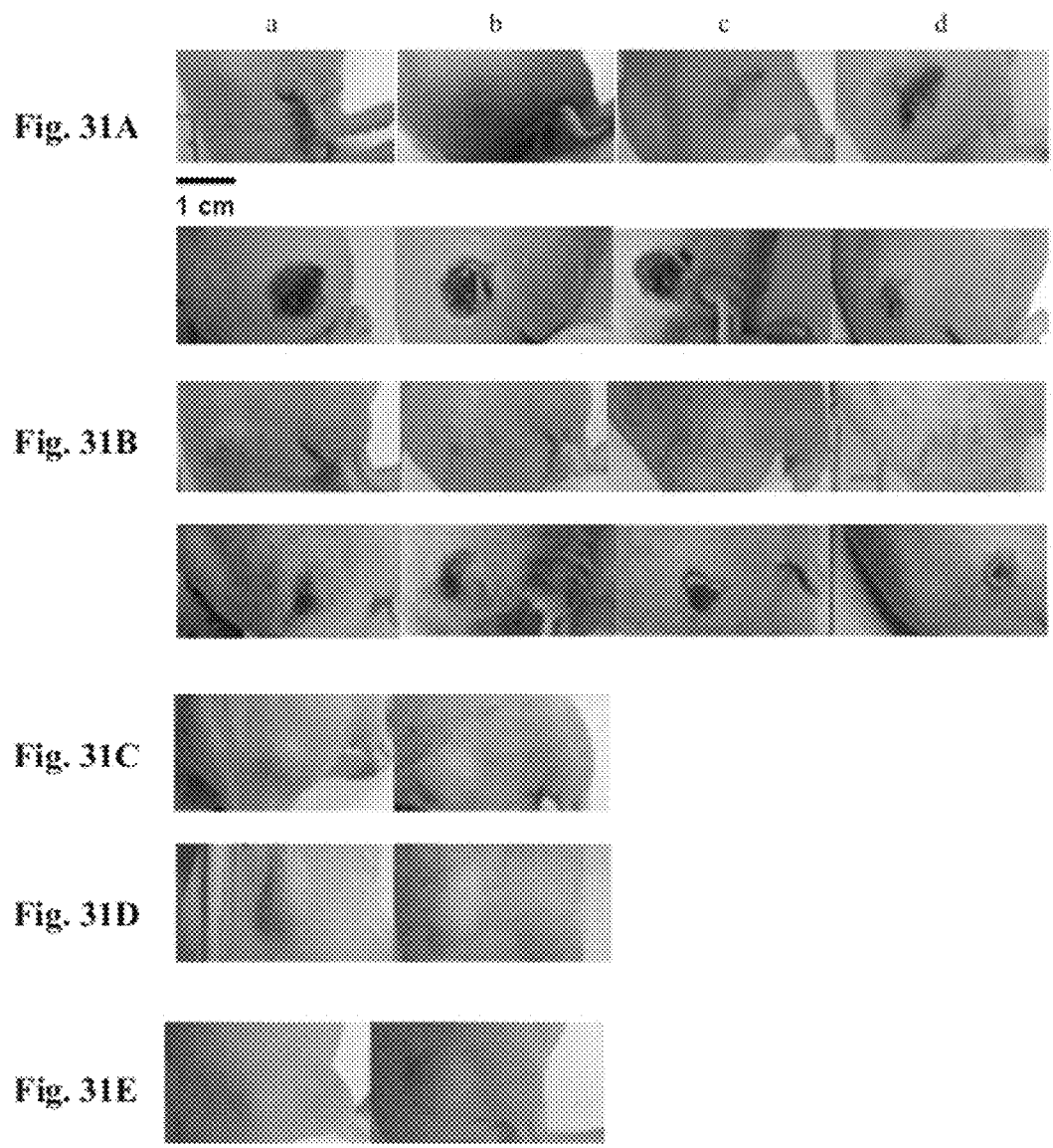

Fig. 39A
Fig. 39B
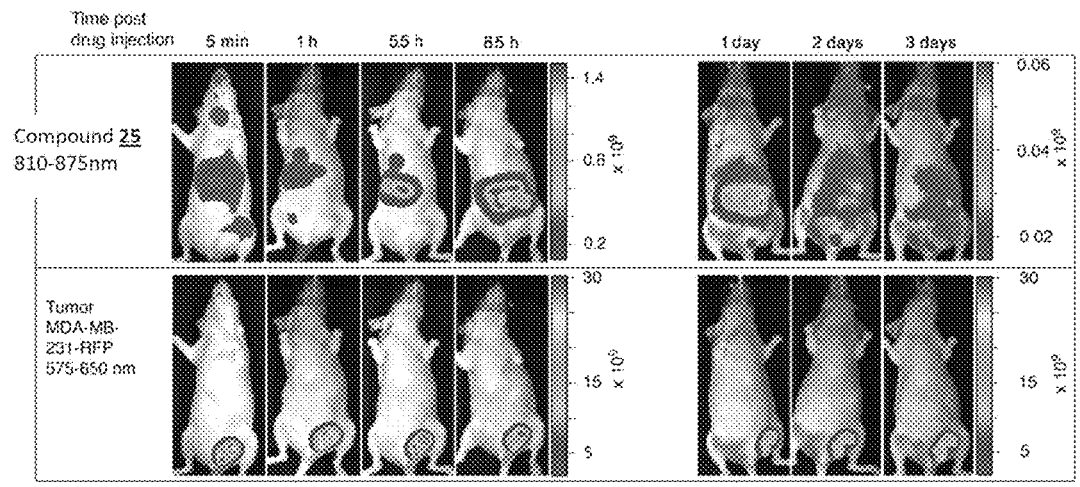
Fig. 40A
Fig. 40B
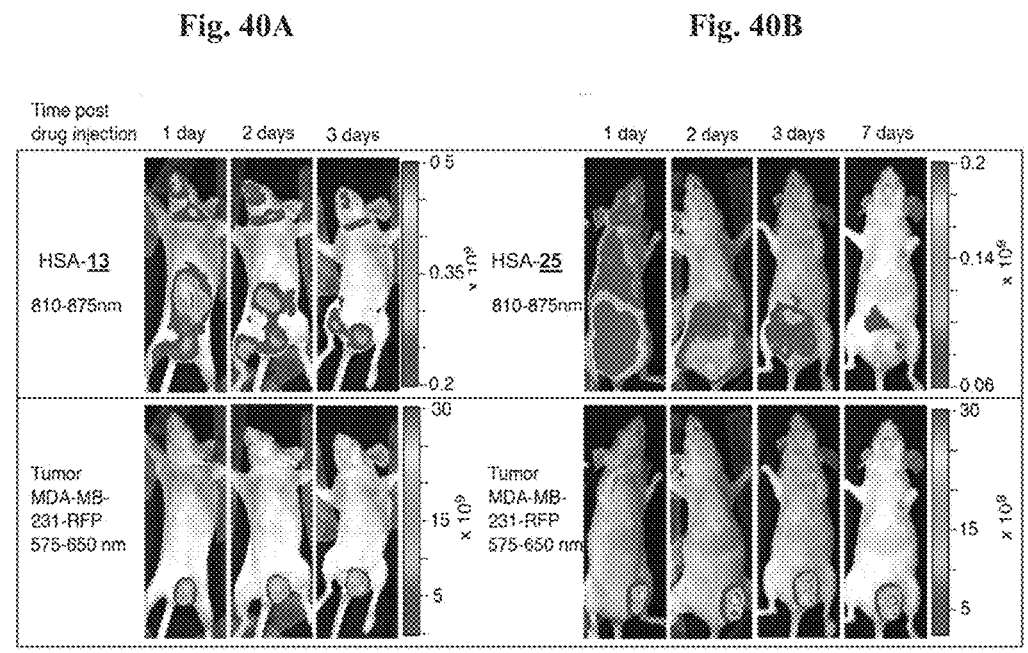

```
                        SEQUENCE LISTING

<160> NUMBER OF SEQ ID NOS: 8

<210> SEQ ID NO 1
<211> LENGTH: 5
<212> TYPE: PRT
<213> ORGANISM: Artificial
<220> FEATURE:
<223> OTHER INFORMATION: INTEGRIN BINDING MOTIF
<220> FEATURE:
<221> NAME/KEY: CYCLO
<222> LOCATION: (1)..(5)
<220> FEATURE:
<221> NAME/KEY: D-AMINO ACID
<222> LOCATION: (4)..(4)

<400> SEQUENCE: 1

Arg Gly Asp Phe Lys
1               5

<210> SEQ ID NO 2
<211> LENGTH: 9
<212> TYPE: PRT
<213> ORGANISM: Artificial
<220> FEATURE:
<223> OTHER INFORMATION: INTEGRIN BINDING MOTIF
<220> FEATURE:
<221> NAME/KEY: CYCLIC
<222> LOCATION: (1)..(9)
<223> OTHER INFORMATION: spontaneous oxidative formation of disulfide
      bonds

<400> SEQUENCE: 2

Cys Asp Cys Arg Gly Asp Cys Phe Cys
1               5

<210> SEQ ID NO 3
<211> LENGTH: 6
<212> TYPE: PRT
<213> ORGANISM: Artificial
<220> FEATURE:
<223> OTHER INFORMATION: INTEGRIN BINDING MOTIF
<220> FEATURE:
<221> NAME/KEY: LINEAR
<222> LOCATION: (1)..(6)

<400> SEQUENCE: 3

Gly Arg Gly Asp Ser Pro
1               5

<210> SEQ ID NO 4
<211> LENGTH: 4
<212> TYPE: PRT
<213> ORGANISM: Artificial
<220> FEATURE:
<223> OTHER INFORMATION: INTEGRIN BINDING MOTIF
<220> FEATURE:
<221> NAME/KEY: CYCLO
<222> LOCATION: (1)..(4)

<400> SEQUENCE: 4

Arg Gly Asp Lys
1
```

```
<210> SEQ ID NO 5
<211> LENGTH: 7
<212> TYPE: PRT
<213> ORGANISM: Artificial
<220> FEATURE:
<223> OTHER INFORMATION: INTEGRIN BINDING MOTIF

<400> SEQUENCE: 5

Gly Arg Gly Asp Ser Pro Lys
1               5

<210> SEQ ID NO 6
<211> LENGTH: 25
<212> TYPE: PRT
<213> ORGANISM: Artificial
<220> FEATURE:
<223> OTHER INFORMATION: INTEGRIN BINDING MOTIF

<400> SEQUENCE: 6

Gly Arg Gly Asp Ser Pro Gly Arg Gly Asp Ser Pro Gly Arg Gly Asp
1               5                   10                  15

Ser Pro Gly Arg Gly Asp Ser Pro Lys
            20                  25

<210> SEQ ID NO 7
<211> LENGTH: 5
<212> TYPE: PRT
<213> ORGANISM: Artificial
<220> FEATURE:
<223> OTHER INFORMATION: INTEGRIN BINDING MOTIF
<220> FEATURE:
<221> NAME/KEY: CYCLIC
<222> LOCATION: (1)..(5)
<220> FEATURE:
<221> NAME/KEY: N-METHYL
<222> LOCATION: (4)..(5)
<220> FEATURE:
<221> NAME/KEY: D-AMINO ACID
<222> LOCATION: (4)..(4)

<400> SEQUENCE: 7

Arg Gly Asp Phe Lys
1               5

<210> SEQ ID NO 8
<211> LENGTH: 5
<212> TYPE: PRT
<213> ORGANISM: Artificial
<220> FEATURE:
<223> OTHER INFORMATION: INTEGRIN BINDING MOTIF
<220> FEATURE:
<221> NAME/KEY: CYCLIC
<222> LOCATION: (1)..(5)
<220> FEATURE:
<221> NAME/KEY: D-AMINO ACID
<222> LOCATION: (4)..(4)

<400> SEQUENCE: 8

Arg Gly Asp Tyr Lys
1               5
```

CONJUGATES OF RGD PEPTIDES AND PORPHYRIN OR (BACTERIO)CHLOROPHYLL PHOTOSYNTHESIZERS AND THEIR USES

CROSS REFERENCE TO RELATED APPLICATIONS

The present application is a continuation-in-part of application Ser. No. 11/843,996, filed Aug. 23, 2007, now abandoned, the entire contents of which are hereby incorporated by reference. Parent application Ser. No. 11/843,996 claimed the benefit of provisional application No. 60/839,409, filed Aug. 23, 2006, the entire contents of which are also hereby incorporated herein by reference.

FIELD OF THE INVENTION

The present invention relates to photosensitizers and in particular to novel conjugates of porphyrin, chlorophyll and bacteriochlorophyll derivatives with peptides containing the RGD motif or with RGD peptidomimetics, to their preparation and their use in methods of in-vivo photodynamic therapy and diagnosis of tumors and different vascular diseases such as age-related macular degeneration.

DEFINITIONS AND ABBREVIATIONS

AMD: age-related macular degeneration; Bchl a: bacteriochlorophyll a: pentacyclic 7,8,17,18-tetrahydroporphyrin with a $5^{th}$ isocyclic ring, a central Mg atom, a phytyl or geranylgeranyl group at position $17^3$, a $COOCH_3$ group at position $13^2$, an H atom at position $13^2$, methyl groups at positions 2, 7, 12, 18, an acetyl group at position 3, and an ethyl group at position 8, herein compound 1; Bphe: bacteriopheophytin a (Bchl in which the central Mg is replaced by two H atoms); Bpheid: bacteriopheophorbide a (the C-$17^2$-free carboxylic acid derived from Bphe without the central metal atom); Chl: chlorophyll; EC: endothelial cells; ECM: extracellular matrix; NIR: near-infrared; Pd-Bpheid: Pd-bacteriopheophorbide a; PDT: photodynamic therapy; RGD-4C: the cyclic nonapeptide CDCRGDCFC-NH$_2$; Rhodobacterioehlorin: tetracyclic 7,8,17,18-tetrahydroporphyrin having a —CH$_2$CH$_2$COOH group at position 17, a —COOH at position 13, methyl groups at positions 2, 7, 12, 8, and ethyl groups at positions 3 and 8; ROS: reactive oxygen species; VTI: vascular-targeted imaging; VTP: vascular-targeted PDT.

IUPAC numbering of the bacteriochlorophyll derivatives is used throughout the specification. Using this nomenclature, the natural bacteriochlorophylls carry two carboxylic acid esters at positions $13^2$ and $17^2$, however they are esterified at positions $13^3$ and $17^3$.

BACKGROUND OF THE INVENTION

Photodynamic therapy (PDT) is a non-surgical treatment of tumors in which non-toxic drugs and non-hazardous photosensitizing irradiation are combined to generate cytotoxic reactive oxygen species in situ. This technique is more selective than the commonly used tumor chemotherapy and radiotherapy.

PDT of tumors involves the combination of administered photosensitizer and local light delivery, both innocuous agents by themselves, but in the presence of molecular oxygen they are capable of producing cytotoxic reactive oxygen species (ROS) that can inactivate cells. Being a binary treatment modality, PDT allows for greater specificity and has the potential of being more selective, yet not less destructive, when compared with commonly used chemotherapy or radiotherapy (Dougherty et al., 1998; Bonnett et al., 1999; Kessel and Dougherty, 1999; Mazon, 1999; Hahn and Glatstein, 1999).

Porphyrins have been employed as the primary photosensitizing agents in clinics. Optimal tissue penetration by light apparently occurs between 650-800 nm. Porfimer sodium (Photofrin®, a trademark of Axcan Pharma Inc.), the world's first approved photodynamic therapy agent, which is obtained from hematoporphyrin-IX by treatment with acids and has received FDA approval for treatment of esophageal and endobronchial non-small cell lung cancers, is a complex and inseparable mixture of monomers, dimers, and higher oligomers.

Large amounts of work have been devoted to the synthesis of single pure compounds—so-called "second generation" sensitizers—which absorb at long wavelength, have well established structures and exhibit better differentiation between their retention in tumor cells and their retention in skin or other normal tissues. In order to optimize the performance of the porphyrin drugs in therapeutics and diagnostics, several porphyrin derivatives have been proposed in which, for example, there is a central metal atom (other than Mg) complexed to the four pyrrole rings, and/or the peripheral substituents of the pyrrole rings are modified and/or the macrocycle is dihydrogenated to chlorophyll derivatives (chlorins) or tetrahydrogenated to bacteriochlorophyll derivatives (bacteriochlorins).

Due to their intense absorption in favorable spectral regions (650-850 nm) and their ready degradation after treatment, chlorophyll (Chl) and bacteriochlorophyll (BChl) derivatives have been identified as excellent sensitizers for PDT of tumors and to have superior properties in comparison to porphyrins. Bacteriochlorophylls are of potential advantage compared to the chlorophylls because they show intense near-infrared bands, i.e., at considerably longer wavelengths than chlorophyll derivatives.

Tumor Vascular Targeting

Targeting photodynamic reagents for destruction of the tumor vasculature, as opposed to the tumor cells themselves, may offer therapeutic advantages since tumor-cell growth and development critically depend on continuous oxygen and nutrient supply (Ruoslahti, 2002). Such vascular damage may include thrombus formation and further restrict tumor blood perfusion (Huang et al., 1997). Furthermore, targeting the tumor vascular endothelial cell (EC) layer is expected to circumvent the poor penetration of tumor stroma by the therapeutic macromolecules (Huang et al., 1997; Burrows and Thorpe 1994). Although tumor blood vessels might be affected by the tumor microenvironment and acquire a tumor associated "signature", they are not malignant and less likely to develop drug resistance. Furthermore, when a targeted antivascular agent is also active against the tumor cells, additional gains in efficacy can be expected. Thus, by combining antivascular properties with antitumor cytotoxic activities in one drug, its efficacy can be expected to increase and, consequently, decrease the required effective cytotoxic dose. In addition to ECs, tumor cells have also been shown in one case to comprise part of the luminal surface mosaic of the tumor blood vessels (Ruoslahti, 2002; Chang at al, 2000). Consequently these tumor cells are thought to be directly exposed to the blood and freely interact with therapeutic macromolecules that otherwise are unable to cross the endothelial barrier.

Selective vascular targeting can rely on the differential susceptibility and consequent response to therapeutic agents of tumor and normal blood vessels. Alternatively, differential endocytosis may promote selective uptake of cytotoxic or other therapeutic agents. Recent studies have suggested organ/tissue specific properties for vascular ECs (Ruoslahti, 2002). The blood vessels in different tissues are likely to express tissue specific endothelial markers that are mostly unknown. Pathological processes such as inflammation, ischemia and malignancy can also impose their signature on the respective vasculature (Ruoslahti, 2002; Ruoslahti and Rajotte, 2000; Ruoslahti, 2000; Rajotte et al., 1998; Arap et al., 1998). The biochemical features that characterize blood vessels in tumors may include angiogenesis-related molecules such as certain integrins. The integrins $\beta_v\beta_3$, $\alpha_v\beta_5$ and $\alpha_5\beta_1$ have been identified in expression patterns typical for angiogenic vascular ECs associated with tumors, wounds, inflammatory tissue, and during vascular remodeling (Brooks et al, 1994a; Brooks et al, 1994b; Brooks et al, 1995; Elceiri and Cheresh, 1999). Endothelial-cell growth factor receptors, proteases, peptidases, cell surface proteoglycans and extracellular matrix (ECM) components have also been described (Ruoslahti, 2000). This rich repertoire of heterogenic molecules and processes may provide new opportunities for targeted delivery of therapies.

Different strategies have been pursued to achieve this goal. Circulating peptides, peptidomimetics or antibodies that target specific sites in the vasculature are attractive as carriers for therapeutics and diagnostic agents offering theoretical advantages over such conjugates that directly target tumor cells, mostly situated beyond physiological barriers such as the blood vessel wall.

Chaleix et al., 2003, disclose the synthesis of RGD-porphyrin conjugates as potential candidates for PDT application, in which the unmetalated porphyrin macrocycle is substituted at each of the positions 10, 15, 20 by 4-methylphenyl or acetylatedglucosyloxyphenyl and at position 5 by a residue of a linear RGD-containing peptide linked to the macrocycle via a spacer arm.

Selective Uptake of RGD-Containing Peptides by Endothelial and Tumor Cells Via $\alpha_v\beta_3$ and $\alpha_v\beta_5$ Integrins The arginine-glycine-aspartic acid Arg-Gly-Asp (RGD) motif of ECM components, like fibronectin (Pierschbacher and Ruoslahti, 1984) and vitronectin, binds to integrins (Ruoslahti and Pierschbacher, 1987; D'Souza S E et al., 1991; Joshi et al, 1993; Koivunen et al., 1994). Integrin-mediated adhesion leads to intracellular signaling events that regulate cell survival, proliferation, and migration. Some 25 integrins are known, and at least eight of them bind the RGD motif as the primary recognition sequence in their ligands.

Data obtained by phage display methods (Pasqualini and Ruoslahti, 1996) screening for ROD-containing peptides, have shown their selective binding to endothelial lining of tumor blood vessels (Ruoslahti, 1996; Pasqualini et al., 1997). Because the expression of integrins is reported to be high on activated, but more restricted on quiescent, ECs, small synthetic RGD-containing peptides have been proposed as antagonists impairing the growth of vascular endothelial and tumor cells. RGD peptides also retard signal transmission, affect cell migration and induce tumor cell regression or apoptosis (Su et al., 2002). RGD-analogues are used in tumor imaging (Haubner et al., 2001), anti-angiogenesis approaches (Kawaguchi et al., 2001; Pasqualini et al., 2000), and in tumor targeting of radionucleotides (van Hagen et al., 2000) and chemotherapeutic drugs (Arap et al., 1998; Zitzmann et al., 2002).

Integrins are also expressed on cancer cells and therefore play an important role in the invasion, metastasis, proliferation and apoptosis of cancer cells. Metastasis invasion of tumor cells into preferred organs may represent cell-homing phenomena that depend on the adhesive interaction between the tumor cells and organ-specific endothelial markers (Ruoslahti and Rajotte, 2000). By binding to integrin of either endothelial or tumor cells, RGD peptides are capable of modulating in vivo cell traffic by inhibition of tumor cell-ECM and tumor cell-EC attachments, which are obligatory for metastatic processes. Several studies have indicated that RGD-containing compounds can interfere with tumor cell metastatic processes in vitro (Goligorsky et al., 1998; Romanov and Goligorsky 1999) and in vivo (Saiki et al., 1989; Hardan et al., 1993).

Peptides that are specific for individual integrins are of considerable interest and of possible medical significance. The $\alpha_v\beta_3$ integrin was the first integrin shown to be associated with tumor angiogenesis. RGD peptides that specifically block the $\alpha v\beta 3$ integrin show promise as inhibitors of tumor and retinal angiogenesis, of osteoporosis and in targeting drugs to tumor vasculature (Assa-Munt et al., 2001). Coupling of the anticancer drug doxorubicin or a pro-apoptotic peptide to an $\alpha v\beta 3$ integrin-binding RGD peptide yields compounds that are more active and less toxic than unmodified drugs when tested against xenograft tumors in mice (Ruoslahti, 2000; Arap et al., 1998; Arap et al., 2002; Ellerby et al., 1999).

U.S. Pat. No. 6,576,239, EP 0927045 B1 and WO 98/010795 (all of The Burnham Institute, Inventors: E. Ruoslahti and R. Pasqualini) disclose a conjugate comprising a tumor homing peptide comprising the amino acid sequence RGD or NGR, said tumor homing peptide linked to a therapeutic or diagnostic moiety, provided said moiety is not a phage particle. The therapeutic moiety may be a cytotoxic agent or a cancer chemotherapeutic agent such as doxorubicin. The conjugate selectively homes to angiogenic vasculature upon in vivo administration. The tumor homing peptide may be a peptide of up to 20 or 30 amino acids or of 50 to 100 amino acids in length, linear or cyclic. One preferred peptide is the cyclic nonapeptide, CDCRGDCFC or H-Cys*-Asp-Cys*-Arg-Gly-Asp-Cys*-Phe-Cys-NH$_2$.

Selective Vascular Response Induced in Tumors by Photodynamic Therapy (PDT)

Application of novel bacteriochlorophyll (Bchl) derivatives as sensitizers in PDT has been reported by our group in recent years in the scientific literature (Zilberstein et al., 2001; Schreiber et al., 2002; Gross et al., 1997; Zilberstein et al., 1997; Rosenbach-Belkin et al., 1996; Gross et al., 2003a; Koudinova et al., 2003; Preise et al., 2003; Gross et al., 2003b) and in the patent publications U.S. Pat. No. 5,726,169 U.S. Pat. No. 5,650,292, U.S. Pat. No. 5,955,585, U.S. Pat. No. 6,147,195, U.S. Pat. No. 6,740,637, U.S. Pat. No. 6,333,319, U.S. Pat. No. 6,569,846, U.S. Pat. No. 7,045,117, DE 41 21 876, EP 1 246 826, WO 2004/045492, WO 2005/120573. The spectra, photophysics, and photochemistry of Bchl derivatives have made them optimal light-harvesting molecules with clear advantages over other sensitizers presently used in PDT. These Bchl derivatives are mostly polar and remain in the circulation for a very short time with practically no extravasations into other tissues (Brandis et al., 2003). Therefore, these compounds are good candidates for vascular-targeted PDT that relies on short (5-10 min) temporal intravascular encounter with light and higher susceptibility of the tumor vessels to the PDT-generated cytotoxic ROS.

Recent studies performed by our group showed that primary photosensitization is intravascular with rapid development of ischemic occlusions and stasis within the illumination period. This process also induces photochemically induced lipid peroxidation (LPO) and early EC death that is primarily confined to the tumor vasculature (Gross et al., 2003a; Koudinova et al., 2003). Due to light independent progression of free radical chain reactions along with developing hypoxia, LPO and cell death spread beyond the vascular compartment to cover the entire tumor interstitium until complete necrosis of the tumor is attained around 24 hours post PDT. Hence, the primary action of PDT blocks blood supply and induces hypoxia that initiates, in a secondary manner, a series of molecular and pathophysiological events that culminate with tumor eradication.

Mitochondria, lysosomes, plasma membrane, and nuclei of cells have been evaluated as potential PDT targets. Since most PDT sensitizers do not accumulate in cell nuclei, PDT has a generally low potential of causing DNA damage, mutations, and carcinogenesis. Hydrophilic sensitizers are likely to be taken up by pinocytosis and/or endocytosis and therefore become localized in lysosomes or endosomes. Light exposure will then permeabilize the lysosomes so that sensitizers and hydrolytic enzymes are released into the cytosol (Dougherty et al., 1998).

PDT damage to plasma membrane can be observed within minutes after light exposure. This type of damage is manifested as swelling, shedding of vesicles containing plasma membrane marker enzymes, cytosolic enzymes and lysosomal enzymes, reduction of active transport, depolarization of plasma membrane, inhibition of the activities of plasma membrane enzymes, changes in intracellular $Ca^{2+}$, up- and down-regulation of surface antigens, LPO that may lead to protein crosslinking, and damage to multidrug transporters (Dougherty et al., 1998).

Reports that PDT could rapidly induce apoptosis, both in vitro and in vivo, have provided insight into the nature of the photokilling mechanisms. Insight into the mechanism of apoptosis after PDT has perhaps been provided by reports that indicate an association between mitochondrial photodamage and apoptotic responses. Recent studies performed by our group showed that the Bchl based photosensitizers induce the activation of the apoptotic pathway. However, apoptosis is probably not the cause for cell death, since inhibiting the apoptotic pathways did not rescue the cells (Mazor et al. 2003, unpublished).

Reference is made to the following patents and patent applications of the applicants of the present application, the contents of all these patents and patent applications being hereby incorporated by reference in their entirety as if fully disclosed herein: U.S. Pat. No. 5,726,169 U.S. Pat. No. 5,650,292, U.S. Pat. No. 5,955,585, U.S. Pat. No. 6,147,195, U.S. Pat. No. 6,740,637, U.S. Pat. No. 6,333,319, U.S. Pat. No. 6,569,846, U.S. Pat. No. 7,045,117, DE 41 21 876, EP 1 246 826, WO 2004/045492, WO 2005/120573.

SUMMARY OF THE INVENTION

The present invention relates to a conjugate of a RGD-containing peptide or RGD peptidomimetic and a photosensitizer selected from the group consisting of porphyrin, chlorophyll and bacteriochlorophyll, excluding the conjugates wherein the photosensitizer is unmetalated porphyrin substituted at each of the positions 10, 15, 20 by 4-methylphenyl or acetylated glucosyloxyphenyl and at position 5 by a residue of a linear RGD-containing peptide linked to the porphyrin macrocycle via a spacer arm.

In one embodiment, the photosensitizer is a porphyrin, preferably a tetraarylporphyrin. In another embodiment, the photosensitizer is a chlorophyll or bacteriochlorophyll, preferably of the formulas I, II and III herein.

The invention further provides a diagnostic, therapeutic or radiotherapeutic composition for visualization, PDT therapy or radiotherapy of tissues or organs comprising an effective amount of a photosensitizer-RGD peptide conjugate of the invention and a pharmaceutically acceptable carrier.

The conjugates of the invention can be used in methods for tumor diagnosis using different diagnostic techniques and in methods of photodynamic therapy of tumors and vascular diseases and in tumor radiotherapy.

BRIEF DESCRIPTION OF THE FIGURES

The present patent or application file contains at least one drawing executed in color. Copies of this patent or patent application publication with color drawings will be provided by the Office upon request and payment of the necessary fee.

FIG. 1A: Mass spectrometry measurement. FIG. 1B: Spectrophotometry analysis. FIG. 1C: HPLC results after synthesis (conjugate 11 is peak number 3).

FIG. 2A: Electronic spectrum in acetone. FIG. 2B: Mass spectrum: ESI-MS (+) 679 (M), 702 (M+Na) m/z.

FIG. 3A: Chromatography of Eu-RGD-4C (a single pick). FIG. 3B: Mass spectrometry analysis (MW of isothiocyanatophenyl-DTPA-Eu-RGD-4C=1498, arrow).

FIG. 8 shows the effect of RGD-4C on HUVEC detachment. The morphological changes of the cells were documented using light microscopy. The upper panels a-e represent the phase contrast microscopy of cell detachment in the presence of increasing concentrations of RGD-4C (a: control; b: 25 µM; c: 50 µM; d: 100 µM; e: 200 µM). The lower panels represent the recovery of the cells 24 h after replacement of the medium with a fresh one.

FIG. 14A ICP-MS results for conjugate 42. Each time point represents 2 mice. FIG. 14B shows the same results with focus on specific organs of interest (blood, tumor, liver, kidneys and muscle) compared to the results obtained for RGDconjugate 24 (see FIGS. 11A-11C).

FIGS. 23A-23I are a series of photographs (a), bioluminescence (b) and fluorescence (c) images of CT26luc lung metastases in CD-1 nude male mice 24 hours (A,B), 9 hours (C,D), 4 hours (E,F) after the i.v. injection of conjugate 24 (15 mg/kg). Images G,H are of CT26luc lung metastases in CD-1 nude male mice that were not injected with the conjugate. Image I is of CD-1 nude male mouse without lung metastases 24 hours after the i.v. injection of conjugate 24. The middle image is the bioluminescence signal originated from the reaction of lucifern with the luciferase transfected tumor cells. The right image is the NIR fluorescence signal originated from 24 taken using Xenogen IVIS® Imaging System 100. The arrows indicate the lung metastases.

(FIG. 27A) or 4°

C. (FIG. 27B) with 0-20 µM conjugate 23 in 10% FCS in medium in the absence or presence of excess free cyclo-RGDfK (100 fold up to 1 mM). Cell survival was determined using Neutral Red viability assay. The points represent average results of triplicates.

FIGS. 31A-31E are pictures of C6 glioma tumor xenografts treated with conjugate 24 or compound 8. CD-1 nude male mice bearing C6 glioma xenografts were treated as follows: 31A. conjugate 24 was i.v. injected 15 mg/kg, 15-min illumination (90 J/cm$^2$) 8 hours post injection; upper panels: (a) pre PDT; (b) 2 days post PDT; (c) 3 days post PDT; (d) 4 days post PDT; lower panels: (a) 7 days post PDT; (b) 9 days post PDT; (c) 14 days post PDT; (d) 18 days post PDT. 31B. conjugate 24 was i.v. injected 24 mg/kg, 10-min illumination (60 J/cm$^2$) 8 hours post injection; a, b, c and d in upper and lower panels as for 31A. 31C. Dark control—conjugate 24 was i.v. injected without illumination; a) pre PDT, b) 5 days post PDT. 31D. Light control—illumination without injection of photosensitizer; a) pre PDT, b) 5 days post PDT. 31E. Unconjugated photosensitizer control—compound 8 was i.v. injected 9 mg/kg, 10 min illumination (60 J/cm$^2$) 8 hours post injection, a) pre PDT, b) 11 days post PDT. Images were taken at indicated time post PDT.

FIGS. 39A-39B are fluorescence images showing accumulation of compound 25 in CD-1 nude female mice grafted with an orthotopically large MDA-MB-231-RFP tumors. Images were taken within few hour after i.v. injection of 9 mg/kg compound 25 (39A) and accumulation of 25 was then monitored for up to three days (39B). Upper panel-near infrared (NIR) fluorescence images indicating compound 25 distribution; lower panel-Red fluorescence images indicating tumor location.

FIGS. 40A-40C are fluorescence images showing accumulation of conjugate 13 and compound 25 covalently bound to HSA in large MDA-MB-231-RFP tumors in CD-1 nude female mice, following i.v. injection of 0.7 nmol of HSA-conjugate 13 (A) or HSA-compound 25 (B). Images of the tumors were taken at the indicated times post-injection. Upper panel—near infrared (NIR) fluorescence images indicating compound distribution; lower panel—red fluorescence images indicating tumor size and location. Longitudinal accumulation of conjugate 13 covalently bound to HSA and compound 25 covalently bound to HSA in large tumors is presented in graph 40C. Total fluorescence intensity within the individual tumor boundaries at the indicated times was normalized per unit area and expressed as photon/(sec×cm²).

DETAILED DESCRIPTION OF THE INVENTION

Figure 1A:
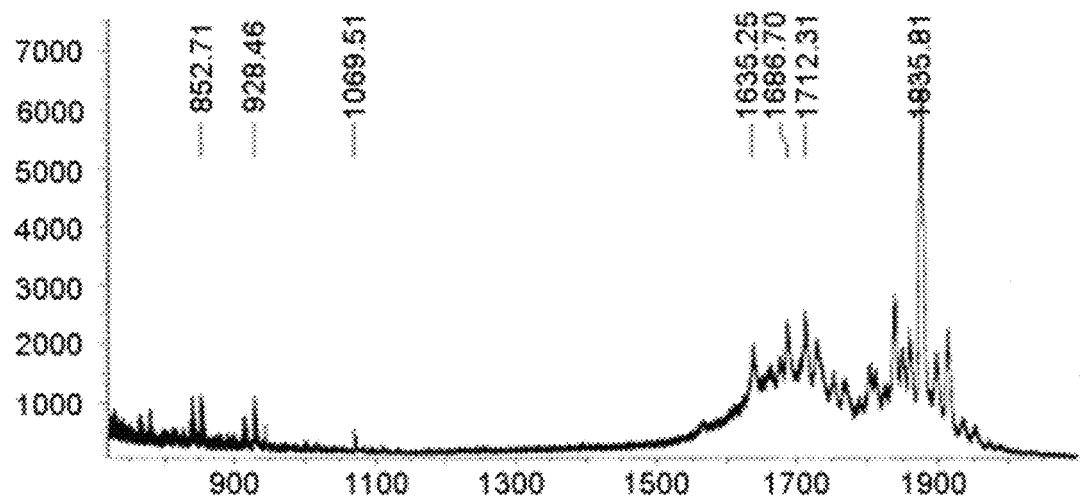
FIGS. 1A-1C show characterization spectra of conjugate 11.

In a broad aspect, the present invention relates to a conjugate of a photosensitizer selected from porphyrin, chlorophyll (Chl) and bacteriochlorophyll (BChl) and an RGD-containing peptide or an RGD peptidomimetic It is one object of the present invention to provide conjugates of photosensitizers that specifically target the sensitizer to the tumor vasculature. There are some advantages for vascular photosensitizer targeting over vascular targeting with conventional chemotherapy. First, during accumulation of a targeted conventional drug, it is often active, unless it is a prodrug, while the targeted photosensitizer is not active until locally illuminated. Second, a targeted conventional drug will bind and act also at undesirable targets presenting the homing address whereas the targeted photosensitizer will be activated only at the relevant illuminated site. Furthermore, PDT with photosensitizers targeted to the neovascular endothelial signatures in tumor may be remarkably selective in inducing photodynamic EC injury.

The integrin $\alpha_v\beta_3$ receptor has been reported to play an important role in tumor metastasis and angiogenesis, which involves growth of new blood vessels from preexisting vasculatures during tumor growth. This integrin may be a viable marker for tumor growth and spread. Therefore, noninvasive imaging methods for visual monitoring of integrin $\alpha_v\beta_3$ expression in real-time provides opportunities for assessing therapeutic intervention as well as for detection of metastasis.

Integrins mediate the attachment between a cell and the tissue surrounding it which may be another cell or the extracellular matrix (ECM). Integrins bind peptides and proteins which comprise the RGD motif within. RGD peptides interact with the integrin receptor sites, which can initiate cell-signaling processes and influence many different diseases. Thus, the integrin RGD binding site is an attractive pharmaceutical target. The integrin $\alpha_v\beta_3$ has an RGD binding site and peptides containing the sequence RGD home to, and act as antagonists of, $\alpha_v\beta_3$ integrin. Thus, in one preferred embodiment of the invention, the RGD-containing peptide is an antagonist of an integrin receptor.

In the bifunctional conjugates of the invention, the homing property is provided by the RGD-containing peptide while the PDT effect is provided by the photosensitizer. These conjugates should be able to target the sensitizer to neovessels of primary solid tumors and possibly respective metastases for the purpose of diagnosis and for photodynamic destruction. They can further act as antiangiogenic agents and initiate apoptotic destruction of neoendothelial and blood exposed tumor cells.

The terms "RGD-containing peptide" or "RGD peptide" are used herein interchangeably and mean a peptide containing the RGD sequence, also referred to as RGD motif. The term "RGD peptidomimetic" as used herein refers to compounds, particularly, non-peptidic compounds, that mimic peptides having the RGD motif.

The RGD-containing peptide may be a linear or cyclic peptide composed of 4-100, preferably 5-50, 5-30, 5-20 or, more preferably, 5-10, amino acid residues. In preferred embodiments, the RGD peptide is composed of 4, 5, 6, 7, 9 or 25, most preferably 5 amino acid residues.

As used herein, the term "amino acid" includes the 20 naturally occurring amino acids as well as non-natural amino acids.

Examples of natural amino acids suitable for the invention include, but are not limited to, Ala, Arg, Asp, Cys, Gln, Glu, Gly, Ile, Leu, Lys, Met, Phe, Pro, Ser, Thr, Tyr, and Val.

Examples of non-natural amino acids include, but are not limited to, 4-aminobutyric acid (Abu), 2-aminoadipic acid, diaminopropionic (Dap) acid, hydroxylysine, homoserine, homovaline, homoleucine, norleucine (Nle), norvaline (Nva), ornithine (Orn), TIC, naphthylalanine (NaI), ring-methylated derivatives of Phe, halogenated derivatives of Phe or o-methyl-Tyr.

The term "amino acid" herein includes also modified amino acids such as modifications that occur post-translationally in vivo, for example, hydroxyproline, phosphoserine and phosphothreonine; D-modification; N-alkylation, preferably N-methylation, of the peptide bond; acylation or alkylation of the amino terminal group or of the free amino group of Lys; esterification or amidation of the carboxy terminal group or of a free carboxy group of Asp or Glu; and esterification or etherification of the hydroxyl group of Ser or Tyr.

The term "amino acid" includes both D- and L-amino acids. Thus, the peptides used in the conjugates of the invention can be all-D (except for glycine), all-L or L,D-amino acids. D-modifications as well as N-alkylation of the peptide bond are most beneficial to prevent peptide cleavage by enzymes in the organism. In the present invention, a D-amino acid is indicated by a small letter as for the D-phenylalanine 'f' residue in the peptide cycloRGDfK of SEQ ID NO:1 used herein.

The present invention includes also cyclic peptides. Peptides can be cyclized by a variety of methods such as formation of disulfides, sulfides and, especially, lactam bonds between carboxyl and amino functions of the N- and C-termini or amino acid side chains. Cyclization can be obtained by any method known in the art, for example, through amide bond formation, e.g., by incorporating Glu, Asp, Lys, Orn, diamino butyric (Dab) acid, diaminopropionic (Dap) acid at various positions in the chain (—CO—NH or —NH—CO bonds). Backbone to backbone cyclization can also be obtained through incorporation of modified amino acids of the formulas H—N(CH$_2$)$_n$—COOH)—C(R)H—COOH or H—N((CH$_2$)$_n$—NH$_2$)—C(R)H—COOH, wherein n=1-4, and further wherein R is any natural or non-natural side chain of an amino acid.

Cyclization can also be obtained via formation of S—S bonds through incorporation of two Cys residues. Additional side-chain to side chain cyclization can be obtained via formation of an interaction bond of the formula —(CH$_2$)$_n$—S—CH$_2$—CO—, wherein n=1 or 2, which is possible, for example, through incorporation of Cys or homoCys and reaction of its free SH group with, e.g., bromoacetylated Lys, Orn, Dab or Dap.

In some embodiments, the RGD peptides may be those described in U.S. Pat. No. 6,576,239 and EP 0927045, herein incorporated by reference in their entirety as if fully disclosed herein.

In one preferred embodiment, the peptide used according to the invention is the cyclic pentapeptide RGDfK of SEQ ID NO:1, wherein 'f' indicates a D-Phe residue.

In another preferred embodiment, the peptide is the cyclic nonapeptide CDCRGDCGC of SEQ ID NO:2, herein designated 'RGD-4C', which contains four cysteine residues forming two disulfide bonds in the molecule, and is one of the promising peptides with integrin specificity. This peptide was shown to be a selective and potent ligand (affinity constant of ~100 nM) of the $\alpha_v\beta_5$ and $\alpha_v\beta_3$ integrins (Ruoslahti, 2002; Elceiri and Cheresh, 1999).

The aspartic acid residue of the RGD motif is highly susceptible to chemical degradation, leading to the loss of biological activity, and this degradation could be prevented by cyclization via disulfide linkage (Bogdanowich-Knipp et al., 1999). Along with improving stability, double cyclic peptides show higher potency compared to single disulphide-bridge and linear peptides in inhibiting the attachment of vitronectin to cells. The high activity of double cyclic RGD peptide is likely to be due to an appropriately restrained conformation not only of the RGD motif but also of the flanking amino acids. The number and nature of residues flanking the RGD sequence in synthetic peptides have a significant influence on how that sequence is recognized by individual integrin receptors (Koivunen et al., 1995; Pierschbacher and Ruoslahti, 1987). An aromatic residue may be particularly significant in making favorable contacts in the binding site of integrin (Koivunen et al., 1995). Cyclic RGD peptides targeted for $\alpha_v\beta_3$ internalize by an integrin independent fluid-phase endocytosis pathway that does not alter the number of functional integrin receptors on the cell surface. Additionally, cyclic RGD peptides remain or degrade in the lysosome, in a process that reaches saturation after 15 minutes, and only a small portion can leave the lysosome and reach the cell cytoplasm. This explains why cyclic RGD peptides are found in the cell cytoplasm only after a certain period of time (48 to 72 hours) (Hart et al., 1994; Castel et al., 2001).

In other preferred embodiments, the RGD peptide is selected from the cyclic peptides: (i) tetrapeptide cyclo-RGDK (SEQ ID NO:4), pentapeptide cycloRGDf-n(Me)K (SEQ ID NO:7), wherein f indicates D-Phe and the peptide bond between f and K is methylated; and pentapeptide cycloRGDyK (SEQ ID NO:8), wherein y indicates D-Tyr.

In another embodiment, the RGD-containing peptide is linear and may be selected from the hexapeptide GRGDSP (SEQ ID NO:3), the heptapeptide GRGDSPK (SEQ ID NO:5), and the 25-mer (GRGDSP)$_4$K (SEQ ID NO:7)

In one embodiment of the invention, the RGD peptide is linked directly to the photosensitizer porphyrin, chlorophyll or bacteriochlorophyll macrocycle via a functional group in its periphery, for example, COOH, forming an amide CO—NH$_2$ group with the amino terminal group or a free amino group of the RGD peptide.

In another embodiment, the RGD peptide is linked to the photosensitizer macrocycle via a spacer arm/bridging group such as, but not limited to, a $C_1$-$C_{25}$ hydrocarbylene, preferably a $C_1$-$C_{10}$ alkylene or phenylene, substituted by an end functional group such as OH, COOH, SO$_3$H, COSH or NH$_2$, thus forming an ether, ester, amide, thioamide or sulfonamide group.

In some embodiments, the photosensitizer is conjugated to a RGd peptidomimetic.

In one preferred embodiment the RGD peptidomimetic is a non-peptidic compound comprising a guanidine and a carboxyl terminal groups spaced by a chain of 11 atoms, at least of said atoms being carbon atoms, and said chain comprises one or more O, S or N atoms and may optionally be substituted by oxo, thioxo, halogen, amino, C1-C6 alkyl, hydroxyl, or carboxy or one or more atoms of said chain may form a 3-6 membered carbocyclic or heterocyclic ring. Compounds of this type are described in WO 93/09795 of the same applicant, herein incorporated by reference in its entirety as if fully disclosed herein.

In preferred embodiments, the RGD peptidomimetic above comprises in the chain N atoms and is substituted by an oxo group.

In a more preferred embodiment, the RGD peptidomimetic has the formula shown in conjugate 40 herein:

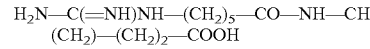

H$_2$N—C(=NH)NH—(CH$_2$)$_5$—CO—NH—CH
(CH$_2$)—(CH$_2$)$_2$—COOH

In another embodiment, the RGD peptidomimetic has the formula shown in conjugate 41 herein.

In one embodiment, the photosensitizer is a porphyrin that may be metalated or unmetalated and optionally substituted in the periphery by different substituents such as alkyl, aryl, heteroaryl and or functional groups. Most preferred porphyrins used in accordance with the present invention are water-soluble porphyrins.

In preferred embodiments, the porphyrin macrocycle is substituted by 4 aryl groups at positions 5, 10, 15, 20.

In one preferred embodiment, the photosensitizer is a tetraarylporphyrin of the formula:

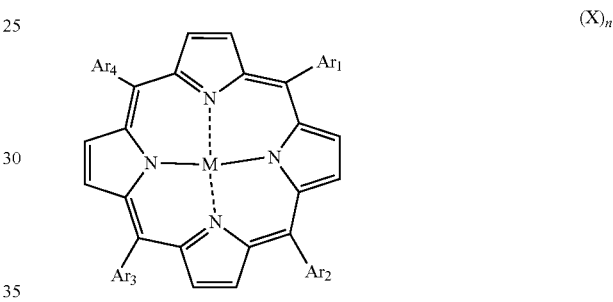

wherein

Ar$_1$, Ar$_2$, Ar$_3$, and Ar$_4$, the same or different, are each an aryl radical selected from a carbocyclic aryl, a heteroaryl and a mixed carboaryl-heteroaryl radical, each of the aryl radicals is unsubstituted or is substituted by one or more substituents selected from halogen atoms, $C_2$-$C_8$ alkyl when the aryl is phenyl, $C_1$-$C_8$ alkyl when the aryl is heteroaryl or mixed carboaryl-heteroaryl, $C_1$-$C_8$ alkoxy, carboxy, $C_1$-$C_8$ alkylamino, amino-($C_1$-$C_8$) alkylamino, tri-($C_1$-$C_8$) alkylammonium, hydroxy, and CONH$_2$, and at least one of Ar$_1$, Ar$_2$, Ar$_3$, and Ar$_4$ is substituted by an RGD-containing peptide or an RGD peptidomimetic linked to said at least one aryl group via one of its substituents or via a bridging group;

n is 0 when the substituents are neutral, or n is an integer from 1 to 4;

X is a pharmaceutically acceptable anion, when the aryl groups are positively charged, or a pharmaceutically acceptable cation, when the aryl groups are negatively charged; and M is 2H or is an atom selected from the group consisting of Mg, Pd, Pt, Co, Ni, Sn, Cu, Zn, Mn, In, Eu, Fe, Au, Al, Gd, Er, Yb, Lu, Ga, Y, Rh, Ru, Si, Ge, Cr, Mo, P, Re, Tl and Tc and isotopes thereof.

In preferred embodiments, the RGD-porphyrin conjugates are utilized in diagnosis and/or radiotherapy. According to these embodiments, the porphyrins are metalated porphyrins wherein the metal atom is preferably Mn, Cu, or Ni. When the conjugates of the invention are utilized for diagnosis, for example, of tumors, the porphyrins are metalated with radioisotopes such as $^{103}$Pd, $^{195}$Pt, $^{106}$Rh, $^{188}$Re, $^{177}$Lu, $^{164}$Er, $^{117m}$Sn, $^{153}$Sn, $^{90}$Y, $^{67}$Cu and $^{32}$P.

In certain other embodiments, the RGD-porphyrin conjugates are utilized in photodynamic therapy (PDT). The preferred porphyrins according to these embodiments are non-metalated porphyrins or porphyrin containing certain metal atoms selected from Co, Pd, Pt or Ru. Cytotoxicity of metalated porphyrins may be enhanced by introduction of positively or negatively charged groups thereto.

Photophysical properties (visible absorption, fluorescence and triplet lifetime) of the metalated metalloporphyrin derivatives are determined by the central metal. Ando et al. (Ando et al., 1993) showed that a Zn-porphyrin derivative had longer triplet lifetimes (>1 ms) and the triplet lifetime of the Ga porphyrin was even longer (40.3 ms). On the other hand, Cu-porphyrin had a much shorter triplet lifetime than other metalated porphyrins. In fact, the triplet lifetimes of Mn-, Fe- and Ni-porphyrins were unmeasurable because they did not emit any detectable fluorescence or phosphorescence. This means that they have triplet lifetimes shorter than 0.1 µs. The absence of fluorescence and phosphorescence of these derivatives can be connected with increase of the radiationless decay from the lowest singlet state as well as from the lowest excited triplet state to result in significant reduction of the triplet lifetime.

Thus, apparently, porphyrins containing metal atom such as Mn, Cu, Gd, Zn, Fe(II) or Ni do not react well with tissue oxygen and, therefore, do not generate the critical amount of reactive oxygen species (ROS) needed to elicit an efficient PDT effect. Indeed, it was shown (Ali and van Lier, 1999; Tomoyuki et al., 1993) that $^{67}$Cu- and Ni-porphyrins are non-toxic and exhibit good in vivo stability, and Mn(III)-porphyrins are usually not active as photosensitizers and thus avoid side effects such as skin photosensitivity.

Based on such observations, the present inventors designed tetrarylporphyrin derivatives metalated with Mn, Ni, Cu, Gd, Zn or Fe(II) as diagnostic agents, suitable for concomitant use in diagnostic techniques such as, but not limited to, magnetic resonance imaging.

The carbocyclic aryl radical by itself or as part of the mixed carboaryl-heteroaryl radical may be a substituted or unsubstituted monocyclic or bicyclic aromatic radical and said heteroaryl radical by itself or as part of a mixed carboaryl-heteroaryl radical may be a substituted or unsubstituted 5-6 membered aromatic ring containing 1-3 heteroatoms selected from O, S and/or N.

Examples of carbocyclic aryl radical include phenyl, biphenyl and naphthyl and of heteroaryl include furyl, thienyl, pyrrolyl, imidazolyl, thiazolyl, pyridyl, pyrimidyl, and triazinyl. The carbocyclic aryl and/or heteroaryl radical may be unsubstituted or substituted by one or more halogen atoms, $C_1$-$C_8$ alkyl, $C_1$-$C_8$ alkoxy, carboxy, $C_1$-$C_8$alkylamino, amino-($C_1$-$C_8$) alkylamino, and tri-($C_1$-$C_8$) alkylammonium radicals, carboxy, $CONH_2$, with the proviso that M is not 2H when the carbocyclic aryl is phenyl substituted by methyl or tetraacetylglucosyloxy and the RGD peptide is linear.

In the tetraaryl porphirins above M is preferably 2H, Pd, Cu, Mn or Gd.

In one preferred embodiment, the RGD peptide in the conjugate containing a porphyrin photosensitizer is the peptide of SEQ ID NO:1, preferably linked to at least one aryl group of the porphyrin moiety via a —CO—NH— group.

In preferred embodiments, the RGD peptide-porphyrin conjugates comprise a non-metalated or metalated tetraarylporphyrin conjugated to the peptide of SEQ ID NO:1:Meso-5-(4-cycloRGDfK-benzamido)-10,15,20-tris(4-carboxyphenyl)porphine (20); Copper(II) meso-5-(4-cycloRGDfK-benzamido)-10,15,20-tris(4-carboxyphenyl)porphine (21); and Gadolinium(III)meso-5-(4-cycloRGDfK-benzamido)-10,15,20-tris(4-carboxyphenyl)porphine (22).

In another embodiment, the photosensitizer is a chlorophyll or bacteriochlorophyll derivative that may be a natural or a synthetic non-natural derivative of chlorophyll or bacteriochlorophyll, including compounds in which modifications have been made in the macrocycle, and/or in the periphery and/or the central Mg atom may be absent or it is replaced by other metal atom suitable for the purpose of diagnosis and/or for the purpose of PDT.

In preferred embodiments, the invention relates to a conjugate wherein the photosensitizer is a chlorophyll or bacteriochlorophyll of the formula I, II or III:

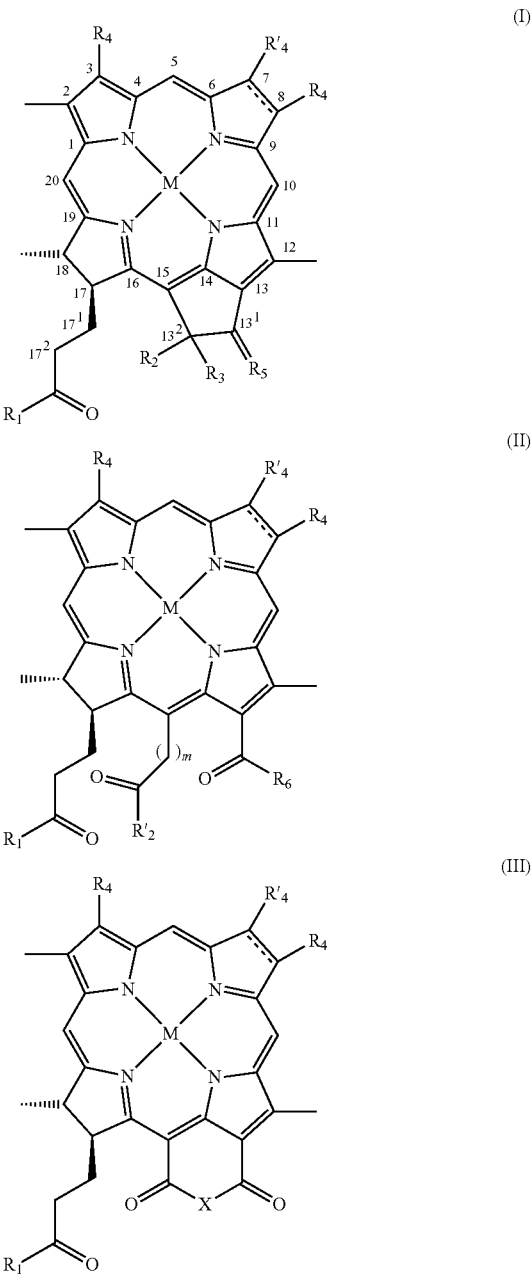

wherein

M represents 2H or an atom selected from the group consisting of Mg, Pd, Pt, Co, Ni, Sn, Cu, Zn, Mn, In, Eu, Fe, Au, Al, Gd, Er, Yb, Lu, Ga, Y, Rh, Ru, Si, Ge, Cr, Mo, P, Re and Tc and isotopes thereof;

X is O or N—$R_7$;

$R_1$, $R'_2$ and $R_6$ each independently is Y—$R_8$, —$NR_9R'_9$ or —$N^+R_9R'_9R''_9A^-$ or $R_1$ and $R_6$ in formula II together with the carbon atoms to which they are attached form a ring comprising an RGD peptide or RGD peptidomimetic;

Y is O or S;

$R_2$ is H, OH or $COOR_9$;

$R_3$ is H, OH, $C_1$-$C_{12}$ alkyl or $C_1$-$C_{12}$ alkoxy;

$R_4$ is —CH=$CR_9R'_9$, —CH=$CR_9$Hal, —CH=CH—$CH_2$—$NR_9R'_9$, —CH=CH—$CH_2$—$N^+R_9R'_9R''_9$ $A^-$, —CHO, —CH=$NR_9$, —CH=$N^+R_9R'_9$ $A^-$, —$CH_2$—$OR_9$, —$CH_2$—$SR_9$, —$CH_2$-Hal, —$CH_2$—$R_9$, —$CH_2$—$NR_9R'_9$, —$CH_2$—$N^+R_9R'_9R''_9$ $A^-$, —$CH_2$—$CH_2R_9$, —$CH_2$—$CH_2$Hal, —$CH_2$—$CH_2OR_9$, —$CH_2$—$CH_2SR_9$, —$CH_2$—$CH_2$—$NR_9R'_9$, —$CH_2$—$CH_2$—$N^+R_9R'_9R''_9$ $A^-$, —$COCH_3$, $C(CH_3)$=$CR_9R'_9$, —$C(CH_3)$=$CR_9$Hal, —$C(CH_3)$=$NR_9$, —$CH(CH_3)$=$N^+R_9R'_9A^-$, —$CH(CH_3)$-Hal, —$CH(CH_3)$—$OR_9$, —$CH(CH_3)$—$SR_9$, —$CH(CH_3)$—$NR_9R'_9$, —CH($CH_3$)—$N^+R_9R'_9R'_9A^-$, or —C≡$CR_9$;

$R'_4$ is methyl or formyl;

$R_5$ is =O, =S, =N—$R_9$, =$N^+R_9R'_9$ $A^-$, =$CR_9R'_9$, or =$CR_9$-Hal;

$R_7$, $R_8$, $R_9$, $R'_9$ and $R''_9$ each independently is:

(a) H;

(b) $C_1$-$C_{25}$ hydrocarbyl;

(c) $C_1$-$C_{25}$ hydrocarbyl, preferably $C_1$-$C_{25}$ alkyl, alkenyl or alkynyl, more preferably $C_1$-$C_{10}$ or $C_1$-$C_6$ alkyl, substituted by one or more functional groups selected from the group consisting of halogen, nitro, oxo, OR, SR, epoxy, epithio, —NRR', —CONRR', —CONR—NRR', —NHCONRR', —NHCONRNRR', —COR, COOR", —$OSO_3R$, —$SO_3R''$, —$SO_2R$, —$NHSO_2R$, —$SO_2NRR'$, =N—OR, —$(CH_2)_n$—CO—NRR', —O—$(CH_2)_n$—OR, —O—$(CH_2)_n$—O—$(CH_2)_n$—R, —$OPO_3RR'$, —$PO_2HR$, and —$PO_3R''R''$, wherein R and R' each independently is H, hydrocarbyl or heterocyclyl and R" is hydrocarbyl or heterocyclyl;

(d) $C_1$-$C_{25}$ hydrocarbyl, preferably $C_1$-$C_{25}$ alkyl, more preferably $C_1$-$C_{10}$ or $C_1$-$C_6$ alkyl, substituted by one or more functional groups selected from the group consisting of acidic groups that are converted to negatively charged groups under physiological conditions;

(e) $C_1$-$C_{25}$ hydrocarbyl, preferably $C_1$-$C_{25}$ alkyl, more preferably $C_1$-$C_{10}$ or $C_1$-$C_6$ alkyl, containing one or more heteroatoms and/or one or more carbocyclic or heterocyclic moieties;

(f) $C_1$-$C_{25}$ hydrocarbyl, preferably $C_1$-$C_{25}$ alkyl, more preferably $C_1$-$C_{10}$ or $C_1$-$C_6$ alkyl, containing one or more heteroatoms and/or one or more carbocyclic or heterocyclic moieties and substituted by one or more functional groups as defined in (c) and (d) above;

(g) $C_1$-$C_{25}$ hydrocarbyl, preferably $C_1$-$C_{25}$ alkyl, more preferably $C_1$-$C_{10}$ or $C_1$-$C_6$ alkyl substituted by a residue of an amino acid, a peptide, a protein, a monosaccharide, an oligosaccharide, a polysaccharide, or a polydentate ligand and its chelating complex with metals; or (h) a residue of an amino acid, a peptide, a protein, a monosaccharide, an oligosaccharide, a polysaccharide, or a polydentate ligand and its chelating complex with metals;

$R_7$ may further be —NRR', wherein R and R' each is H or $C_1$-$C_{25}$ hydrocarbyl, preferably $C_1$-$C_{25}$ alkyl, more preferably $C_1$-$C_{10}$ or $C_1$-$C_6$ alkyl, optionally substituted by a negatively charged group, preferably $SO_3$;

$R_8$ may further be $H^+$ or a cation $R^+_{10}$ when $R_1$, $R'_2$ and $R_6$ each independently is Y—$R_8$;

$R^+_{10}$ is a metal, an ammonium group or an organic cation;

$A^-$ is a physiologically acceptable anion;

m is 0 or 1;

the dotted line at positions 7-8 represents an optional double bond; and pharmaceutically acceptable salts and optical isomers thereof;

and said chlorophyll or bacteriochlorophyll derivative of formula I, II or III contains at least one RGD-containing peptide residue.

In one embodiment, the dotted line at positions 7-8 represents a double bond and the photosensitizer is a chlorophyll of the formula I, II or III. The compounds of formula I wherein M is Mg, $R_1$ at position $17^3$ is phytyloxy, $R_2$ at position $13^2$ is $COOCH_3$, $R_3$ at position $13^2$ is an H atom, $R_5$ is O, $R_4$ at position 3 is vinyl, the dotted line at positions 7-8 represents a double bond, and either $R'_4$ is methyl at position 7 and $R_4$ is ethyl at position 8 or $R'_4$ is formyl at position 7 and $R_4$ is ethyl at position 8, are chlorophyll a and b, respectively, and their derivatives will have different metal atom and/or different substituents $R_1$, $R_2$, $R_3$, $R_4$, $R'_4$ and/or $R_5$.

In another embodiment, the positions 7-8 are hydrogenated and the photosensitizer is a bacteriochlorophyll of the formula I, II or III. The compounds of formula I wherein M is Mg, $R_1$ at position $17^3$ is phytyloxy or geranylgeranyloxy, $R_2$ at position $13^2$ is $COOCH_3$, $R_3$ at position $13^2$ is an H atom, $R_5$ is O, $R_4$ at position 3 is acetyl and at position 8 is ethyl, and the dotted line at positions 7-8 is absent are bacteriochlorophyll a, and their derivatives will have different metal atom and/or different substituents $R_1$, $R_2$, $R_3$, $R_4$, and/or $R_5$.

As used herein, the term "hydrocarbyl" means any straight or branched, saturated or unsaturated, acyclic or cyclic, including aromatic, hydrocarbyl radicals, of 1-25 carbon atoms, preferably of 1 to 20, more preferably 1 to 6, most preferably 2-3 carbon atoms. The hydrocarbyl may be an alkyl radical, preferably of 1-4 carbon atoms, e.g. methyl, ethyl, propyl, butyl, or alkenyl, alkynyl, cycloalkyl, aryl such as phenyl or an aralkyl group such as benzyl, or at the position 17 it is a radical derived from natural Chl and Bchl compounds, e.g. geranylgeranyl (2,6-dimethyl-2,6-octadienyl) or phytyl (2,6,10,14-tetramethyl-hexadec-14-en-16-yl).

As used herein, the term "carbocyclic moiety" refers to a monocyclic or polycyclic compound containing only carbon atoms in the ring(s). The carbocyclic moiety may be saturated, i.e. cycloalkyl, or unsaturated, i.e. cycloalkenyl, or aromatic, i.e. aryl.

The term "alkoxy" as used herein refers to a group ($C_1$-$C_{25}$)alkyl-O—, wherein $C_1$-$C_{25}$ alkyl is as defined above. Examples of alkoxy are methoxy, ethoxy, n-propoxy, isopropoxy, butoxy, isobutoxy, tert-butoxy, pentoxy, hexoxy, —$OC_{15}H_{31}$, —$OC_{16}H_{33}$, —$OC_{17}H_{35}$, —$OC_{18}H_{37}$, and the like. The term "aryloxy" as used herein refers to a group ($C_6$-$C_{18}$)aryl-O—, wherein $C_6$-$C_{18}$ aryl is as defined above, for example, phenoxy and naphthoxy.

The terms "heteroaryl" or "heterocyclic moiety" or "heteroaromatic" or "heterocyclyl", as used herein, mean a radical derived from a mono- or poly-cyclic heteroaromatic ring containing one to three heteroatoms selected from the group consisting of O, S and N. Particular examples are pyrrolyl, furyl, thienyl, pyrazolyl, imidazolyl, oxazolyl, thiazolyl, pyridyl, quinolinyl, pyrimidinyl, 1,3,4-triazinyl, 1,2,3-triazinyl, 1,3,5-triazinyl, benzofuryl, isobenzofuryl, indolyl, imidazo[1,2-a]pyridyl, benzimidazolyl, benzthiazolyl and benzoxazolyl.

Any "carbocyclic", "aryl" or "heteroaryl" may be substituted by one or more radicals such as halogen, $C_6$-$C_{14}$ aryl, $C_1$-$C_{25}$ alkyl, nitro, OR, SR, —COR, —COOR, —SO$_3$R, —SO$_2$R, —NHSO$_2$R, —NRR', —(CH$_2$)$_n$—NR—COR', and —(CH$_2$)$_n$—CO—NRR'. It is to be understood that when a polycyclic heteroaromatic ring is substituted, the substitutions may be in any of the carbocyclic and/or heterocyclic rings.

The term "halogen", as used herein, refers to fluoro, chloro, bromo or iodo.

In one embodiment of the invention, the photosensitizer of the conjugate is a chlorophyll or bacteriochlorophyll of the formula I, II or III containing at least one negatively charged group and/or at least one acidic group that is converted to a negatively charged group at the physiological pH.

As defined herein, "a negatively charged group" is an anion derived from an acid and includes carboxylate (COO$^-$), thiocarboxylate (COS$^-$), sulfonate (SO$_3^-$), and phosphonate (PO$_3^{2-}$), and the "acidic group that is converted to a negatively charged group under physiological conditions" include the carboxylic (—COOH), thio-carboxylic (—COSH), sulfonic (—SO$_3$H) and phosphonic (—PO$_3$H$_2$) acid groups. BChl derivatives with negatively charged groups or groups converted thereto under physiological conditions have been described in WO 2004/045492 of the same applicant, herewith incorporated by reference in its entirety as if fully disclosed herein.

In another embodiment of the invention, the photosensitizer of the conjugate is a chlorophyll or bacteriochlorophyll of the formula I, II or III containing at least one positively charged group and/or at least one basic group that is converted to a positively charged group at the physiological pH.

As defined herein, "a positively charged group" denotes a cation derived from a N-containing group or from an onium group not containing N. Since tumor endothelium is characterized by an increased number of anionic sites, positively charged groups or basic groups that are converted to positively charged groups under physiological conditions, may enhance the targeting efficiency of the conjugates of the present invention.

A "cation derived from a N-containing group" as used herein denotes, for example, but is not limited to, an ammonium —N$^+$(RR'R"), hydrazinium —(R)N—N$^+$(R'R"), ammoniumoxy O←N$^+$(RR')—, iminium>C=N$^+$(RR'), amidinium —C(=RN)—N$^+$R'R" or guanidinium —(R)N—C(=NR)—N$^+$R'R" group, wherein R, R' and R" each independently is H, hydrocarbyl, preferably $C_1$-$C_6$ alkyl as defined herein, phenyl or benzyl, or heterocyclyl, or in the ammonium group one of R, R' and R" may be OH, or two of R, R' and R" in the ammonium group or R and R' in the hydrazinium, ammoniumoxy, iminium, amidinium or guanidinium groups, together with the N atom to which they are attached, form a 3-7 membered saturated ring, optionally containing one or more heteroatoms selected from the group consisting of O, S or N and optionally further substituted at the additional N atom, or said cation is derived from a compound containing one or more N atoms in a heteroaromatic ring.

In one more preferred embodiment, the conjugate of the present invention contains an ammonium group of the formula —N$^+$(RR'R"), wherein each of R, R' and R" independently is H or optionally substituted hydrocarbyl or heterocyclyl, as defined herein, or one of them may be OH. The —N$^+$(RR'R") ammonium group may be a secondary ammonium, wherein any two of the radicals R, R' or R" are H; a tertiary ammonium, wherein only one of R, R' or R" is H; or a quaternary ammonium, wherein each of R, R' or R" is an optionally substituted hydrocarbyl or heterocyclyl group as defined herein. When one of R, R' or R" is OH, the group is a hydroxylammonium group. Preferably, the ammonium group is a quaternary ammonium group wherein R, R' and R" each is $C_1$-$C_6$ alkyl such as methyl, ethyl, propyl, butyl, hexyl. As mentioned hereinabove, the ammonium group may be an end group in the molecule or it may be found within an alkyl chain in the molecule.

In the hydrazinium —(R)N—N$^+$(R'R"), amidinium —C(=NR)—N$^+$R'R" and guanidinium —(R)N—C(=NR)—N$^+$R'R" groups, R, R' and R" may each independently be H or hydrocarbyl or heterocyclyl, or R' and R" together with the N atom to which they are attached form a 3-7 membered saturated ring, as defined herein. Examples of such groups include those wherein R is H, and R' and R" each is $C_1$-$C_6$ alkyl such as methyl, ethyl, propyl, butyl, hexyl.

In the ammoniumoxy O←N$^+$(RR')— and iminium>C=N$^+$(RR') groups, R and R' may each independently be H or hydrocarbyl, preferably $C_1$-$C_6$ alkyl, or heterocyclyl, or R and R' together with the N atom to which they are attached form a 3-7 membered saturated ring, as defined herein.

In another preferred embodiment, the bacteriochlorophyll derivative contains a cyclic ammonium group of the formula —N$^+$(RR'R"), wherein two of R, R' and R" together with the N atom form a 3-7 membered saturated ring defined hereinbelow.

As defined herein, "a 3-7 membered saturated ring" formed by two of R, R' and R" together with the N atom to which they are attached may be a ring containing only N such as aziridine, pyrrolidine, piperidine, piperazine or azepine, or it may contain a further heteroatom selected from O and S such as morpholine or thiomorpholine. The further N atom in the piperazine ring may be optionally substituted by alkyl, e.g. $C_1$-$C_6$ alkyl, that may be substituted by halo, OH or amino. The onium groups derived from said saturated rings include aziridinium, pyrrolidinium, piperidinium, piperazinium, morpholinium, thiomorpholinium and azepinium.

As defined herein "a cation derived from a N-containing heteroaromatic radical" denotes a cation derived from a N-heteroaromatic compound that may be a mono- or polycyclic compound optionally containing O, S or additional N atoms. The ring from which the cation is derived should contain at least one N atom and be aromatic, but the other ring(s), if any, can be partially saturated. Examples of N-heteroaromatic cations include pyrazolium, imidazolium, oxazolium, thiazolium, pyridinium, pyrimidinium, quinolinium, isoquinolinium, 1,2,4-triazinium, 1,3,5-triazinium and purinium.

The at least one positively charged group may also be an onium group not containing nitrogen such as but not limited to, phosphonium [—P$^+$(RR'R")], arsonium [—As$^+$(RR'R")], oxonium [—O$^+$(RR')], sulfonium [—S$^+$(RR')], selenonium [—Se$^+$(RR')], telluronium [—Te$^+$(RR')], stibonium [—Sb$^+$(RR'R")], or bismuthonium [—Bi$^+$(RR'R")] group, wherein each of R, R' and R", independently, is H, hydrocarbyl or heterocyclyl, preferably $C_1$-$C_6$ alkyl such as methyl, ethyl, propyl, butyl, pentyl or hexyl, or aryl, preferably, phenyl.

Examples of phosphonium groups of the formula —P$^+$(RR'R") include groups wherein R, R' and R" each is methyl, ethyl, propyl, butyl or phenyl, or R is methyl, ethyl, propyl, butyl or hexyl and R' and R" both are phenyl. Examples of arsonium groups of the formula —As$^+$(RR'R") include groups wherein R, R' and R" each is methyl, ethyl, propyl, butyl or phenyl. Examples of sulfonium groups of the formula —S$^+$(RR') include groups wherein R and R' each is methyl, ethyl, propyl, butyl, phenyl, benzyl, phenethyl, or a substituted hydrocarbyl group.

As defined herein, "a basic group that is converted to a positively charged group under physiological conditions" is, at least theoretically, any basic group that will generate under physiological conditions a positively charged group as defined herein. It is to be noted that the physiological conditions, as used herein, do not refer solely to the serum, but to different tissues and cell compartments in the body.

Examples of such N-containing basic groups include, without being limited to, any amino group that will generate an ammonium group, any imine group that will generate an iminium group, any hydrazine group that will generate a hydrazinium group, any aminooxy group that will generate an ammoniumoxy group, any amidine group that will generate an amidinium group, any guanidine group that will generate a guanidinium group, all as defined herein. Other examples include phosphino and mercapto groups.

Thus, the conjugates of the present invention may contain at least one basic group that is converted to a positively charged group under physiological conditions such as —NRR', —C(=NR)—NR'R", —NR—NR'R", —(R)N—C(=NR)—NR'R", O←NR—, or >C=NR, wherein each of R, R' and R" independently is H, hydrocarbyl, preferably $C_1$-$C_{25}$ alkyl, more preferably $C_1$-$C_{10}$ or $C_1$-$C_6$ alkyl, or heterocyclyl, or two of R, R' and R" together with the N atom form a 3-7 membered saturated ring, optionally containing an O, S or N atom and optionally further substituted at the additional N atom, or the basic group is a N-containing heteroaromatic radical.

The 3-7 membered saturated ring may be aziridine, pyrrolidine, piperidine, morpholine, thiomorpholine, azepine or piperazine optionally substituted at the additional N atom by $C_1$-$C_6$ alkyl optionally substituted by halo, hydroxyl or amino, and the N-containing heteroaromatic radical may be pyrazolyl, imidazolyl, oxazolyl, thiazolyl, pyridyl, quinolinyl, isoquinolinyl, pyrimidyl, 1,2,4-triazinyl, 1,3,5-triazinyl or purinyl.

BChl derivatives with positively charged groups or groups converted thereto under physiological conditions have been described in WO 2005/120573 of the same applicant, herewith incorporated by reference in its entirety as if fully disclosed herein.

In one embodiment, the photosensitizer is a chlorophyll or bacteriochlorophyll of formula II and $R_6$ is a basic group —NR$_9$R'$_9$ wherein $R_9$ is H and R'$_9$ is $C_1$-$C_6$ alkyl substituted by a basic group —NH—(CH$_2$)$_{2-6}$—NRR' wherein each of R and R' independently is H, $C_1$-$C_6$ alkyl optionally substituted by NH$_2$ or R and R' together with the N atom form a 5-6 membered saturated ring, optionally containing an O or N atom and optionally further substituted at the additional N atom by —(CH$_2$)$_{2-6}$—NH$_2$.

In another embodiment, the photosensitizer is a bacteriochlorophyll of formula II and R6 is —NH—(CH$_2$)$_3$—NH—(CH$_2$)$_3$—NH$_2$, —NH—(CH$_2$)$_2$-1-morpholino, or —NH—(CH$_2$)$_3$—. piperazino-(CH$_2$)$_3$—NH$_2$ or R1 and R6 together form a cyclic ring comprising an RGD peptide or RGD peptidomimetic.

In another embodiment, the photosensitizer is a chlorophyll or bacteriochlorophyll of formula III, X is —NR$_7$, R$_7$ is —NRR', R is H and R' is $C_{2-6}$-alkyl substituted by SO$_3$— or an alkaline salt thereof, preferably the photosensitizer is a bacteriochlorophyll and X is —NR$_7$ and R$_7$ is —NH—(CH$_2$)$_3$—SO$_3$K.

In another embodiment, $R_7$, $R_8$, $R_9$ or R'$_9$ each is a $C_{1-6}$-alkyl substituted by one or more —OH groups. For example, the photosensitizer is a chlorophyll or bacteriochlorophyll of formula II and $R_6$ is —NR$_9$R'$_9$, $R_9$ is H and R'$_9$ is HOCH$_2$—CH(OH)—CH$_2$—.

In another embodiment, the photosensitizer is a chlorophyll or bacterio-chlorophyll of formula II and $R_6$ is —NR$_9$R'$_9$, $R_9$ is H and R'$_9$ is $C_{1-6}$-alkyl substituted by a polydentate ligand or its chelating complexes with metals. Examples of polydentate ligands include, without being limited to, EDTA (ethylenediamine tetraacetic acid), DTPA (diethylene triamine pentaacetic acid) or the macrocyclic ligand DOTA. In one preferred embodiment the polydentate ligand is DTPA, $R_6$ is —NH—(CH$_2$)$_3$—NH-DTPA, and the metal is Gd.

The cation $R_8^+$ may be a monovalent or divalent cation derived from an alkaline or alkaline earth metal such as K$^+$, Na$^+$, Li$^+$, NH$_4^+$, Ca$^{2+}$, more preferably K$^+$; or $R_8^+$ is an organic cation derived from an amine or from a N-containing group As defined herein, the $C_1$-$C_{25}$ hydrocarbyl defined for $R_7$, $R_8$, $R_9$ and R'$_9$ may optionally be substituted by one or more functional groups selected from halogen, nitro, oxo, OR, SR, epoxy, epithio, aziridine, —CONRR', —COR, COOR, —OSO$_3$R, —SO$_3$R, —SO$_2$R, —NHSO$_2$R, —SO$_2$NRR'—NRR', =N—OR, =N—NRR', —C(=NR)—NRR', —NR—NRR', —(R)N—C(=NR)—NRR', O←NR—, >C=NR, —(CH$_2$)$_n$—NR—COR', —(CH$_2$)$_n$—CO—NRR', —O—(CH$_2$)$_n$—OR, —O—(CH$_2$)$_n$—O—(CH$_2$)$_n$—R, —PRR', —OPO$_3$RR', —PO$_2$HR, —PO$_3$RR'; one or more negatively charged groups such as COO$^-$, COS$^-$, —OSO$_3^-$, —SO$_3^-$, —OPO$_3$R$^-$, —PO$_2$H$^-$, —PO$_3^{2-}$ and —PO$_3$R$^-$; and/or one or more positively charged groups such as —P$^+$(RR'R"), —As$^+$(RR'R"), —O$^+$(RR'), —S$^+$(RR'), —Te$^+$(RR'), —Sb$^+$(RR'R"), —Bi$^+$(RR'R"), O←N$^+$(RR')—, >C=N$^+$(RR'), —N$^+$(RR'R"), —(R)N—N$^+$(RR'R"), —(R)N—C(=HN)—N$^+$RR'R", —C(=NH)—N$^+$(RR'R"), or a N-heteroaromatic cation such as pyrazolium, imidazolium, oxazolium, thiazolium, pyridinium, quinolinium, pyrimidinium, 1,2,4-triazinium, 1,3,5-triazinium and purinium; wherein n is an integer from 1 to 6, R, R' and R" each independently is H, hydrocarbyl or heterocyclyl, or two of R, R' and R" together with the N atom to which they are attached form a 3-7 membered saturated ring, optionally containing one or more heteroatoms selected from the group consisting of O, S or N and optionally further substituted at the additional N atom. The $C_1$-$C_{25}$ hydrocarbyl defined for $R_7$, $R_8$, $R_9$ and R'$_9$ may also be substituted by the residue of a mono-, oligo- or polysaccharide such as glycosyl, or of an amino acid, peptide or protein. In addition, $R_8$, $R_9$ and R'$_9$ each may independently be a residue of a mono-, oligo- or polysaccharide such as glycosyl, or of an amino acid, peptide or protein, or a polydentate ligand such as DTPA, DOTA, EDTA and the like and their chelating complexes with metals.

In the groups OR and SR, when R is H, the groups hydroxy and mercapto are represented, respectively, and when R is other than H, ethers and sulfides are represented. In the group —PRR', the phosphino group is represented when R and R' are H. In the group —COR, when R is H, the formyl group —CHO of an aldehyde is represented, while when R is other than H, this is the residue of a ketone such as alkylcarbonyl and arylcarbonyl groups. In the group COOR, when R is not H, this is a carboxylic acid ester group such as the alkoxycarbonyl and aryloxycarbonyl groups. Similarly, esters are represented in the groups —OSO$_3$R, —SO$_3$R, —SO$_2$R, —OPO$_3$RR', —PO$_2$HR and —PO$_3$RR' when R and R' are other than H.

In one preferred embodiment of the invention, the photosensitizer is unmetalated, namely, M is 2H. In other preferred embodiments, the photosensitizer is metalated as defined hereinabove, more preferably M is Pd, Cu or Mn, most preferably Pd.

In some preferred embodiments of the invention, the photosensitizer is a bacteriochlorophyll of the formula I, II or III, more preferably formula II, and M is 2H, Cu, Mn, more preferably Pd. In other embodiments, the photosensitizer is a chlorophyll of the formula I, II or III, more preferably formula II, and M is 2H, Cu or Mn.

In some preferred embodiments, the conjugate comprises a photosensitizer bacteriochlorophyll of the formula II wherein M is Pd, Mn, Cu or 2H; m is 0; R$_1$ is NH—P, wherein P is the residue of an RGD-containing peptide or RGD peptidomimetic linked directly to the NH— or via a spacer; R'$_2$ is methoxy; R$_4$ at position 3 is acetyl and at position 8 is ethyl; R'$_4$ is methyl; and R$_6$ is —NH—(CH$_2$)$_2$—SO$_3^-$Me$^+$, wherein Me$^+$ is Na$^+$ or K$^+$.

In other preferred embodiments, the conjugate comprises a photosensitizer bacteriochlorophyll of the formula II wherein M is Pd or 2H; m is 0; R$_1$ is NH—P, wherein P is the residue of an RGD-containing peptide or RGD peptidomimetic linked directly to the NH— or via a spacer; R'$_2$ is methoxy; R$_4$ at position 3 is acetyl and at position 8 is ethyl; R'$_4$ is methyl; and R$_6$ is —NH—CH$_2$—CH(OH)—CH$_2$—OH.

In another embodiment, the conjugate comprises a bacteriochlorophyll of the formula III wherein M is Pd; R$_1$ is NH—P, wherein P is the residue of an RGD-containing peptide or RGD peptidomimetic linked directly to the NH— or via a spacer; R$_4$ at position 3 is acetyl and at position 8 is ethyl; R'$_4$ is methyl; X is N—R$_7$ and R$_7$ is —NH—(CH$_2$)$_3$—SO$_3^-$Me$^+$, wherein Me$^+$ is Na$^+$ or K$^+$.

In another embodiment, the conjugate comprises a bacteriochlorophyll of the formula I wherein M is Mn; R$_1$ is NH—P, wherein P is the residue of an RGD-containing peptide or RGD peptidomimetic linked directly to the NH— or via a spacer; R$_2$ is OH; R$_3$ is COOCH$_3$; R$_4$ at position 3 is acetyl and at position 8 is ethyl; R'$_4$ is methyl; and R$_5$ is O.

In another embodiment, the conjugate comprises a chlorophyll of the formula II wherein M is selected from Mn, Cu or 2H; R$_1$ is NH—P, wherein P is the residue of an RGD-containing peptide or RGD peptidomimetic linked directly to the NH— or via a spacer; R$_4$ at position 3 is vinyl and at position 8 is ethyl; R'$_4$ is methyl; and R$_6$ is —NH—(CH$_2$)$_2$—SO$_3^-$Me$^+$, wherein Me$^+$ is Na$^+$ or K$^+$.

In another embodiment, the conjugate comprises a bacteriochlorophyll of the formula II wherein M is 2H; m is 0; R$_1$ is NH—P, wherein P is the residue of an RGD-containing peptide or RGD peptidomimetic linked directly to the NH— or via a spacer; R'$_2$ is methoxy; R$_4$ at position 3 is acetyl and at position 8 is ethyl; R'$_4$ is methyl; and R$_6$ is —NH—(CH$_2$)$_3$—NH—(CH$_2$)$_3$—NH$_2$.

In another embodiment, the conjugate comprises a bacteriochlorophyll of the formula II wherein M is 2H; m is 0; R$_1$ is NH—P, wherein P is the residue of an RGD-containing peptide or RGD peptidomimetic linked directly to the NH— or via a spacer; R'$_2$ is methoxy; R$_4$ at position 3 is acetyl and at position 8 is ethyl; R'$_4$ is methyl; and R$_6$ is —NH—(CH$_2$)$_2$-morpholino.

In another embodiment, the conjugate comprises a bacteriochlorophyll of the formula II wherein M is 2H; m is 0; R$_1$ is NH—P, wherein P is the residue of an RGD-containing peptide or RGD peptidomimetic linked directly to the NH— or via a spacer; R'$_2$ is methoxy; R$_4$ at position 3 is acetyl and at position 8 is ethyl; R'$_4$ is methyl; and R$_6$ is —NH—(CH$_2$)$_3$-piperazino-(CH$_2$)$_3$—NH$_2$.

In another embodiment, the conjugate comprises a bacteriochlorophyll of the formula II wherein M is Pd; m is 0; R$_1$ is wherein P is the residue of the RGD-peptidomimetic; R'$_2$ is methoxy; R$_4$ at position 3 is acetyl and at position 8 is ethyl; R'$_4$ is methyl; and R$_6$ is —NH—(CH$_2$)$_2$—SO$_3$K (conjugate 40).

In another embodiment, the conjugate comprises a bacteriochlorophyll of the formula II wherein M is Pd; m is 0; R$_1$ is NH—P, wherein P is the residue of the RGD-peptidomimetic; R'$_2$ is methoxy; R$_4$ at position 3 is acetyl and at position 8 is ethyl; R'$_4$ is methyl; and R$_6$ is —NH—(CH$_2$)$_2$—SO$_3$K (conjugate 41).

In another embodiment, R$_1$ and R$_6$ together form a cyclic ring comprising —NH-RGD-CO—NH—(CH$_2$)$_2$—NH— or —NH-RGD-CO—NH—(CH$_2$)$_2$-piperazino-(CH$_2$)$_2$—NH—. In one embodiment, the conjugate comprises a bacteriochlorophyll of the formula II wherein m is 0; R'$_2$ is methoxy; R$_4$ at position 3 is acetyl and at position 8 is ethyl; R'$_4$ is methyl; and either R$_1$ and R$_6$ together form a cyclic ring comprising —NH-RGD-CO—NH—(CH$_2$)$_2$—NH— and M is Pd (Conjugate 37) or M is 2H (Conjugate 38) or R$_1$ and R$_6$ together form a cyclic ring comprising —NH-RGD-CO$_7$NH—(CH$_2$)$_2$-piperazino-(CH$_2$)$_2$—NH— and M is Pd (Conjugate 31).

In another embodiment, the conjugate comprises a chlorophyll of the formula II wherein M is 2H; R$_1$ is NH—P, wherein P is the residue of the RGD-containing peptide of SEQ ID NO:1; R$_4$ at position 3 is vinyl and at position 8 is ethyl; R'$_4$ is methyl; and R$_6$ is —NH—(CH$_2$)$_2$—SO$_3$K (Conjugate 16).

In another embodiment, the conjugate comprises a chlorophyll of the formula II wherein M is Mn; R$_1$ is NH—P, wherein P is the residue of the RGD-containing peptide of SEQ ID NO:1; R$_4$ at position 3 is vinyl and at position 8 is ethyl; R'$_4$ is methyl; and R$_6$ is —NH—(CH$_2$)$_2$—SO$_3$K (Conjugate 17).

In another embodiment, the conjugate comprises a chlorophyll of the formula II wherein M is Cu; R$_1$ is NH—P, wherein P is the residue of the RGD-containing peptide of SEQ ID NO:1; R$_4$ at position 3 is vinyl and at position 8 is ethyl; R'$_4$ is methyl; and R$_6$ is —NH—(CH$_2$)$_2$—SO$_3$K (Conjugate 18).

In another embodiment, the conjugate comprises a bacteriochlorophyll of the formula I wherein M is Mn; R$_1$ is NH—P, wherein P is the residue of the RGD-containing peptide of SEQ ID NO:1; R$_2$ is OH; R$_3$ is COOCH$_3$; R$_4$ at position 3 is acetyl and at position 8 is ethyl; R'$_4$ is methyl; and R$_5$ is O (Conjugate 12).

In another embodiment, the conjugate comprises a bacteriochlorophyll of the formula I wherein M is 2H; R$_1$ is NH—P, wherein P is the residue of the RGD-containing peptide of SEQ ID NO:1; R$_2$ is OH; R$_3$ is COOCH$_3$; R$_4$ at position 3 is acetyl and at position 8 is ethyl; R'$_4$ is methyl; and R$_5$ is O (Conjugate 27).

In another embodiment, the conjugate comprises a bacteriochlorophyll of the formula I wherein M is 2H; R$_1$ is NH—(CH$_2$)$_2$—NH—CO—P, wherein P is the residue of the ROD-containing peptide of SEQ ID NO:4; R$_2$ is OH; R$_3$ is COOCH$_3$; R$_4$ at position 3 is acetyl and at position 8 is ethyl; R'$_4$ is methyl; and R$_5$ is O (Conjugate 32).

In another embodiment, the conjugate comprises a bacteriochlorophyll of the formula II wherein M is Pd; m is 0; $R_1$ is NH—P, wherein P is the residue of the RGD-containing peptide of SEQ ID NO:2; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 11).

In another embodiment, the conjugate comprises a bacteriochlorophyll of the formula II wherein M is 2H; m is 0; $R_1$ is NH—P, wherein P is the residue of the RGD-containing peptide of SEQ ID NO:1; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 13).

In another embodiment, the conjugate comprises a bacteriochlorophyll of the formula II wherein M is Mn; m is 0; $R_1$ is NH—P, wherein P is the residue of the RGD-containing peptide of SEQ ID NO:1; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 14).

In another embodiment, the conjugate comprises a bacteriochlorophyll of the formula II wherein M is Cu; m is 0; $R_1$ is NH—P, wherein P is the residue of the RGD-containing peptide of SEQ ID NO:1; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 15).

In another embodiment, the conjugate comprises a bacteriochlorophyll of the formula II wherein M is Pd; m is 0; $R_1$ is NH—P, wherein P is the residue of the RGD-containing peptide of SEQ ID NO:1; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 24).

In another embodiment, the conjugate comprises a bacteriochlorophyll of the formula II wherein M is Pd; m is 0; $R_1$ is NH—P, wherein P is the residue of the RGD-containing peptide of SEQ ID NO:1; $R'_2$ is methoxy; $R_4$ at position 3 is acetyl and at position 8 is ethyl; $R'_4$ is methyl; and $R_6$ is —NH—$(CH_2)_3$—$SO_3$K (Conjugate 19).

In another embodiment, the conjugate comprises a bacteriochlorophyll of the formula II wherein M is 2H; m is 0; $R_1$ is NH—P, wherein P is the residue of the RGD-containing peptide of SEQ ID NO:3; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 26).

In another embodiment, the conjugate comprises a bacteriochlorophyll of the formula II wherein M is Pd; m is 0; $R_1$ is NH—P, wherein P is the residue of the RGD-containing peptide of SEQ ID NO:5; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 33).

In another embodiment, the conjugate comprises a bacteriochlorophyll of the formula II wherein M is Pd; m is 0; $R_1$ is NH—P, wherein P is the residue of the RGD-containing peptide of SEQ ID NO:6; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 34).

In another embodiment, the conjugate comprises a bacteriochlorophyll of the formula II wherein M is Pd; m is 0; $R_1$ is NH—P, wherein P is the residue of the RGD-containing peptide of SEQ ID NO:7; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 35).

In another embodiment, the conjugate comprises a bacteriochlorophyll of the formula II wherein M is Pd; m is 0; $R_1$ is NH—CH $[(—(CH_2)_2—CO—NH—P]_2$, wherein P is the residue of the RGD-containing peptide of SEQ ID NO:8; $R'_2$ is methoxy; $R_4$ at position 3 is acetyl and at position 8 is ethyl; $R'_4$ is methyl; and $R_6$ is —NH—$(CH_2)_2$—$SO_3$K (Conjugate 36).

In another embodiment, the conjugate comprises a bacteriochlorophyll of the formula II wherein M is PD; m is 0; $R_1$ is NH—P, wherein P is the residue of the RGD-containing peptide of SEQ ID NO:1; $R'_2$ is methoxy; $R_4$ at position 3 is acetyl and at position 8 is ethyl; $R'_4$ is methyl; and $R_6$ is —NH—$CH_2$—CH(OH)—$CH_2$OH. (Conjugate 26).

In another embodiment, the conjugate comprises a bacteriochlorophyll of the formula II wherein M is 2H; m is 0; $R_1$ is NH—P, wherein P is the residue of the RGD-containing peptide of SEQ ID NO:1; $R'_2$ is methoxy; $R_4$ at position 3 is acetyl and at position 8 is ethyl; $R'_4$ is methyl; and $R_6$ is —NH—$(CH_2)_3$—NH—CO-DTPA (Conjugate 43) or its chelate complex with Gd (Conjugate 44).

The invention further provides the novel bacteriochlorophyll of the formula II, wherein M is Pd; $R_1$ is COOH; $R'_2$ is methoxy; $R_4$ at position 3 is acetyl and at position 8 is ethyl; $R'_4$ is methyl; and $R_6$ is —NH—$CH_2$—CH(OH)—$CH_2$—OH (compound 10).

In another aspect, the present invention provides a pharmaceutical composition comprising a conjugate of an RGD-containing peptide or an RGD peptidomimetic and a photosensitizer selected from a porphyrin, a chlorophyll or a bacteriochlorophyll as defined herein and a pharmaceutically acceptable carrier.

In one embodiment, the pharmaceutical composition comprises a conjugate comprising a porphyrin photosensitizer as defined herein or a pharmaceutically acceptable salt thereof. In another embodiment, it comprises a conjugate comprising a chlorophyll or a bacteriochlorophyll photosensitizer of formula I, II or III as defined herein or a pharmaceutically acceptable salt thereof.

In one preferred embodiment the pharmaceutical composition comprises a conjugate in which the chlorophyll has formula II, more preferably selected from the conjugates 16, 17 and 18.

In another preferred embodiment the pharmaceutical composition comprises a conjugate in which the bacteriochlorophyll has the formula I, more preferably selected from the conjugates 12, 27 and 32.

In another preferred embodiment the pharmaceutical composition comprises a conjugate in which the bacteriochlorophyll has the formula III, more preferably the conjugate 19.

In another more preferred embodiment the pharmaceutical composition comprises a conjugate in which the bacteriochlorophyll has the formula II conjugated with an RGD peptide, more preferably with the RGD peptide of SEQ ID NO:1, more preferably selected from the conjugates 13, 15, 23, 28, 29, 30, 31 and 44 and more preferably the conjugate 24.

In another embodiment the pharmaceutical composition comprises a conjugate in which the bacteriochlorophyll has the formula II conjugated with an RGD peptide of any of SEQ ID NO:2-8, more preferably the conjugates 11, 22, 33, 34, 35, and 36.

In another embodiment the pharmaceutical composition comprises a conjugate in which the bacteriochlorophyll has the formula II conjugated with an RGD peptidomimetic, more preferably the conjugates 40 and 41.

In one embodiment, the pharmaceutical composition is for use in photodynamic therapy (PDT), more particularly for vascular-targeted PDT (VTP).

In one embodiment, the pharmaceutical composition is for use in oncology, particularly for VTP of tumors. Any suitable solid tumor is encompassed by the invention, bith primary tumors and metastasis, of tumors selected from, but not limited to, from melanoma, colon, breast, lung, prostate, brain or head and neck cancer.

In another embodiment, the pharmaceutical composition is for use in non-oncologic diseases, for VTP of non-neoplastic tissue or organ. In one embodiment, the pharmaceutical composition is used for treatment of vascular diseases such as age-related macular degeneration (AMD) or disorders such as obesity by limiting vascular supply to adipose tissue and thus inhibiting its growth.

The pharmaceutical composition of the invention is also used for diagnostic purposes, for visualization of organs and tissues. It can be used in methods of vascular-targeted imaging (VTI).

In one embodiment, the pharmaceutical composition is used for diagnosis of tumors using several techniques. Several diagnostic techniques can be applied in accordance with the invention, by adapting the central metal atom to the particular technique.

For tumor diagnosis by dynamic fluorescence imaging, M in the photosensitizer is 2H or a metal selected from Cu, Pd Gd, Pt, Zn, Al, Eu, Er, Yb or isotopes thereof.

For tumor diagnosis by radiodiagnostic technique, M in the photosensitizer is a radioisotope selected from $^{64}$Cu, $^{67}$Cu, $^{99m}$Tc, $^{67}$Ga, $^{201}$Tl, $^{195}$Pt, $^{60}$Co, $^{111}$In and $^{51}$Cr.

In one embodiment, the radiodiagnostic technique is positron emission tomography (PET) and M is $^{64}$Cu or $^{67}$Cu. In another embodiment, the radiodiagnostic technique is single photon emission tomography (SPET) and M is a radioisotope selected from $^{99m}$Tc, $^{67}$Ga, $^{195}$Pt, $^{111}$In, $^{51}$Cr and $^{60}$Co.

For tumor diagnosis by molecular magnetic resonance imaging (MM), M is a paramagnetic metal selected from $Mn^{3+}$, $Cu^{2+}$, $Fe^{3+}$, $Eu^{3+}$, $Gd^{3+}$ and $Dy^{3+}$, or the photosensitizer is substituted by a metal chelate complex of a polydentate ligand and the metal is as defined hereinbefore.

The present invention also provides a pharmaceutical composition for tumor radiotherapy, wherein M is a radioisotope selected from $^{103}$Pd, $^{195}$Pt, $^{105}$Rh, $^{106}$Rh, $^{188}$Re, $^{177}$Lu, $^{164}$Er, $^{117m}$Sn, $^{153}$Sm, $^{90}$Y, $^{67}$Cu and $^{32}$P.

The present invention further provides the novel bacteriochlorophyll of the formula II, wherein M is Pd; $R_1$ is COOH; $R'_2$ is methoxy; $R_4$ at position 3 is acetyl and at position 8 is ethyl; $R'_4$ is methyl; and $R_6$ is —NH—CH(OH)—CH$_2$—OH herein identified as compound 10.

According to one embodiment, the invention relates to a method for tumor diagnosis by dynamic fluorescence imaging, which comprises: (a) administering to a subject suspected of having a tumor a RGD peptide-photosensitizer conjugate of the invention in which M is 2H or a metal selected from Cu, Pd Gd, Pt, Zn, Al, Eu, Er, Yb or an isotopes thereof; and (b) irradiating the subject by standard procedures and measuring the fluorescence of the suspected area, wherein a higher fluorescence indicates tumor sites.

In another embodiment, the invention provides a method for tumor diagnosis by radiodiagnostic technique, which comprises: (a) administering to a subject suspected of having a tumor a RGD peptide-photosensitizer conjugate of the invention in which M is a radioisotope selected from $^{64}$Cu, $^{67}$Cu, $^{99m}$Tc, $^{67}$Ga, $^{195}$Pt, $^{201}$Tl, $^{60}$Co, $^{111}$In, $^{51}$Cr; and (b) scanning the subject in an imaging scanner and measuring the radiation level of the suspected area, wherein an enhanced radiation indicates tumor sites. In a preferred embodiment, the radiodiagnostic technique is positron emission tomography (PET) and M is $^{64}$Cu or $^{67}$Cu. In another preferred embodiment, the radiodiagnostic technique is single photon emission tomography (SPET) and M is a radioisotope selected from the group consisting of $^{99m}$Tc, $^{67}$Ga, $^{195}$Pt, $^{111}$In, $^{51}$Cr and $^{60}$Co.

In a further embodiment, the invention provides a molecular magnetic resonance imaging (MRI) method for tumor diagnosis comprising the steps of: (a) administering to a subject suspected of having a tumor a RGD peptide-photosensitizer conjugate of the invention wherein M is a paramagnetic metal; and (b) subjecting the patient to magnetic resonance imaging by generating at least one MR image of the target region of interest within the patient's body prior to said administration and one or more MR images thereafter. The paramagnetic metal may be any suitable metal for MRI including, but not limited to, $Mn^{3+}$, $Cu^{2+}$, $Fe^{3+}$, $Eu^{3+}$, or $Dy^{3+}$ and, preferably, $Gd^{3+}$.

In one preferred embodiment, the MRI method includes the steps: (a) administering to the subject a RGD peptide-photosensitizer conjugate of the invention wherein M is a paramagnetic metal, preferably, $Mn^{3+}$, $Cu^{2+}$, $Fe^{3+}$, $Eu^{3+}$, or $Dy^{3+}$ and, more preferably, $Gd^{3+}$; (b) generating an MR image at zero time and at a second or more time points thereafter; and (c) processing and analyzing the data to diagnose the presence or absence of a tumor.

In still another embodiment, the invention provides a method for diagnosis of tumors by fluorescence imaging using a photosensitizer, when the improvement is use of a RGD peptide-photosensitizer conjugate of the invention.

The invention further provides a method for diagnosis of tumors by PET or SPET scanning using a photosensitizer, when the improvement is use of a RGD peptide-photosensitizer conjugate of the invention.

Further provided is a method for diagnosis of tumors by MRI using a photosensitizer, when the improvement is use of a RGD peptide-photosensitizer conjugate of the invention.

The RGD peptide-photosensitizer conjugates of the invention are particularly suitable for vascular-targeting PDT (VTP) and are useful for treatment of diseases associated with angiogenesis/neovascularization and new blood vessel growth such as cancer, diabetic retinopathy, macular degeneration and arthritis. In one most preferred embodiment of the present invention, the target for treatment with the sensitizers of the invention are abnormal blood vessels, particularly blood vessels of solid tumors, age-related macular degeneration, restenosis, acute inflammation or atherosclerosis (Dougherty and Levy, 2003), due to the inherent difference of sensitivity of normal and abnormal blood vessels to the suggested PDT protocols described herein.

Thus, in one embodiment, the conjugates of the invention are useful in the oncological field for treatment by PDT of precancerous states and several cancer types such as, but not limited to, melanoma, prostate, brain, colon, ovarian, breast, head and neck, chest wall tumors arising from breast cancer, skin, lung, esophagus and bladder cancers and tumors. The compounds are useful for treatment of primary as well as metastatic tumors.

In this aspect, the invention relates to a method for tumor photodynamic therapy, which comprises: (a) administering to an individual in need a RGD peptide-photosensitizer conjugate according to the invention; and (b) irradiating the local of the tumor.

The invention further relates to tumor therapy without PDT, namely, to a method for tumor radiotherapy, which comprises administering to an individual in need a RGD peptide-photosensitizer conjugate according to the invention wherein M is $^{103}$Pd, $^{195}$Pt, $^{105}$Rh, $^{106}$Rh, $^{188}$Re, $^{177}$Lu, $^{164}$Er, $^{117m}$Sn, $^{153}$Sm, $^{90}$Y, $^{67}$Cu, or $^{32}$P.

In another embodiment, the compounds of the invention are useful in non-oncological areas. Besides the efficient destruction of unwanted cells, like neoplasms and tumors, by PDT, the compounds of the invention can also be used against proliferating cells and blood vessels, which are the main cause of arteriosclerosis, arthritis, psoriasi, obesity and macular degeneration. In addition, the compounds can be used in the treatment of non-malignant tumors such as benign prostate hypertrophy.

In one preferred embodiment, the conjugates of the invention can be used in PDT for treatment of cardiovascular diseases mainly for vessel occlusion and thrombosis in coronary artery diseases, intimal hyperplasia, restenosis, and atherosclerotic plaques. In a more preferred embodiment, the compounds of the invention are used for preventing or reducing in-stent restenosis in an individual suffering from a cardiovascular disease that underwent coronary angiography. In another preferred embodiment, the compounds of the invention can be used in a method for the treatment of atherosclerosis by destruction of atheromatous plaque in a diseased blood vessel.

In another preferred embodiment, the compounds of the invention can be used in PDT for treatment of dermatological diseases, disorders and conditions such as acne, acne scarring, psoriasis, athlete's foot, warts, actinic keratosis, and port-wine stains (malformations of tiny blood vessels that connect the veins to the arteries (capillaries) located in the upper levels of the skin).

In another preferred embodiment, the conjugates of the invention can be used in PDT for treatment of ophthalmic diseases, disorders and conditions such as corneal and choroidal neovascularization and, more preferably, age-related macular degeneration (AMD).

The amount of the conjugate to be administered for PDT therapy will be established by the skilled physician according to the experience accumulated with porphyrin, Chl and BChl derivatives used in PDT, and will vary depending on the choice of the derivative used as active ingredient, the condition to be treated, the mode of administration, the age and condition of the patient, and the judgement of the physician.

The wavelength of the irradiating light is preferably chosen to match the maximum absorbance of the photosensitizer. The suitable wavelength for any of the compounds can be readily determined from its absorption spectrum. In a preferred embodiment, a strong light source is used, more preferably lasers at 720-790 nm when the photosensitizer is a BChl derivative.

The conjugates of the invention may be further used in photodynamic therapy as an adjuvant to another current therapy used for the treatment of a disease, disorder or condition, to make it more effective. For example, they may be used intraoperatively in combination with surgery, to help prevent the recurrence of cancer on large surface areas such as the pleura (lining of the lung) and the peritoneum (lining of the abdomen), common sites of spread for some types of cancer, in intraoperative treatment of recurrent head and neck carcinomas, or following femoral artery angioplasty to prevent restenosis. The conjugates may be also used in intraoperative PDT tumor diagnosis, for example, of brain tumors.

Another possibility according to the invention is to use the conjugates of the invention in PDT of large solid tumors by interstitial therapy, a technique that involves feeding optic fibers directly into tumors using needles guided by computed tomography (CT). This may be especially useful in areas that require extensive surgery such as in head and neck tumors.

The amount of conjugate to be administered and the route of administration will be determined according to the kind of disease, stage of the disease, age and health conditions of the patient, but will be much lower than the currently used dosage of Photofrin II® (about 5-40 mg HpD/kg body weight) or Tookad® (about 2-10 mg/kg body weight).

The pharmaceutical compositions of the invention are administered to the patient by standard procedures used in PDT, for example, systemically, particularly by injection, more preferably by intravenous injection, locally by direct injection into the solid tumor, or topically for treatment of skin diseases and conditions.

Preferred photosensitizers for the purpose of the present invention are water-soluble porphyrin, chlorophyll and bacteriochlorophyll derivatives. The present inventors have previously shown (Mazor et al, 2005, Brandis et al. 2005) that water-soluble bacteriochlorins such as WST-11 (herein designated compound 8) circulate as non-covalent complexes with serum albumin (SA) until clearance, but despite this association they show no accumulation in the tumor tissue and rapidly clear from the treated subject.

Insufficient vascularization, linked with enhanced interstitial fluid pressure due to the lack of lymphatic drainage in the tumor vicinity, interfere with the convectional uptake of small molecules used as therapeutic or contrast agents in known diagnostic protocols, thereby impairing the efficiency of in situ diagnostic and prognosis techniques such as magnetic resonance imaging (MRI), blood oxygenation level dependent-MRI, diffusion-weighted MRI and positron emission tomography (PET). At the same time, enhanced tumor vascular permeability in these regions drives extravasation of macromolecules such as serum albumin (SA) from the circulation into the tumor tissue, while the poor lymphatic drainage fosters their retention within the tumor compartment (Minchinton and Tannock, 2006, Iyer et al., 2006). Consequently, the "enhanced permeability and retention (EPR) effect", has been proposed as the basis for nonspecific targeting of drugs comprising large molecules to tumor tissue and has given rise to a new approach for tumor-targeting drug design based on macromolecular, micellar and lipidic particles.

In their quest for new imaging avenues, the present inventors found that small contrast and/or therapeutic agents, such as water-soluble porphyrin, chlorophyll and bacteriochlorophyll derivatives designed to have the dual capacity of moderate association affinity to SA and high affinity to tumor-specific receptors, would allow for their prolonged accumulation in tumors. It was assumed that the EPR effect would assist agent extravasation and retention in the tumor interstitium upon forming a complex with SA. Once in the tumor tissue, the modified agents will dissociate from the SA and preferentially bind to specific receptors, ensuring active agent accumulation. It was found in accordance with the present invention that by covalent binding of the water-soluble photo sensitizers mentioned above to the RGD-containing peptides and peptidomimetics, which are ligands of the tumor-abundant cell receptors integrins, while retaining their SA complexation ability, contrast and therapeutic agents are obtained that selectively and synergistically accumulate and retain in the tumor and enable highly efficient in vivo imaging of such tumors.

The invention will now be illustrated by the following non-limiting Examples.

EXAMPLES

I Chemical Section

In the Examples herein, the intermediates and compounds 1-10 and the conjugates of the invention (11-24) will be presented by their respective Arabic numbers in bold and underlined according to the following List of Compounds and the Appendix. The formulas of all the compounds and conjugates are presented in the Appendix at the end of the description, just before the References.

List of Compounds
1. Bacteriochlorophyll a (Bchl a)
2. $13^2$-OH-Bacteriochlorophyll a ($13^2$-OH-Bchl a)
3. Bacteriopheophorbide a (Bpheid a)
4. $13^2$-OH-Bacteriopheophorbide a ($13^2$-OH-Bpheid a)
4a. Bacteriopurpurin 18 (BPP 18)
5. Chlorophyll a (Chl a)
6. Pheophorbide a (Pheid a)
7. Palladium Bacteriopheophorbide a (Pd-Bpheid)
8. Palladium $3^1$-oxo-15-methoxycarbonylmethyl-Rhodobacteriochlorin $13^1$-(2-sulfoethyl)amide potassium salt
9. Manganese(III) $13^2$-OH-Bacteriopheophorbide a (Mn(III) $13^2$-OH-Bpheid a)
10. Palladium $3^1$-oxo-15-methoxycarbonylmethyl-Rhodobacteriochlorin-$13^1$-(2,3-dihydroxypropyl)amide potassium salt
11. Palladium $3^1$-oxo-15-methoxycarbonylmethyl-Rhodobacteriochlorin $13^1$-(2-sulfoethyl)amide-$17^3$-(RGD-4C)amide potassium salt
12. Manganese(III) $13^2$-OH-Bacteriopheophorbide-$17^3$-(cycloRGDfK)amide
13. $3^1$-oxo-15-methoxycarbonylmethyl-Rhodobacteriochlorin $13^1$-(2-sulfoethyl)amide-$17^3$-(cycloRGDfK)amide potassium salt
14. Manganese(III) $3^1$-oxo-15-methoxycarbonylmethyl-Rhodobacteriochlorin $13^1$-(2-sulfoethyl)amide-$17^3$-(cycloRGDfK)amide potassium salt
15. Copper(II) $3^1$-oxo-15-methoxycarbonylmethyl-Rhodobacteriochlorin $13^1$-(2-sulfoethyl)amide-$17^3$-(cycloRGDfK)amide potassium salt
16. $3^1,3^2$-Didehydrorhodochlorin $13^1$-(2-sulfoethyl)amide-$17^3$-(cycloRGDfK)amide potassium salt
17. Manganese(III) $3^1,3^2$-Didehydrorhodochlorin $13^1$-(2-sulfoethyl)amide-$17^3$-(cycloRGDfK)amide potassium salt
18. Copper(II) $3^1,3^2$-Didehydrorhodochlorin $13^1$-(2-sulfoethyl)amide-$17^3$-(cycloRGDfK)amide potassium salt
19. Palladium Bacteriopurpurin N-(3-sulfopropylamino)imide-$17^3$-(cycloRGDfK)amide potassium salt
20. Meso-5-(4-cycloRGDfK-benzamido)-10,15,20-tris(4-carboxyphenyl)porphine
21. Copper(II) meso-5-(4-cycloRGDfK-benzamido)-10,15,20-tris(4-carboxyphenyl)porphine
22. Gadolinium(III)meso-5-(4-cycloRGDfK-benzamido)-10,15,20-tris(4-carboxy phenyl)porphine
23. Palladium $3^1$-oxo-15-methoxycarbonylmethyl-Rhodobacteriochlorin-$13^1$-(2,3-dihydroxypropyl)amide-$17^3$-(cycloRGDfK)amide
24. Palladium $3^1$-oxo-15-methoxycarbonylmethyl-Rhodobacteriochlorin $13^1$-(2-sulfoethyl)amide-$17^3$-(cycloRGDfK)amide potassium salt.
25. $3^1$-oxo-15-methoxycarbonylmethyl-Rhodobacteriochlorin $13^1$-(2-sulfoethyl)amide potassium salt.
26. $3^1$-oxo-15-methoxycarbonylmethyl-Rhodobacteriochlorin $13^1$-(2-sulfoethyl)amide-$17^3$-(GRGDSP)amide potassium salt
27. Bacteriopheophorbide-$17^3$-(cycloRGDfK)amide
28. $3^1$-oxo-15-methoxycarbonylmethyl-Rhodobacteriochlorin $13^1$-(3-[(3-aminopropyl)amino]propyl)amide-$17^3$-(cycloRGDfK)amide
29. $3^1$-oxo-15-methoxycarbonylmethyl-Rhodobacteriochlorin $13^1$-(2,3-dihydroxypropyl)amide-$17^3$-(cycloRGDfK)amide
30. $3^1$-oxo-15-methoxycarbonylmethyl-Rhodobacteriochlorin $13^1$-(2-morpholino-N-ethyl)amide-$17^3$-(cycloRGDfK)amide
31. $3^1$-oxo-15-methoxycarbonylmethyl-Rhodobacteriochlorin $13^1$-{3-[4-(3-aminopropyl)-piperazin-1-yl]-propyl}amide-$17^3$-(cycloRGDfK)amide
32. Bacteriopheophorbide-$17^3$-(2-cycloRGDK-amido-N-ethyl)amide
33. Palladium $3^1$-oxo-15-methoxycarbonylmethyl-Rhodobacteriochlorin $13^1$-(2-sulfoethyl)amide-$17^3$-(GRGDSPK)amide potassium salt
34. Palladium $3^1$-oxo-15-methoxycarbonylmethyl-Rhodobacteriochlorin $13^1$-(2-sulfoethyl)amide-$17^3$-[(GRGDSP)$_4$K]amide potassium salt
35. Palladium $3^1$-oxo-15-methoxycarbonylmethyl-Rhodobacteriochlorin $13^1$-(2-sulfoethyl)amide-$17^3$-(cycloRGDf-N(Me)K)amide potassium salt
36. Palladium $3^1$-oxo-15-methoxycarbonylmethyl-Rhodobacteriochlorin $13'$-(2-sulfoethyl)-$17^3$-N-[4-heptanedioic acid bis-(cycloRGDyK-amido)]amide potassium salt
37. Palladium $3^1$-oxo-15-methoxycarbonylmethyl-Rhodobacteriochlorin $13^1,17^3$-cyclo(2-RGD-amido-N-ethyl)diamide
38. $3^1$-oxo-15-methoxycarbonylmethyl-Rhodobacteriochlorin $13^1,17^3$-cyclo(2-RGD-amido-N-ethyl)diamide
39. Palladium $3^1$-oxo-15-methoxycarbonylmethyl-Rhodobacteriochlorin $13^1,17^3$-cyclo{3-[4-(3-aminopropyl-DGR-amido)-piperazin-1-yl]-propyl}diamide
40. Palladium $3^1$-oxo-15-methoxycarbonylmethyl-Rhodobacteriochlorin $13^1$-(2-sulfoethyl)amide-$17^3$-[4-(methyl-5-(6-guanidino-hexanoylamino)-pentanoic acid)]amide potassium salt
41. Palladium $3^1$-oxo-15-methoxycarbonylmethyl-Rhodobacteriochlorin $13^1$-(2-sulfoethyl)amide-$17^3$-[7-amido-3-[[1-(4-guanidino-butyryl)-piperidine-3-carbonyl]-amino]-heptanoic acid] potassium salt
42. Palladium $3^1$-oxo-15-methoxycarbonylmethyl-Rhodobacteriochlorin $13^1$-(2-sulfoethyl)amide-$17^3$-(cycloRADfK)amide potassium salt
43. $3^1$-oxo-15-methoxycarbonylmethyl-Rhodobacteriochlorin $13^1$-(3-DTPA-amido-N-propyl)amide-$17^3$-(cycloRGDfK)amide
44. $3^1$-oxo-15-methoxycarbonylmethyl-Rhodobacteriochlorin $13^1$-(3-Gd-DTPA-amido-N-propyl)amide-$17^3$-(cycloRGDfK)amide Materials and Methods (i) Bacteriochlorophyll a (Bchl a), L was obtained as described by Scherz and Parson, 1984. The procedure started from extraction of pigments from dry (lyophilized) cells of the photosynthetic bacteria *Rhodovulum sulfidophilum*. Purification of the crude pigment extract was carried out by DEAE-Sepharose column chromatography according to Omata and Murata, 1983. Briefly, DEAE-Sepharose was washed with distilled water and then converted to an acetate form by suspending it in a 1M sodium acetate buffer (pH=7). The slurry was washed 3 times with acetone and finally suspended in methanol-acetone (1:3, v:v) for storage at 5° C.

The purity was checked by thin layer chromatography (TLC). Detailed description of TLC conditions can be found in Fiedor et al., 1992.

(ii) $13^2$-OH-Bacteriochlorophyll a ($13^2$-OH-Bchl), 2, was produced by allomerization of Bchl a by stirring a methanol solution of Bchl a (1 g/ml) in the dark, in contact with air, as described in Struck et al., 1992.

(iii) Bacteriopheophorbide (Bpheid), 3, and $13^2$-OH-Bacteriopheophorbide ($13^2$-OH-Bpheid) 4 were synthesized following Wasielewski and Svec, 1980, by demetallation-deesterification of the corresponding Bchl a or $13^2$-OH-Bchl a with 80% aqueous trifluoroacetic acid. Purification of synthesized Bpheid or $13^2$-OH-Bpheid is carried out on Silica ("Kieselgel 60", Merck, Germany) column with gradient of methanol in chloroform (0 to 15/25% vol.) as eluent.

(iv) Chlorophyll a (Chl), 5, and (v) Pheophorbide a (Pheid), 6. Chl was obtained from cyanobacteria *Spirulina platensis* following the same routine for obtaining Bchl (see above). Further, Chl is converted into Pheid following the same procedure as described for Bpheid above.

(vi) Palladium Bacteriopheophorbide a (Pd-Bpheid), 7, was synthesized as described in WO 2000/033833 (Example 2 therein)

(vii) Palladium $3^1$-oxo-15-methoxycarbonylmethyl-Rhodobacteriochlorin $13^1$-(2-sulfoethyl)amide potassium salt, 8, was synthesized as described in WO 2004/045492 (Example 1, synthesis of compound 4).

(viii) $3^1$-oxo-15-methoxycarbonylmethyl-Rhodobacteriochlorin $13^1$-(2-sulfoethyl)amide dipotassium salt, 25, was synthesized by reaction of Bpheid with taurine as described in WO 2004/045492 (Example 2, synthesis of compound 5).

(ix) Bacteriopurpurin 18 (BPP18), 4a was synthesized as described by Mironov et al., 1992.

(x) The resin, the amino acid derivatives, N-hydroxybenzotriazole (HOBt) and benzotriazole-1-yl-oxy-tris-pyrrolidino-phosphonium hexafluorophosphate (PyBOP) were purchased from Novabiochem; N,N-Diisopropylethylamine (DIEA), N,N'-diisopropylcarbodiimide (DIC) ethylenediamine, 1,4-bis(3-aminopropyl)-piperazine, 1,3-dimethylbarbituric acid (DMBA), diethyldithiocarbamic acid, sodium salt (DEDTC), 2,2,2-trifluoroethanol (TFE), triisopropylsilane (TIS), 1,2-ethanedithiol (EDT), trifluoroacetic acid (TFA), meso-tetra(4-carboxy-phenyl)porphine, sodium L-ascorbate and 4-oxoheptanedioic acid, were purchased from Aldrich (USA); N-hydroxysuccinimide (NHS) was purchased from Sigma (USA); N-hydroxysulfosuccinimide (sulfo-NHS), 1,3-dicyclohexylcarbodiimide (DCC), N-(3-dimethylaminopropyl)-N'-ethylcarbodiimide (EDC), N-Fmoc-6-aminohexanoic acid, $N^\beta$-Fmoc-$N^\omega$-Boc-β-L-homolysine, and N-Fmoc-piperidine-3-carboxylic acid were purchased from Fluka (Switzerland); cadmium acetate, copper acetate and manganese(II) chloride were from Merck (Germany); and tetrakis (triphenylphosphine) palladium was obtained from Acros.

Chemicals and solvents of analytical grade were generally used except when performing HPLC, where HPLC-grade solvents are applied.

(xi) Peptide synthesis—Peptides were synthesized by solid phase methods via Fmoc chemistry using protected amino acids and cyclicized according to procedures common in the art. Removal of Fmoc-group and completion of couplings were monitored by the ninhydrin (Kaiser) test. TFA or a cocktail solution of TFA/thioanisole/$H_2O$/triisopropylsilane (TIS) was used for peptide removal from the resin simultaneously with deprotection (Arg-pentamethylchroman-6-ylsulfonyl (Pmc) or 2,2,4,6,7-pentamethyldihydro benzofuran-5-sulfonyl (Pbf); Asp-OtBu; Ser-tert-butyl (tBu); Lys-tert-butyloxycarbonyl (Boc), allyloxycarbonyl (Alloc) or Dde).

(i) Linear peptides GRGDSPK, $(GRGDSP)_4K$ or GRGDSP were obtained using Fmoc-Lys(Boc)-Wang resin or 2-chlorotrityl chloride resin, respectively.

(ii) Cyclic peptides (cycloRGDfK), (cycloRGDyK), (cycloRADfK) and (cycloRGDf-N(Me)K) were prepared by synthesis of pentapeptides on 2-chlorotrityl chloride resin and their subsequent cyclization in solution as described in Haubner et al., 1999. $N^\alpha$-methyl protected lysine was prepared from 2-aminoheptanedioic acid as described previously (Freidinger et al., 1983). Another method of synthesis of cycloRGDfK by cyclization on the resin is described in Example 13 herein.

(iii) Cyclic peptide RGD-4C was prepared by synthesis of CDCRGDCFCG by standard solid phase synthesis protocol and its cyclicization by spontaneous oxidative formation of disulfide bonds (Koivunen et al. 1995).

(iv) Cyclic peptidyl-amine cycloRGDK-$NH_2$ was synthesized on chlorotrityl-resin (protections: Arg-Pbf; Asp-OtBu; $N^\epsilon$-Lys-Alloc). Then, N-terminal Fmoc group and the Alloc protecting group on the ε-amino of the lysine residue were cleaved, and the cyclization between the two aminos through an urea bond using N,N'-carbonyldiimidazole (CDI) was allowed for 12-16 h. The cyclic peptide was cleaved from the support and the lysine carboxylate was reacted with 1,2-diaminoethane (DCC activation) to obtain the required peptidylamine.

(v) Cyclopeptide dimer $(cycloRGDyK)_2$. 4-Oxoheptanedioic acid was converted into 4-aminoheptanedioic acid according to Wanunu et al., 2005. Then the amino group was Boc-protected and carboxylic moieties were activated with NHS/DCC in DMF. The diester was purified on silica column with chloroform-methanol, and then reacted with cycloRGDyK in DMF containing DIEA overnight. The Boc protection was cleaved with TFA-water-dichloromethane (DCM) (90:5:5). The desired compound was purified by HPLC.

(vi) RGD-Peptidomimetics (RGD-PMI, RGD-PM2) were obtained according to WO 93/09795. Namely, one amino group of ethyl 5-amino-4-aminomethyl)pentanoic acid (Vaillancourt et al. 2001 and refs therein) was protected with equimolar amount of Boc anhydride and the carboxylic group was protected with tert-butyl alcohol. The product was purified on silica column, and coupled with N-Fmoc-6-aminohexanoic acid followed by Fmoc-deprotection and conversion of the amine to guanidinium with 3,5-dimethylpyrazole 1-carboxamidine nitrate (pH 9.5; 50° C.). Finally, the N-Boc and O-tBu were removed with TFA, and the product RGD-PMI was purified by HPLC. The synthesis of RDG-PM1 is depicted in Scheme 3. For the synthesis of RGD-PM2 (see Scheme 3), $N^\beta$-Fmoc-$N^\omega$-Boc-β-L-homolysine was attached to Wang-resin. Next, couplings with N-Fmoc-piperidine-3-carboxylic acid and N-Fmoc-4-aminobutyric acid were performed using solid phase methods. After guanidinium formation (as described above), the resulting material was deprotected and removed from the resin with TFA, and the product RGD-PM2 was purified by HPLC.

(xii) TLC: silica plates (Kieselgel-60, Merck, Germany); chloroform-methanol (4:1, v/v).

(xiii) The extinction coefficients of the metallocomplexes were determined by correlating the central metal concentration (using flame photometry with metal salt as a standard) with the optical density of the examined solution at the particular wavelength.

(xiv) Mass spectra. Electrospray ionization mass spectra (ESI-MS) were recorded on a platform LCZ spectrometer (Micromass, England). The Matrix-assisted laser desorption/ionization mass spectra (MALDI-TOF-MS) measurements were performed on Bruker REFLEX time-of-flight instrument (Bruker Daltonics, USA).

(xv) Optical absorption (UV-VIS) spectra of the different complexes were recorded with either Genesis-2 (Milton Roy, England), V-570 (JASCO, Japan) or Shimadzu UV-1650PC (Japan) spectrophotometers.

(xvi) HPLC was performed using an LC-900 instrument (JASCO, Japan) equipped with a UV-915 diode-array detector, or a Waters Delta Prep 4000 system equipped with a Waters 486 UV-VIS tunable absorbance detector and a Waters fraction collector, controlled by Millennium v3.05 program. The flow rate was set to 75 ml/min, using a preparative column (Vydac C18, 218TP101550, 50×250 mm, 10-15 µm), the detector was set at wavelength 380 nm and the fraction collector was set at a time mode of 6 s/fraction. Solvents used in the HPLC purification were as follows: solvent A: 50 mM solution of ammonium acetate in $H_2O$; solvent B: acetonitrile.

(xvii) LC-MS API 150EX (Applied Biosystems/MDS SCIEX), was performed using YMS-Pack Pro C18 column. Mobile phase: solvent A: 0.2% AcOH/0.12% $NH_4OH/H_2O$; solvent B: 4.75% A/0.2% AcOH/acetonitrile. Flow rate: 200 µl/min. Gradient: 20% B (0-2 min) to 95% B (25-30 min).

Example 1. Synthesis of Conjugate 11

Figure 1B:
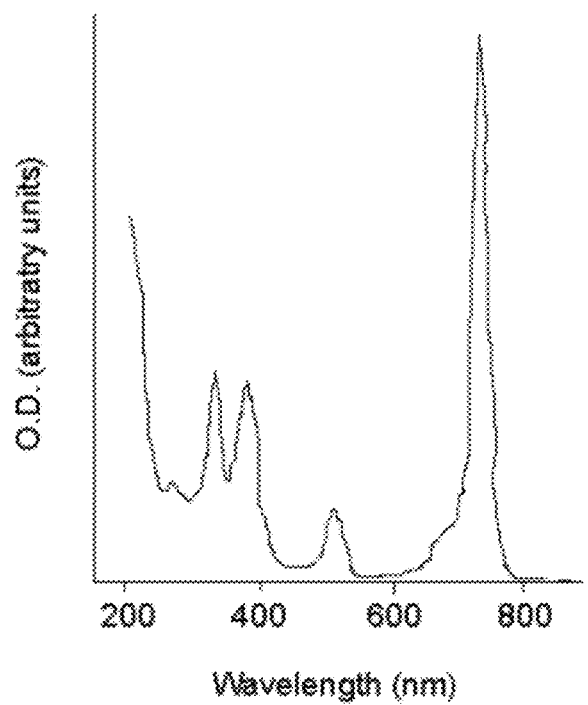
Figure 1C:
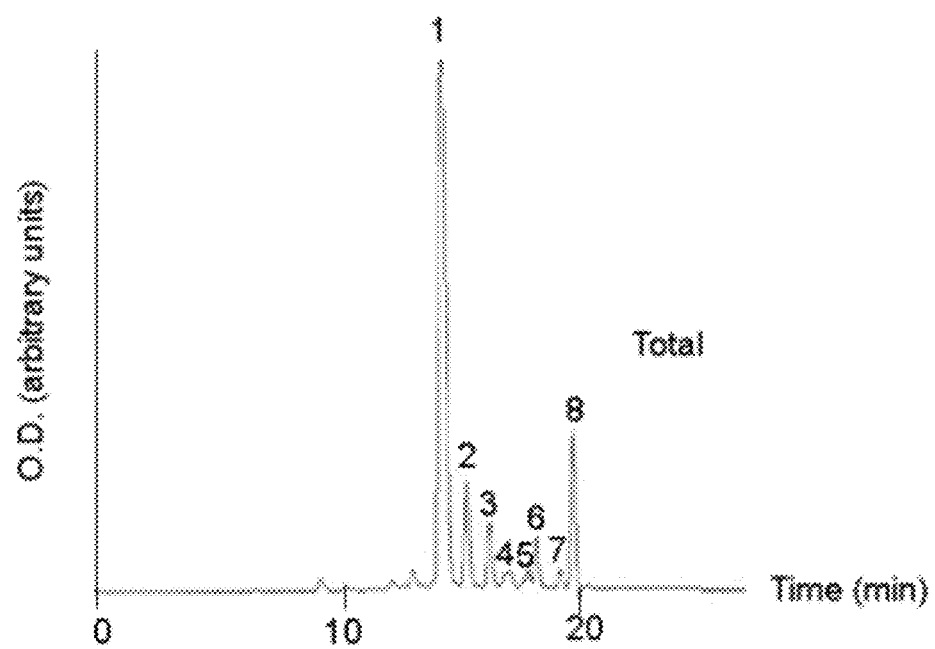

Compound 8, obtained as described in Material and Methods, was directly conjugated to the cyclic peptide RGD-4C as described in Scheme 1 as follows: compound 8 (10 mg) was reacted overnight with NHS (20 mg) in the presence of EDC (20 mg) in DMSO (3 ml). The obtained activated succinimide ester (Bauminger and Wilchek, 1980) was purified on a silica column using $CHCl_3$:MeOH (6:1, vol.), dried and kept under argon in the dark until further use. RGD-4C (2 mg, 1.97 µmoles) was dissolved in 800 µl DMSO and added to the activated ester (4.8 mg, 5.13 µmoles in 800 µl DMSO and 400 µl $NaHCO_3$ buffer 0.1 M pH 8.5). The reaction mixture was incubated at room temperature for 24 hours, and stirred under argon. The obtained conjugate 11 was purified using HPLC and identified by mass spectroscopy (1837 m/z) (FIGS. 1A-1C). Yield: 18%.

Example 2. Synthesis of Conjugate 12

Conjugate 12 was prepared starting from the synthesis of compound 9.
(i) Synthesis of Compound 9
Compound 4 (20 mg), obtained as described in Materials and Methods, was dissolved in DMF (8 ml) that was previously passed through Alumina B column (1×5 cm), and bubbled with Argon for 5-10 minutes. Cadmium acetate (85 mg, 10 eq. to 4) was added and the reaction mixture heated to 110° C. The reaction progress was monitored spectrally (in acetone). Metalation occurred within 5 minutes. $MnCl_2.2H_2O$ (55 mg, 10 eq.) was added while stirring until the reaction was completed (within additional 5-10 minutes). To remove inorganic salts, the reaction solution was evaporated; the solid was re-dissolved in acetonitrile, the solution was filtered through Whatman paper on Buchner funnel and evaporated. Finally, HPLC of the crude product re-dissolved in water was performed (LC-phase at a flow of 8 ml/min, and the pure product 9 was eluted at 10.5-13.5 min., providing a full separation of the product from chlorin admixtures and by-products. Yield: 88%.

Figure 2A:
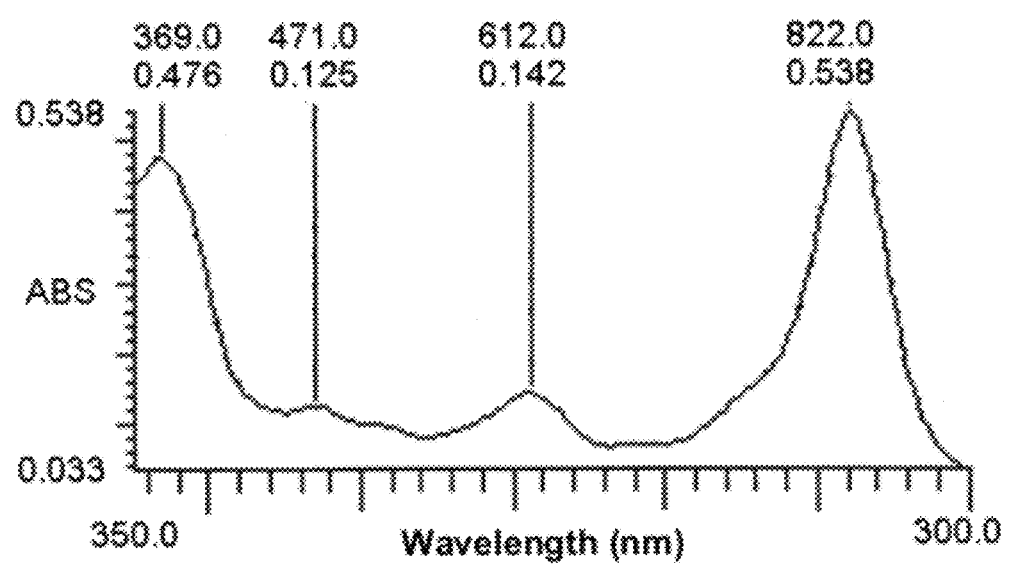
FIGS. 2A-2B show characterization spectra of conjugate 9.
Figure 2B:
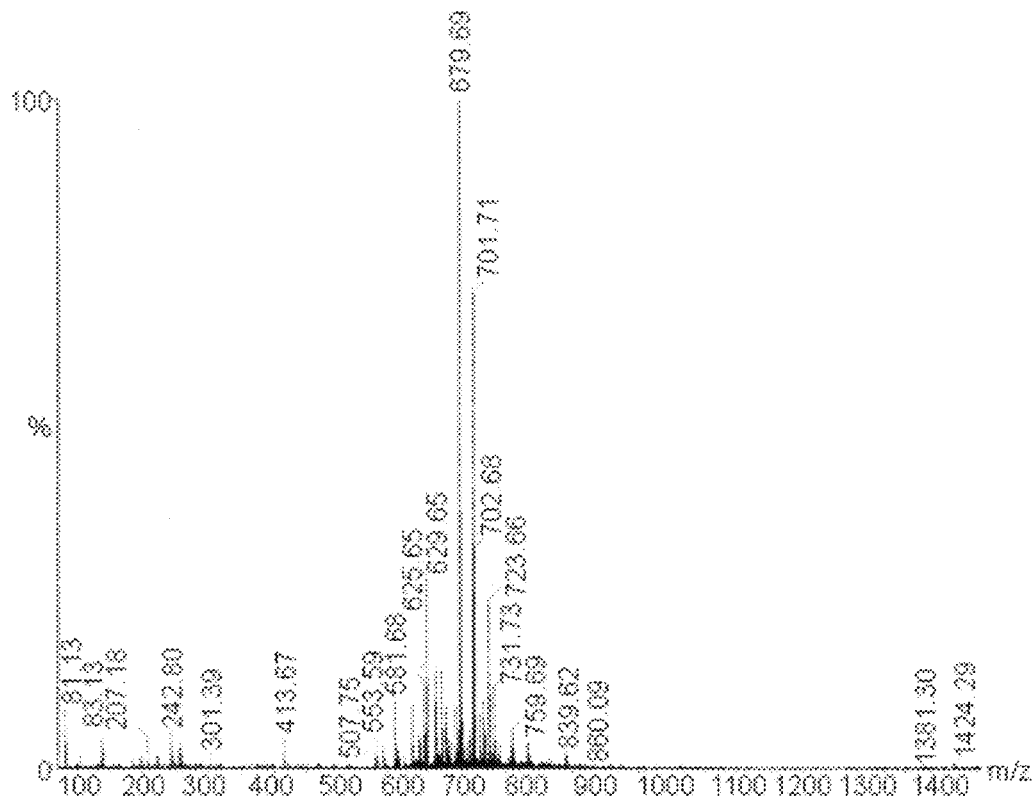

The structure of compound 9 was confirmed spectrally (see electronic spectrum depicted in FIG. 2A) and by mass spectrum (FIG. 2B, ESI-MS, positive mode and also negative mode to check for the absence of $MnCl_2$; 679 m/z).
(ii) Synthesis of Conjugate 12
Compound 9 (15 mg) was dissolved in DMSO with sulfo-NHS (30 mg) and DCC (24 mg), the reaction mixture was stirred at room temperature under argon atmosphere overnight, evaporated, re-dissolved in 5 mM phosphate buffer pH 8.0 (1.5 ml) and filtered. CycloRGDfK (30 mg) in DMSO (2.5 ml) was added to the filtrate, the mixture was stirred under argon atmosphere for 6 hrs, evaporated, re-dissolved in water (2 ml), and purified on HPLC on preparative $C_{18}$ column using a gradient elution of acetonitrile in water, 10-40%, during 15 min., flow 7 ml/min. The purified conjugate 12 was dried under reduced pressure and stored at −20° C. under argon atmosphere till application.

Example 3. Synthesis of Conjugate 14

The title compound was prepared starting from the synthesis of the unmetalated conjugate 13, as follows.
(i) Synthesis of Conjugate 13
Bpheid (compound 3) (40 mg), prepared as described in Materials and Methods above, was activated with NHS (80 mg) and DCC (60 mg) in chloroform (5 ml) under stirring, at room temperature overnight. The obtained activated ester was purified on silica column using chloroform as eluent, and then reacted with cycloRGDfK (40 mg) in DMSO (5 ml) under stirring and argon atmosphere overnight. Then, taurine (50 mg) dissolved in 1M dipotassium hydrogen phosphate (1.5 ml, pH adjusted to 8.2) was added to the reaction, and the mixture was evaporated, leading to the putative compound 13. The product was purified by HPLC on reversed phase using gradient elution with 5 mM phosphate buffer, pH 8.0, and methanol, as described previously (Brandis et al., 2005). Yield: 52%.
(ii) Synthesis of Conjugate 14
Manganese was inserted into compound 13 using the procedure employed in Example 2. The product, conjugate 14 was purified by HPLC using gradient elution with acetonitrile and water as described previously (Brandis et al., 2005).

Example 4. Synthesis of Conjugate 15

An aqueous solution of copper acetate (2 mg) was added to a mixture of conjugate 13 (3 mg) (prepared in Example 3 (i)) and sodium ascorbate (2 mg) in water. The reaction was immediately monitored by spectrophotometry. After copper insertion into the macrocycle, the product was purified on a RP-18 cartridge (Lichrolut, Merck), first using water to wash out non-reacted copper acetate and ascorbates, and then methanol for the elution of the main compound, conjugate 15, which was collected and evaporated. Yield: 86%.

For the preparation of radioactive conjugates, the same procedure is used with water-soluble salts other than acetate of freshly-prepared radioactive isotope $^{64}Cu$ or $^{67}Cu$ ($t_{1/2}$ is 12.70 h and 2.58 d, respectively).

Example 5. Synthesis of Conjugate 17

The title compound was prepared starting from the preparation of the unmetalated conjugate 16.

(i) Synthesis of Conjugate 16

Conjugate 16 was prepared as in Example 3(i), but using Pheid (compound 6) as the starting material instead of Bpheid.

(ii) Synthesis of Conjugate 17

Conjugate 17 was synthesized according to the procedure described in Example 3(ii), using conjugate 16 obtained above as the starting material.

Example 6. Synthesis of Conjugate 18

The title compound was synthesized following the procedure of Example 5 above, using compound 16 as the starting material.

Example 7. Synthesis of Conjugate 19

The preparation of conjugate 19 is schematically described in Scheme 2 hereinafter.

Bacteriopurpurin 18 (BPP 18), 4a (20 mg) obtained as described in Materials and Methods, and palladium acetate (10 mg) in chloroform (8 ml) were mixed with palmitoyl ascorbate (25 mg) in methanol (12 ml). After 20 min. of stirring, the reaction was completed (monitoring was carried out by spectrophotometry), and the mixture was shaken with chloroform/water. The organic layer was collected, dried over sodium sulfate, evaporated, and purified on silica column with chloroform-acetone elution, to obtain Pd-BPP 18. UV-VIS Spectrum: 342, 414, 534 and 810 nm in chloroform.

Pd-BPP 18 (18 mg) was stirred with hydrazine hydrate (12 µl) in pyridine (8 ml) for 35 min, the reaction mixture was poured into chloroform (30 ml) and 1N HCl (30 ml), and stirred for additional 2 hrs. Then, the organic layer was dried over sodium sulfate, propane sultone (50 mg) was added, and the mixture stirred for 10 min. and evaporated. The residue was treated with aqueous ammonia (28%, 3 ml) for 30 min. to eliminate unreacted sultone by conversion into sulfopropylamine, and the mixture was evaporated again. Water (3 ml) was added to dissolve the residue and the product was purified on a RP-18 cartridge (Lichrolut, Merck), first using water to wash out sulfopropylamine, and then methanol for the elution of the main compound, thus obtaining Pd-Bacteriopurpurin-N-(3-sulfopropylamino)imide (UV-VIS Spectrum: 344, 417, 528 and 822 nm in water).

Pd-Bacteriopurpurin-N-(3-sulfopropylamino)imide (10 mg) was reacted overnight with NHS (20 mg), in the presence of EDC (20 mg) in DMSO (3 ml). The obtained activated ester was purified on a silica column using $CHCl_3$:MeOH (5:1), dried and kept under argon in the dark until further use.

CycloRGDfK (5 mg) was dissolved in 1 ml of DMSO, added to the activated complex (5 mg) in 1 ml of DMSO, and the reaction mixture was incubated at room temperature for 24 hours, and stirred under argon. The obtained conjugate 19 was purified using HPLC, and identified by mass spectroscopy (ESI-MS positive mode, 1415 m/z).

Example 8. Synthesis of Conjugate 21

The title compound was prepared starting from the synthesis of conjugate 20 as follows.

(i) Synthesis of Conjugate 20

Meso-tetra(4-carboxyphenyl)porphine (20 mg, 25 µmol), was mixed with sulfo-NHS (4 mg, 36 µmol) and EDC (6 mg, 30 µmol) in DMSO (6 ml), and stirred at room temperature for 24 hr. Then, cycloRGDfK (20 mg, 33 µmol) was added, the reaction mixture was stirred for further 24 hr, and then evaporated to dryness, re-dissolved in water and purified on HPLC on preparative $C_{18}$ column, using a gradient elution of acetonitrile in 0.2% acetic acid 30-50% during 15 min., flow 6 ml/min. The purified conjugate 20 was dried under reduced pressure and stored at −20° C.

(ii) Synthesis of Conjugate 21

Conjugate 20 (4 mg) was dissolved in 50%-aqueous methanol and aqueous solutions of copper acetate (2 mg) and sodium ascorbate (2 mg) were added. The reaction was completed in 2 min. (monitored by spectrophotometry). The product was purified on RP-18 cartridge (Lichrolut, Merck), first, using water to wash out unreacted copper actetate and ascorbate, and then methanol for the elution of the main compound, conjugate 21, which is collected and evaporated (UV-VIS Spectrum: 418 and 538 nm in water).

Example 9. Synthesis of Conjugate 22

Conjugate 20 (4 mg), obtained in Example 8(i) above, and gadolinium acetylacetonate (10 mg) were heated in imidazole (0.3 g) at 210° C., as previously described (Horrocks et al., 1978). The reaction was completed in 50 min. (monitored by spectrophotometry). After sublimation of imidazole, the product was re-dissolved in water and purified on HPLC, as described in Example 8(i).

Example 10. Synthesis of Conjugate 23

Conjugate 23 was prepared starting from the synthesis of compound 10.

(i) Synthesis of Compound 10

(100 mg) was dissolved in N-methylpyrrolidone (1 ml) and 3-amino-2-propanediol (405 mg) and the solution was mixed during 3 hours at room temperature under argon atmosphere. The product 10 was purified on HPLC using YMC-C18 preparative column with 0.2% acetic acid/acetonitrile. Yield: 86%. Analysis was performed on LC-MS using YMC-C18 analytical column with ammonium acetate, pH 4.5/acetonitrile. ESI-MS positive mode, 805 m/z.

(ii) Synthesis of Conjugate 23

Compound 10 (50 mg), NHS (80 mg) and DCC (216 mg) were dissolved in dry N,N-dimethylformamide (8 ml). The solution was stirred for 90 min at room temperature under argon atmosphere. The active ester formed was purified on HPLC using YMC-C18 preparative column with 0.2% acetic acid/acetonitrile, analyzed on LC-MS using YMC-C18 analytical column with ammonium acetate, pH 4.5/acetonitrile, and identified by mass spectroscopy: ESI-MS positive mode, 902 m/z.

The active ester (10 mg) was dissolved in dry N-methyl-pyrrolidone (1 ml). CycloRGDfK (8 mg) and triethylamine (10 µl) were added and the solution was stirred for 75 min. The product was purified on HPLC using YMC-C18 preparative column with 0.2% acetic acid/acetonitrile. Yield: 50%. Analysis was performed on LC-MS using YMC-C18 analytical column with ammonium acetate pH 4.5/acetonitrile: ESI-MS positive mode, 1393 m/z.

Example 11. Synthesis of Conjugate 24

Compound 8 (100 mg) was activated with NHS (70 mg) and N-cyclohexylcarbodiimide-N'-methyl polystyrene (120 mg) in DMF (5 ml). The solution was stirred at 50° C. during 15 hours and filtered through a sinter glass. CycloRGDfK (100 mg) was dissolved in DMF (5 ml) containing N-methylmorpholine (100 μl) and added to the filtrate. The mixture was stirred under argon atmosphere at room temperature for 24 hours, the solvent was evaporated in vacuum, and the product 24 was purified on HPLC using YMC-C18 preparative column with ammonium acetate pH 4.5/acetonitrile. Yield: 23%. Analysis was performed on LC-MS with YMC-C18 analytical column under the same conditions. UV-VIS spectrum (HPLC): 332, 386, 516, and 750 nm. ESI-MS positive mode, 1425 m/z.

Example 12. Synthesis of Conjugate 26

To the Fmoc-deprotected GRGDSP-resin (0.35 mmol), a mixture of compound 25 (530 mg, 0.7 mmol), HOBt, PyBOP (both 0.7 mmol) and DIEA (2.1 mmol) in 6 ml of DMF was added, and the reaction was agitated during 2 h under argon atmosphere. After washings with DMF (10×5 ml) and DCM (5×5 ml), the resin was dried in vacuum for at least 3 h. The peptide-conjugate was then cleaved from the resin and deprotected (Arg, Pbf; Asp, OtBu) using a cocktail solution of 85:5:5:5 TFA/thioanisole/$H_2O$/triisopropylsilane (TIS) (10 ml) for 10 min at 0° C. and then 1 h at room temperature under Ar atmosphere. The resin was filtered and washed with the cocktail solution (4 ml) and the combined filtrate was evaporated by a stream of $N_2$ to about half of its volume. Upon addition of cold $Et_2O$ (30 ml), a dark precipitate appeared. Centrifugation and decantation of the $Et_2O$ layer and additional treatment with cold $Et_2O$ (2×30 ml) afforded the crude dark solid, which was further purified by RP-HPLC (264 mg; 58%). Analysis was performed on LC-MS using YMC-C18 analytical column with ammonium acetate pH 4.5/acetonitrile: ESI-MS positive mode, 1306 m/z.

Example 13. Synthesis of Conjugates 28-31

The title compounds were prepared starting from the synthesis of the unmetalated Bpheid-cycloRGDfK conjugate n as follows.
(i) Solid Phase Synthesis of cycloRGDfK
Fmoc-$C^α$-allyl protected aspartic acid was attached on 2-chlorotrityl chloride resin. Next, glycine, $N^G$-Pbf arginine, N'-Dde lysine, and phenylalanine were attached on the resin by usual Fmoc chemistry, forming fKRGD peptidyl-resin. Then, the N-terminal Fmoc group was removed with 2%-piperidine/DMF, and the $C^α$-allyl group on aspartic acid residue was removed with tetrakis(triphenylphosphine) palladium and 1,3-dimethylbarbituric acid (DMBA) in DCM. The peptide was cyclized in the presence of HOBt/PyBOP and DIEA. The ε-amine of the lysine residue was cleaved with 4%-hydrazine/DMF.
(ii) Synthesis of Conjugate 27
Bpheid (3, 0.6 mmol) was bound to ε-$NH_2$-Lys on the fKRGD peptidyl-resin (0.3 mmol) in DMF using PyBOP/HOBt (0.6 mmol) as coupling agents and DIEA (1.8 mmol) as a base, thus obtaining conjugate 27.
(iii) Synthesis of Conjugates 28-31
Conjugate 27 (0.1 mmol) was treated on the resin with the appropriate amine in Table 1 (5-6 mmol) in DMF at room temperature during 2 h. Then, the amine excess was washed off, the product was disconnected from the resin, deprotected with the TFA-containing cocktail, and finally purified by RP-HPLC. Analysis was performed on LC-MS using YMC-C18 analytical column with ammonium acetate pH 4.5/acetonitrile. The results are shown in Table 1.

TABLE 1

Yield and ESI-MS of Conjugates 28-31

| Conjugate | Amine | Yield, mg (%) | ESI-MS (+), m/z |
|---|---|---|---|
| 28 | bis(3-aminopropyl)amine | 71 (53) | 1327 |
| 29 | 3-amino-1,2-propanediol | 63 (49) | 1287 |
| 30 | N-(2-aminoethyl)morpholine | 75 (56) | 1326 |
| 31 | 1,4-bis(3-aminopropyl)piperazine | 75 (54) | 1396 |

Example 14. Synthesis of Conjugate 32

Conjugate 32 was obtained by coupling peptidylamine cycloRGDK-$NH_2$ (obtained as described in Material and Methods) and Bpheid a (1) in DMF solution in the presence of DCC, followed by Pbf and O-tBu deprotection with TFA. The product was purified by RP-HPLC. Yield: 53%. Analysis was performed on LC-MS using YMC-C18 analytical column with ammonium acetate pH 4.5/acetonitrile: ESI-MS positive mode, 1135 m/z.

Example 15. Synthesis of Conjugate 33

Conjugate 33 was obtained by conjugating compound 8 with the linear peptide GRGDSPK (obtained as described in Material and Methods) similarly to the method described for conjugate 24 in Example 11. Yield: 55%. Analysis was performed on LC-MS using YMC-C18 analytical column with ammonium acetate pH 4.5/acetonitrile: ESI-MS positive mode, 1537 m/z.

Example 16. Synthesis of Conjugate 34

Conjugate 34 was obtained by conjugating compound 8 with the linear peptide $(GRGDSP)_4K$ (obtained as described in Material and Methods) similarly to the method described for conjugate 24 in Example 11. Yield: 41%. Analysis was performed on LC-MS using YMC-C18 analytical column with ammonium acetate pH 4.5/acetonitrile. MALDI-MS positive mode, 3291 (M+2Na) m/z.

Example 17. Synthesis of Conjugate 35

Conjugate 35 was obtained by conjugating compound 8 with cycloRGDf-N(Me)K (obtained as described in Material and Methods) similarly to the method described for conjugate 24 in Example 11. Yield: 58%. Analysis was performed on LC-MS using YMC-C18 analytical column with ammonium acetate pH 4.5/acetonitrile: ESI-MS positive mode, 1439 m/z.

Example 18. Synthesis of Conjugate 36

Conjugate 36 was obtained by conjugating compound 8 with the cyclic dimer peptide $(cycloRGDyK)_2$ (obtained as described in Material and Methods) similarly to the method described for conjugate 24 in Example 11. Yield: 27%. Analysis was performed on LC-MS using YMC-C18 analytical column with ammonium acetate pH 4.5/acetonitrile. MALDI-MS positive mode, 2245 (M+2Na) m/z.

Example 19. Synthesis of Conjugate 37

The conjugate 37 was synthesized from Pd-Bpheid (compound 7) and the peptide RGD. The peptide was prepared by the solid phase procedure by coupling of Fmoc-Arg (Pbf)-Gly-OH to a resin bound H-Asp-O-Allyl residue.

(i) Preparation of Protected Dipeptide Arg-Gly

A solution of Fmoc-Gly-OH (4.162 g; 14 mmol) and DIEA (9.755 g; 56 mmol) in 100 ml of dry DCM was stirred with 10 g of 2-chlorotrityl chloride resin (1.4 mmol/g) for 1 h at room temperature (rt). The Fmoc group was removed by treatment with 5% piperidine in DMF/DCM (1:1), followed by 20% piperidine in DMF. Then, Fmoc-Arg (Pbf)-OH (18.17 g; 28 mmol) in DMF (130 ml) was activated with HOBt (4.29 g; 28 mmol) and DIC (4.34 ml; 28 mmol) for 15 min at rt and added to the reaction vessel. The mixture was stirred for 2 h at rt. The peptidyl-resin was washed and dried in vacuum for 3 h. The protected dipeptide was cleaved from the resin by stirring with a cocktail solution of AcOH/2,2,2-trifluoroethanol (TFE)/DCM (1:1:3) for 1 h at rt. Upon treatment with cold $Et_2O$ (11), the oily residue solidified. Filtration and washings with cold $Et_2O$ afforded the white precipitate (8.64 g; 87.5%) with homogeneity of about 99% (HPLC).

(ii) Synthesis of the Tripeptide RGD

Attachment of the third amino acid to the dipeptide obtained in step (i) above started by stirring 2-chlorotrityl chloride resin (0.5 g; 1.4 mmol/g) with a solution of Fmoc-Asp-O-Allyl (138.4 mg; 0.35 mmol) and DIEA (244 μl; 1.4 mmol) in DCM during 1 h at rt to give a loading of about 0.7 mmol/g. Then, the resin was washed and Fmoc was removed as described above. Fmoc-Arg (Pbf)-Gly-OH (371 mg; 0.525 mmol), HOBt (80.4 mg; 0.525 mmol) and DIC (81 μl; 0.525 mmol) were dissolved in 2.5 ml DMF and stirred at rt for 20 min. The resulting solution was added to the washed H-Asp-O-Allyl-resin, and the mixture was agitated for 2 h at rt. The peptidyl-resin was washed, and Fmoc was removed.

(iii) Synthesis of Conjugate 37

A mixture of compound 7 (268 mg; 0.375 mmol), HOBT (57.4 mg; 0.375 mmol) and DIC (58 μl; 0.375 mmol) in 3 ml of DMF was stirred for 30 min at rt and added to an aliquot of Fmoc-deprotected tripeptidyl-resin obtained in (ii) above (about 0.125 mmol). The mixture was agitated for 2 h at rt, and the conjugate of 7 with the linear tripeptide RGD was obtained. This reaction and all following operations with modified peptidyl-resin were performed in Argon atmosphere in the dark. After washing, the resin was treated with ethylenediamine (25 μl; 375 mmol) in DMF during 1 h at it, then washed. In order to remove the allyl-protecting group, the resin was reacted with a solution of $[(C_6H_5)_3P]_4Pd^0$ (87 mg; 0.075 mmol) and DMBA (137 mg; 0.875 mmol) in DCM during 2 h at rt.

On-resin cyclization was accomplished by binding the deprotected Asp residue to the ethylenediamino moiety using a solution of PyBOP (195 mg; 0.375 mmol) and DIEA (131 μl; 0.75 mmol) in DMF for 2 h at rt. The resin was washed and dried in vacuum for 3 h. The peptide conjugate was cleaved from the resin using a cocktail solution TFA/Thioanisole/$H_2O$/TIS/EDT (82.5:5:5:5:2.5) for 10 min at 0° C. and then 1 h at rt. Upon the addition of cold $Et_2O$ (25 ml), a dark solid was obtained. The crude product (95 mg) was purified by RP-HPLC to give 2 mg of pure (98%) cyclic RGD conjugate 37. ESI-MS 1087 (M+H) m/z.

Example 20. Synthesis of Conjugate 38

The synthesis was carried out on a 0.175 mmol scale using the same procedure as described in Example 19, but starting from the compound Bpheid 3 instead of Pd-Bpheid 7. The crude product (160 mg) was purified by RP-HPLC to give 17 mg of pure (98%) cyclic RGD conjugate 38. ESI-MS 982 (M+H) m/z.

Example 21. Synthesis of Conjugate 39

The procedure is similar as in Example 19, but 1,4-bis (3-aminopropyl)-piperazine was used for "bridge"-formation between the Bpheid residue and the Asp-residue instead of ethylenediamine. The crude product (158 mg) was purified by RP-HPLC to give 12.5 mg of pure (99%) cyclic RGD conjugate 39. ESI-MS 1122 (M+H) m/z.

Example 22. Synthesis of Conjugate 40

Conjugate 40 was obtained by a method similar to that described for conjugate 24, but using the linear RGD-peptidomimetic 5-(6-guanidino-hexanoylamino)-pentanoic acid (RGD-PM1). Yield: 42%. Analysis was performed on LC-MS using YMC-C18 analytical column with ammonium acetate pH 4.5/acetonitrile: ESI-MS positive mode, 1123 m/z.

Example 23. Synthesis of Conjugate 41

Conjugate 41 was obtained by a method similar to that described for conjugate 24, but using the linear RGD-peptidomimetic 1-(4-guanidino-butyryl)-piperidine-3-carbonyl]-amino]-heptanoic acid (RGD-PM2). Yield: 66%. Analysis was performed on LC-MS using YMC-C18 analytical column with ammonium acetate pH 4.5/acetonitrile: ESI-MS positive mode, 1220 m/z.

Example 24. Synthesis of Conjugate 42

Conjugate 42 was obtained by a method similar to that described for conjugate 24 in Example 11, but using the peptide cycloRADfK. Yield: 30%. Analysis was performed on LC-MS using YMC-C18 analytical column with ammonium acetate pH 4.5/acetonitrile: ESI-MS positive mode, 1439 m/z.

Example 25. Synthesis of Conjugate 43

The title compound was prepared starting from the synthesis of the Bacteriopheophorbide-173-(cycloRGDfK) amide conjugate 27, as described in Example 13.

Conjugate 27 (0.1 mmol) was treated on the resin with an 1,3-propylene diamine (6 mmol) in DMF at room temperature during 2 h. Then, the amine excess was washed off, and DTPA dianhydride (0.2 mmol) and triethylamine (100 ml) in anhydrous DMF (30 ml) was added. After 1-h agitation under argon atmosphere, distilled water (50 ml) was added, followed by additional agitation for 30 min. The product 43 was disconnected from the resin, deprotected with the TFA-containing cocktail, and finally purified by RP-HPLC (61 mg, 37%). Analysis was performed on LC-MS using YMC-C18 analytical column with water/acetonitrile. ESI-MS negative mode, 1643 m/z.

Example 26. Synthesis of Conjugate 44

Gadolinium chloride (0.1 mmol) in a sodium acetate buffered aqueous solution (0.1 N, pH 5.5) was added into a solution of conjugate 43 (6 μmol) in 2 mL of DMF. The mixture was allowed to stand at ambient temperature for overnight with stirring. The formation of the metal chelates was verified by LC-MS (1799 m/z). The reaction mixture was evaporated, and the product was purified on a RP-18 cartridge (Lichrolut, Merck), first using water to wash out non-reacted gadolinium salt, and then methanol for the elution of the main compound, conjugate 44, which was collected and evaporated (8 mg, 73%).

II. Biological Section

Materials and Methods (i) Eu-labeled RGD-4C.

RGD-4C (20 nmole in 10 µl DDW) was added to 100 µl of K-phosphate buffer (0.1 M, pH 8.5) containing isothiocyanatophenyl-DTPA-Eu (150 nmole, 50 µl). The mixture was incubated overnight at room temperature with constant stirring. To terminate the reaction, 1 µl of Tris-Cl (1 M, pH 7.5) was added, the mixture was stirred for 5 min, then loaded on Sep-Pak C-18 cartridge and washed with DDW to elute the free Eu. The Column was then washed with 50% aqueous ethanol, fractions (250-500 µl) were collected and their fluorescence measured.

(ii) Covalent Attachment to Human Serum Albumin (HSA).

HSA (90 mg) was activated with sulfoNHS and 1-ethyl-3-(3-dimethylaminopropyl)carbodiimide hydrochloride (EDAC) (sulfoNHS:EDAC:HSA=1000:500:1 molar ratio) in 50 mM phosphate buffer, pH 5.0. After 45 minutes, a sample of the reaction mixture (about 1 ml) was passed through PD-10 column (Sephadex G-25M, GE Healthcare, Uppsala, Sweden) using 5 ml of the same buffer to recover the protein fraction (HSA-sNHS). Photosensitizers, conjugated or non-conjugated to RGD-containing peptide (about 20 mg each), were dissolved in DMF (2 ml) and added to 2 ml HSA-sNHS, diluted with 4 ml of 50 mM phosphate buffer, pH 8.0, and 1 ml of 5% mannitol. Reaction mixtures were sonicated and stirred overnight under argon atmosphere, then evaporated to remove DMF, re-dissolved in water and passed again through PD-10 column for collection of photosensitizer-HSA-conjugates. To remove non-covalently bound photosensitizers, the products were evaporated and extracted several times with methanol. The extent of HSA conjugation was calculated from the molar ratios between the photosensitizer and HSA parts, determined spectrophotometrically and by Bradford assay, respectively. Approximately 10% of HSA was conjugated. Aliquots of conjugates equal to 0.7 nmol photosensitizer, were prepared for injections.

(iii) Association Constants of Photosensitizers to HSA.

Association constants of photosensitizers, conjugated or non-conjugated to an RGD-containing peptide, were deduced from spectroscopic measurements of the ratio between the photosenstizer and HSA for different concentrations of HSA using both factor analysis, as previously described (Brandis et al., 2005) and by monitoring changes in the near infrared (NIR) absorption of the photosensitizers during titration with HSA. Briefly, all photosensitizers (PhSs) present broad NIR absorption with reduced intensity in SA-free aqueous solutions. Upon addition of SA, they form 1:1 complexes with the added protein (PhS/SA) with strong and narrow NIR absorption bands. The narrow-band absorption is proportional to the (PhS/SA) concentration enabling calculation of the association constant Ka through the following equation:

$$K_a = \frac{[PhS/SA]}{\{[SA]_0 - [PhS/SA]\} \times [PhS]}$$

where $[SA]_0$ is the analytical concentration of the added SA and $[PhS/SA]$ is the concentration of the photosensitizer complexed with SA calculated from the spectral changes.

In Vitro Studies (iv) Cell Culture.

Mouse embryonic heart endothelial cells (H5V) monolayers were cultured in Dulbecco's modified Eagle's medium (DMEM)/F12 containing 25 mM HEPES, pH 7.4, 10% fetal calf serum (FCS), 2 mM glutamine, 0.06 mg/ml penicillin and 0.1 mg/ml streptomycin at 37° C., in 8% $CO_2$. Human umbilical vein endothelial cells (HUVEC) were maintained in M199 medium (with glutamine and EARLE's salts) containing 10 mM HEPES, pH 7.4, 20% heat inactivated FCS (56° C., 30 min), 2 mM glutamine, 50 mg/ml gentamycin, 25 µg/ml endothelial cell growth factor (ECGF), 5 IU/ml heparin at 37° C., in 5% $CO_2$. H5V cells were kindly provided by Dr. Annunciata Vecci, Instituto Mario Negri, Milan, Italy. HUVEC cells were obtained from Rambam Medical Center, Haifa, Israel.

(v) Solubilization of Sensitizers, Peptides and their Conjugates for In Vitro Cell Culture Experiments.

Water-soluble compound 8 and conjugate 11 were dissolved in culture medium (DMEM/F12) or 10% FCS in medium or 10 µM BSA in medium or PBS prior to use, as described for each experiment. Water insoluble compounds (RGD-4C, cycloRGDfK, compound 10 and conjugate II) were dissolved in 100% DMSO before use and diluted in culture medium or PBS to a final DMSO concentration of 2% v/v. Compound 24 was dissolved in 100% DMSO before use and diluted in saline to a final DMSO concentration of 5% v/v.

(vi) Light Source.

The light source for in vitro studies was home-built 100-W halogen lamp equipped with a high-pass filter (λ>650 nm, Safelight filter IA Eastman Kodak Co., Rochester, N.Y., USA) and a 4-cm water filter. The lamp was used to illuminate (20 mW/$cm^2$/10 min (12 J/$cm^2$)) the culture plates from the bottom at room temperature in a dark room.

(vii) Phototoxicity Assay of the RGD Peptide Photosensitizer Conjugates.

To determine the pigment photodynamic efficacy in vitro under standard conditions, cells were cultured in 96-well plates and preincubated for 15 or 90 min at 37° C. or 4° C., according to the indicated experiment protocol, with 0-25 µM conjugated or non-conjugated photosensitizer in different media conditions (culture medium DMEM/F12; 10% FCS in medium or 10 µM BSA in medium) in the absence or presence of excess free peptide (100 fold up to 1 mM). The cells were washed and illuminated (20 mW/$cm^2$ for 10 min). Plates were placed back in the culture incubator for 24 h. Cell survival was determined using Neutral Red cell viability assay. Cell survival was calculated as the percent of the dye accumulated in the untreated controls. Triplicate determinations were conducted and representative experiments are shown. Three kinds of controls were used: (i) light control: cells illuminated in the absence of pigments; (ii) dark control: cells treated with pigments but kept in the dark; and (iii) untreated cells that were kept in the dark.

(viii) Neutral Red Cell Viability Assay.

Following photosensitization and a 24-h incubation period (37° C.), cell survival was determined by Neutral Red (Fluka Chemie, Buchs, Switzerland) accumulation. After subtraction of assay blanks, net optical density (570 nm) was computed as the average value of triplicates determinations. Cell survival was calculated as the percent of the dye accumulated in the untreated controls.

(ix) Cell Detachment (Rounding) Assay:

H5V cells were cultured as monolayers in 3-cm dish for 24-48 h, and further incubated for 1 h with 100 μM RGD-4C at 4° C. or 37° C. The cells were washed once and re-incubated for three hours with fresh culture medium at 37° C. In the same fashion, HUVEC were cultured as monolayers in 6-well plate pre-coated with gelatin for 48 h, and incubated for 1 h with 100 μM RGD-4C at 37° C. The cells were washed once and re-incubated for 24 h with fresh culture medium at 37° C. The morphological changes of the cells were documented using light microscopy.

In Vivo Studies (x) Animals:

Male CD1 nude mice (7-8-week old, ~30 g) were housed and handled with free access to food and water in the animal facility according to the guidelines (1996) of the Institutional Animal Care and Use Committee of the Weizmann Institute of Science, Rehovot, Israel.

(xi) Xenograft, Graft and Metastases Tumor Models.

Cultured rat C6 glioma cell monolayers were scraped under saline with a rubber policeman. Single-cell suspensions of rat C6 glioma (2-4×10$^6$ cells/mouse, 50 μl) were implanted subcutaneously (s.c.) on the backs of the mice. The glial cell strain, C6, was cloned from a rat glial tumor induced by N-nitrosomethylurea after a series of alternate culture and animal passages. Tumors reached treatment size, i.e. diameter of 7-9 mm, within 2-3 weeks. Rat C6 glioma cells were kindly provided by Prof. Michal Neeman, Weizmann Institute of Science, Rehovot, Israel.

Cultured BALB/c CT26luc colon carcinoma cell monolayers transfected with luciferase were scraped under saline with a rubber policeman. Single-cell suspensions of CT26luc (2-4×10$^6$ cells/mouse, 50 μl) were implanted subcutaneously (s.c.) on the backs of the mice. CT26 is an N-nitroso-N-methylurethane-(NNMU) induced, undifferentiated colon carcinoma cell line. It was cloned to generate the cell line designated CT26WT, which was stably transduced with luciferase to obtain the lethal subclone CT26luc. Tumors reached treatment size, i.e. diameter of 7-9 mm, within 1.5-2 weeks. CT26luc cells were kindly provided by Dina Preise, Weizmann Institute, Rehovot, Israel.

Cultured BALB/cfC3H 4T1luc mammary gland tumor cell monolayers transfected with luciferase were scraped under saline with a rubber policeman. Single-cell suspensions of 4T1 luc (2-4×10$^6$ cells/mouse, 50 μl) were implanted subcutaneously (s.c.) on the backs of the mice. 4T1 is a 6-thioguanine resistant cell line selected from the 410.4 tumor without mutagen treatment, which was stably transduced with luciferase to obtain the lethal subclone 4T1luc (kindly provided by Shimrit Ben-Zaken, Weizmann Institute, Rehovot, Israel). Tumors reached treatment size, i.e. diameter of 7-9 mm, within 1 week.

Mammary fat pads (left, bottom nipple) of female mice were inoculated with harvested MDA-MB-231-RFP human breast cancer cells (4×10$^6$ in 100 ml saline). Tumors were classified as 'small' (~100 mm$^3$) at one to two weeks from time of cell injection, or 'large' after three to four weeks (necrotic tumors, 250 to 500 mm$^3$). To avoid tumor burden, mice were sacrificed (cervical dislocation) when tumor size reached 10% of body weight or at 90 days post-implantation. External caliper measurements, length (L), width (W) and depth (D) were used to calculate in vivo tumor volume according to the formula: $V=L/2 \cdot W/2 \cdot D/2 \cdot \pi \cdot 4/3$.

Cultured metastatic human breast cancer MDA-MB-231 cell (ATCC, USA) monolayers were scraped under saline with a rubber policeman. Single-cell suspensions of rat human breast cancer (2-4×10$^6$ cells/mouse, 50 μl) were implanted s.c. on the backs of the mice. Tumors reached treatment size, i.e. diameter of 7-9 mm, within 1 week.

Cultured human OVCAR-8 ovarian adenocarcinoma cell monolayers (kindly provided by Prof. Mordechai Liscovitz, Weizmann Institute, Rehovot, Israel) were scraped under saline with a rubber policeman. Single-cell suspensions of human OVCAR-8 ovarian adenocarcinoma (2-4×10$^6$ cells/mouse, 50 μl) were implanted s.c. on the backs of the mice. OVCAR-8 are derived from a chemotherapy-treated patient with a metastatic disease. Tumors reached treatment size, i.e. diameter of 7-9 mm, within 3-4 weeks.

Cultured MLS human carcinoma cell monolayers (kindly provided by Prof. Michal Neeman, Weizmann Institute, Rehovot, Israel) were scraped under saline with a rubber policeman. Single-cell suspensions of human MLS cells (2-4×10$^6$ cells/mouse, 50 μl) were implanted s.c. on the backs of the mice. Tumors reached treatment size, i.e. diameter of 7-9 mm, within one week.

Groin Metastases.

Cultured CT26luc cells (1×10$^6$ cells/mouse, 20 μl) collected in saline were s.c. injected in the distal dorsal foot of the hindleg of anesthetized mice. When the needle was injected below the skin, the handle of the syringe was withdrawn to verify that it had not penetrated a blood vessel. In this way, systemic dissemination of tumor cells was avoided. Primary tumors grew to a size of 6-8 mm within 3 weeks. Metastases in the groin were inspected using Xenogen IVIS® Imaging System as described herein and by palpation.

Lung Metastases Model.

Cultured CT26luc or 4T1luc cells (0.8-1×10$^6$ cells/mouse, 300 μl) collected in saline were i.v.-injected in the tail vain of anesthetized mice. Lung metastases in the lungs were inspected using Xenogen IVIS® Imaging System as described herein, 2-3 weeks after cells injection.

The mice were sacrificed (according to the guidelines of the Weizmann Institute of Science) when tumors reached the diameter of >15 mm.

(xii) Anesthesia:

Mice were anesthetized by an intraperitoneal (i.p.) injection of a mixture of 50 μl ketamine (100 mg/ml; Rhone Merieux, Lyon, France) and xylazine (2%; Vitamed, Benyamina, Israel) (85:15, vol:vol).

(xiii) Light Source:

The light source for in vivo studies is a 763 nm or 755 nm diode laser (1W; Ceramoptec, Bonn, Germany) according to the photosensitizer in use.

(xiv) Solubilization of Sensitizers and their Conjugates for Animal Experiments.

The water-soluble conjugates were dissolved in PBS or in 5% aqueous mannitol prior to use. The pH was adjusted to a pH of 7.2 to 7.4 with Tris HCl (10 mM tris(hydroxymethyl)aminomethane (when dissolved in 5% aqueous mannitol). The water-insoluble conjugates were dissolved in 100% DMSO before use and diluted in saline or PBS to a final DMSO concentration of 5% v/v. The obtained solutions were filtered through 0.2 μm polytetrafluoroethylene (PTFE) filters (National Scientific, Rockwood Tenn., USA). Concentrations were spectrophotometrically determined in methanol at 747 nm, using molar extinction coefficients of $1.2 \times 10^5$ M$^{-1}$ cm$^{-1}$ for Pd-containing and $6.3 \times 10^4$ cm$^{-1}$ for Pd free compounds. The solutions were stored in the dark at −20° C. until use.

(xv) Biodistribution Studies.

Anesthetized mice were i.v. injected (tail vein) with the different photosensitizer (pigment) conjugates (control group: untreated). The mice were sacrificed at indicated time points and samples of the indicated organs and tissues (blood, tumor, intestine, liver, spleen, kidneys, testies, heart, lung, brain, skin, muscle and fat) were placed in pre-weighted vials and immediately frozen and stored at −20° in the dark until analyzed. Three methods were used for sample preparation: (1) Each sample was thawed and homogenized in DDW (1:10 w/v). Aliquots of the homogenate (5000) were lyophilized in Eppendorf test tubes. Then, 60 μl of $HNO_3$ (70%, TraceSelect, Fluka) were added to each dry sample, incubated for 1 h at 90° C. and diluted with DDW to 3 ml. (2) Each sample was diluted (1:2 w/v) in $HNO_3$ (70%, TraceSelect, Fluka). The samples were sonicated for 30 min in boiled water, and left for at least 48 h at room temperature. (3) Applied for assessment of non-metalated conjugates. Each sample was thawed and homogenized in methanol (100 mg tissue/ml) and extracted the next morning by centrifugation (13,000×g, five minutes) at room temperature. In methods (1) and (2), 140 μl from each sample was added to 3.36 ml DDW to give total volume of 3.5 ml and incubated for 1 h at 90° C. Pd concentrations were determined by ICP-MS. According to method (3), the supernatants were diluted in methanol by a factor of two and the drug concentration was determined by fluorescence measurements (Varian-Cary Eclipse spectrofluorimeter, Palo Alto, Calif., USA) at 750 nm (peak values). Drug concentrations were interpolated from a fluorescence calibration curve, based on predetermined drug concentrations using absorption spectroscopy.

(xvi) Inductively-Coupled Plasma Mass Spectrometry (ICP-MS)

was performed for determination of Pd concentrations using an ELAN-6000 instrument (Perkin Elmer, CT).

(xvii) In Vivo Whole Body Fluorescence Imaging.

The in Vivo Optical Imaging System (IVISR100/XFO-12, Xenogen Corp., Alameda, Calif., USA) was used to acquire fluorescent images of the RFP-expressing tumors, as well as photosensitizers associated with tissues and organs after their intravenous (i.v.) infusion to the tested animals. The field-of-view was 15 cm. Two images were taken; the first image is black and white, providing a photograph of the animal. The second image is a colored overlay of the emitted photon data, in the present case the NIR fluorescence of the compound (680-720 nm excitation filter and a 780-810 nm emission filter) or bioluminescence (560 nm) as described below. The CCD integration time was 10-20 sec in order to maintain a high signal-to-noise ratio.

RFP fluorescence, in units of photons/sec, was detected using 525/50 nm and 612/75 nm filter sets for excitation and emission, respectively, with one second integration time. NIR fluorescence of the different photosensitizers, in units of photons/sec, was detected using 680/30 nm and 847/75 nm filter sets for excitation and emission, respectively, at an integration time of five seconds. Background fluorescence for all quantitative analyses was calculated by recording the average fluorescence (photons/sec)/cm² from three animals in three different areas around and within the tumor of untreated animals provided with a similar diet for three days before measurements. Drug accumulation was determined following i.v. administration of molar equivalents of the photosensitizer to the tail vein of mice fed with a chlorophyll-free, purified diet for three days before administration (in order to reduce skin and food autofluorescence). Before imaging, mice were anesthetized by intraperitoneum injection of a 30 μl mixture of 85:15 ketamine:xylazine.

Dynamic fluorescence images were acquired immediately following the injection of a conjugate of the invention and continued for approximately 2 hours. Fluorescence images were also obtained under isoflurane anesthesia for up to 72 hr after initial injection of the conjugate. The injected dose varied from 140 to 250 nmol per animal. Xenogen Living Image Software (Xenogen Corp., Alameda, Calif., USA) was used for sequential fluorescent image acquisition and superimposition of photographic images of mice and color-coded fluorescent images. Statistical analysis was performed using Origin8.1 (OriginLab, Northampton, Mass., USA) and SPSS15 (SPSS Inc, Chicago, Ill., USA) softwares.

(xviii) Luciferin Assay.

Localization and viability of CT26luc and 4T1luc tumor cells transplanted in mice were accurately assessed by in vivo bioluminescence imaging (BLI). According to the present invention, BLI relies on the light-emitting properties of the reporter enzyme firefly luciferase, which catalyses the transformation of its substrate D-luciferin into oxyluciferin leading to the emission of photons. Luciferin is a chemical substance found in the cells of various bioluminescent organisms. When luciferin is oxidized under the catalytic effects of luciferase and ATP, a bluish-green light is produced. Firefly luciferin is a particularly good reporter for in vivo biophotonic imaging due to properties of its emission spectra. The emission peak of firefly luciferase (560 nm) is contained within the spectrum of visible light and can be detected and quantified with low light imaging systems such as the IVIS system. Prior to imaging, mice were injected intraperitoneally with D-luciferin (for whole body imaging: 55 mg/kg of body weight; for lungs and lymph node metastases imaging: 77 mg/kg of body weight). In vivo images were acquired with the Xenogen IVIS® Imaging System 100 Series and analyzed with the Living Image® 2.5 software. Luciferin can be used in a number of ways. It can be used to monitor light production in vivo, and can be monitored with a Xenogen IVIS® Imaging System.

(xix) PDT Protocol.

CD-1 nude male mice bearing the different tumor xenografts were anesthetized and 24 (5-24 mg/kg body weight) or 8 (9 mg/kg body weight) were i.v. injected via the tail vein. The tumors were trans-cutaneously illuminated after 3.5, 6, 8, 12 and 24 hours for 5-30 min at light doses of 30-360 J/cm². Intensity of illumination: 100-200 mW/cm². After treatment, the mice were returned to the cage. The mice were considered cured if tumor free for 90 days after treatment. Mice were euthanatized when the tumor diameter reached 15 mm. The controls used were: (1) dark control, the mice were i.v.-injected with pigment and not illuminated; (2) light control, mice were illuminated without pigment injection; (3) untreated control; (4) compound 8 alone: the mice were i.v. injected with 8 and illuminated after indicated time point. (5) Mixture of 8 and cycloRGDfX: the mice were i.v. injected with mixture of 8 with cycloRGDfK and illuminated after indicated time point. (6) cycloRGDfK alone: the mice were i.v. injected with cycloRGDfK and illuminated after indicated time point. Images were taken at indicated time post PDT.

(xx) MRI Measurements.

Conventional spin-echo images are acquired before contrast agent administration, in order to localize the tumor. IR snap images were obtained before and 2, 5, 10, 20 and 30 min after injection of 9. The parameters used for IR snap imaging were: TR/TE=9.2/2.7 ms, field of view (FOV)=5 cm, number of experiments (NEX)=1, image matrix=128× 128, slice thickness 2 mm, and a 10° flip angle. A series of seven images, using inversion times of 0.05 s, 0.25 s, 0.4 s, 1.8 s, 2.5 s, 3.6 s, and 5 s were used for Ti evaluation.

Example 26. Evaluation of Binding Parameters and Biological Activities of the Cyclic Peptide RGD-4C The binding parameters and biological activities of the cyclic nonapeptide RGD-4C were characterized in order to test its suitability for vascular photosensitizer targeting.

Characterization of RGD-4C binding activity (i) Preparation of Eu-Labeled RGD-4C.

Figure 3A:
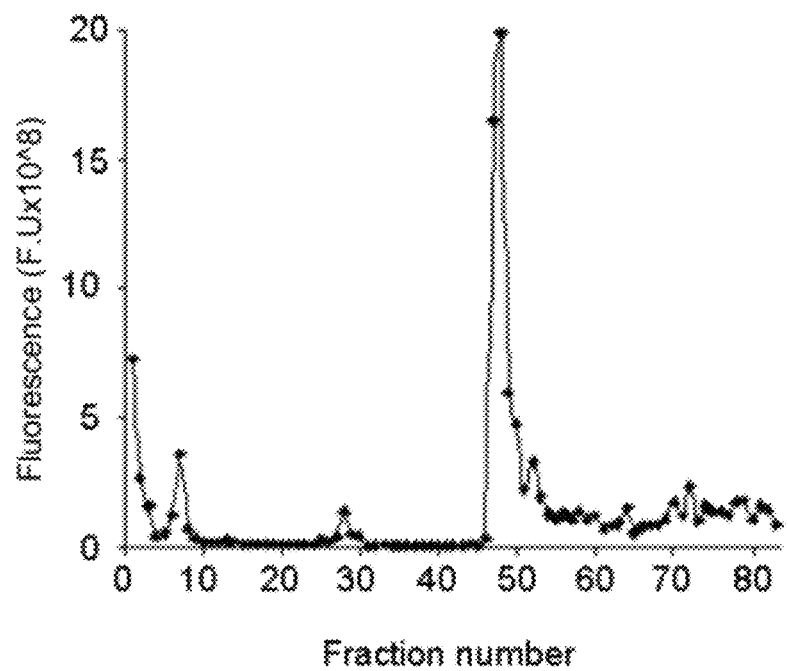
FIGS. 3A-3B show purification and characterization of Eu-RGD-4C.
Figure 3B:
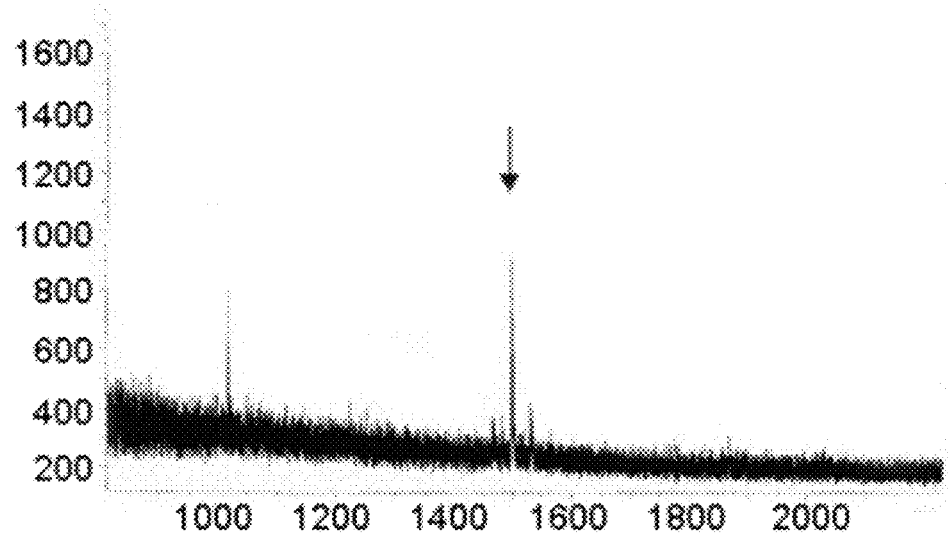

The binding parameters characteristics for the $\alpha_v\beta_3$ integrin receptor expressed on endothelial cells (affinity, specificity and number of receptors/cell) were determined using time resolved emission spectroscopy with Eu-labeled RGD-4C. To this end, RGD-4C was labeled with Eu by direct conjugation of isothiocyanatophenyl-DTPA-Eu as described in Material and Methods. The separation of Eu-RGD-4C from free isothiocyanatophenyl-DTPA-Eu was carried out using Sep-Pak C-18. The column was washed with 50% aqueous ethanol, fractions were collected and their fluorescence measured as described in Materials and Methods. An additional wash with 100% ethanol did not reveal the retention of any significant amount of Eu-containing material in the column. The final product, Eu-RGD-4C, was quantitatively eluted as a single peak (FIG. 3A), as confirmed by mass-spectra analysis (1499 m/z) (FIG. 3B).

(ii) $\alpha_v\beta_3$ Integrin Receptor Binding Assay.

Figure 4:
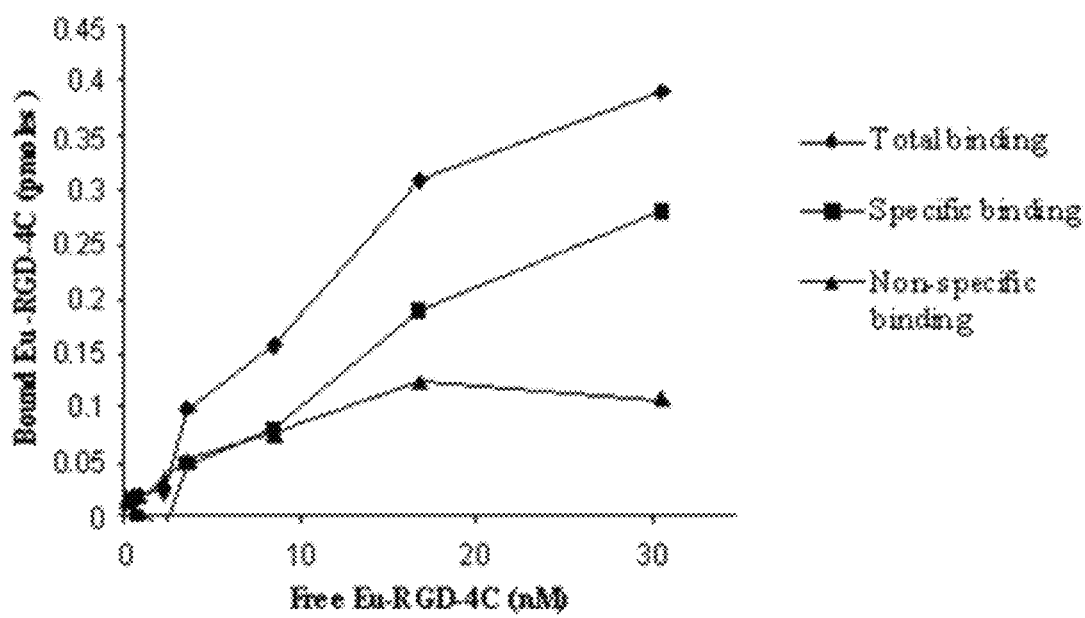
FIG. 4 shows the results of a receptor-binding assay. The specific binding activity of free Eu-RGD-4C to the integrin receptor was measured using H5V cells in the absence (total binding) or presence of 1 µM RGD-4C (non-specific binding).
Figure 5:
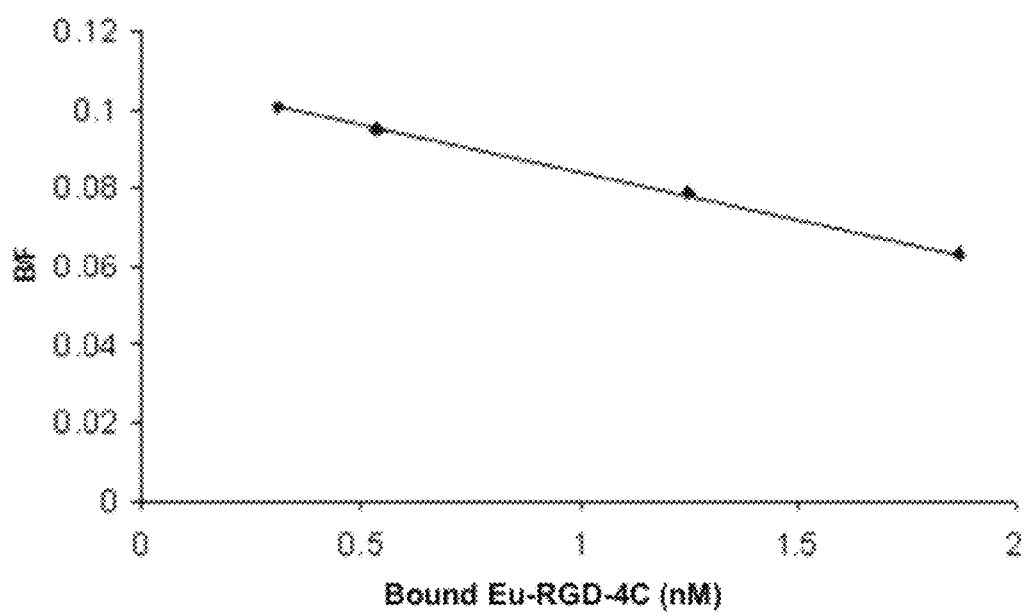
FIG. 5 shows Scatchard analysis of bound (B) and free (F) Eu-RGD-4C based on the results of the receptor-binding assay described in FIG. 4.

The binding activity of Eu-RGD-4C to the integrin receptor was determined using mouse H5V endothelial cells in culture. For the binding assay, H5V cells were plated in 48-well plate ($10^5$/well) for 48 h. The plates were incubated at 4° C. (in order to inhibit receptor endocytosis), washed once with ice cold binding buffer (0.1% BSA in DMEM:F-12) and incubated for 2 h with increasing concentrations of Eu-RGD-4C in the absence (total binding) or presence of 1 µM RGD-4C (non specific binding). The incubation was terminated by triple washing with ice cold binding buffer, and enhancement solution was added (300 µl/well) in order to lyse the cells and release the chelated Eu. Samples (200 µl) were taken from each well and fluorescence was determined using time-resolved fluorometry. Net specific binding was calculated by subtraction of non-specific from total values for each concentration. The percentages of non-specific binding from total added ligand were 4.9%±2.4% (mean±SD). The ratio of total binding to non-specific binding increased from ~1 at low ligand concentrations to ~4 at the highest concentration. The binding results and the Scatchard analysis are presented in FIG. 4 and FIG. 5, respectively, for a representative experiment.

The values for the binding parameters of the ligand were calculated from the Scatchard analysis: ($1/K_d=K_a$, the tested compound's affinity) and $B_{max}$ (the maximal number of binding sites) were 37.2-41.3 nM, and 4.3-7.7 nM (1-1.8 million receptors per cell), respectively. Thus, Eu-RGD-4C binds specifically to H5V endothelial cells. 5 These results confirm reports by others that RGD-4C is a potent ligand for $\alpha_v\beta_3$ integrin receptor (affinity constant of ~100 nM). Specific binding to $\alpha_v\beta_3$ integrin receptor was further demonstrated using isolated $\alpha_v\beta_3$ binding assay as follows.

(iii) Solid-Phase Receptor Assay.

Figure 6:
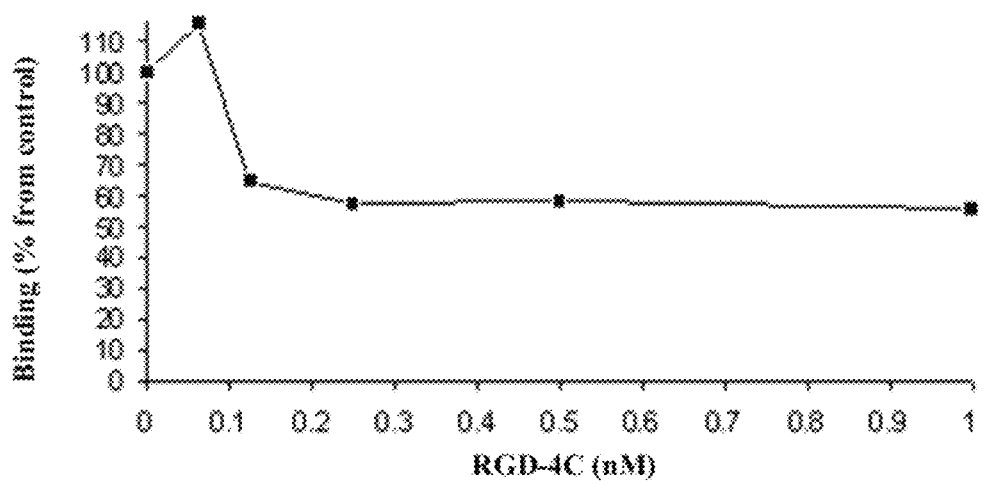
FIG. 6 shows results of a solid phase receptor assay measuring Eu-RGD-4C binding to isolated $\alpha_v\beta_3$ integrin receptor. Time-resolved fluorometry was used for fluorescence determination.

The binding of Eu-RGD-4C to isolated $\alpha_v\beta_3$ integrin receptor was determined using time-resolved fluorometry. Each well of a microtiter plate (Nunc MaxiSorb) was coated with 50 µl of purified receptor (1 µg/ml in PBS) by shaking at 4° C. overnight. The receptor solution was then removed, and each well was blocked with 200 µl of milk (1% w/v milk powder in PBS, 1 hr, room temperature). The plate was then washed with 200 µl of PBS once, and incubated for 1 h at 37° C. with increasing concentrations of RGD-4C in the presence of constant amount of Eu-RGD-4C (10 million F.U./well). The ligand/competitor solution was removed and each well was washed three times with 200 µl PBS. Enhancement solution was added (200 µl/well) to release the chelated Eu. Samples (100 µl) were taken from each well and fluorescence was determined using time-resolved fluorometry (FIG. 6). Under these experimental conditions, 100 µM of RGD-4C reduced by 50% Eu-RGD-4C binding to the isolated receptor. This value represents the highest attenuation of the Eu-RGD-4C binding, even at RGD-4C highest concentrations.

Characterization of RGD-4C Biological Activity

Figure 7A:
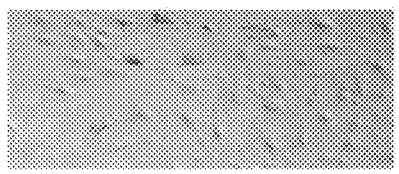
FIGS. 7A-7B show the effect of RGD-4C on H5V endothelial cells detachment. The morphological changes of the cells were documented using light microscopy. 5% of rounded cells (n=200) after incubation in the absence (FIG. 7A) and 99% in the presence of RGD-4C (FIG. 7B). After replacement of the medium with a fresh one and incubation for 3 h at 37° C., the % of rounded cells (n=200) in the absence and in the presence of RGD-4C were 6% and 8%, respectively (not shown).
Figure 7B:

The biological effect of RGD-4C binding was characterized in H5V cells and Human Umbilical Vein Endothelial Cells (HUVEC) using the cell-rounding assay described in Materials and Methods. The morphological changes of the cells were documented using light microscopy. As seen in FIG. 7B, RGD-4C at a concentration of 100 µM induced 99% H5V endothelial cell detachment from the dish (n=200), whereas only 5% rounded cells were observed in the absence of RGD-4C (see FIG. 7A). This effect was reversible as the cells recovered following 3 h re-incubation with fresh culture medium (8% rounded cells in dishes with previous presence of RGD-4C versus 6% in the absence of RGD-4C).

Similarly to H5V cells, 100 µM RGD-4C induced HUVEC detachment from the dish in a reversible manner, since the cells recovered following 24 h re-incubation with fresh culture medium (FIG. 8: upper panels show HUVEC cell detachment in the presence of increasing concentrations of RGD-4C (0-200 µM) while the lower panels show recovery of the cells 24 h after replacement of the medium with a fresh one).

Thus, the effect of RGD-4C is a reversible one since removal of RGD-4C by extensive washing and subsequent maintenance of the tested endothelial cells in culture for 3 h (H5V) or 24 h (HUVEC), results in complete recovery of their adhesive capacities.

Example 27. Binding, Cellular Uptake and Localization In Vitro of Conjugate 24

The binding pattern of the RGD-BChl conjugates is of great importance in understanding their mode of action. Conjugate 24 presents a detectable NIR fluorescence and its cellular binding and localization was determined in vitro using fluorescence microscopy. Cultured H5V endothelial cells were incubated with 25 µM 24 in DMEM/F12 medium with 10% FCS for 2 hours at 37° C. The cell culture was then washed, and PBS++ was added. Using custom made fluorescence microscope, 24 was excited at 520 nm and the emitted fluorescence was detected at 780 nm.

Figure 9:
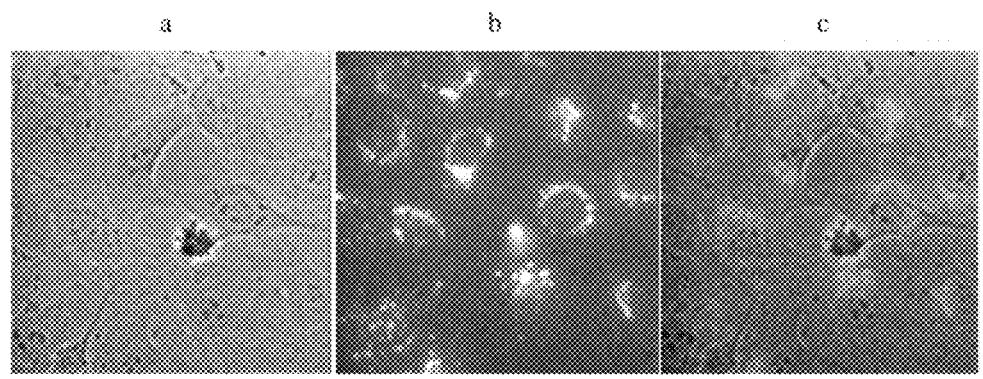
FIG. 9 shows the cellular uptake and localization of conjugate 24 in H5V endothelial cells as depicted in a trans photograph (a), a fluorescence image (b) (excitation filter: 520 nm; emission filter: 780 nm) and a merge of the photograph and image (c).

As shown in FIG. 9, conjugate 24 penetrated into endothelial cells and concentrated around the nucleus in granule-like structures.

Figure 10:
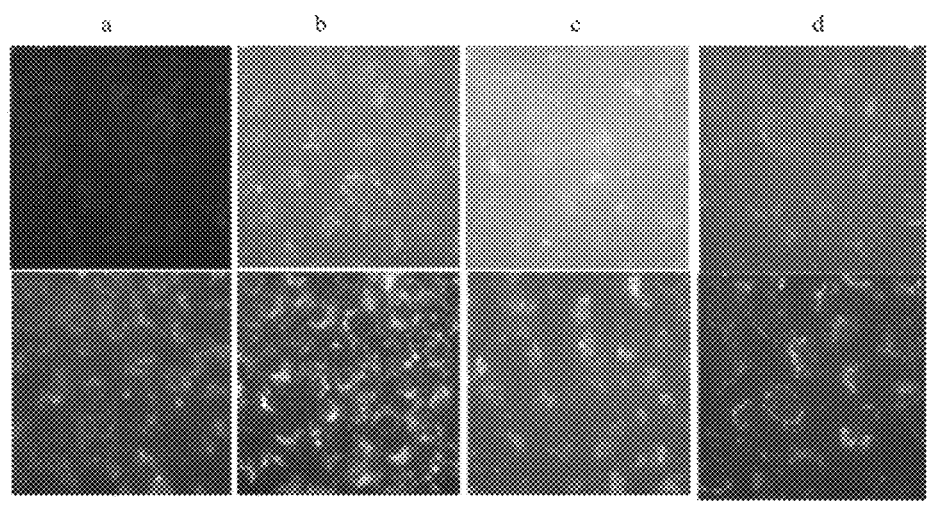
FIG. 10 is a series of fluorescence images showing the cellular uptake and localization of conjugate 24 and compound 8 in H5V endothelial cells measured 20 min (upper panels) or 2.5 hours (lower panels) after incubation with the compounds in a medium containing 10% or 75% FCS (excitation filter: 520 nm; emission filter: 780 nm). (a) 8, 10% FCS; (b) 24, 10% FCS; (c) 8, 75% FCS; (b) 24, 75% FCS.

For comparison purposes, the cellular uptake of non-conjugated compound 8 was measured. Cultured H5V cells were incubated with 25 µM 24 or 8 in DMEM/F12 medium with 10% FCS or 75% FCS for 20 minutes or 2 hours at 37° C. The cell culture was then washed, and PBS++ was added. Excitation was carried out at 520 nm and emitted fluorescence detection at 780 nm. FIG. 10 demonstrates that the conjugate cellular uptake was faster than that of compound 8.

Notably, high serum concentrations (75% vs. 10% FCS) attenuate the cellular uptake of conjugate 24. Quantitative structure function relationship studies done in our group emphasized the role of photosensitizer structure in the interactions with serum proteins. These studies suggest that there is an active involvement of serum albumin in the trafficking of compound 8 both into and out of the treated cells. Further, the cellular uptake of 8 clearance and phototoxicity are mediated by BSA molecules that undergo continuous receptor mediated up-take and secretion. Regarding conjugate 24 the affinity of the bacteriochlorophyll moiety to serum albumin modifies the conjugate bioavailability to the integrin receptor $\alpha_v\beta_3$. This can explain the observed decrease in cellular accumulation in the presence of high serum protein concentrations (FIG. 10). The higher in vitro accumulation of conjugate 24 compared to compound 8 at each time point that was tested could be explained by the fact that the RGD conjugate can enter the cell by integrin receptor mediated endocytosis or/and by non specific endocytosis like the non-conjugated 8.

Example 28. In Vivo Biodistribution of Conjugate 24 and Compound 8

The conjugates of the invention are potential drug carriers. Therefore, their in vivo biodistribution is of great importance. In order to quantify the conjugate levels in target tissues, Ion Coupled Plasma-Mass Spectroscopy (ICP-MS) was used for tracing the central M atom (e.g., Pd, Cu) in the target organ. The stable binding of the central merttal atom enables monitoring and accurate determination of the time dependent concentration of the compound in the target organs. Biodistribution of conjugate 24 and of compound 8 was determined in CD1-nude male mice with tumor xenografts of rat C6 glioma as described in Materials and Methods, using method (2) for sample preparation. Biodistribution of 24 was also determined in CD1-nude male mice bearing tumor grafts of mouse CT26luc colon carcinoma and CD1-nude male mice bearing tumor grafts of mouse of 4T1luc mammary cancer.

Figure 11A:
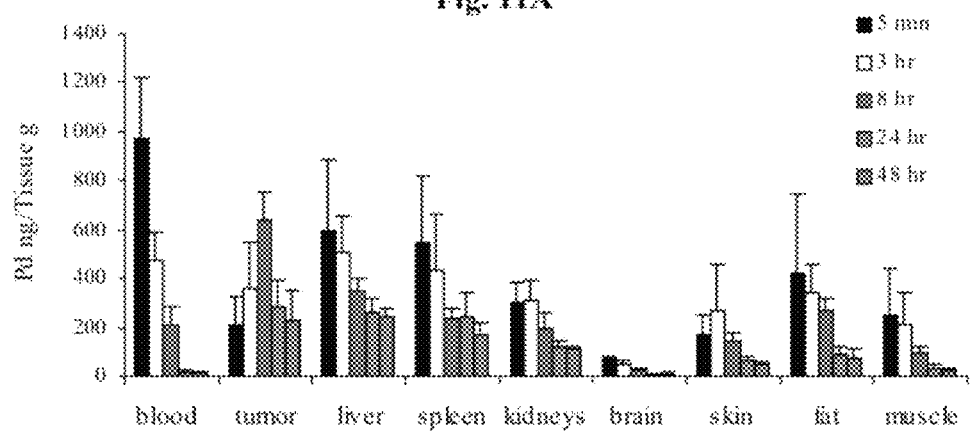
FIGS. 11A-11C are a series of graphs showing the biodistribution of conjugate 24, i.v. injected into CD1 nude male mice with tumor xenografts of rat C6 glioma (11A; each time point represents 6 mice), mouse CT26luc colon carcinoma (11B; each time point represents 2 mice), and mouse 4T1luc carcinoma of the breast (11C; each time point represents 3 mice), sacrificed at the indicated times. Pd concentrations in different organs were determined by ICP-MS. The boxes present time-windows most suitable for PDT and imaging measurements.
Figure 11B:
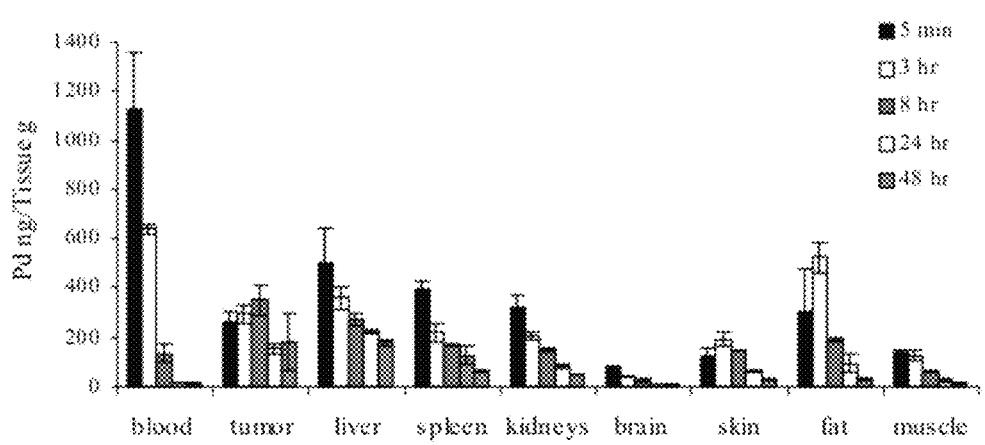
Figure 11C:
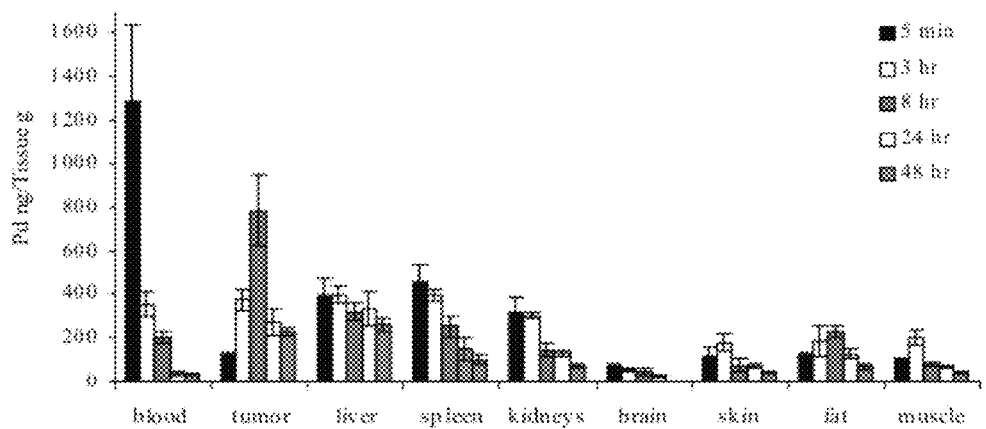

The results, as shown in FIGS. 11A-11C, indicate accumulation of conjugate 24 in the different tumor tissues up to 8 hours post injection accompanied by continuous decrease of the conjugate levels in the blood. Moreover, the biodistribution pattern of 24 appears independent of the tumor's origin (rat C6 glioma (FIG. 11A), mouse CT26luc colon carcinoma (FIG. 11B), and mouse 4T1 carcinoma of the breast (FIG. 11C).

Figure 12:
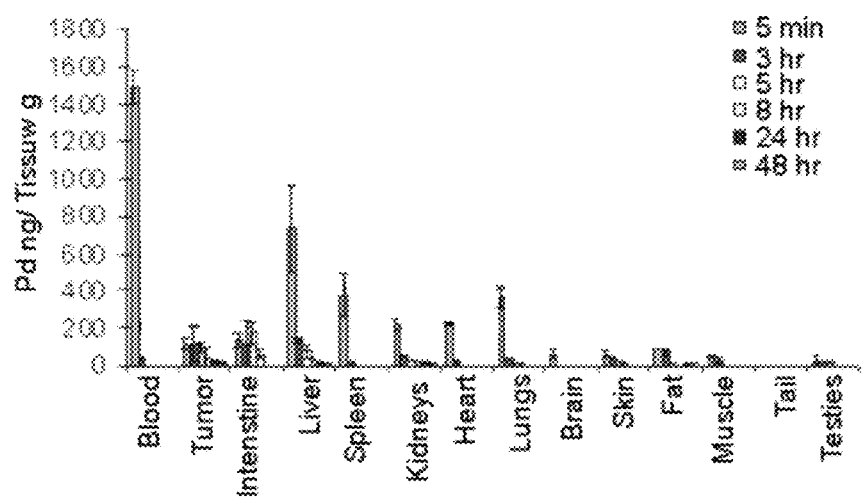
FIG. 12 shows biodistribution of compound 8, i.v. injected (tail vein) into CD1-nude male mice with tumor xenografts of rat C6 glioma, sacrificed at the indicated times. Pd concentrations were determined by ICP-MS.

The biodistribution of compound 8 injected to CD1 nude mice with tumor xenografts of rat C6 glioma presented a completely different picture as shown in FIG. 12: compound 8 cleared rapidly from the subject and at no time showed selective accumulation or retention in the tumor tissue. The accumulation of conjugate 24 in the tumor tissue, with maximal values at 8 h post injection, as opposed to compound 8 (FIG. 12), indicates that the potential drug carrier 24 can be used for drug targeting purposes and can be applied for imaging of tumors and angiogenesis.

Moreover, it is to be noted that the concentrations of accumulated conjugate within the tumor tissue reached the μM level, whereas labeled cycloRGDfK and cycloRGDfK conjugated to other metal chelators were reported by others to reach concentrations only in the nM range (Haubner et al., 2001; Janssen et al., 2002a; Janssen et al., 2002b; Temming, 2005). These reported results demonstrate rapid tumor uptake of the conjugated peptides with maximal peak concentration at 30 min, 1 hour or 2 hours post injection, depending on the conjugate structure. Thus, the markedly increased tumor uptake of the conjugates of the invention compared to either M-Bchl derivative alone or GRD-containing peptide conjugated to other chelators, can be attributed to the conjugation of the RGD-containing peptide to the BChl moiety.

The relative levels of 24 in the tumor tissue and blood are illustrated in FIG. 11A-11C, and it is shown that while 8 hours post injection the conjugate reached maximum concentration in the tumor, at 24 hours post injection its concentration in the tumor relative to the blood and surrounding normal tissue, is still sufficiently high to enable a selective vascular-targeted imaging (VTI) and possibly vascular-targeted PDT (VTP).

It is to be noted that the concentration of the conjugate in the tumor tissue relative to other organs was significantly lower in tumors where the cells are known not to express $\alpha_v\beta_3$ integrin (e.g. CT26luc). Thus, the observed accumulation in $\alpha_v\beta_3$ negative tumors is probably due to their vascular up-take.

Example 29. In Vivo Biodistribution of Conjugate 15

Figure 13:
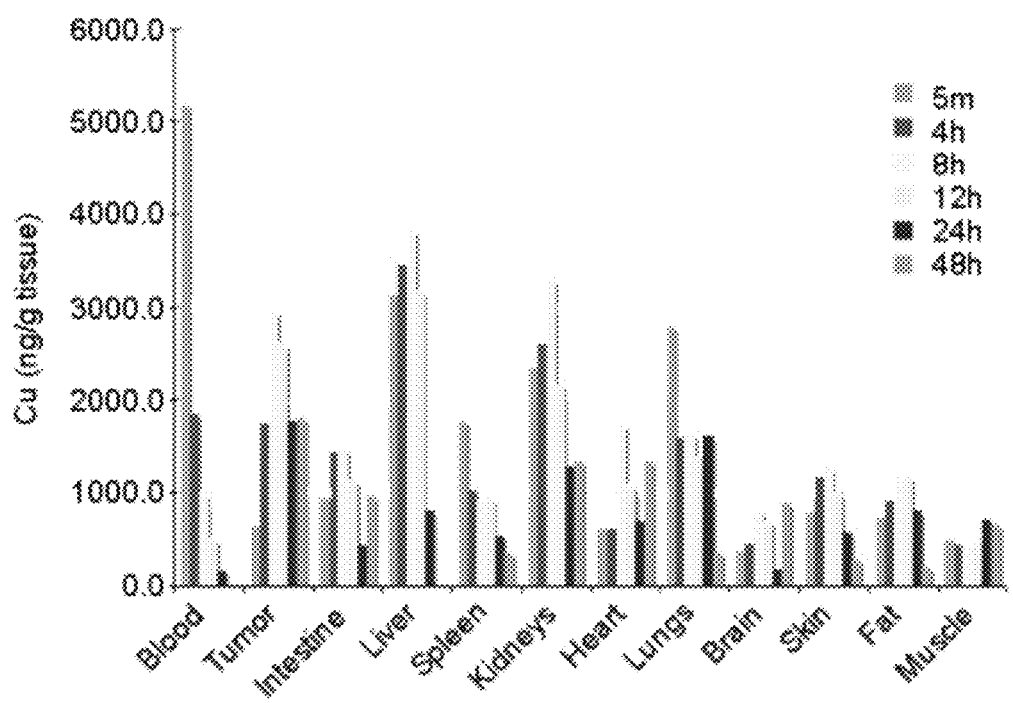
FIG. 13 shows the biodistribution of Cu-conjugate 15 in mice bearing MDA-MB-231 breast tumor. The animals were sacrificed at selected time points. Cu concentrations are shown at selected time point, after the subtraction of time 0, as an average value from three animals.

The biodistribution of Cu-conjugate 15 was determined in female CD-1 nude mice of 6-8 weeks-old, weighing 20-23 g and bearing 6-9-mm³ tumors of human adenocarcinoma cells obtained from breast tissue (MDA-MB-231 cells). The conjugate (30 mg/ml in 5% DMSO/PBS) was injected to the tail vein, and the animals were sacrificed in selected time points. Cu concentrations were determined by ICP-MS as described in Material and Methods. The ICP-MS results after the subtraction of time 0 are shown in FIG. 13.

The obtained data showed an obvious accumulation of 15 in tumor with a peak at 8-12 h after injection of about 3-fold intensity in comparison with surrounding normal tissue.

Example 30. In Vivo Biodistribution of Conjugate 42

Figure 14A:
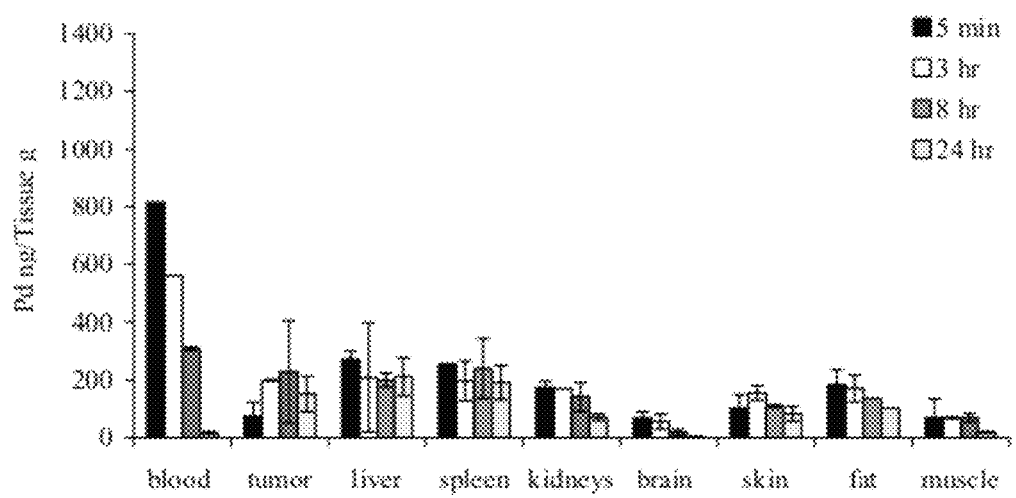
FIGS. 14A-14B are graphs showing the biodistribution of conjugate 42 (that contains the RAD motif), i.v. injected into CD1 nude male mice with tumor grafts of mouse CT26luc colon carcinoma, sacrificed at the indicated times. Pd concentrations in different organs were determined by ICP-MS.

In order to assess the actual role of RGD/integrin recognition, the biodistribution of the conjugate 42 in which glycine in the peptide is replaced with alanine, was measured and compared to the biodistribution of conjugate 24. The substitution of only one amino acid was demonstrated by others to interfere with the integrin recognition (Pierschbacher and Ruoslahti, 1987). Mostly, RAD or RGE peptides were used for this purpose. The biodistribution assay was performed as described in Example 26 above using CD1 nude male mice with tumor grafts of mouse CT26luc colon cancer cells, and Pd concentrations were determined by ICP-MS. The ICP-MS results are shown in FIG. 14A.

Figure 14B:
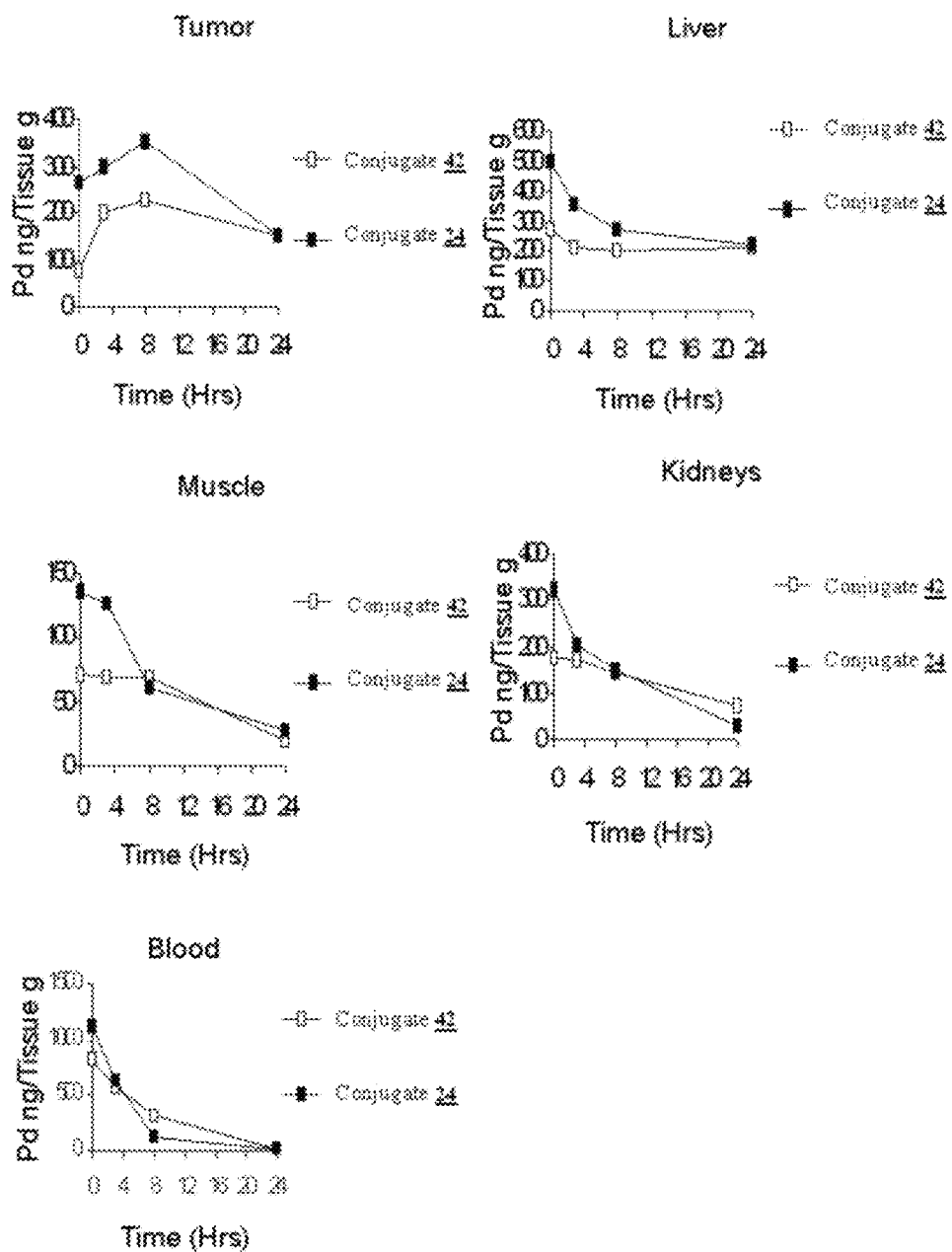

Comparison between the biodistribution of conjugate 24 and the conjugate 42 (FIG. 14B) demonstrates that RGD conjugate uptake in tumor tissue was faster than that of RAD conjugate and to a higher extent up to 24 hours. Conjugate 24 accumulated in the tumor tissue with maximal peak concentration at 8 hours post injection accompanied by a continuous decrease of the conjugate levels in the blood, while the concentrations of 42 in the tumor tissue and blood 8 hours post injection are quite the same. Importantly, both conjugates presented a prolonged basal level after administration due to non-specific binding. However, the accumulation of the RGD conjugate in the tumor site was twice as much compare to the RAD conjugate.

Example 31. In Vivo Fluorescence Imaging of Mice Bearing Rat C6 Glioma Xenografts Following Treatment with Conjugate 24 or Compound 8

Figure 15:
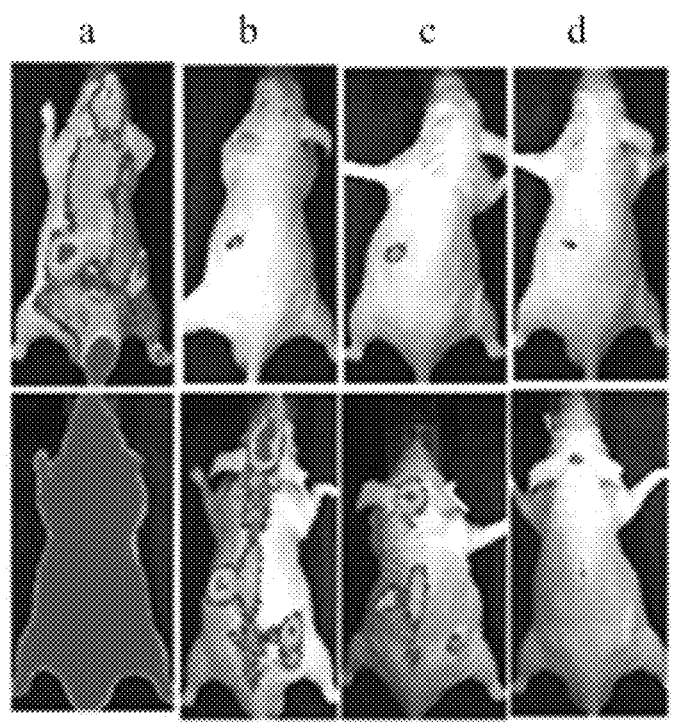
FIG. 15 shows a comparison of whole-body NIR fluorescence imaging after administration of the compound 8 (upper panels) or of conjugate 24. The given images illustrate the fluorescence of a mouse bearing rat C6 glioma xenograft on the back of the right posterior limb (a) 4 hours, (b) 24 hours, (c) 48 hours and (d) 72 hours post injection of 200 nmol dose of conjugate 24 or compound 8. Tumors are indicated by arrows and all images are normalized to the same scale.

Dynamic fluorescence images were obtained from CD-1 nude male mice bearing rat C6 glioma xenografts. The fluorescence images were acquired using IVIS system as described in Materials and Methods. Clearance of the injected photosensitizers (compound 8 or conjugate 24) was measured in mice by fluorescence imaging and is demonstrated in FIG. 15. Mice bearing rat C6 glioma xenografts on the back of the right posterior limb were injected with 200 nmol dose of conjugate 8 (mice in upper pictures) or 200-nmol dose of 24 (mice in lower pictures), and images were taken at 4, 24, 48 and 72 hours post-injection.

Except for a residual fluorescence from the liver and spleen, no specific signal could be seen from the animal treated with the compound 8 at times longer than 4 hours post injection in agreement with the ICP-MS data (FIG. 12). Conjugate 24 appears to accumulate in the tumor, spleen, liver and a fat hump below the animal head. These imaging results, when combined with the ICP-MS results, suggest that the best time window for imaging and probably treatment of the tumor by VTP is at 8-24 hours after drug administration.

Example 32. Dynamic Fluorescence Imaging of Mice Bearing Mouse CT26Luc Colon Cancer Grafts Transfected with Luciferase Following Treatment with Conjugate 24

Cell lines transfected with luciferase generate visible light in the presence of luciferin when alive. The luciferin luminescence enables to monitor viable tumor cells and thus provides the means to validate the conjugate's homing at the tumor site, its imaging capability and the efficacy of VTP.

To avoid the theoretical possibility of conjugate excitation by the luciferin bioluminescence, the fluorescence images were recorded and only then the animals were i.p. injected with luciferin and the bioluminescence of the transfected tumor cells was detected.

The results show that there is a complete overlap between the region of NIR fluorescence signal coming from conjugate 24 and the region of endogenous bioluminescence signal that originates in the tumor cells themselves.

Figure 16A:
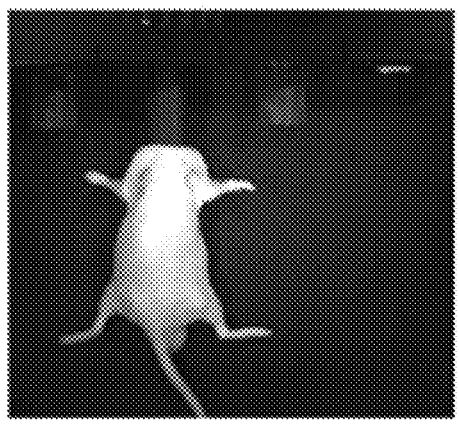
FIGS. 16A-16C are a photograph (16A), a fluorescence image (16B) and a luminescence image (luciferase+luciferin; 16C) of a mouse bearing, on the right anterior limb, a subcutaneous xenograft of CT26luc colon cancer (transfected with luciferase) 24 hr after the injection of 200 nmol dose of conjugate 24. The fluorescence and luminescence images were acquired using IVIS system.
Figure 16B:
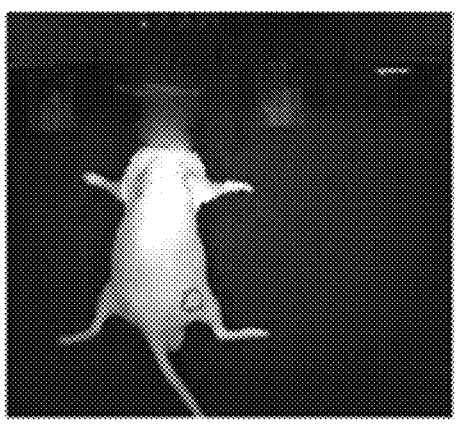
Figure 16C:
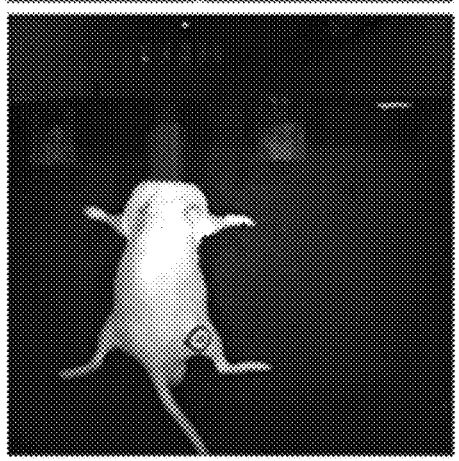

Dynamic fluorescence images were obtained from CD-1 nude male mice bearing grafts of mouse CT26luc colon cancer transfected with luciferase, following the intravenous injection of an integrin receptor targeting conjugate 24. FIGS. 16B-16C depict fluorescence and luminescence images of a mouse bearing a graft on the back of the right posterior limb, 24 hours after injection of 200-nmol dose of conjugate 24. The fluorescence and luminescence images were acquired using Xenogen IVIS® Imaging System as described in Material and Methods.

The results show that there is a complete overlap between the region of NIR fluorescence signal coming from conjugate 24 and the region of endogenous bioluminescence signal that originates in the tumor cells themselves.

Example 33. Dynamic Fluorescence Imaging of Mice Bearing 4T1Luc Mammary Cancer Grafts Transfected with Luciferase Following Treatment with Conjugate 24

Figure 17A:
FIGS. 17A-17C show photographs (17A) and fluorescence (17B) and bioluminescence (17C) images of two mice bearing subcutaneous grafts of mouse 4T1luc mammary gland cancer (transfected with luciferase) on the right anterior limb, 24 hr after the injection of 200 nmol dose of conjugate 24.
Figure 17B:
Figure 17C:

Dynamic fluorescence images were obtained from BALB/c female mice bearing grafts of mouse 4T1luc mammary cancer transfected with luciferase, following the intravenous injection of an integrin receptor targeting conjugate 24. FIGS. 17A-17C show photographs fluorescence and luminescence images of two female mice bearing a subcutaneous mouse 4T1 mammary gland cancer transfected with luciferase grafts on the back of the right posterior limb, 24 hours after the injection of 200-nmol dose of conjugate 24. The fluorescence and luminescence images were acquired using IVIS system as described in Material and Methods.

The results show that there is a complete overlap between the region of NIR fluorescence signal coming from conjugate 24 and the region of endogenous bioluminescence signal that originates in the tumor cells themselves.

Example 34. Dynamic Fluorescence of Mice Bearing Ovarian Carcinoma (MLS) Following Treatment with Conjugate 26

Figure 18:
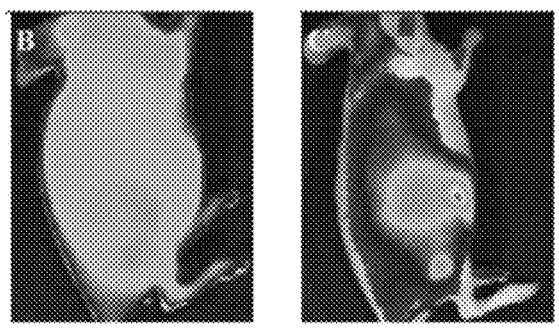
FIG. 18 shows the fluorescence imaging of a mouse bearing ovarian carcinoma MLS xenograft, taken 8 (left panel) and 14 (right panel) hours after i.v. injection of conjugate 31. The fluorescence and luminescence images were acquired using IVIS system.

Conjugate 26 (8 mg/kg) was i.v. injected into animals bearing MLS ovarian carcinoma. Images on IVIS were taken after 8 and 14 hours. As shown in FIG. 18, the conjugate did not present accumulation after 8 hours, but at 14 hours a high level of fluorescence was observed in tumor and liver areas.

Figure 19:
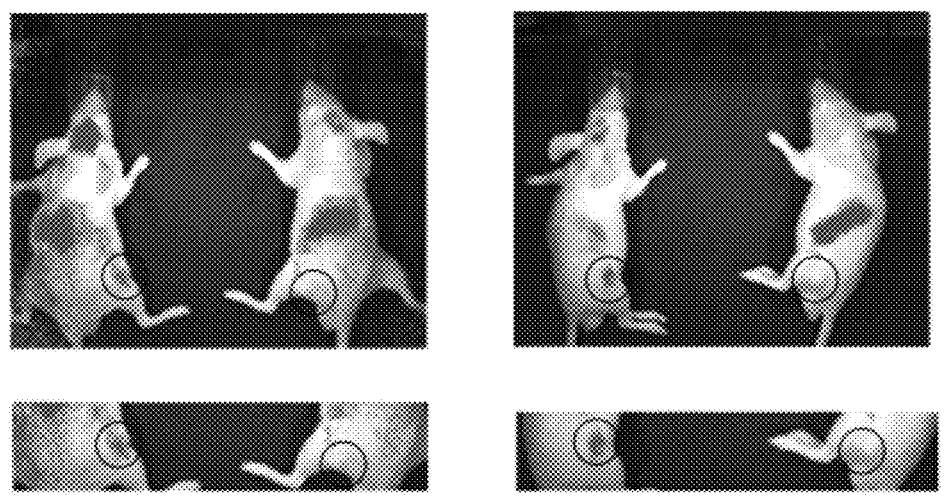
FIG. 19 shows fluorescence images of two mice bearing rat C6 glioma xenograft 24 hours after the administration of 140 nmol of conjugate 24 alone (left mouse), or one hour after injection of 8.5 μmol of cycloRGDfK peptide (right mouse). Each mouse was documented from above (upper panel, left) and from aside (upper panel, right). Zoom in photographs are also shown (lower panel). The circles on the fluorescence images indicate the location of the xenografted rat C6 glioma tumor.

Example 35. Fluorescence Imaging Demonstration of In Vivo Binding Specificity of Conjugate 24 to $\alpha_v\beta_3$ Integrin Receptor Specific binding is defined as one inhibited by the unconjugated sensitizer. Thus, in order to demonstrate the in vivo binding specificity of conjugate 24, attempts to block its accumulation were carried by competing with free cyclo-RGDfK for binding of the same binding sites. Fluorescence imaging was performed 24 hours after administration of 140 nmol of conjugate 24 alone (FIG. 19, left mouse on both panels, with tumor on the back of the right posterior limb), or administration of 140 nmol of conjugate 24 1 hour after injection of excess "free" (8.5 µmol) cycloRGDfK peptide to mice bearing C6 glioma xenografts (FIG. 19, right mouse on both panels, with tumor on the back of the left posterior limb). Fluorescence images of the blocked receptor xenografts with the same exposure time are illustrated in FIG. 19 on the same linear color scale to allow for a qualitative comparison. The fluorescence intensity originating from the tumor was larger when conjugate 24 was administered alone as compared to when the peptide cycloRGDfK was administered one hour prior to imaging agent administration. In normal tissues, the uptake was not influenced by the pre-administration of cycloRGDfK.

The results show that the uptake of conjugate 24 in tumor regions were: (i) significantly greater than in the contralateral normal tissue regions; and (ii) blocked by pre-injection of cycloRGDfK in excess. Taken together, one can conclude that "free" cycloRGDfK inhibits the accumulation of conjugate 24, and the reduced uptake of conjugate 24 resulting from pre-administration of cycloRGDfK in excess validates the in vivo molecular specificity of the conjugate to $\alpha_v\beta_3$ receptors.

Example 36. Dynamic Fluorescence Imaging Following Treatment with Conjugate 42

Figure 20:
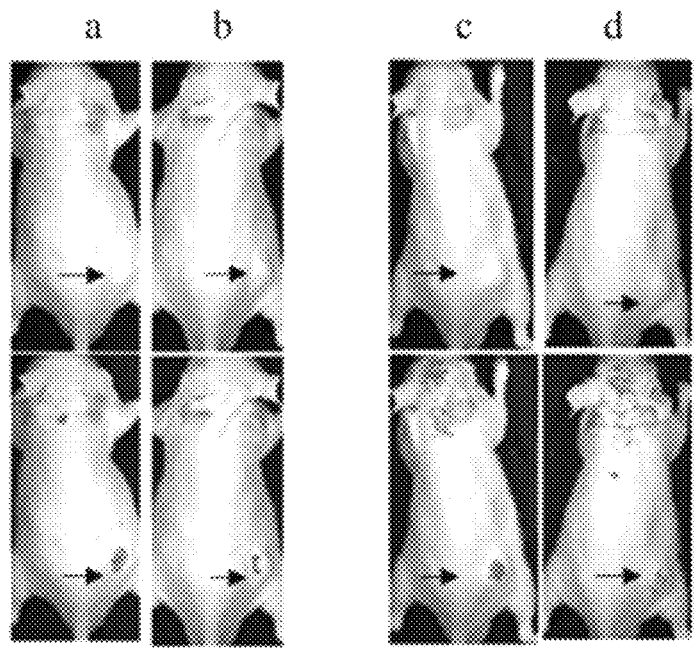
FIG. 20 shows black & white photographs (upper panels) and fluorescence images (lower panels) of CD-1 nude male mice bearing CT26luc xenografts on the back of the posterior limb, 24 hours after the administration of RGD conjugate 24 (panels a,c) or RAD conjugate 42 (panels b,d). Tumors are indicated by arrows and all images are normalized to the same scale. The fluorescence images were acquired using IVIS system.

In order to assess the actual role of RGD/integrin recognition in vivo, dynamic fluorescence images were obtained from CD-1 nude male mice bearing CT26luc grafts on the back of the posterior limb, 24 hours after the administration of conjugate 24 (FIG. 20, left mouse in each panel) or conjugate 42, in which glycine in the peptide is replaced with alanine (cycloRADfK); right mouse in each panel). Since the fluorescence signal of the RGD conjugate at the tumor tissue reaches a maximum at 3.5-4 hours post injection, images are presented taken 4 hours post injection. Importantly, both conjugates present a prolonged basal level of fluorescence after administration due to non-specific binding. However, the fluorescence intensity of the RGD conjugate is clearly higher than that of the RAD conjugate in the tumor site. These results are supported quantitively by ICP-MS measurements showing almost twice as much accumulation of the RGD conjugate in the tumor tissue (see Example 30 above and FIG. 14A).

Since the CT26luc cells lack $\alpha_v\beta_3$ (although they likely express some $\alpha_v\beta_5$) (Yao et al., 2005; Borza et al., 2006), the higher fluorescence of 24 from the tumors probably originates in their ligation (via the RGD tripeptide) to the neoendothelial $\alpha_v\beta_3$ integrins.

Figure 21:
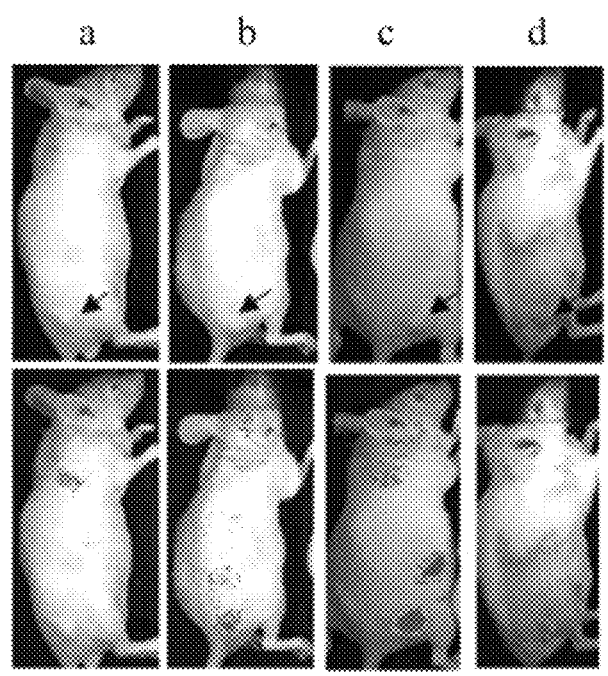
FIG. 21 shows black & white photographs (upper panels) and fluorescence images (lower panels) of mice bearing (a) OVCAR 8, (b) CT26luc, (c) MLS, and (d) 4T1luc xenografts on the back of the posterior limb, 24 hours after the administration of c conjugate 24. Tumors are indicated by arrows and all images are normalized to the same scale.

FIG. 21 depicts the fluorescence images of CD1 nude mice bearing tumors that originate in human ovary adenocarcinoma OVCAR-8, mouse colon cancer CT26luc, human epithelial ovarian carcinoma MLS, and mouse mammary carcinoma 4T1luc cell lines, 24 h after administration of conjugate 24. Integrin $\alpha_v\beta_3$ is expressed on some types of solid tumor cells. Regarding the cell lines above, MLS (Schiffenbauer et al., 2002), and 4T1luc (Mi et al., 2006), overexpress integrin $\alpha_v\beta_3$ receptors on their cell surface, while mouse CT26luc lack integrin $\alpha_v\beta_3$ receptors, but express some $\alpha_v\beta_5$ (Yao et al., 2005; Borza et al., 2006), and OVCAR-8 lack $\alpha_v$ integrins (Ross et al., 2000). Indeed, the fluorescence signal was significantly higher for integrin $\alpha_v\beta_3$ positive cells (MLS and 4T1luc) compared to integrin $\alpha_v\beta_3$ negative cells (CT26luc and OVCAR-8), probably due to additional accumulation in the tumor cells themselves. The observed difference between the compound accumulation in the two $\alpha_v\beta_3$ negative tumors (CT26luc and OVCAR-8) probably reflects (i) a difference in their neovascularization since they both lack the $\alpha_v\beta_3$ integrins, (ii) might be due to additional accumulation in the CT26luc tumor cells themselves, since they express $\alpha_v\beta_5$ that can binds specifically the RGD-BChl conjugate.

Example 37. Dynamic Fluorescence Imaging of Lung Metastases

Figure 22:
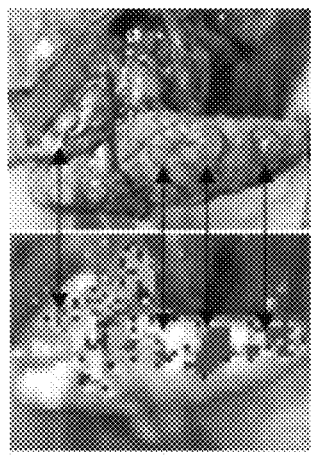
FIG. 22 shows a photograph (upper image, taken using digital camera) and a fluorescence image (lower image) from conjugate 24 localization in lung metastasis of 4T1luc breast cancer tumor in BALB/c female mouse, 24 hr after i.v. injection of conjugate 24 (15 mg/kg). The NIR fluorescence signal originated from localization of conjugate 24 taken using Imaging System Xenogen IVIS® 100.

Detection of a 4T1luc model of breast cancer metastases in the lungs was enabled by conjugate 24.24 h post injection into BALB/c female mouse (15 mg/kg) (FIG. 22). These results show that the uptake of 24 in metastatic regions in the lungs can be monitored by fluorescence at relatively high accuracy.

Next, CT26luc model metastases in the lungs were detected as a function of time post 24 injection (4, 9 and 24 h, 15 mg/kg; FIGS. 23A-23I). CD-1 nude male mice bearing CT26luc lung metastases that were not injected with the conjugate served as controls (FIGS. 23G.23H) and a CD-1 nude male mouse without lung metastases that was i.v. injected with conjugate 24 (FIG. 23I). The fluorescence imaging results show that the uptake of 24 in metastatic regions was significantly higher than by the surrounding normal tissue regions, with best tumor to background ratio at 24 hours after administration.

Example 38. Dynamic Fluorescence Imaging of Lymph Node Metastases

Figure 24:
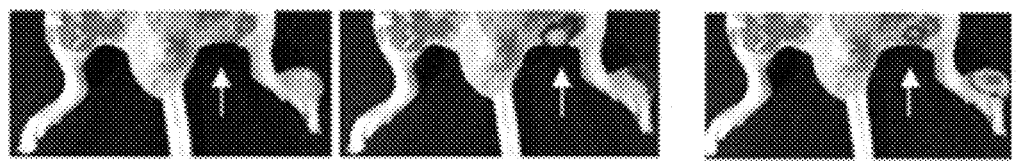
FIG. 24 shows black & white photograpfs (a), bioluminescence (b) and fluorescence (c) images of CD-1 nude male mouse bearing CT26luc primary tumor on the back of its left leg and metastases in the near lymph node, 24 hours after the i.v. injection of conjugate 24 (15 mg/kg). The middle image is the bioluminescence signal originated from the reaction of luciferin with the luciferase transfected tumor cells. The right image is the NIR fluorescence signal originated from conjugate 24 taken using Xenogen IVIS® Imaging System 100. The arrows indicate the lymph node metastases.

CD-1 nude male mouse bearing CT26luc primary tumor on the back of its left leg and metastases in the near lymph node, was imaged and photographed 24 hours after the i.v. injection of conjugate 24 (15 mg/kg). Detection of the CT26luc metastases in the lymph node was abled by localization of conjugate 24. The black & white photograph, bioluminescence signal originated from the reaction of lucifern with the luciferase transfected tumor cells, and the fluorescence image of the mouse are shown in FIG. 24.

These results indicate that tumors in both primary and metastatic regions (lungs, lymph nodes) can be monitored by fluorescence at relatively high accuracy.

Example 39. In Vivo Magnetic Resonance Imaging (MRI) of Mice Bearing Rat C6 Glioma Xenografts Using Compound 9 as a Contrast Agent Measurements were performed on CD1 nude male mice (average weight ~30 g) bearing the C6-glioma xnegratfs (10-15 mm diameter; left flank, subcutaneous). Seven mice were used for MRI enhanced with Mn-13$^2$-OH-Bpheid (compound 9) (15 mmol/kg).

Calculated graphs of signal intensity ratio and relaxivity ratio revealed that compound 9 at a dose of 15 µmol/kg increased the tumor/normal relaxivity ratio from 0.8-1.0 up to ~1.4, in about 10 min after injection of the substance. The contrast effect obtained with 9 was higher than that known for Gd-containing contrast agents.

Taking the higher contrast obtained by compound 9 in comparison with Gd agents and the expected prolonged residence of the corresponding Mn-containing cycloRGDfK conjugate 12 in the tumor, that enables long integration of the MR signal, we anticipate superior imaging with this conjugate over other contrast agents such as Gd-DTPA.

Example 40. In Vitro Targeted Phototoxicity

In order to evaluate the photodynamic potency of the RGD peptide-photosensitizer conjugate versus that of the non-conjugated photosensitizer, the phototoxicity of conjugate 23 and the unconjugated photosensitizer 10 were determined by monitoring the survival of cultured H5V endothelial cells following PDT.

Figure 25A:
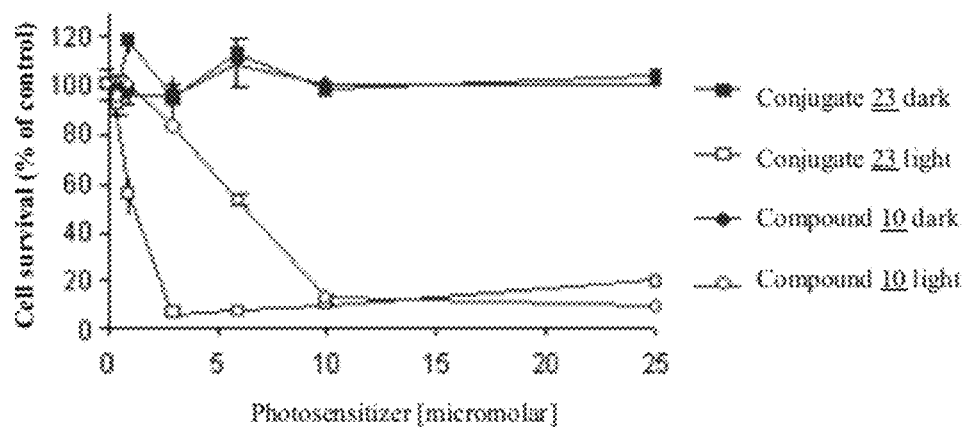
FIGS. 25A-25C show dose-response survival curve of H5V cells incubated for 90 min at 37° C. with 0-25 μM conjugate 23 or compound 10 in different media conditions: 10% FCS in medium (FIG. 25A), culture medium DMEM/F12 (FIG. 25B) or 10 μM BSA in medium (FIG. 25C). Cell survival was determined using Neutral Red viability assay. The points represent average results of triplicates.
Figure 25B:
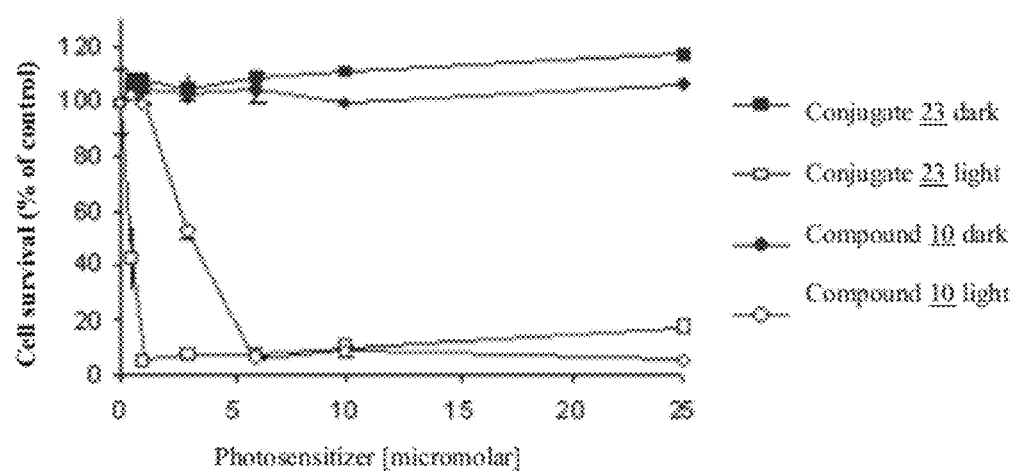
Figure 25C:
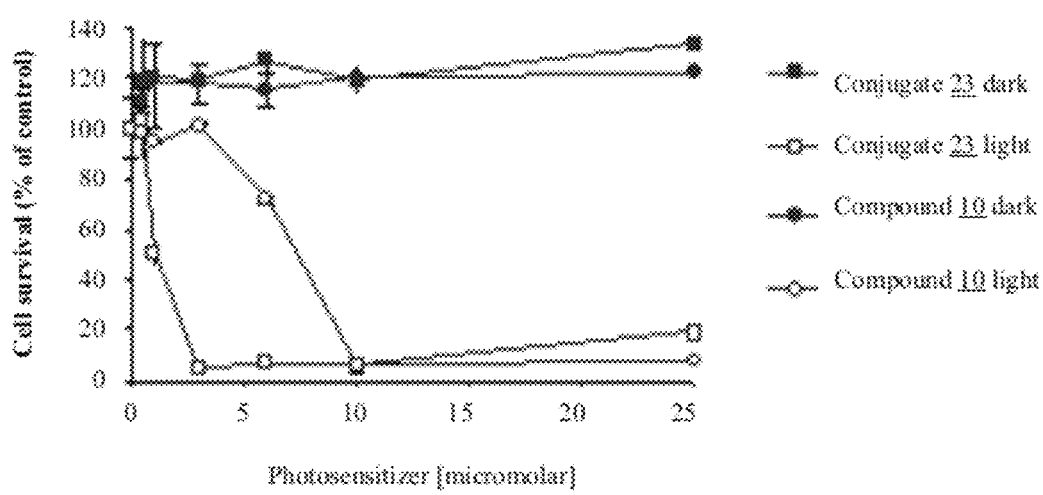
Figure 26A:
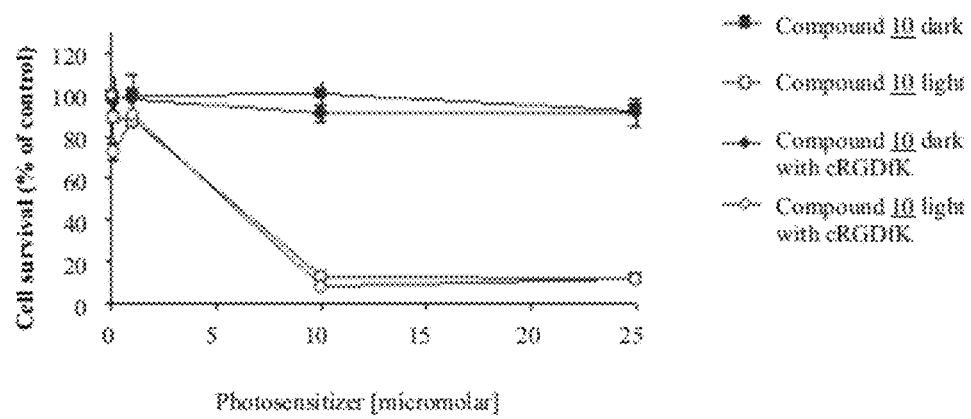
FIGS. 26A-26D show dose-response survival curves of H5V cells incubated for 90 min at 37° C. with 0-25 μM compound 10 (FIGS. 16A, 16B) or conjugate 23 (FIGS. 26C, 26D) in the absence or presence of free cycloRGDfK in excess (100-fold up to 1 mM), in different media conditions (10% FCS in medium (FIGS. 26A, 27C) or 10 μM BSA in medium (FIGS. 26B, 26D)). Cell survival was determined using Neutral Red viability assay. The points represent average results of triplicates.
Figure 26B:
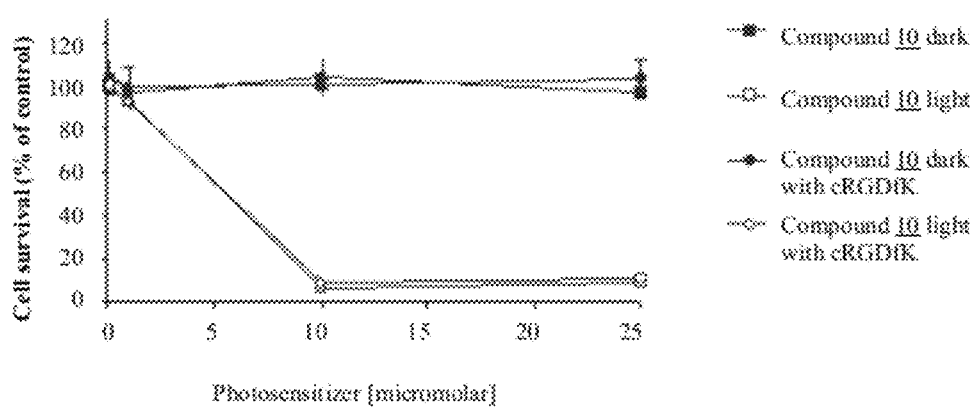
Figure 26C:
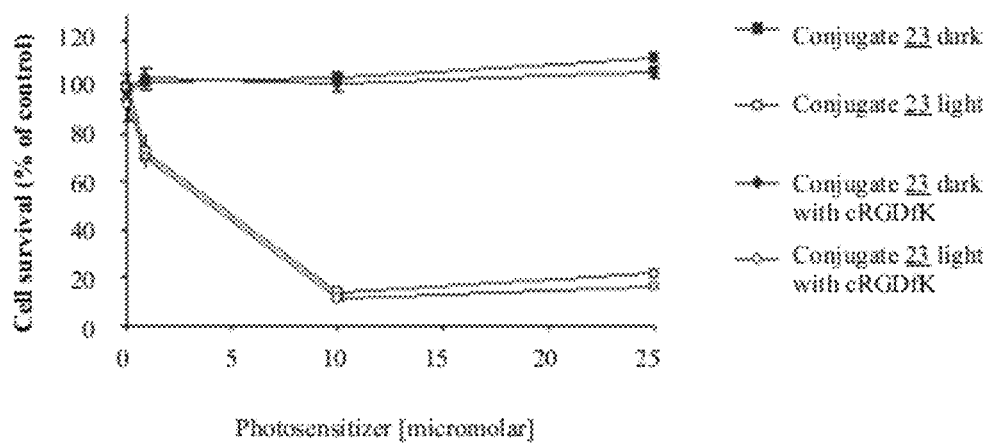
Figure 26D:
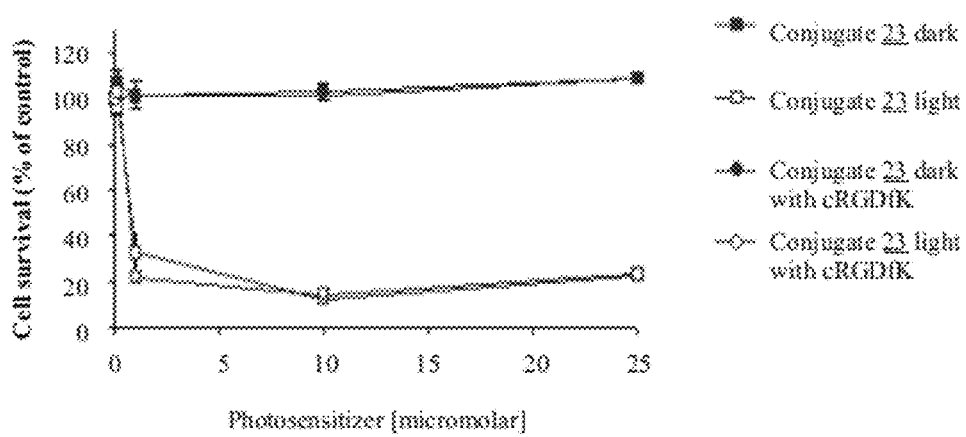

H5V cells were incubated for 90 min at 37° C. with 0-25 µM of conjugate 23 or compound 10 in different media conditions, illuminated and their survival was determined using Neutral Red viability assay as described in Materials and Methods. The dose-response survival curves of the H5V cells treated with the photosensitizers under different conditions are shown in FIGS. 25A-25C: 10% FCS in medium (FIG. 25A), culture medium DMEM/F12 (25B) and 10 µM BSA in medium (25C).

The phototoxic effects of conjugate 23 and compound 10 in different media were found to be light- and drug concentration-dependent. Based on the LD$_{50}$ values we can conclude that the photodynamic potency of the conjugate 23 is higher than that of the non-conjugated photosensitizer 10.

Targeted phototoxicity is defined as one inhibited by the free ligand. Thus, further experiments attempted to block phototoxicity by administration of the free cycloRGDfK, which competes for the cellular binding of conjugate 23. H5V cells were incubated for 90 min at 37° C. with 0-25 µM of compound 10 or conjugate 23 in different media (10% FCS in medium or 10 µM BSA in medium) in the absence or presence of free excess cycloRGDfK (100-fold up to 1 mM). The cells were illuminated and cell survival was determined using Neutral Red viability assay, as described above.

As shown in FIGS. 26A-26D, presenting the dose-response survival curves of treated cells, and as indicated by the LD$_{50}$ values presented in Table 2, the phototoxic effects of 23 and 10 were not influenced by the presence of excess cycloRGDfK.

TABLE 2

LD$_{50}$ values of conjugate 23 and compound 10 in absence and presence of free peptide in excess in different reaction conditions

| Reaction Conditions | Compound | | | |
|---|---|---|---|---|
| | Conj. 23 | Conj. 23 with free peptide in excess | Comp. 10 | Comp. 10 with free peptide in excess |
| 10 µM BSA in medium (90 min, 37° C.) | 0.5-1 µM (FIGS. 16C, 17D) | 1 µM (FIG. 17D) | 3.5-5 µM (FIGS. 16C, 17B) | 5 µM (FIG. 17B) |
| culture medium (90 min, 37° C.) | 1 µM (FIG. 16B) | Not done | 7 µM (FIG. 16B) | Not done |
| 10% FCS (90 min, 37° C.) | 1-4 µM (FIGS. 16A, 17C) | 4 µM (FIG. 17C) | 5-7 µM (FIGS. 16A, 17A) | 5 µM (FIG. 17A) |
| 10% FCS (15 min, 37° C.) | 3.5 µM (FIG. 18A) | 2.4 µM (FIG. 18A) | Not done | Not done |
| 10% FCS (15 min, 4° C.) | 20 µM (FIG. 18B) | 8 µM (FIG. 18B) | Not done | Not done |

These results suggest that the conjugate is entering the cell via integrin-independent fluid-phase endocytosis, thus the free cycloRGDfK cannot compete for the cellular binding with the conjugate. The integrin-independent cell entry can be attributed to either parts of the conjugate, the photosensitizer moiety or the cycloRGDfK peptide. There is one report in the literature indicating that cycloRGDfK internalizes by an integrin-independent fluid-phase endocytosis that does not alter the number of functional integrin receptors on the cell surface (Hart et al., 1994; Castel et al., 2001).

Figure 27A:
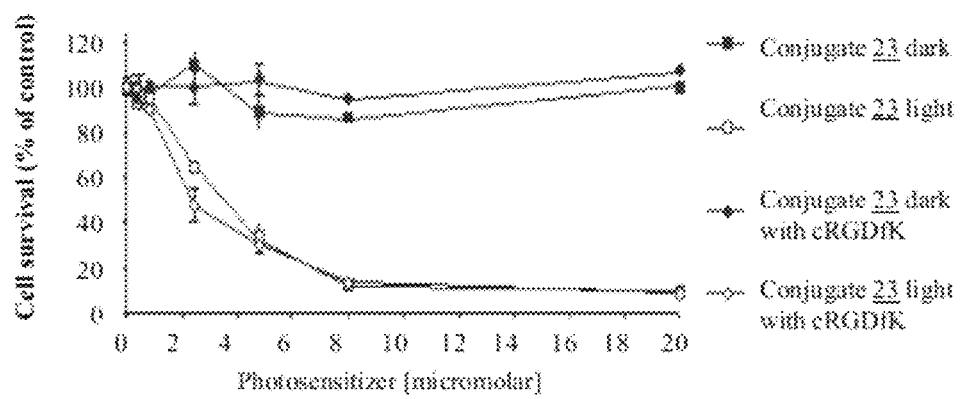
FIGS. 27A-27B show dose-response survival curves of H5V cells incubated for 15 min at 37° C.
Figure 27B:
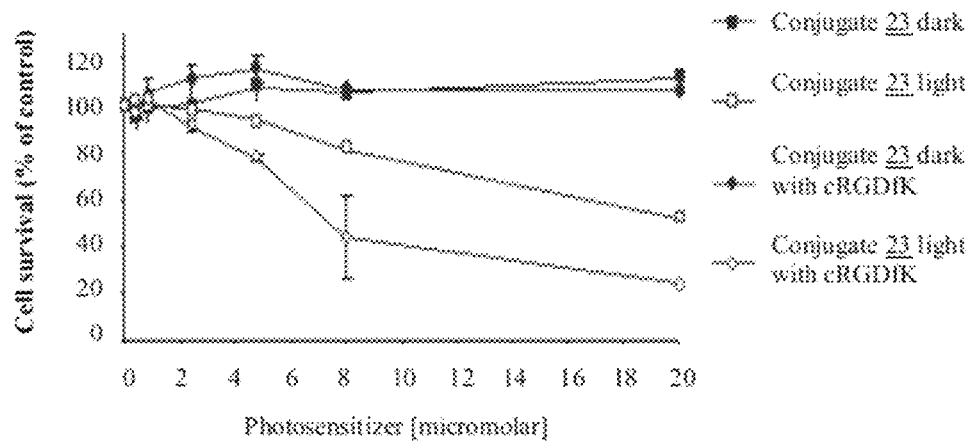

In order to test the endocytosis theory and since the endocytic process is time- and temperature-dependent, H5V cells were incubated at 37° C. and 4° C. for 15 min with 0-20 µM of conjugate 23 in medium containing 10% FCS, in the presence or absence of excess cycloRGDfK (100-fold up to 1 mM). Cells were illuminated and their survival was determined as described above. The dose-response survival curves of the treated H5V cells are shown in FIGS. 27A-27B.

The LD$_{50}$ values measured for 15-min incubation at 37° C. or 4° C. increased relatively to the values obtained upon incubation of the cells at 37° C. for 90 min (Table 2). The LD$_{50}$ values of conjugate 23 changed to 3.5 µM and to 20 µM following 15-min incubation at 37° C. and 4° C., respectively, compared to 1 µM obtained for incubation at 37° C. for 90 min. The increase in LD$_{50}$ values upon lowering the temperature supports the hypothesis of a possible role for endocytosis in the conjugate uptake.

Unexpectedly, not only the photocytotoxic effect of conjugate 23 was un-blocked by the presence of excess cycloRGDfK, but in fact, the photodynamic activity of 23 under 15-min incubation at 37° C. or 4° C. was higher in the presence of free cycloRGDfK. There is a possibility that the excess of free peptide causes the cells to be more sensitive to the PDT effect of the conjugate due to enhanced detachment of the cells from the dish and/or induced apoptotic signal transduction.

The phototoxicity of conjugate 24 was determined by monitoring the survival of cultured H5V endothelial cells following PDT. H5V cells were incubated for 2 hours at 37° C. with 0-25 µM conjugate 24 in culture medium DMEM/F12 with 10% FCS. The cells were illuminated and their survival was determined as described above.

Figure 28:
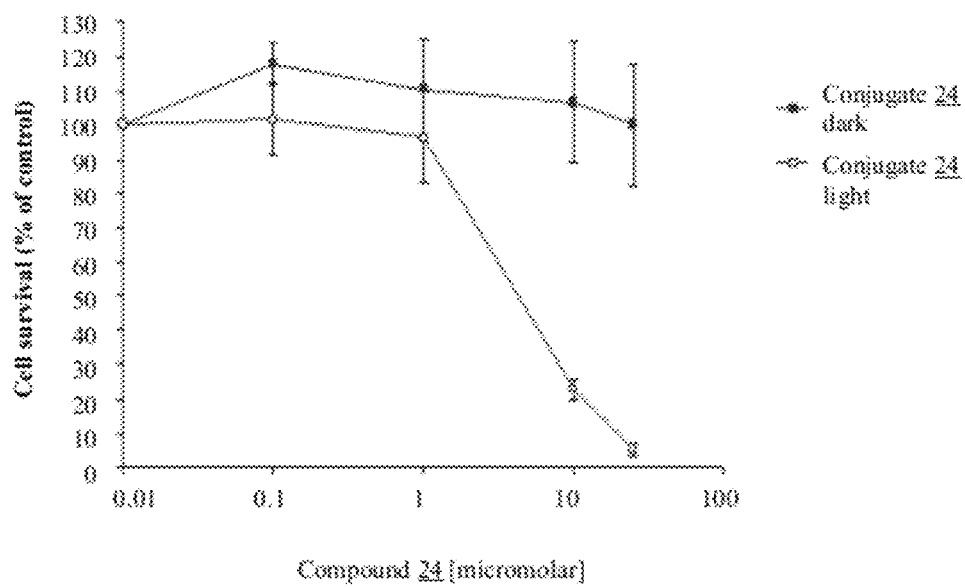
FIG. 28 shows dose-response survival curve of H5V cells incubated for 2 hours at 37° C. with 0-25 µM conjugate 24 in culture medium DMEM/F12 with 10% FCS. Cell survival was determined using Neutral Red viability assay. The points represent average results of triplicates.

As shown in the dose-response survival curve (FIG. 28), the phototoxic effects of conjugate 24 on H5V cells after 2 hr incubation at 37° C. were found to be light- and drug concentration-dependent.

The phototoxicity of a third conjugate, 11, and of compound 8 was also determined using H5V endothelial cells. Cells were incubated for 90 min at 37° C. in the presence of 0-20 µM conjugate 11 or compound 8 in 10 µM BSA in medium, illuminated and their survival was determined as described above.

Figure 29:
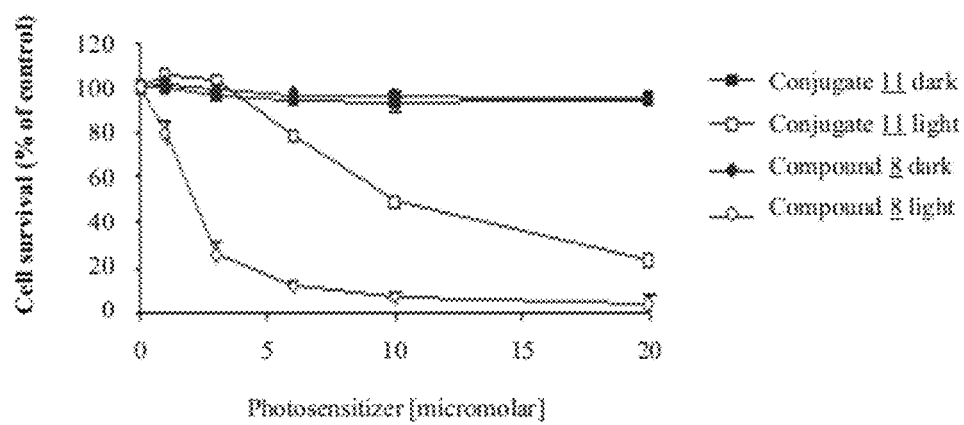
FIG. 29 shows dose-response survival curve of H5V cells incubated 90 min at 37° C. with 0-20 µM conjugate. H or compound 8 (Pd-MLT) in 10 µM BSA in medium. Cell survival was determined using Neutral Red viability assay. The points represent average results of triplicates.

As shown in the dose-response survival curve (FIG. 29), the phototoxic effects of conjugate 11 and compound 8 were found to be light- and drug concentration-dependent. The LD$_{50}$ values are represented in Table 3.

TABLE 3

LD$_{50}$ values of conjugate 11 and compound 8 in absence and presence of free peptide excess

| Reaction Conditions | Compound | | | |
|---|---|---|---|---|
| | Conj. 11 | Conj. 11 with free peptide excess | Comp. 8 | Comp. 8 with free peptide excess |
| 10 µM BSA in medium (90 min, 37° C.) | 7-10 µM (FIGS. 19, 20) | 5 µM (FIG. 20) | 1.8-2 µM (FIGS. 19, 20) | 2 µM (FIG. 20) |

Figure 30A:
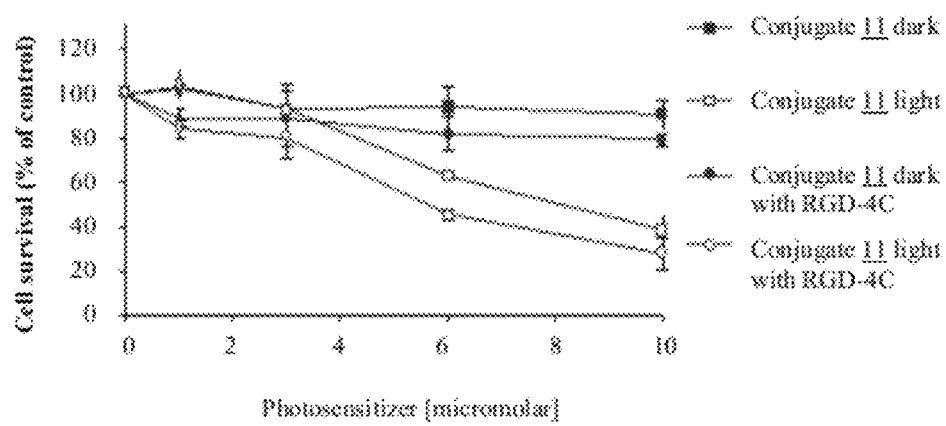
FIGS. 30A-30B show dose-response survival curves of H5V cells incubated for 90 min at 37° C. with 0-10 µM conjugate 11 (FIG. 30A) or compound 8 (FIG. 30B) in 10 µM BSA in medium in the absence or presence of excess RGD-4C (1 mM). Cell survival was determined using Neutral Red viability assay. The points represent average results of triplicates.
Figure 30B:
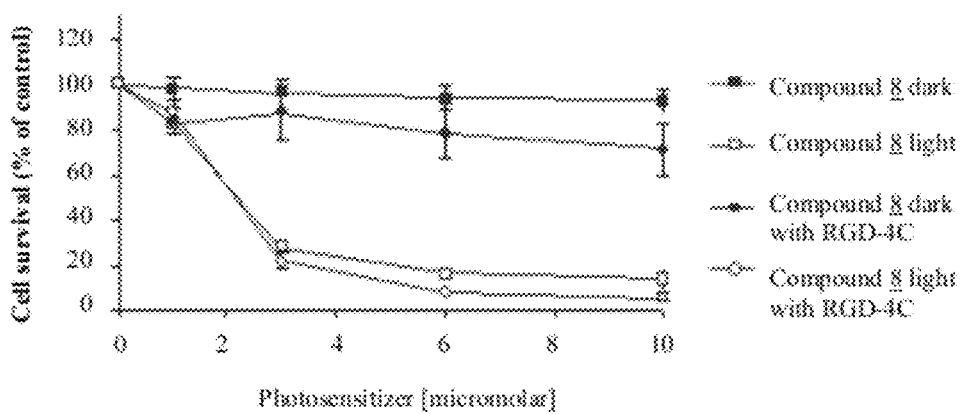

As for the cycloRGDfK peptide, blockage of the phototoxicity of conjugate 11 by adding free cyclic RGD-4C to the cell culture failed (FIGS. 30A-30B, Table 3). H5V cells were incubated for 90 min at 37° C. with 0-10 µM conjugate 11 or compound 8 in 10 µM BSA in medium in the absence or presence of RGD-4C in excess (1 mM). The cells were illuminated and their survival was determinated as described above.

Again, this result suggests that the photosensitizer's moiety (compound 8) determines the cellular uptake of the conjugate 11 via free endocytosis.

Example 41. In Vivo PDT in Rat C6 Glioma Tumor Using Conjugate 24

Based on the results above we developed a new treatment protocols for PDT of solid tumors using conjugate 24. The protocol parameters should include: Time of treatment (drug-light interval)—Illumination 3 to 24 hours post-drug administration; Dose (mg/kg)—5-24 mg/kg; Duration of illumination (min)—5-30 min; Intensity of illumination (mW/cm$^2$)-100-200 mW/cm$^2$; Delivered energy (J/cm$^2$)—30-360 J/cm$^2$.

The initial tumor models used comprised rat C6 glioma tumor xenografts, since these tumor cells express $\alpha_v\beta_3$ (Zhang et al., 2006) and $\alpha_v\beta_5$ integrins (Milner et al., 1999) in addition to integrin $\alpha_v\beta_3$ expressed on the tumor neovasculature.

CD-1 nude male mice bearing C6 glioma grafts were i.v. injected with 15 or 24 mg/kg body doses of conjugate 24 or 9 mg/kg body dose of compound 8.

For each protocol we used at least 3 animals, but due to high mortality rate we were left with limited number of animals. The results are presented in Table 4.

TABLE 4

Therapeutic results of different VTP protocols applying conjugate 24 to mice bearing rat C6 glioma.

| Time to treatment (hours) | Dose (mg/kg) | Duration of illumination (min) | Intensity of illumination (mW) | Delivered energy (J/cm$^2$) | comments | No. of animals |
|---|---|---|---|---|---|---|
| 3.5 | 15 | 5 | 100 | 30 | Extensive necrosis | 2 |
| 6 | 15 | 10 | 100 | 60 | Extensive necrosis | 2 |
| 8 | 15 | 5 | 100 | 30 | Limited necrosis | 2 |
| 8 | 15 | 10 | 100 | 60 | Limited necrosis | 1 |
| 8 | 24 | 10 | 100 | 60 | Limited necrosis | 1 |
| 8 | 24 | 10 | 100 | 60 | Extensive necrosis | 1 |
| 8 | 15 | 15 | 100 | 90 | Extensive necrosis | 1 |

The protocols that appeared optimal and provided the best therapeutic results appear in bold in Table 4: 15 mg/kg, 15-min illumination (90 J/cm$^2$) 8 hours post injection, and 24 mg/kg, 10-min illumination (60 J/cm$^2$) 8 hours post injection.

FIGS. 31A and 31B show the therapeutic results of those protocols, respectively. In dark control (FIG. 31C), the mice were i.v. injected with conjugate 24 and not illuminated; In light control (FIG. 31D), mice were illuminated without conjugate 24 injection; and in unconjugated photosensitizer control (FIG. 31E), the mice were i.v. injected with compound 8 and illuminated after 8 hours.

The different controls showed no PDT effect. In contrast, the animals treated with conjugate 24 and light presented extensive edema few hours post PDT treatment that developed to inflammation and necrosis below the skin at 3 days post PDT. Tumor flattening and long period of tumor regression as well as wound healing was observed.

Example 42. In Vivo PDT in Mouse CT26 Colon Tumor Using Conjugate 24

Using the rat C6 glioma model we could not get immediate assessment of VTP outcome, a major disadvantage in course of a screening process. To overcome this problem we used the mouse CT26luc colon carcinoma model consisting of luciferase transfected cells, which enable fast evaluation of the therapeutic effect.

CD-1 nude male mice bearing CT26luc tumors were subjected to different protocols of PDT with conjugate as shown in Table 5.

TABLE 5

Therapeutic results of different VTP protocols applying conjugate 24 to mice bearing mice CT26luc colon cancer.

| Time to treatment (hrs) | Dose (mg/kg) | Duration of illumination (min) | Intensity of illumination (mW) | Delivered energy (J/cm$^2$) | Comments | No. of animals |
|---|---|---|---|---|---|---|
| 8 | 9 | 15 | 100 | 90 | Reduction in luminescence signal, no necrosis | 3 |
| 8 | 9 | 10 | 100 | 60 | Reduction in luminescence signal, no necrosis* | 5 |
| 8 | 11 | 10 | 100 | 60 | Reduction in luminescence signal, extensive necrosis | 4 |
| 8 | 12 | 10 | 100 | 60 | Reduction in luminescence signal, extensive necrosis | 3 |
| 8 | 15 | 10 | 100 | 60 | Reduction in luminescence signal, extensive necrosis | 4 |
| 12 | 15 | 15 | 100 | 90 | Reduction in luminescence signal, limited necrosis* | 5 |
| 24 | 15 | 30 | 200 | 360 | Reduction in luminescence signal, no necrosis* | 3 |
| 24 | 15 | 30 | 100 | 180 | Reduction in luminescence signal, no necrosis | 2 |
| 24 | 24 | 30 | 100 | 180 | Reduction in luminescence signal, no necrosis | 2 |

TABLE 5-continued

Therapeutic results of different VTP protocols applying conjugate 24 to mice bearing mice CT26luc colon cancer.

| Time to treatment (hrs) | Dose (mg/kg) | Duration of illumination (min) | Intensity of illumination (mW) | Delivered energy (J/cm$^2$) | Comments | No. of animals |
|---|---|---|---|---|---|---|
| 24 | 24 | 30 | 150 | 270 | Reduction in luminescence signal, no necrosis | 2 |
| 24 | 24 | 30 | 200 | 360 | Reduction in luminescence signal, limited necrosis | 2 |

FIGS. 32A-32F show the therapeutic results of applying 15 mg/kg, 10 min illumination (60 J/cm$^2$), 8 hours post injection of conjugate 24 to mice bearing CT26luc tumors (bolded protocol in Table 5). 32A—conjugate 24 was i.v. injected 15 mg/kg, 10 min illumination (60 J/cm$^2$) 8 hours post injection. 32B—overlaid images taken after i.p. injection of luciferin to the mouse described in 32A, using the IVIS system. The first image is black and white, which gives the photograph of the animal. The second image is color overlay of the emitted photon data. All images are normalized to the same scale. 32C—Bioluminescence signal quantification (photon/sec/cm$^2$) of the data shown in B. 32D control with compound 8 alone: the mice were i.v. injected with compound 8 and illuminated after 8 hours. 32E—control with mixture of compound 8 and cycloRGDfK: the mice were i.v. injected with mixture of compound 8 with cycloRGDfK and illuminated after 8 hours. 32F—control with cycloRGDfK alone: the mice were i.v. injected with cycloRGDfK and illuminated after 8 hours. Images were taken at indicated time post PDT.

Figure 32A:
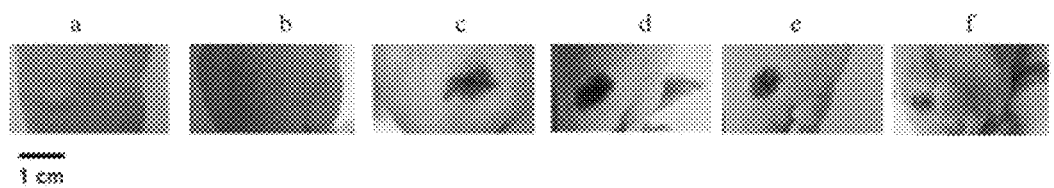
FIGS. 32A-32F show the therapeutic results of applying 15 mg/kg, 10 min illumination (60 J/cm$^2$), 8 hours post injection of conjugate 24 to mice bearing CT26luc tumors. 32A—conjugate 24 was i.v. injected 15 mg/kg, 10 min illumination (60 J/cm$^2$) 8 hours post injection; a) pre PDT, b) 1 day post PDT; (c) 4 days post PDT; (d) 8 days post PDT; (e) 12 days post PDT; (f) 19 days post PDT. 32B—overlaid images taken after i.p. injection of luciferin to the mouse described in 32A, using the IVIS system. The first image is black and white, which gives the photograph of the animal. The second image is color overlay of the emitted photon data. All images are normalized to the same scale; (a) pre PDT; (b) 1 day post PDT; (c) 4 days post PDT; (d) 8 days post PDT. 32C—Bioluminescence signal quantification (photon/sec/cm$^2$) of the data shown in 32B. 32D—control with compound 8 alone: the mice were i.v. injected with compound 8 and illuminated after 8 hours; (a) pre PDT; (b) 2 days post PDT. 32E—control with mixture of compound 8 and cycloRGDfK: the mice were i.v. injected with mixture of compound 8 with cycloRGDfK and illuminated after 8 hours; (a) pre PDT; (b) 2 days post PDT. 32F—control with cycloRGDfK alone: the mice were i.v. injected with cyclo-RGDfK and illuminated after 8 hours; (a) pre PDT; (b) 2 days post PDT. Images were taken at indicated time post PDT.
Figure 32B:
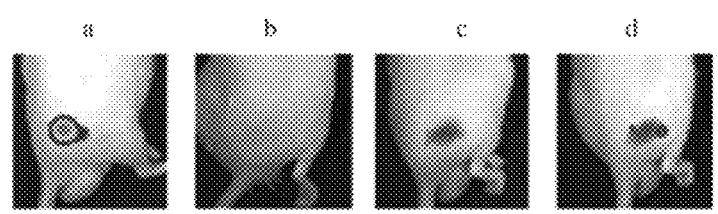
Figure 32C:
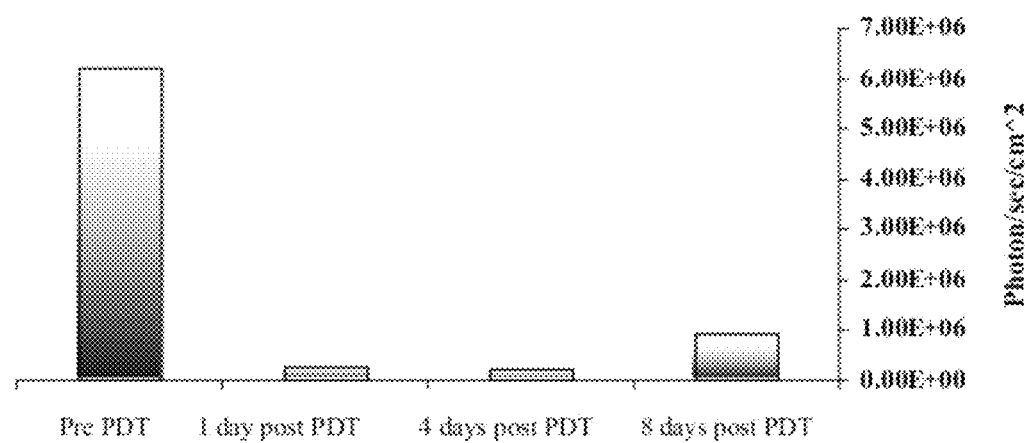
Figure 32D:
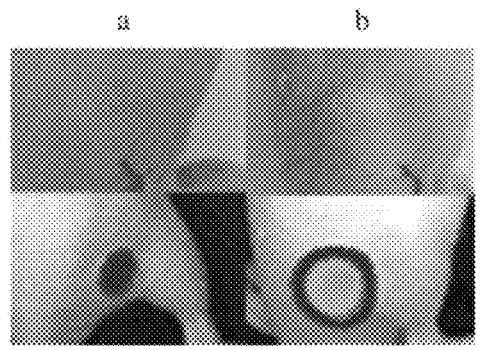
Figure 32E:
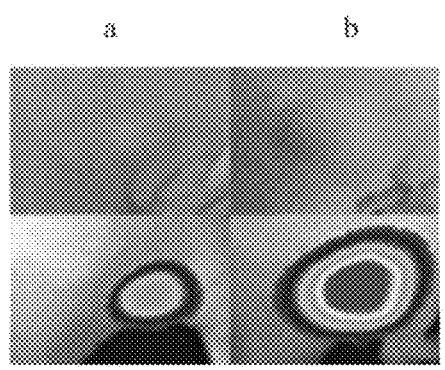
Figure 32F:
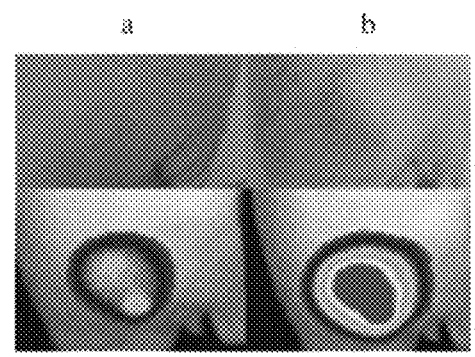

FIG. 32B shows overlaid images taken with the IVIS system after i.p. injection of luciferin to the mouse depicted in FIG. 32A. FIG. 32C provides quantitative description of the bioluminescence shown in FIG. 32 B. The controls used were (1) compound 8 alone (FIG. 32D); (2) mixture of unconjugated compound 8 and cycloRGDfK (FIG. 32E); and (3) cycloRGDfK alone (FIG. 32F). The different controls showed no PDT effect. In contrast, the animals treated with the targeted conjugate developed necrosis within 4 days post PDT (FIG. 32A). Significant bioluminescence signal from residual tumor cells appear 8 days post PDT (FIG. 32B), although no tumor was palpated or visually detected. Wound healing and tumor flattening were observed in all responding animals.

Figure 33:
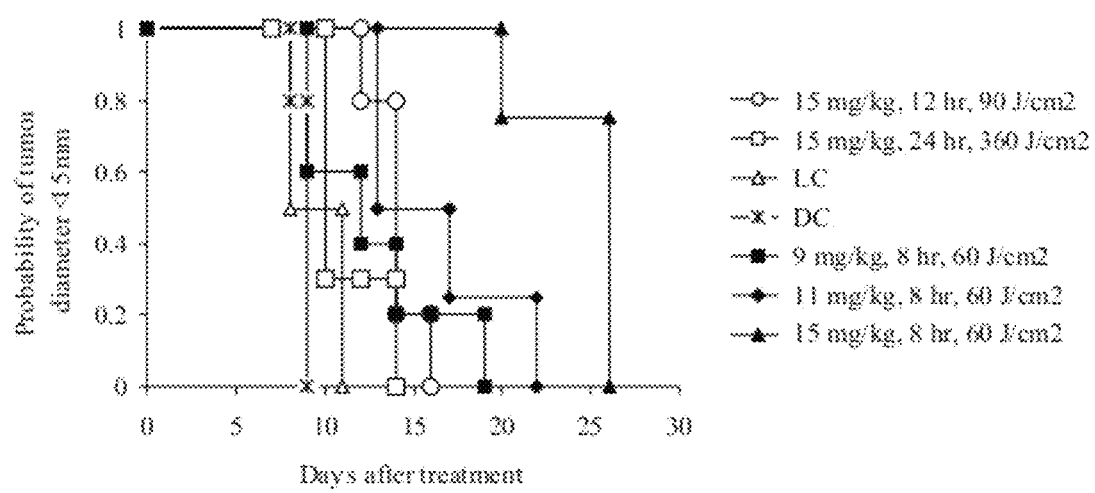
FIG. 33 shows the Kaplan-Mayer curve for the protocols indicated in the Table 5 with asterisk.

FIG. 33 shows the Kaplan-Mayer curve for the protocols indicated in the Table 5 with asterisk.

Example 43. Tumor Diagnosis and Pdt Treatment of Breast Tumors with Conjugate 13

Human breast cancer MDA-MB-231 cells (ATCC) were transfected with red fluorescent protein (RFP) as follows.

Plasmids—
the plasmid that was used for the transfection of the cells was pDsRed-Monomer-Hyg-C1 (Clontech, Palo Alto, Calif.) that carries the RFP gene and resistance gene for hygromycin in which the DsRed-Monomer gene was replaced with pDsRed2 (from the pDsRed2-N1 plasmid).

Transfection Process—
For the transfection process, Lipofectamine™ 2000 (Invitrogen) was used according to the manufacturer protocol: 4 μg DNA were incubated for 5 min with 250 μl Opti-MEM medium (supplied by the manufacturer Invitrogen). In a separate test tube, 10 μl of Lipofectamine were incubated for 5 min with 250 μA Opti-MEM medium. After incubation, the DNA and Lipofectamine solutions were mixed and incubated for 20 min at room temperature and the content was evenly scattered on one out of a 6-well plate that was 50-60% confluent with the MDA-MB-231 cells.

Figure 34A:
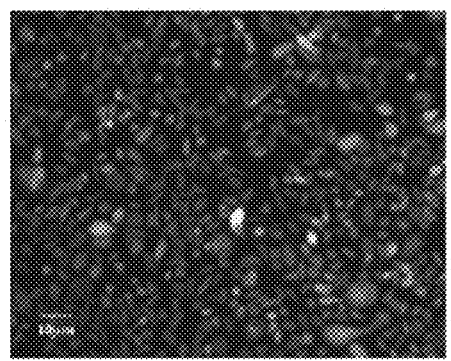
FIGS. 34A-34B show the fluorescent mammary cancer MDA-MB-231 RFP clone 3 (resistant to hygromycin) after 1 sec and 3 sec exposure, respectively.
Figure 34B:
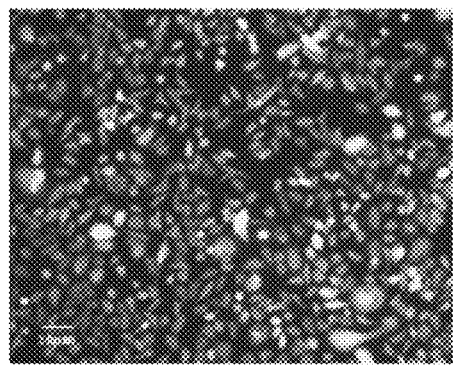

Selection of Stable Clone—
24 hr after the transfection of the MDA-MB-231 cells, the plate was checked under a fluorescence microscope (Nikon). A transient transfection was detectable at this stage. The medium was replaced with fresh medium containing antibiotics (hygromycin) at a concentration of 250 μg/ml. When the plates reached confluency, the cells were detached from the culture plate following a 30-60 sec treatment with trypsin, and plated in a 96-well plate at a concentration of 0.5 cells/well. Wells that contained one clone only and the clone was fluorescent, were collected and plated in a 6-well plate. After reaching confluency they were further plated in a 10 cm plate. FIGS. 34A-34B show the fluorescent MDA-MB-231 RFP clone 3 (resistant to hygromycin) after 1 sec and 3 sec exposure, respectively.

For the PDT experiments, MDA-MB-231 RFP cells (4×10$^6$) were implanted subcutaneously on the backs of the mice and tumors developed to the treatment size (6-8 mm) within 2-3 weeks.

PDT Protocol:
Anaesthetized mice were i.v. injected with conjugate 13 (7.5 mg drug/kg body weight). The tumors were illuminated for 10 min. The drug light interval used was 8 hr post drug injection. Transdermal illumination through the mouse skin with 755 nm diode laser at 100 mW/cm$^2$ (CeramOptec, Germany) was used. After the treatment, the mice were returned to the cage. In the dark control group, the mice were i.v. injected with the sensitizer conjugate 13 and placed in dark cage for 24 hr. In the light control group, the mice were illuminated for 10 min with 100 mW/cm$^2$. During the first 2 days post PDT, as needed, the mice received analgesia (2.5 mg/kg Flunexin daily) and 3 days Oxycode in the drinking water. The end point of animal survival is when the size of the tumor reaches 10% of animal weight. Mice are sacrificed at this time (up to 90 days) by cervical dislocation.

Figure 35A:
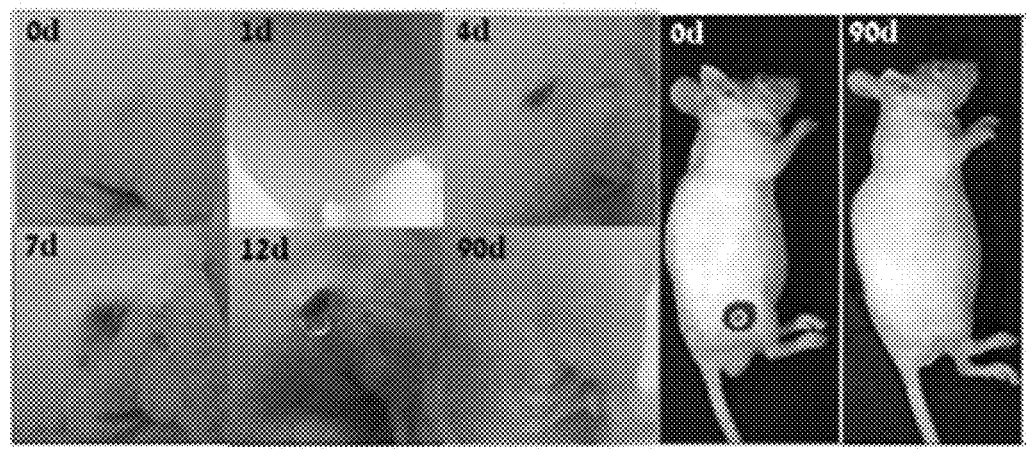
FIGS. 35A-35B show two representative examples to local response of human mammary cancer MDA-MB-231-RFP to PDT. Mice with MDA-MB-231-RFP xenografts (~0.5 cm3) on their backs were i.v. injected with 7.5 mg/kg of conjugate 13 and illuminated 8 h later through the mouse skin. 35A—Photographs taken from (a) day 0 (before treatment) and after treatment at (b) 1, (c) 4, (d) 7, (e) 12 and (f) 90 days. By day 4 partial necrosis was seen, by day 7 tumor flattening was observed, after 90 days the wound healed and the animal was cured. At the right, photographs of the mouse at day 0 and after 90 days. 35B—In vivo whole-body red fluorescence imaging of CD-1 nude male mice bearing MDA-MB-231-RFP orthotopic tumor. The photos were taken at the times like in 35A. No signal was detected 90 days after treatment.
Figure 35B:
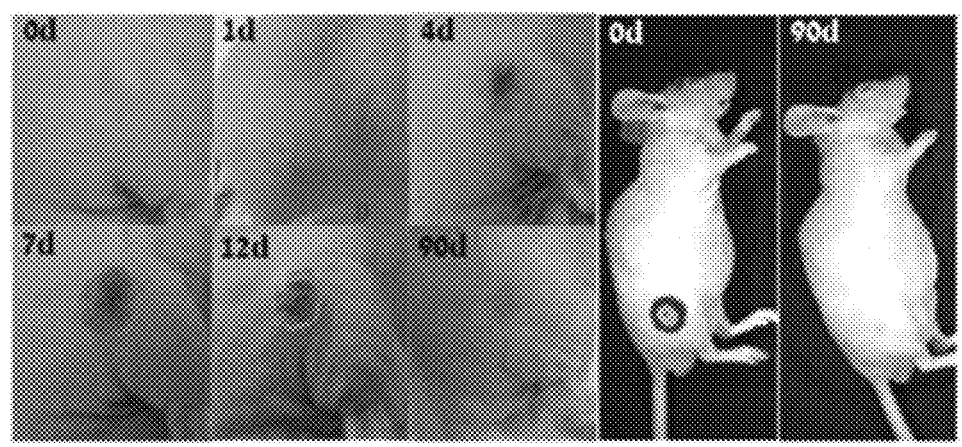

FIGS. 35A-35B show two representative examples to local response of human MDA-MB-231-RFP to PDT. Mice with MDA-MB-231-RFP xenografts (~0.5 cm$^3$) on their backs were i.v. injected with 7.5 mg/kg of conjugate 13 and illuminated 8 h later through the mouse skin with 755 nm diode laser at 100 mW/cm². 35A—Photographs taken from day 0 (before treatment) and after treatment at 1, 4, 7, 12 and 90 days. By day 4 partial necrosis was seen, by day 7 tumor flattening was observed, after 90 days the wound healed and the animal was cured. 35B—In vivo whole-body red fluorescence imaging of CD-1 nude male mice bearing MDA-MB-231-RFP orthotopic tumor. No signal was detected 90 days after treatment.

In order to study the accumulation of the photosensitizer in primary mammary tumors, the MDA-MB-231-RFP cells ($4 \times 10^6$) were implanted orthotopicaly in the mammary pad of the mice. Tumors developed to the wanted size, bigger than 1 cm³, within 3-4 weeks.

For the accumulation assessment, mice were anesthetized by i.p. injection of 30 mixture of 85:15 ketamine:xylazine, and received an i.v. injection to the tail vein of 15 mg drug/kg body weight conjugate 13. Fluorescence of both tumor cells and conjugate 13 are monitored by IVIS®100. Imaging system (Xenogen). Tumor imaging main filter set comprised: excitation filter 500-550 nm, emission filter 575-650 nm; Background filter set for subtraction the tissue auto fluorescence: excitation filter 460-490 nm, emission filter 575-650 nm. Photosensitizer imaging main filter set: excitation filter 665-695 nm, emission filter 810-875 nm.

Images were taken at these time points post drug injection: 15 min, 1, 2, 3, 4.5, 6, 7.5, 9, 24 hr, 2, 3, 4, 5, 6, 7 days. The results are shown in FIGS. 36 and 37.

Figure 36:
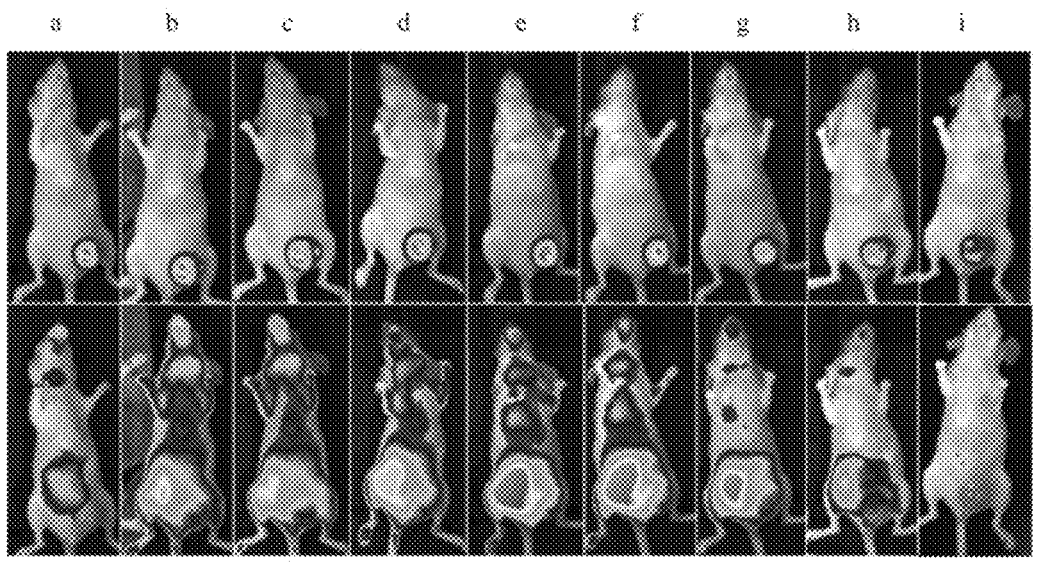
FIG. 36 shows accumulation of conjugate 13 in orthotopic human breast MDA-MB-231-RFP primary tumor (tumor size ~1 cm$^3$). Images were taken from 15 min to 24 hr post drug injection. Upper panels—In vivo whole-body red fluorescence imaging of CD-1 nude female mice bearing MDA-MB-231-RFP orthotopic tumor. Lower panels—In vivo whole-body NIR fluorescence imaging of conjugate 13 accumulation. The drug shows no specific accumulation in the tumor during the first 24 hours. a to i—15 min, 1 h, 2 h, 3 h, 4.5 h, 6 h, 7.5 h, 9 h, 24 h

FIG. 36 shows accumulation of conjugate 13 in orthotopic human breast MDA-MB-231-RFP primary tumor (tumor size ~1 cm³). Images were taken from 15 min to 24 hr post drug injection. Top panel—In vivo whole-body red fluorescence imaging of CD-1 nude female mice bearing MDA-MB-231-RFP orthotopic tumor. Bottom panel—In vivo whole-body NIR fluorescence imaging of conjugate 13 accumulation. The drug shows no specific accumulation in the tumor during the first 24 h.

Figure 37:
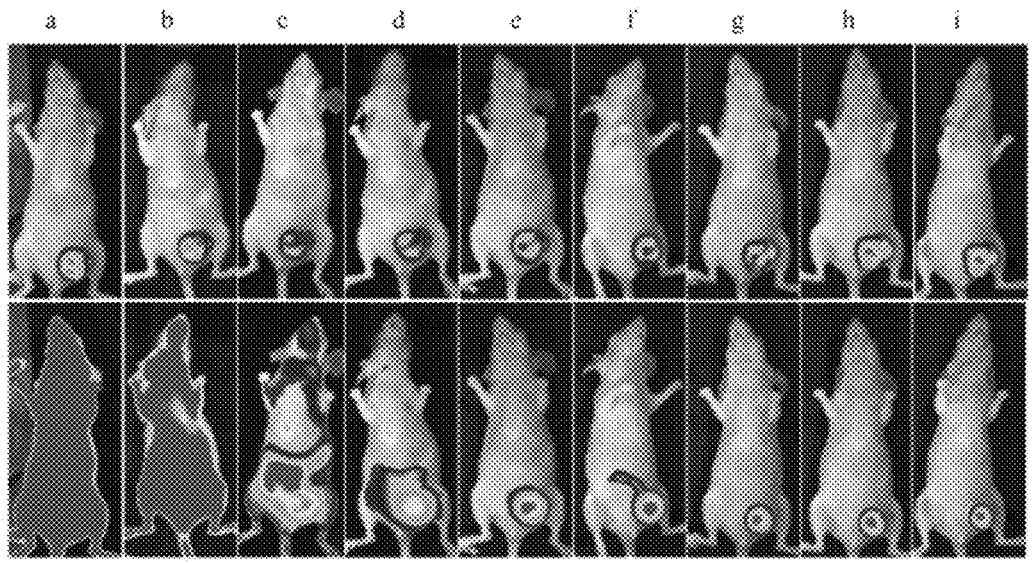
FIG. 37 shows accumulation of conjugate 13 in orthotopic human breast MDA-MB-231-RFP primary tumor (tumor size ~1 cm$^3$). Images were taken from day 1 to 6 post drug injection. Top panel—In vivo whole-body red fluorescence imaging of CD-1 nude female mice bearing MDA-MB-231-RFP orthotopic tumor. Bottom panel—In vivo whole-body NIR fluorescence imaging of conjugate 13 accumulation. The drug shows accumulation in the tumor, reaching peak concentration specifically in the tumor from day 2 post injection a to i—1 h, 9 h, 1 day, 2 days, 3 days, 4 days, 5 days, 6 days, 7 days.

FIG. 37 shows accumulation of conjugate 13 in orthotopic human breast MDA-MB-231-RFP primary tumor (tumor size ~1 cm³). Images were taken from day 1 to 6 post drug injection. Top panel—In vivo whole-body red fluorescence imaging of CD-1 nude female mice bearing MDA-MB-231-RFP orthotopic tumor. Bottom panel—In vivo whole-body MR fluorescence imaging of conjugate 13 accumulation. The drug shows accumulation in the tumor, reaching peak concentration specifically in the tumor from day 2 post injection.

Example 44. Biodistribution and Pharmacokinetics of Conjugate 13

Figure 38A:
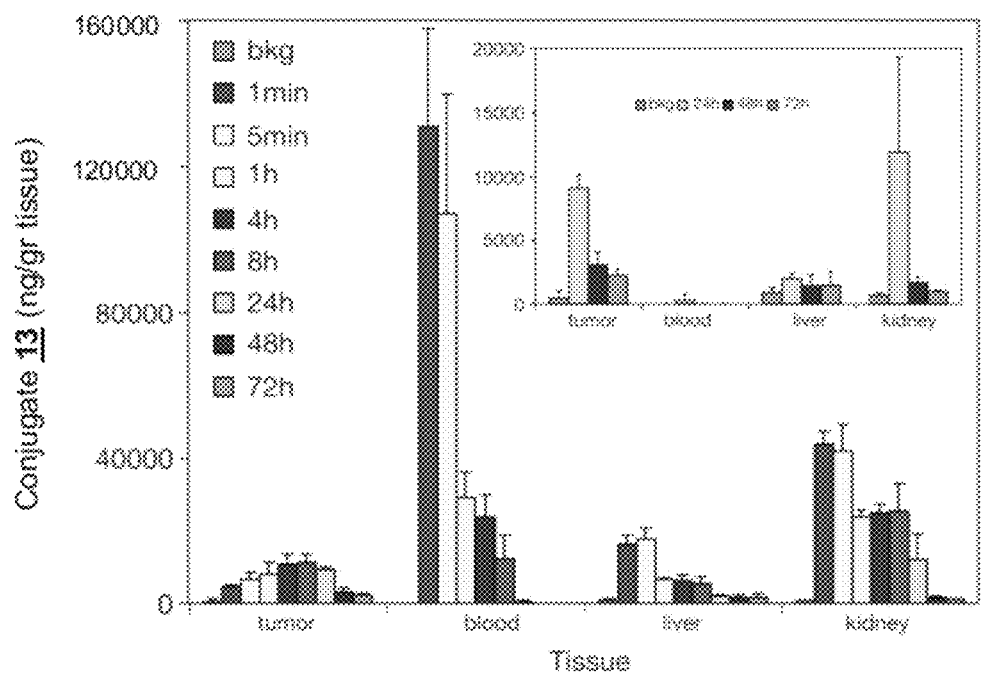
FIGS. 38A-38B present the biodistribution of conjugate 13 and non-conjugated compound 25 in MDA-MB-231-RFP tumor-bearing CD-1 nude, female mice (n=3 for each time point), that were intravenously injected with: (A) 15 mg/kg conjugate 13 or, (B) 9 mg/kg compound 25 and sacrificed at the indicated times. Values represent averaged fluorescence intensities (±standard deviation)

Levels of conjugate 13 in blood, liver, kidney and large MDAMB-231-RFP tumors were assessed at the indicated time points after i.v. injection of 15 mg/kg (n=27; FIG. 38A). Conjugate 13 reached peak concentrations in the tumors at eight hours post-injection (11 µg drug/gr tumor tissue; about 3.0% of the initial drug dose), while its levels in the normal tissues examined peaked at less than five minutes post-injection and cleared to nearly background levels within less than 72 hours. The levels of 13 in the tumor were about two orders of magnitude higher than in the blood during the 48 to 72 hours post-administration period (FIG. 38A, insert), about 10-fold higher than in the spleen, heart, brain, fat and muscle (data not shown), and approximately two-fold higher than in the kidney, liver, intestines, lung and skin (data not shown). Conjugate 13 underwent rapid hepatic clearance with a $t_{1/2}$ of about four hours. These results clearly show that 13 and similar agents can be used for selective imaging of tumors.

Figure 38B:
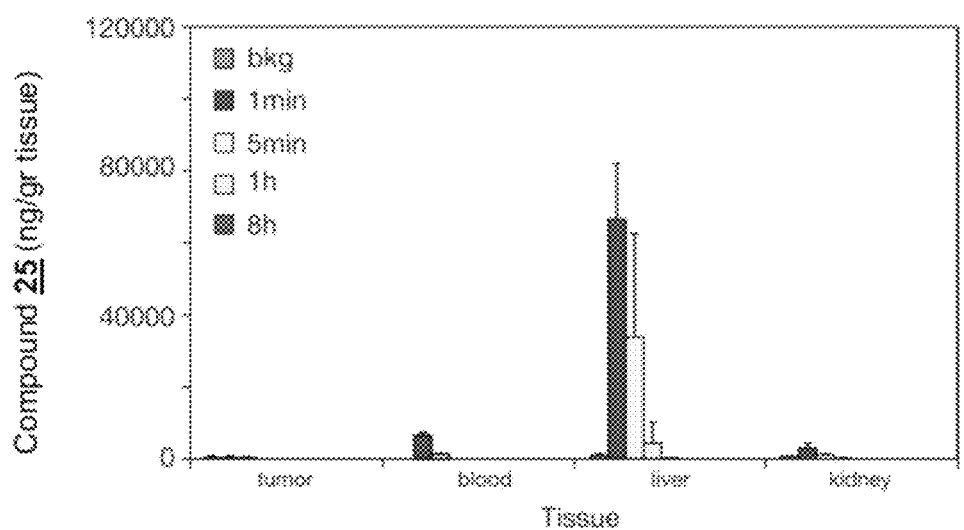

Example 45. The c(RGDfK) Moiety is Essential for Conjugate 13 Uptake by Tumor In order to determine whether the RGD moiety is imperative for the selective uptake of conjugate 13 by the tumor, its time-dependent accumulation within MDA-MB-231-RFP tumors was compared with that of the RGD-free compound 25. Quantitative assessment of the compound fluorescence intensity from tissue extracts was performed showing no accumulation of 25 in the tumor at any time longer than one hour post administration (FIG. 38B). No specific tumor fluorescence of 25 was seen even in mice bearing large, necrotic tumors, already at one hour post i.v. injection.

Similar results were obtained in mice bearing small tumors (data not shown). These findings clearly indicate that the c(RGDfK) moiety is imperative to tumor-specific bacteriochlorophyll derivative accumulation and retention.

Figure 40C:
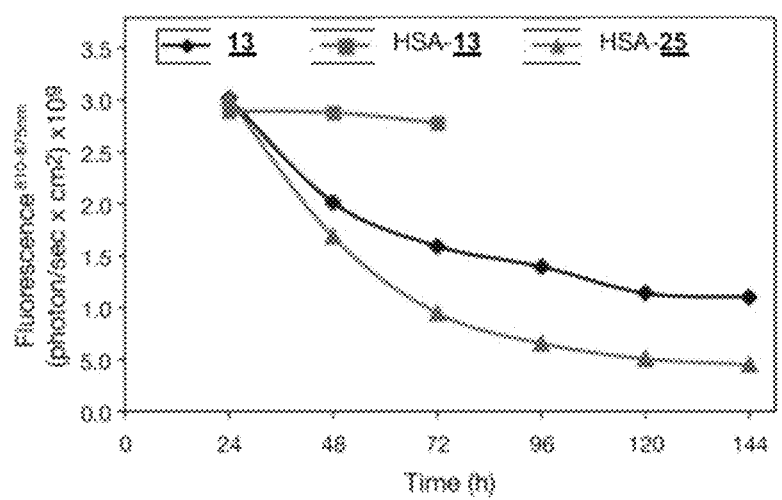

Example 46. Association of Bacteriochlorophyll Derivatives to Serum Albumin (SA) Plays a Role in their Uptake and Prolonged Accumulation in Tumors In previous studies (Mazor et al., 2005, Brandis et al., 2005), the present inventors have demonstrated that the water soluble compound 8 (WST-11) is primarily carried in the circulation through non-covalent associations with SA. However, such non-covalent association appears insufficient to drive tumor accumulation and retention of compounds 8 (Rubinstein et al., 2007) and 25 (FIGS. 38B and 39A-B). On the other hand when 25 was covalently bound to human serum albumin (HSA), it presented some accumulation and prolonged retention in the MDA-MB-231-RFP tumor (FIGS. 40B and 40C) and conjugate 13 covalently bound to HSA appears to clear extremely slowly, if at all, from the tumor (FIGS. 40A and 40C).

These findings corroborate with the aforementioned finding that covalent binding or non-covalent association of contrast agents with SA, significantly enhances their uptake by tumors (Chen et al., 2009).

All together, the above findings indicate that the enhanced permeability and retention (EPR) effect may support mobilization of SA-associating therapeutic and imaging agents into the tumor. However, interactions with tumor-specific receptors are required for the prolonged retention and accumulation of these compounds within the tumor.

Example 47. Conjugation of Photosensitizer to c(RGDfK) does not Increase its Binding Affinity to SA Following the findings disclosed in Example 46 above, it may be suggested that stronger binding of conjugate 13 to SA compared with RGD-free compound 25 analogue accounts for the increased accumulation of the former in tumors. Therefore, the association constants of compounds 8 and 25 and conjugates 13 and 24 were determined. The derived constants $Ka_{(HSA)}$ (0.54±0.07; 0.44±0.09; 0.12±10.04; and 0.09±0.04, respectively) were found to be within the same order of magnitude. In fact, those for the RGDconjugates were four to six fold lower than the association constants of their RGD-free analogues, ruling out stronger SA association as the sole basis for RGD-conjugates retention in the tumor.
Thus, association to SA appears to be important for the uptake of bacteriochlorophyll derivatives to tumors but is not enhanced by the RGD moiety.
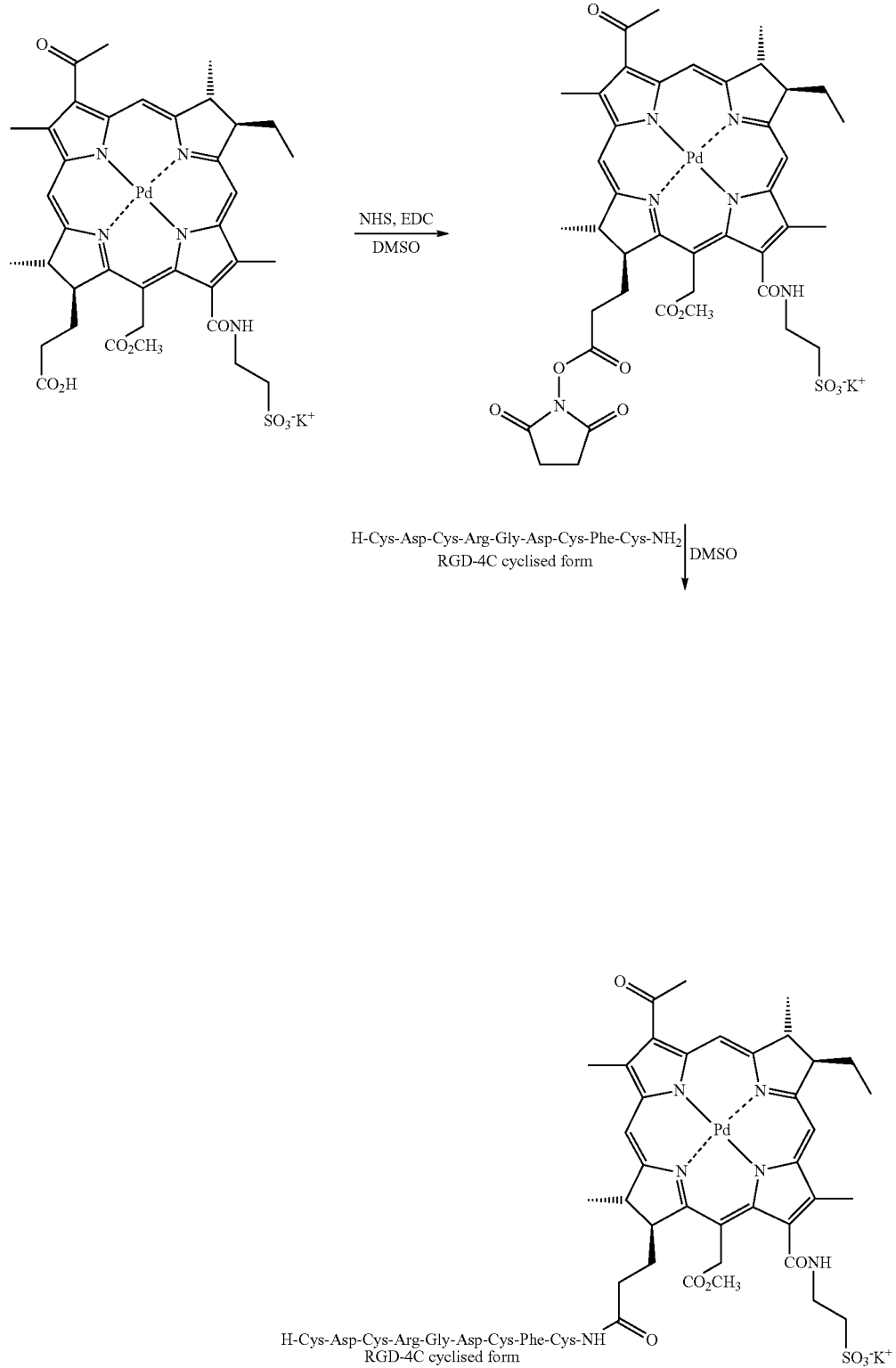
Scheme 1

Scheme 2
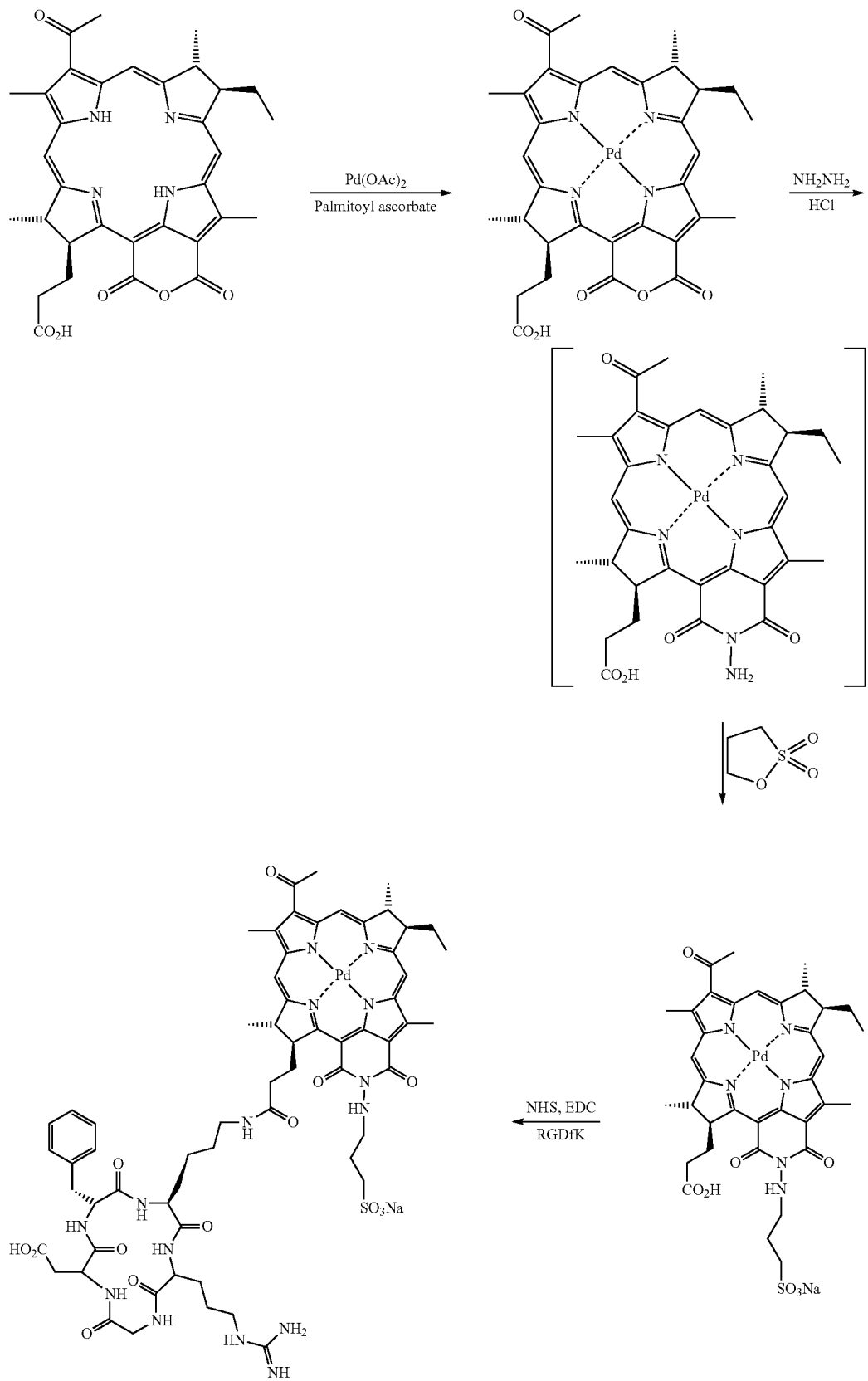

Scheme 3
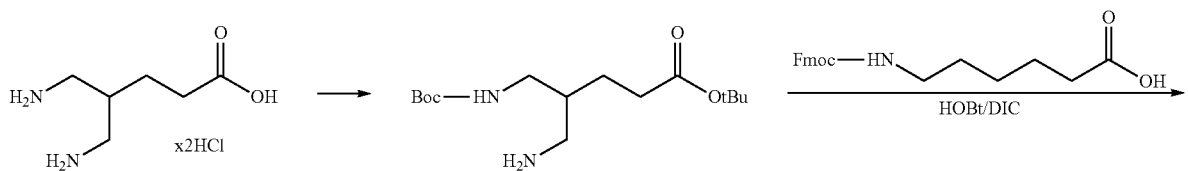
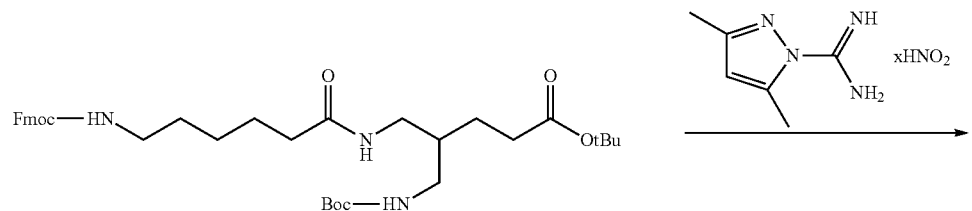
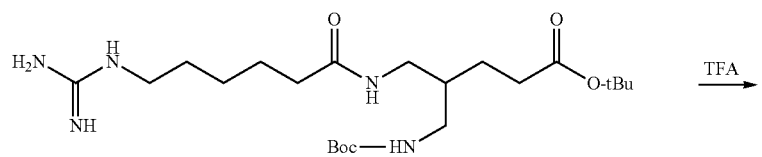
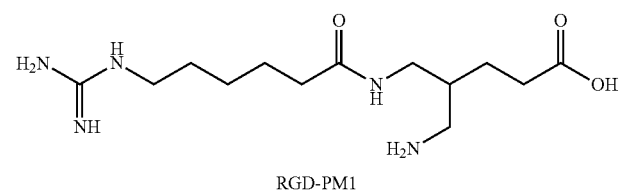
RGD-PM1
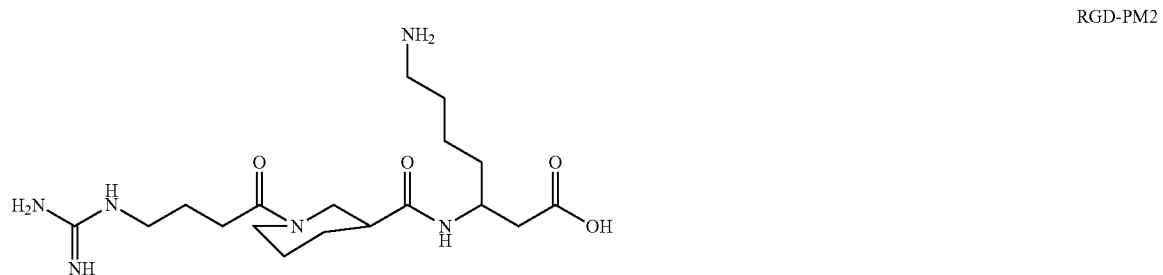
RGD-PM2

APPENDIX
| Compound Number | Chemical Name | Structure |
|---|---|---|
| 1 | Bacteriochlorophyll a | 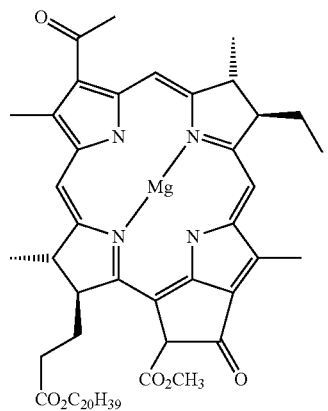 |
| 2 | $13^2$-OH-Bacteriochlorophyll a | 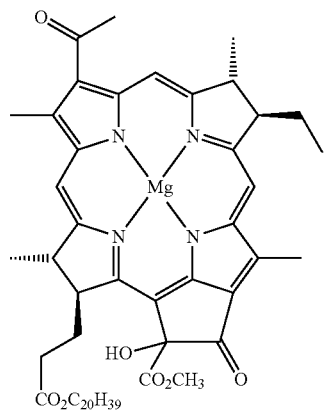 |
| 3 | Bacteriopheophorbide a | 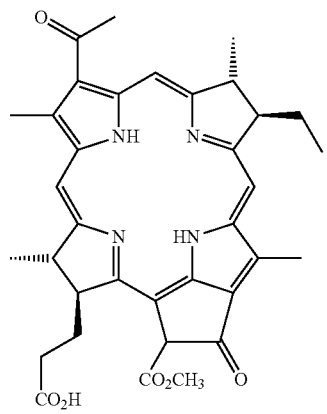 |

APPENDIX-continued
| Compound Number | Chemical Name | Structure |
|---|---|---|
| 4 | $13^2$-OH-Bacteriopheophorbide a | 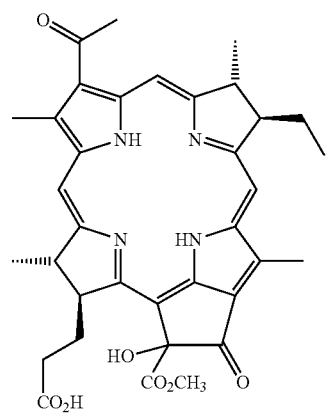 |
| 4a | Bacteriopurpurin 18 | 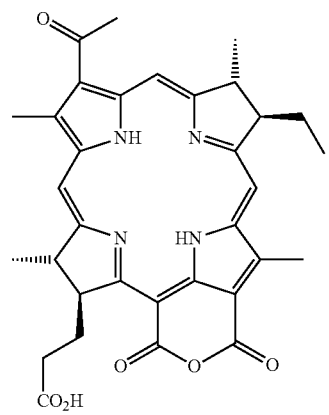 |
| 5 | Chlorophyll a | 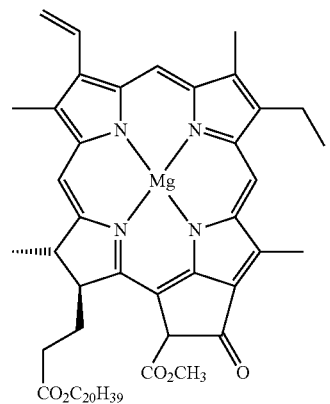 |

APPENDIX-continued
| Compound Number | Chemical Name | Structure |
|---|---|---|
| 6 | Pheophorbide a | 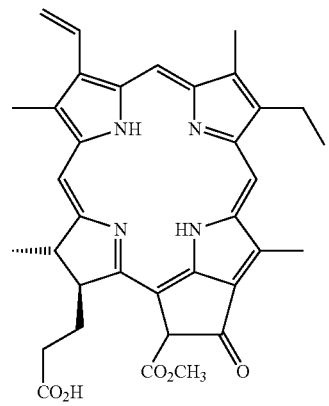 |
| 7 | Palladium Bacteriopheophorbide a | 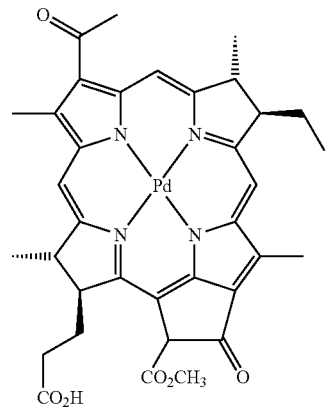 |
| 8 | Palladium $3^1$-oxo-15-methoxycarbonylmethyl-Rhodobacteriochlorin $13^1$-(2-sulfoethyl)amide potassium salt | 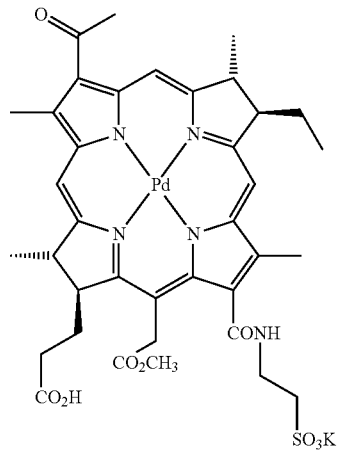 |

APPENDIX-continued

| Compound Number | Chemical Name | Structure |
|---|---|---|
| 9 | Manganese(III) $13^2$-OH-Bacteriopheophorbide a | 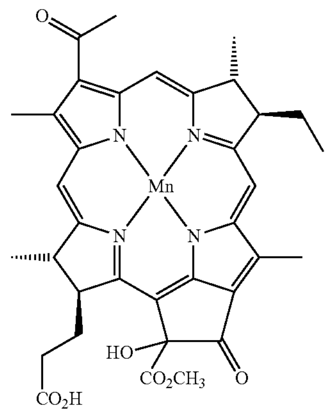 |
| 10 | Palladium $3^1$-oxo-15-methoxycarbonylmethyl-Rhodobacteriochlorin-$13^1$-(2,3-dihydroxypropyl)amide potassium salt | 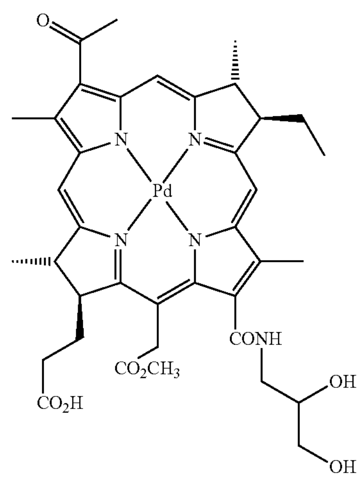 |
| 11 | Palladium $3^1$-oxo-15-methoxycarbonylmethyl-Rhodobacteriochlorin $13^1$-(2-sulfoethyl)amide-$17^3$-(RGD-4C)amide potassium salt | 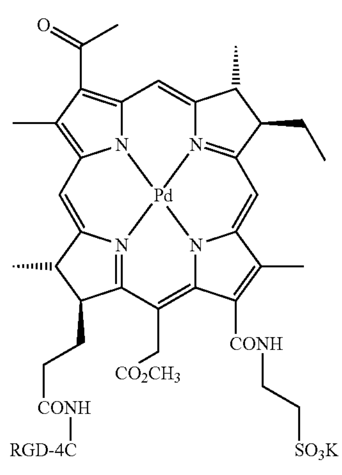 |

APPENDIX-continued
| Compound Number | Chemical Name | Structure |
|---|---|---|
| 12 | Manganese(III) 13²-OH-Bacteriopheophorbide-17³-(cycloRGDfK)amide | 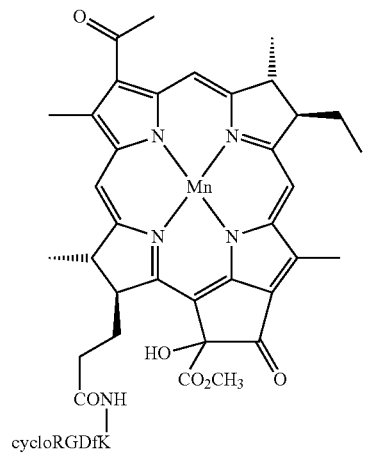 |
| 13 | 3¹-oxo-15-methoxycarbonylmethyl-Rhodobacteriochlorin 13¹-(2-sulfoethyl)amide-17³-(cycloRGDfK)amide potassium salt | 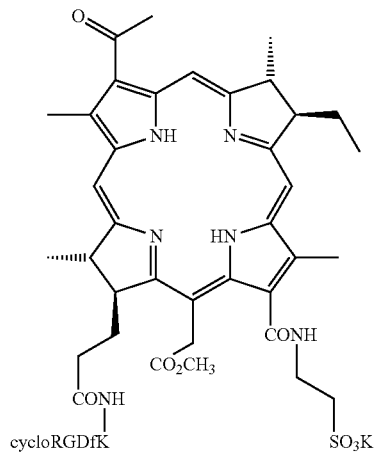 |
| 14 | Manganese(III) 3¹-oxo-15-methoxycarbonylmethyl-Rhodobacteriochlorin 13¹-(2-sulfoethyl)amide-17³-(cycloRGDfK)amide potassium salt | 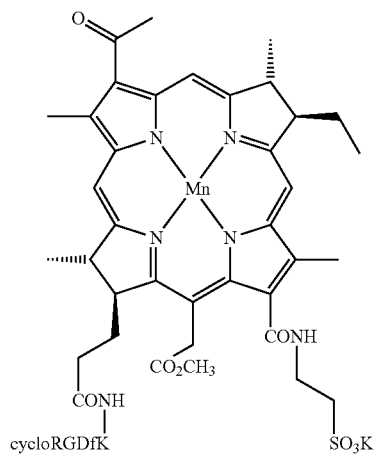 |

APPENDIX-continued

| Compound Number | Chemical Name | Structure |
|---|---|---|
| 15 | Copper(II) $3^1$-oxo-15-methoxycarbonylmethyl-Rhodobacteriochlorin $13^1$-(2-sulfoethyl)amide-$17^3$-(cycloRGDfK)amide potassium salt | 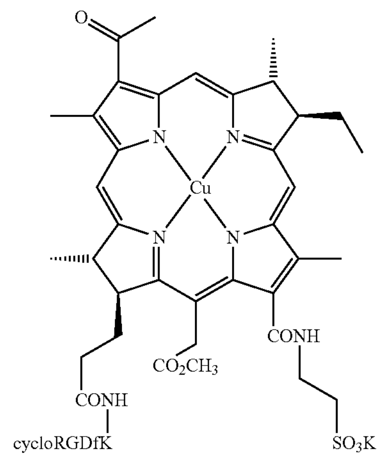 |
| 16 | $3^1,3^2$-Didehydrorhodochlorin $13^1$-(2-sulfoethyl)amide-$17^3$-(cycloRGDfK)amide potassium salt | 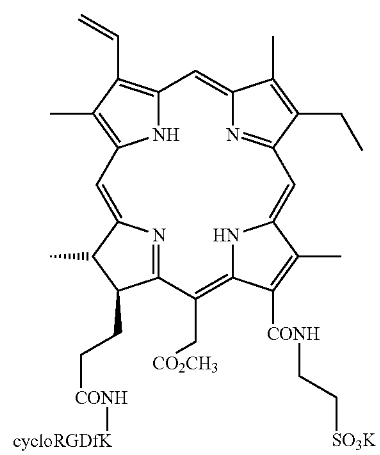 |
| 17 | Manganese(III) $3^1,3^2$-Didehydrorhodochlorin $13^1$-(2-sulfoethyl)amide-$17^3$-(cycloRGDfK)amide potassium salt | 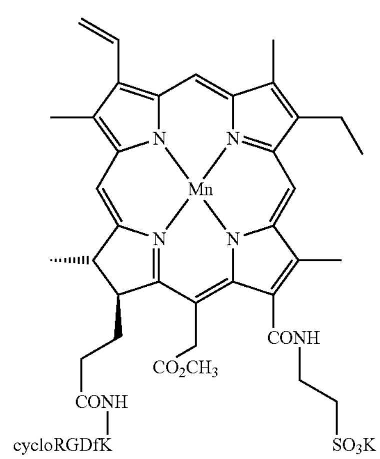 |

APPENDIX-continued

| Compound Number | Chemical Name | Structure |
|---|---|---|
| 18 | Copper(II) $3^1,3^2$-Didehydrorhodochlorin $13^1$-(2-sulfoethyl)amide-$17^3$-(cycloRGDfK)amide potassium salt | 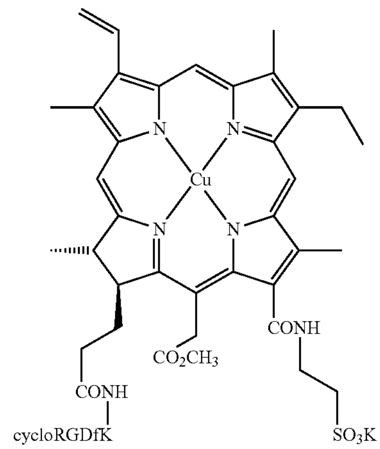 |
| 19 | Palladium Bacteriopurpurin N-(3-sulfopropylamino)imide-$17^3$-(cycloRGDfK)amide potassium salt | 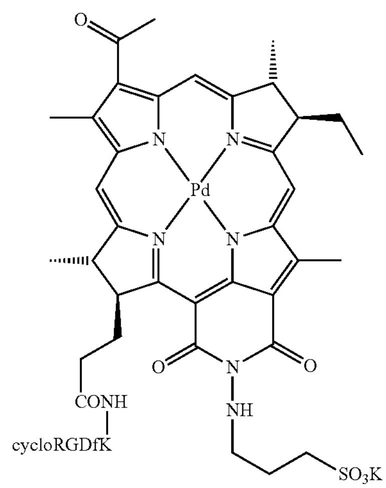 |
| 20 | Meso-5-(4-cycloRGDfK-benzamido)-10,15,20-tris(4-carboxyphenyl)porphine | 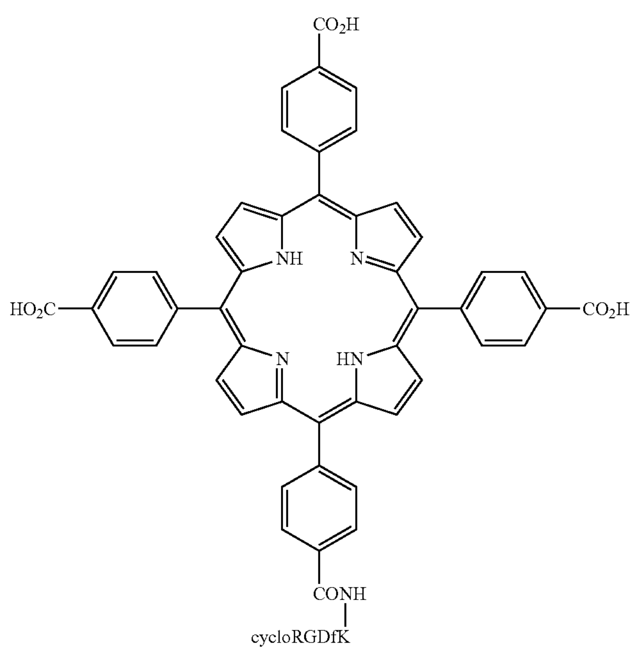 |

APPENDIX-continued
| Compound Number | Chemical Name | Structure |
|---|---|---|
| 21 | Copper(II) meso-5-(4-cycloRGDfK-benzamido)-10,15,20-tris(4-carboxyphenyl) porphine | 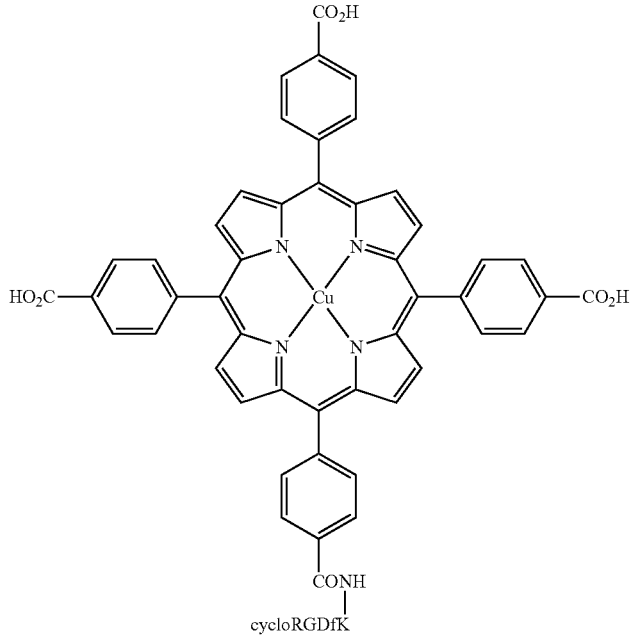 |
| 22 | Gadolinium(III) meso-5-(4-cycloRGDfK-benzamido)-10,15,20-tris(4-carboxyphenyl) porphine | 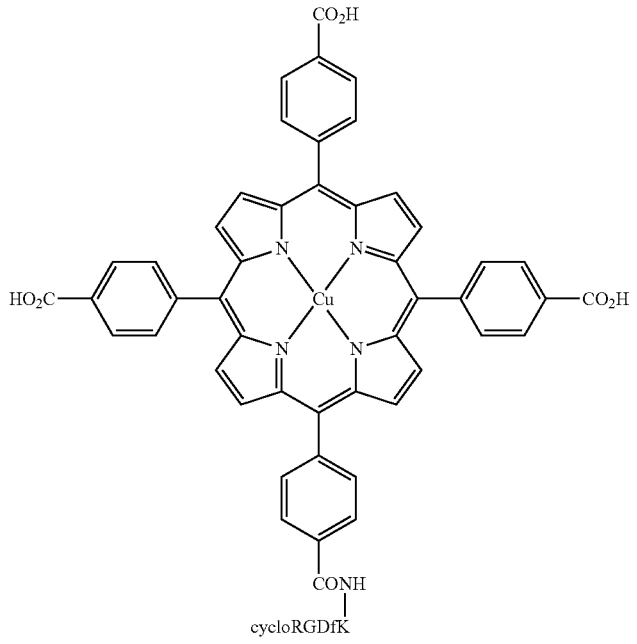 |

APPENDIX-continued

| Compound Number | Chemical Name | Structure |
|---|---|---|
| 23 | Palladium $3^1$-oxo-15-methoxycarbonylmethyl-Rhodobacteriochlorin-$13^1$-(2,3-dihydroxypropyl)amide-$17^3$-(cycloRGDfK)amide | 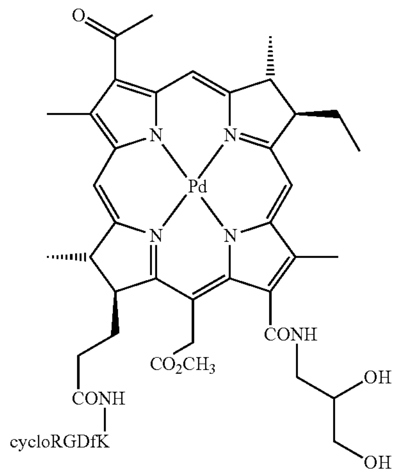 |
| 24 | Palladium $3^1$-oxo-15-methoxycarbonylmethyl-Rhodobacteriochlorin $13^1$-(2-sulfoethyl)amide-$17^3$-(cycloRGDfK)amide potassium salt | 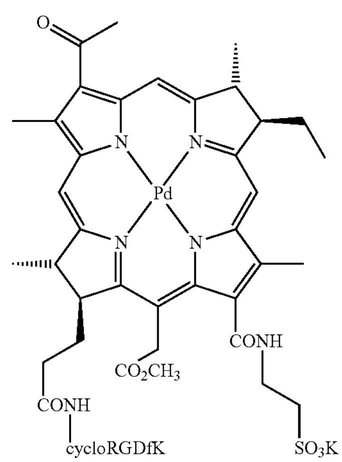 |
| 25 | $3^1$-oxo-15-methoxycarbonylmethyl-Rhodobacteriochlorin $13^1$-(2-sulfoethyl)amide potassium salt | 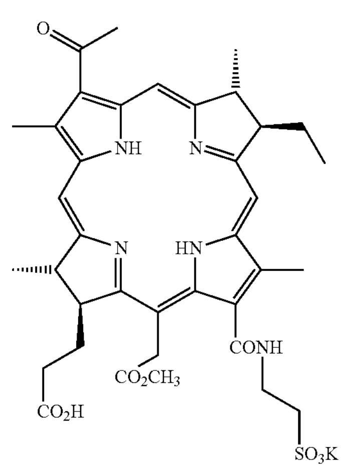 |

APPENDIX-continued

| Compound Number | Chemical Name | Structure |
|---|---|---|
| 26 | $3^1$-oxo-15-methoxycarbonylmethyl-Rhodobacteriochlorin $13^1$-(2-sulfoethyl)amide-$17^3$-(GRGDSP)amide potassium salt | 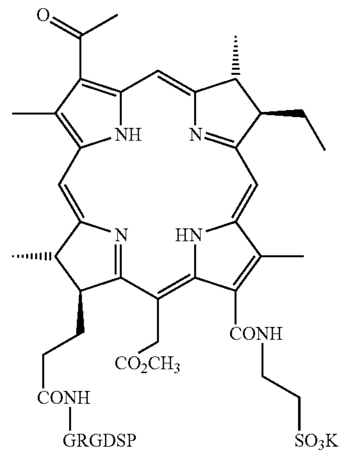 |
| 27 | Bacteriopheophorbide-$17^3$-(cycloRGDfK)amide | 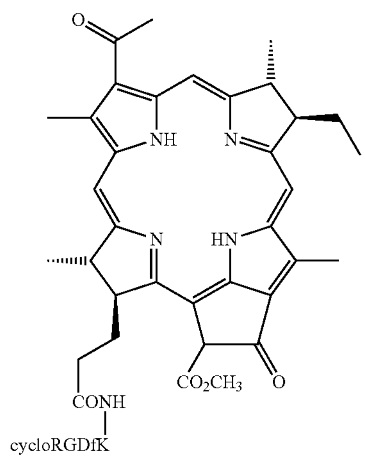 |
| 28 | $3^1$-oxo-15-methoxycarbonylmethyl-Rhodobacteriochlorin $13^1$-(3-[(3-aminopropyl)amino]propyl)amide-$17^3$-(cycloRGDfK)amide | 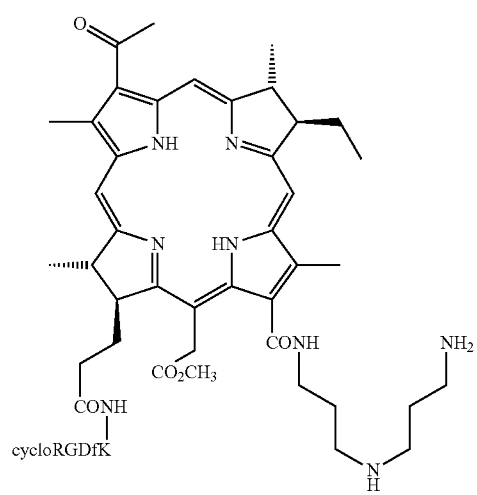 |

APPENDIX-continued

| Compound Number | Chemical Name | Structure |
|---|---|---|
| 29 | 3¹-oxo-15-methoxycarbonylmethyl-Rhodobacteriochlorin 13¹-(2,3-dihydroxypropyl)amide-17³-(cycloRGDfK)amide | 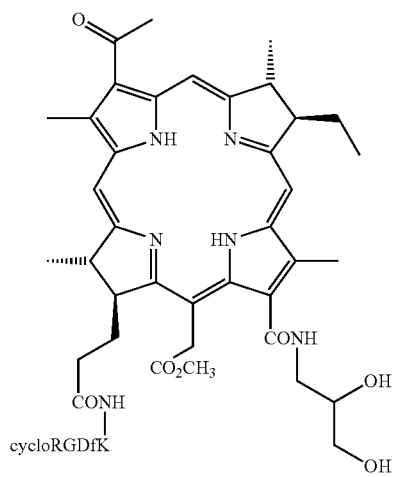 |
| 30 | 3¹-oxo-15-methoxycarbonylmethyl-Rhodobacteriochlorin 13¹-(2-morpholino-N-ethyl)amide-17³-(cycloRGDfK)amide | 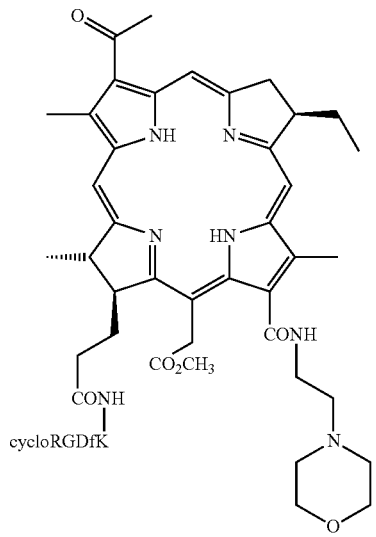 |
| 31 | 3¹-oxo-15-methoxycarbonylmethyl-Rhodobacteriochlorin 13¹-{3-[4-(3-aminopropyl)-piperazin-1-yl]-propyl}amide-17³-(cycloRGDfK)amide | 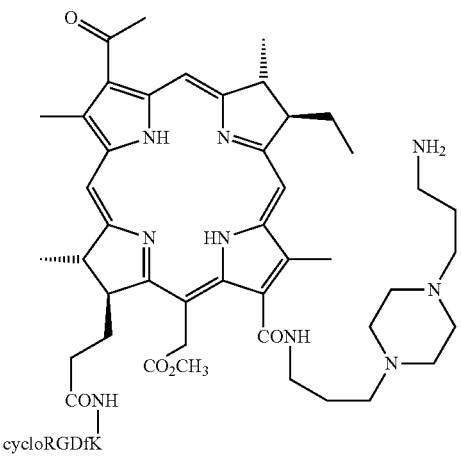 |

APPENDIX-continued

| Compound Number | Chemical Name | Structure |
|---|---|---|
| 32 | Bacteriopheophorbide-$17^3$-(2-cycloRGDK-amido-N-ethyl)amide | 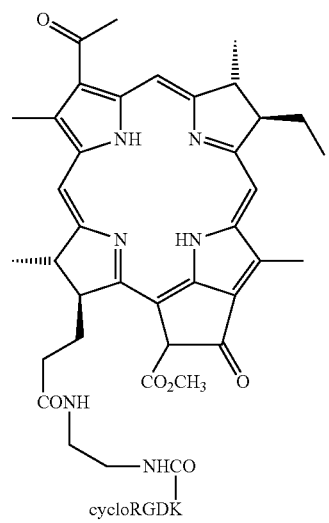 |
| 33 | Palladium $3^1$-oxo-15-methoxycarbonylmethyl-Rhodobacteriochlorin $13^1$-(2-sulfoethyl)amide-$17^3$-(GRGDSPK)amide potassium salt | 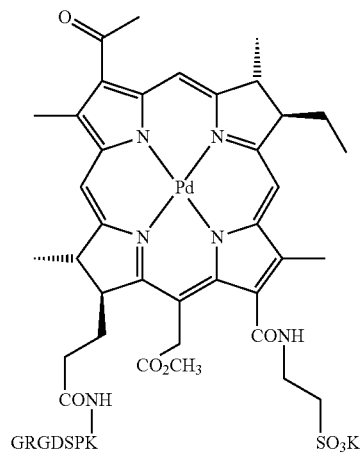 |
| 34 | Palladium $3^1$-oxo-15-methoxycarbonylmethyl-Rhodobacteriochlorin $13^1$-(2-sulfoethyl)amide-$17^3$-[(GRGDSP)$_4$K]amide potassium salt | 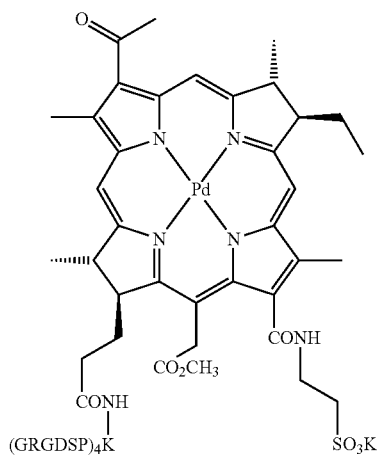 |

APPENDIX-continued

| Compound Number | Chemical Name | Structure |
|---|---|---|
| 35 | Palladium $3^1$-oxo-15-methoxycarbonylmethyl-Rhodobacteriochlorin $13^1$-(2-sulfoethyl)amide-$17^3$-(cycloRGDf-N(Me)K)amide potassium salt | 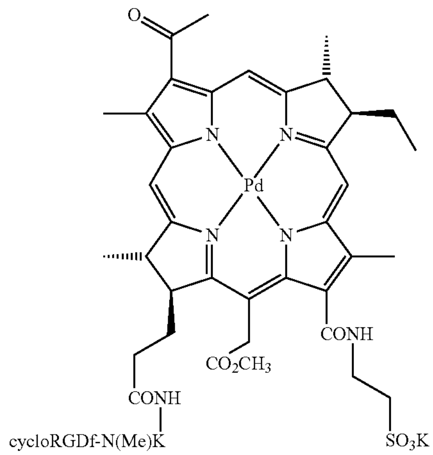 |
| 36 | Palladium $3^1$-oxo-15-methoxycarbonylmethyl-Rhodobacteriochlorin $13^1$-(2-sulfoethyl)-$17^3$-N-[4-heptanedioic acid bis-(cycloRGDyK-amido)]amide potassium salt | 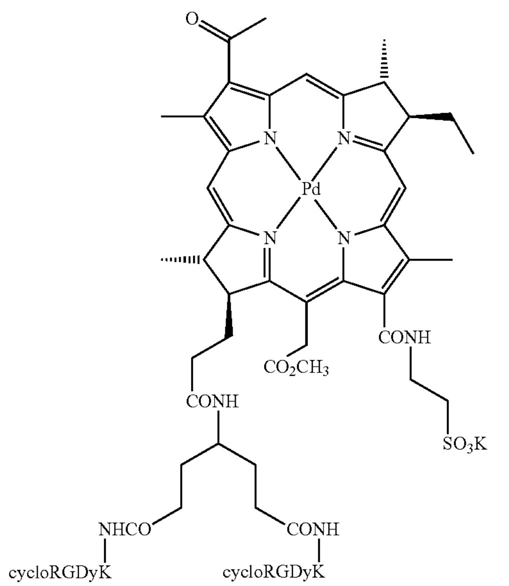 |
| 37 | Palladium $3^1$-oxo-15-methoxycarbonylmethyl-Rhodobacteriochlorin $13^1,17^3$-cyclo(2-RGD-amido-N-ethyl)diamide | 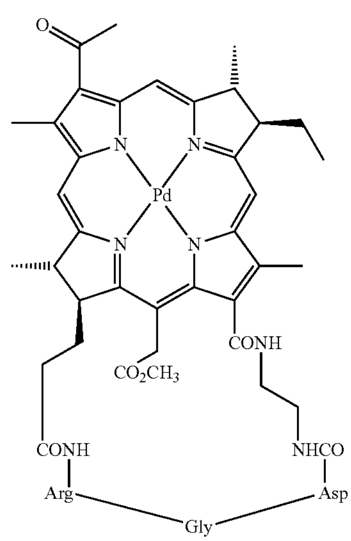 |

APPENDIX-continued
| Compound Number | Chemical Name | Structure |
|---|---|---|
| 38 | 3$^1$-oxo-15-methoxycarbonylmethyl-Rhodobacteriochlorin 13$^1$,17$^3$-cyclo(2-RGD-amido-N-ethyl)diamide | 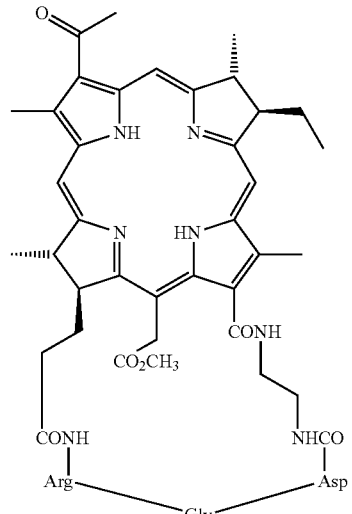 |
| 39 | Palladium 3$^1$-oxo-15-methoxycarbonylmethyl-Rhodobacteriochlorin 13$^1$,17$^3$-cyclo{3-[4-(3-aminopropyl-RGD-amido)-piperazin-1-yl]-propyl}diamide | 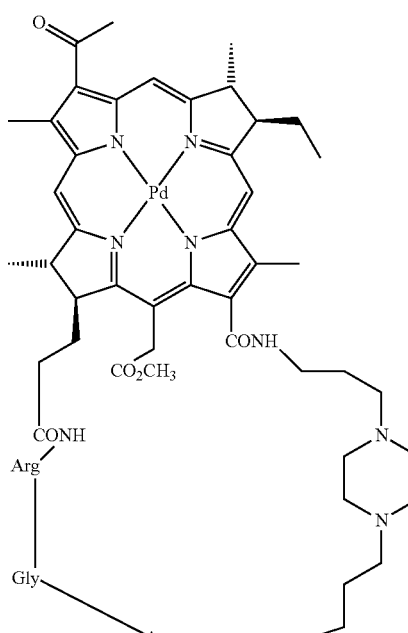 |

APPENDIX-continued

| Compound Number | Chemical Name | Structure |
|---|---|---|
| 40 | Palladium $3^1$-oxo-15-methoxycarbonylmethyl-Rhodobacteriochlorin $13^1$-(2-sulfoethyl)amide-$17^3$-[4-(methyl-5-(6-guanidino-hexanoylamino)-pentanoic acid)]amide potassium salt | 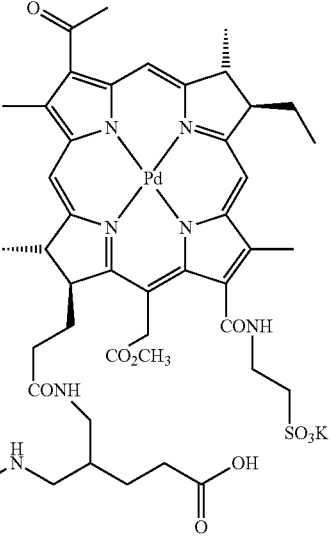 |
| 41 | Palladium $3^1$-oxo-15-methoxycarbonylmethyl-Rhodobacteriochlorin $13^1$-(2-sulfoethyl)amide-$17^3$-[7-amido-3-[[1-(4-guanidino-butyryl)-piperidine-3-carbonyl]-amino]-heptanoic acid] potassium salt | 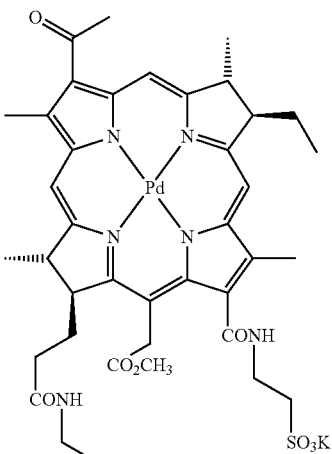 |

APPENDIX-continued

| Compound Number | Chemical Name | Structure |
|---|---|---|
| 42 | Palladium $3^1$-oxo-15-methoxycarbonylmethyl-Rhodobacteriochlorin $13^1$-(2-sulfoethyl)amide-$17^3$-(cycloRADfK)amide potassium salt | 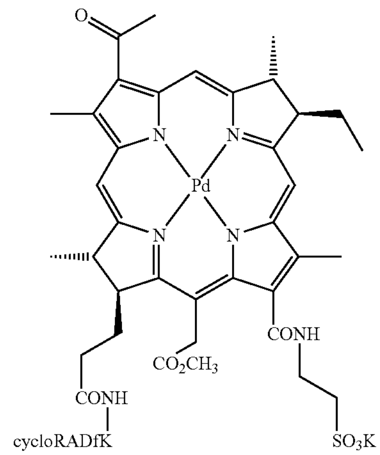 |
| 43 | $3^1$-oxo-15-methoxycarbonylmethyl-Rhodobacteriochlorin $13^1$-(3-DTPA-amido-N-propyl)amide-$17^3$-(cycloRGDfK)amide | 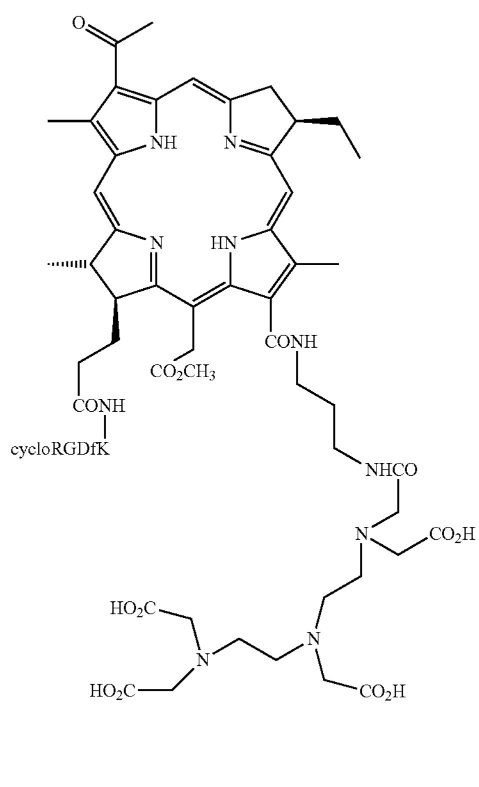 |

APPENDIX-continued

| Compound Number | Chemical Name | Structure |
|---|---|---|
| 44 | $3^1$-oxo-15-methoxycarbonylmethyl-Rhodobacteriochlorin $13^1$-(3-Gd-DTPA-amido-N-propyl)amide-$17^3$-(cycloRGDfK)amide | 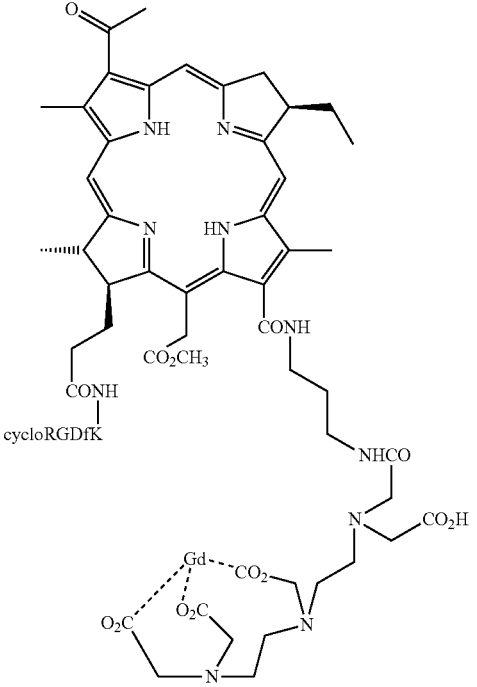 |

REFERENCES

Ali H. and van Lier J. E., (1999) "Metal Complexes as Photo- and Radiosensitizers", Chem. Rev. 99: 2379-2450.

Ando T., Irie K., Koshimizu K., Takemura T., Nishino H., Iwashima A, Takeda N., Nakajima S, and Sakata I, (1993) "Photocytotoxicity of Water-Soluble Metalloporphyrin Derivatives", Photochemistry and Photobiology, 57(4): 629-633.

Arap W., Haedicke W., Bernasconi M., Kain R., Rajotte D., Krajewski S., Ellerby H. M., Bredesen D. E., Pasqualini R. and Ruoslahti E. (2002) "Targeting the prostate for destruction through a vascular address", Proc. Natl. Acad. Sci. U.S.A., 99(3):1527-1531.

Arap W., Pasqualini R. and Ruoslahti E. (1998) "Cancer treatment by targeted drug delivery to tumor vasculature in a mouse model", Science, 279:377-380.

Assa-Munt N., Jia X., Laakkonen P. and Ruoslahti E. (2001) "Solution structures and integrin binding activities of an RGD peptide with two isomers", Biochemistry, 40:2373-2378.

Bauminger S. and Wilchek M. (1980) "The use of carbodiimides in the preparation of immunizing conjugates. Methods Enzymol", 70(A):151-159.

Bogdanowich-Knipp S. J., Jois D. S. and Siahaan T. J. (1999) "The effect of conformation on the solution stability of linear vs. cyclic RGD peptides", J. Pept. Res., 53(5):523-9.

Bonnett R. (1999) "Photodynamic therapy in historical perspective", Rev. Contemp. Pharmacother., 10:1-17.

Borza C M, Pozzi A, Borza D B, Pedchenko V, Hellmark T, Hudson B G, Zent R. (2006) "Integrin alpha3beta1, a novel receptor for alpha3(IV) noncollagenous domain and a trans-dominant Inhibitor for integrin alphavbeta3", J Biol. Chem. 281(30):20932-20939.

Brandis A., Mazor O., Gross S., Koudinova N., Hami R., Kalin-Kammhuber N., Rosenbach-Belkin V., Greenwald M., Bondon A., Simonneaux G., Scheer H., Salomon Y. and Scherz A. (2003) "Novel palladium-bacteriochlorophyll derivatives for antivascular Photodynamic therapy: synthesis, phototoxicity, pharmacokinetics and efficacy", J. Med. Chem. submitted.

Brandis A., Mazor O., Neumark E., Rosenbach-Belkin V., Salomon Y. and Scherz A. (2005) "Novel water-soluble bacteriochlorophyll derivatives for vascular-targeted photodynamic therapy: synthesis, solubility, phototoxicity, and the effect of serum proteins", Photochem Photobiol., 81, 983-993.

Brooks P. C., Clark R. A. and Cheresh D. A. (1994a) "Requirement of vascular integrin alpha v beta 3 for angiogenesis", Science, 264(5158):569-571.

Brooks P. C., Montgomery A. M., Rosenfeld M., Reisfeld R. A., Hu T., Klier G. and Cheresh D. A. (1994b) "Integrin alpha v beta 3 antagonists promote tumor regression by inducing apoptosis of angiogenic blood vessels", Cell, 79(7):1157-1164.

Brooks P. C., Stromblad S., Klemke R., Visscher D., Sarkar F. H. and Cheresh D. A. (1995) "Antiintegrin alpha v beta 3 blocks human breast cancer growth and angiogenesis in human skin", J. Clin. Invest., 96(4):1815-1822.

Burrows F. J. and Thorpe P. E. (1994) "Vascular targeting—a new approach to the therapy of solid tumors", Pharmacol. Ther., 64(1):155-74.

Castel S., Pagan R., Mitjans F., Piulats J., Goodman S., Jonczyc A., Huber F., Vilaro S. and Reina M. (2001) "RGD peptides and monoclonal antibodies, antagonists of α$_v$-integrin, enter the cells by independent endocytic pathways", Lab. Invest., 81(12):1615-1626.

Chaleix V., Sol V., Huang Y. M., Guilloton M., Granet R., Blais J. C., and Krausz P. (2003) "RGD-porphyrin conjugates: synthesis and potential application in photodynamic therapy", Eur. J. Org. Chem., 1486-1493.

Chang Y. S., di Tomaso E., McDonald D. M., Jones R. and Jain R. K. (2000) "Mosaic blood vessels in tumors: frequency of cancer cells in contact with flowing blood", Proc. Acad. Sci. U.S.A., 97(26):14608-14613.

Chen K., Xie J., Chen X., (2009) "RGD-human serum albumin conjugates as efficient tumor targeting probes", Mol Imaging, 8:65-73.

Dougherty D. J., Gomer C. J., Henderson B. W., Joni G., Kessel D., Korbelik M., Moan J. and Qian P. (1998) "Photodynamic therapy", JNCI, 90(12):889-905.

D'Souza S. E., Ginsberg M. H. and Plow E. F. (1991) "Arginyl-glycyl-aspartic acid (RGD): a cell adhesion motif", Trends Biochem. Sci., 16(7):246-250.

Elceiri B. P. and Cheresh D. A. (1999) "The role of alphav integrins during angiogenesis: insights into potential mechanisms of action and clinical development", J. Clin. Invest., 103(9):1227-1230.

Ellerby H. M., Arap W., Ellerby L. M., Kain R., Andrusiak R., Del Rio G., Krajewski S., Rao R., Ruoslahti E., Bredesen D. E. and Pasqualini R. (1999) "Anti-cancer activity of targeted pro-apoptotic peptides", Nat. Med., 5(9):1032-1038.

Fiedor L., Rosenbach-Belkin V. and Scherz A. (1992) "The stereospecific interaction between chlorophylls and chlorophyllase. Possible implication for chlorophyll biosynthesis and degradation", J. Biol. Chem. 267:22043-22047.

Freidinger R. M., Hinkle J. S., Perlow D. S., and Arison B. H. (1983) "Synthesis of 9-Fluorenylmethyloxycarbonyl-Protected N-Alkyl Amino Acids by Reduction of Oxazolidinones", J. Org. Chem. 48: 77-81.

Goligorsky M. S., Kessler H. and Romanov V. I. (1998) "Molecular mimicry of integrin ligation:therapeutic potential of arginine-glycine aspartic acid (RGD) peptides", Nephrol. Dial. Transplant., 13:254-263.

Gross S., Brandis A., Chen L., Rosenbach-Belkin V., Roehrs S., Scherz A., and Salomon Y. (1997) "Protein-A-mediated targeting of bacteriochlorophyll-IgG to *Staphylococcus aureus*: a model for enhanced site-specific photocytotoxicity", Photochem Photobiol., 66(6):871-8.

Gross S., Gilead A. Scherz A. Neeman M. and Salomon Y. (2003b) "Monitoring Photodynamic Therapy of Solid Tumors Online by BOLD Contrast MRI", Nature Medicine in Press.

Gross S., Gilead A., Brandis A., Schreiber S., Machluf Y., Neeman M., Scherz A. and Salomon Y. (2003a) "Selective vascular and tumor responses of photodynamic therapy (PDT) with Pd bacteriopheophorbide (TOOKAD®): online and offline analyses", Proceedings of the 94th annual meeting of the American association for cancer research (AACR), Toronto, April 5-9, 44: 27.

Hahn S. M. and Glatstein E. (1999) "The emergence of photodynamic therapy as a major modality in cancer treatment", Rev. Contemp. Pharmacother., 10:69-74.

Hardan I., Weiss L., Hershkovitz R., Greenspoon N., Alon R., Cahalon L., Reich S., Slavin S, and Lider O. (1993) "Inhibition of metastatic cells colonization in murine lungs and tumor-induced morbidity by non-peptidic Arg-Gly-Asp mimetics", Int. J. Cancer, 55:1023-1028.

Hart S. L., Knight A. M., Harbottle R. P., Mistry A., Hunger H. D., Cutler D. F., Williamson R. and Coutelle C. (1994) "Cell binding and internalization by filamentous phage displaying a cyclic Arg-Gly-Asp-containing peptide", J. Biol. Chem., 269(17):12468-12474.

Haubner R. et al. (1999) "Radiolabeled α$_v$ β$_3$ integrin antagonists: a new class of tracers for tumor targeting", J Nucl Med. 40:1061-1071

Haubner R., Wester H. J., Weber W. A., Mang C., Ziegler S. L., Goodman S. L., Senekowitsch-Schmidtke R., Kessler H. and Schwaiger M. (2001) "Noninvasive imaging of αvβ3 integrin expression using 18F-labeled RGD-containing glycopeptide and positron emission tomography", Cancer res., 61:1781-1785.

Horrocks W. D. Jr. and Hove E. G., 1978, "Water-Soluble Lanthanide Porphyrins: Shift Reagents for Aqueous Solution", Journal of the American Chemical Society, 100: 4386-4392.

Huang X., Molema G., King S., Watkins L., Edgington T. S, and Thorpe P. E. (1997) "Tumor infarction in mice by antibody-directedtargeting of tissue factor to tumor vasculature", Science, 275:547-550.

Iyer A. K., Khaled G., Fang J., Maeda H., (2006) "Exploiting the enhanced permeability and retention effect for tumor targeting", Drug Discov Today 11:812-818.

Janssen M. L., Oyen W. J., Dijkgraaf I., Massuger L. F., Frielink C., Edwards D. S., Rajopadhye M., Boonstra H., Corstens F. H., Boerman O. C. (2002a) "Tumor Targeting with Radiolabeled αvβ3 Integrin Binding Peptides in a Nude Mouse Model", Cancer research 62: 6146-6151.

Janssen M, Oyen W J, Massuger L F, Frielink C, Dijkgraaf I, Edwards D S, Radjopadhye M, Corstens F H, Boerman O C. (2002b) Comparison of a monomeric and dimeric radiolabeled RGD-peptide for tumor targeting. Cancer Biother Radiopharm. 17(6):641-646.

Joshi P., Chung C. Y., Aukhil I. and Erickson H. P. (1993) "Endothelial cells adhere to the RGD domain and the fibrinogen-like terminal knob of tenascin. J", Cell Sci., 106 (Pt 1):389-400.

Kawaguchi M., Hosotani R., Ohishi S., Fujii N., Tulachan S. S., Koizumi M., Toyoda E., Masui T., Nakajima S., Tsuji S., Ida J., Fujimoto K., Wada M., Doi R., and Imamura M. (2001) "A novel synthetic Arg-Gly-Asp-containing peptide cyclo(-RGDf=V-) is the potent inhibitor of angiogenesis", Biochem. Biophys. res. com., 288:711-717.

Kessel D. and Dougherty T. J. (1999) "Agents used in Photodynamic therapy", Rev. Contemp. Pharmacother, 10:19-24.

Koivunen E., Wang B. and Ruoslahti E. (1995) "Phage libraries displaying cyclic peptides with different ring sizes: ligand specificities of the RGD-directed integrins", Biotechnology (N Y), 13(3):265-70.

Koivunen E., Wang B., Dickinson C. D. and Ruoslahti E. (1994) "Peptides in cell adhesion research", Methods Enzymol., 245:346-369.

Koudinova N. V., Pinthus J. H., Brandis A., Brenner O., Bendel P., Ramon J., Eshhar Z., Scherz A. and Salomon Y. (2003) "Photodynamic therapy with Pd-Bacteriopheophorbide (TOOKAD): successful in vivo treatment of human prostatic small cell carcinoma xenografts", Int J Cancer., 104(6):782-789.

Mazon M. D. (1999) "Cellular aspects of photodynamic therapy for cancer", Rev. Contemp. Pharmacother., 10:25-37.

Mazor O., Brandis A., Plaks V., Neumark E., Rosenbach-Belkin V., Salomon Y.; Scherz A., (2005) "WST11, a novel water-soluble bacteriochlorophyll derivative; cellular uptake, pharmacokinetics, biodistribution and vasculartargeted photodynamic activity using melanoma tumors as a model", Photochem. Photobiol., 81:342-351.

Mi Z., Guo H., Wai P. Y., Gao C., Kuo P. C. (2006) "Integrin-linked kinase regulates osteopontin-dependent MMP-2 and uPA expression to convey metastatic function in murine mammary epithelial cancer. cells", Carcinogenesis. 27(6):1134-1145.

Minchinton A. I, Tannock I. F. (2006) "Drug penetration in solid tumours", Nat. Rev. Cancer, 6:583-592.

Mironov A. F. et al. (2003) "New bacteriochlorin derivatives with a fused N-aminoimide ring", J. Porphyrins Phthalocyanins, 7: 725-730.

Mironov A. F., Kozyrev A. N. and Brandis A. S. (1992) "Sensitizers of second generation for photodynamic therapy of cancer based on chlorophyll and bacteriochlorophyll derivatives", Proc. SPIE, 1922:204-208.

Omata T. and Murata N. (1983) "Preparation of Chlorophyll a, Chlorophyll b and Bacteriochlorophyll a by column chromatography with DEAE-Sepharose C1-6B and Sepharose C1-6B", Plant Cell Physiol., 24:1093-1100

Pasqualini R. and Ruoslahti E. (1996) "Organ targeting in vivo using phage display peptide libraries", Nature, 380 (6572):364-366.

Pasqualini R., Koivunen E. and Ruoslahti E. (1997) "Alpha v integrins as receptors for tumor targeting by circulating ligands", Nat. Biotechnol., 15(6):542-546.

Pasqualini R., Koivunen E., Kain R, Landenranta J., Sakamoto M., Stryhn A., Ashmun R. H., Shapiro L. H., Arap W. and Rouslahti E. (2000) "Aminopeptidase N is a receptor for tumor-homing peptides and a target for inhibiting angiogenesis", Cancer res., 60:722-727.

Pierschbacher M. and Ruoslahti E. (1984) "Cell attachment activity of fibronectin can be duplicated by small synthetic fragments of the molecule", Nature, 309:30-33.

Pierschbacher M. D. and Rouslahti E. (1987) "Influence of stereochemistry of the sequence Arg-Gly-Asp-Xaa on binding specificity in cell adhesion", J. Biol. Chem., 262(36):17294-17298.

Preise D., Mazor O., Koudinova N., Liscovitch M., Scherz A. and Salomon Y. (2003) "Bypass Of Tumor Drug Resistance By Antivascular Therapy", Neopliasia, in Press.

Rajotte D., Arap W., Hagedorn M., Koivunen E., Pasqualini R. and Ruoslahti E. (1998) "Molecular Heterogeneity of the vascular endothelium revealed by in vivo phage display", J. Clin. Invest., 102:430-437.

Romanov V. I. and Goligorsky M. S. (1999) "RGD-recognizing integrins mediate interactions of human prostate carcinoma cells with endothelial cells in vitro", The prostate, 39:108-118.

Rosenbach-Belkin V., Chen L., Fiedor L., Tregub I., Paviotsky F., Brumfeld V., Salomon Y. and Scherz A. (1996) "Serine conjugates of chlorophyll and bacteriochlorophyll: photocytotoxicity in vitro and tissue distribution in mice bearing melanoma tumors", Photochem Photobiol., 64(1):174-181.

Ross D. T. et al., (2000) "Systematic variation in gene expression patterns in human cancer cell lines", Nat. Genet. 24(3):227-235.

Rubinstein E., (2007) "Targeted photodynamic drugs: Design, Synthesis and Applications. In PhD thesis Weizmann Institute of Science.

Ruoslahti E. (1996) "RGD and other recognition sequences for integrins", Annu. Rev. Cell Dev. Biol., 12:697-715.

Ruoslahti E. (2000) "Targeting tumor vasculature with homing peptides from phage display", Seminars in cancer biology, 10:435-442.

Ruoslahti E. (2002) "Drug targeting to specific vascular sites", DDT, 7(22):1138-1143.

Ruoslahti E. and Pierschbacher M. D. (1987) "New perspectives in cell adhesion: RGD and integrins", Science, 238(4826):491-497.

Ruoslahti E. and Rajotte D. (2000) "An address system in the vasculature of normal tissues and tumors", Annu. Rev. Immunol., 18:813-827.

Saiki I., Murata J., Iida J., Sakurai T., Nishi N., Matsuno K. and Azuma I. (1989) "Antimetastatic effects of synthetic polypeptides containing repeated structures of the cell adhesive Arg-Gly-Asp (RGD) and Tyr-Ile-Gly-Ser-Arg (YIGSR) sequence", Br. J. Cancer, 60:722-728.

Scherz A. and Parson W. W. (1984) "Oligomers of bacteriochlorophyll and bacteriopheophytin with spectroscopic properties resembling those found in photosynthetic bacteria", Biochim. Biophys. Acta, 766:653-665.

Schiffenbauer Y S, Meir G, Maoz M, Even-Ram S C, Bar-Shavit R, Neeman M. (2002) "Gonadotropin stimulation of MLS human epithelial ovarian carcinoma cells augments cell adhesion mediated by CD44 and by alpha (v)-integrin", Gynecol. Oncol. 84(2):296-302.

Schreiber S., Gross S., Brandis A., Harmelin A., Rosenbach-Belkin V., Scherz A. and Salomon Y. (2002) "Local photodynamic therapy (PDT) of rat C6 glioma xenografts with Pd-bacteriopheophorbide leads to decreased metastases and increase of animal cure compared with surgery", Int. J. Cancer, 99: 279-285.

Struck A., Cmiel E., Katheder I., Schafer W. and Scheer H. (1992) "Bacteriochlorophylls modified at position C-3: long-range intramolecular interaction with position C-13 [2]", Biochimica et Biophysica Acta, 1101 (3): 321-328.

Su Z. F., Liu G., Gupta S., Zhu Z., Rusckowski M. and Hnatowich D. J. (2002) "In vitro and in vivo evaluation of a Technetium-99m-labeled cyclic RGD peptide as a specific marker of alpha(V)beta(3) integrin for tumor imaging", Bioconjug. Chem., 13(3):56'-570.

Temming K. et al. (2005) RGD-based strategies for selective delivery of therapeutics and imaging agents to the tumour vasculature. Drug resistance updates. 8(6):381-402.

Vaillancourt V. A. et al. (2001) "Synthesis and Biological Activity of Aminoguanidine and Diaminoguanidine Analogues of the Antidiabetic/Antiobesity Agent 3-Guanidinopropionic Acid", J. Med. Chem., 44:1231-1248.

van Hagen P. M., Breeman W. A., Bernard H. F., Schaar M., Mooij C. M., Srinivasan A., Schmidt M. A., Krenning E. P. and de Jong M. (2000) "Evaluation of a radiolabelled cyclic DTPA-RGD analogue for tumour imaging and radionuclide thrapy", Int. J. Cancer, 90:186-198.

Wanunu M., Vaskevich A., Cohen S. R., Cohen H., Arad-Yellin R., Shanzer A., Rubinstein I. (2005) "Branched Coordination Multilayers on Gold", JACS, 127: 17877-17887.

Wasielewski M. R. and Svec W. A. (1980) "Synthesis of Covalently Linked Dimeric Derivatives of Chlorophyll a, Pyrochlorophyll a, Chlorophyll b, and Bacteriochlorophyll a", J. Org. Chem., 45(10):1969-1974.

Yao B. et al. (2005) "Enhanced antitumor effect of the combination of tumstatin gene therapy and gemcitabine in murine models", Hum Gene Ther. 16(9):1075-1086.

Zhang S. Z., Lipsky M. M., Trump B. F. and Hsu I. C. (1990) "Neutral Red (NR) assay for cell viability and xenobiotic-induced cytotoxicity in primary cultures of human and rat hepatocytes", Cell. Biol. Toxicol., 6:219-234.

Zilberstein J., Bromberg A., Frantz A., Rosenbach-Belkin V., Kritzmann A., Pfefermann R., Salomon Y. and Scherz A. (1997) "Light-dependent oxygen consumption in bacteriochlorophyll-serine-treated melanoma tumors: on-line determination using a tissue-inserted oxygen microsensor", Photochem Photobiol., 65(6):1012-1019.

Zilberstein J., Schreiber S., Bloemers M. C. W. M., Bendel P., Neeman M., Schechtman E., Kohen F., Scherz A. and Salomon Y. (2001) "Antivascular treatment of solid melanoma tumors with bacteriochlorophyll-serine-based photodynamic therapy", Photochem. Photobiol., 73: 257-266.

Zitzmann S., Ehemann V. and Schwab M. (2002) "Arginine-Glycine-Aspartic acid (RGD)-peptide bind to both tumor and tumor-endothelial cells in vivo", Cancer res., 62:5139-5143.

The invention claimed is:
1. A conjugate of at least one RGD-containing peptide or RGD-peptidomimetic and a water soluble photosensitizer of the formula II:

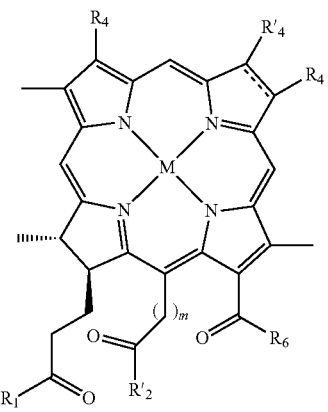

(II)

wherein
M represents 2H or an atom selected from the group consisting of Mg, Pd, Pt, Co, Ni, Sn, Sm, Cu, Zn, Mn, In, Eu, Fe, Au, Al, Gd, Dy, Er, Yb, Lu, Ga, Y, Rh, Ru, Si, Ge, Cr, Mo, P, Re, Tc, Tl and isotopes thereof;
$R_1$, is —NH—P, wherein P is a residue of an RGD-containing peptide or an RGD-peptidomimetic;
$R_6$ is —$NR_9R'_9$ or —$N^+R_9R'_9R''_9A^-$, wherein $R_1$ and $R_6$ may together form a ring;
$R'_2$ is —O—$R_8$;
$R_4$ is —CH=$CR_9R'_9$, —CH=$CR_9$Hal, —CH=CH—$CH_2$—$NR_9R'_9$, —CH=CH—$CH_2$—$N^+R_9R'_9R''_9A^-$, —CHO, —CH=$NR_9$, —CH=$N^+R_9R'_9A^-$, —$CH_2$—$OR_9$, —$CH_2$—$SR_9$, —$CH_2$—Hal, —$CH_2$—$R_9$, —$CH_2$—$NR_9R'_9$, —$CH_2$—$N^+R_9R'_9R''_9A^-$, —$CH_2$—$CH_2R_9$, —$CH_2$—$CH_2$Hal, —$CH_2$—$CH_2OR_9$, —$CH_2$—$CH_2SR_9$, —$CH_2$—$CH_2$—$NR_9R'_9$, —$CH_2$—$CH_2$—$N^+R_9R'_9R''_9A^-$, —$COCH_3$, $C(CH_3)$=$CR_9R'_9$, —$C(CH_3)$=$CR_9$Hal, —$C(CH_3)$=$NR_9$, —$CH(CH_3)$=$N^+R_9R'_9A^-$, —$CH(CH_3)$—Hal, —$CH(CH_3)$—$OR_9$, —$CH(CH_3)$—$SR_9$, —$CH(CH_3)$—$NR_9R'_9$, —$CH(CH_3)$—$N^+R_9R'_9R''_9A^-$, or —C≡$CR_9$;
$R'_4$ is methyl or formyl;
$R_8$, $R_9$, $R'_9$ and $R''_9$ each independently is:
(a) H;
(b) $C_1$-$C_{25}$ hydrocarbyl;
(c) $C_1$-$C_{25}$ hydrocarbyl substituted by one or more functional groups selected from the group consisting of halogen, nitro, oxo, —OR, —SR, epoxy, epithio, —NRR', —CONRR', —CONR—NRR', —NHCONRR', —NHCONRNRR', —COR, COOR, —$OSO_3$R, —$SO_3$R, —$SO_2$R, —$NHSO_2$R, —$SO_2$NRR', =N—OR, —$(CH_2)_n$—CO—NRR', —O—$(CH_2)_n$—OR, —O—$(CH_2)$, —O—$(CH_2)$, —R, —$OPO_3$RR', —$PO_2$HR, and —$PO_3$RR', wherein R and R' each independently is H, hydrocarbyl or heterocyclyl, R may further be a cation, R' may further be a residue of an RGD peptide or RGD peptidomimetic, or R and R' together with the N atom to which they are attached form a 5-7 membered saturated ring optionally containing a further heteroatom selected from O, S and N, wherein the further N atom may be substituted, and n is 1 to 6;
(d) $C_1$-$C_{25}$ hydrocarbyl substituted by one or more functional groups selected from the group consisting of positively charged groups, negatively charged groups, basic groups that are converted to positively charged groups under physiological conditions, and acidic groups that are converted to negatively charged groups under physiological conditions;
(e) $C_1$-$C_{25}$ hydrocarbyl containing one or more heteroatoms and/or one or more carbocyclic or heterocyclic moieties;
(f) $C_1$-$C_{25}$ hydrocarbyl containing one or more heteroatoms and/or one or more carbocyclic or heterocyclic moieties and substituted by one or more functional groups as defined in (c) and (d) above;
(g) $C_1$-$C_{25}$ hydrocarbyl substituted by a residue of an amino acid, a peptide, a protein, a monosaccharide, an oligosaccharide, a polysaccharide, or a polydentate ligand and its chelating complexes with metals; or
(h) a residue of an amino acid, a peptide, a protein, a monosaccharide, an oligosaccharide, a polysaccharide; or a polydentate ligand and its chelating complexes with metals;
$A^-$ is a physiologically acceptable anion;
m is 0 or 1;
the dotted line at positions 7-8 represents an optional double bond; and
pharmaceutically acceptable salts and optical isomers thereof;
wherein each said RGD-containing peptide or RGD-peptidomimetic is:
(A) a cyclic RGD-containing peptide selected from the group consisting of:
(i) the pentapeptide cycloRGDfK (SEQ ID NO:1), wherein f indicates D-Phe;
(ii) the nonapeptide herein designated RGD-4C (SEQ ID NO:2);
(iii) the tetrapeptide cycloRGDK (SEQ ID NO:4);
(iv) the pentapeptide cycloRGDf-N(Me)K (SEQ ID NO:7), wherein f indicates D-Phe; and
(v) the pentapeptide cycloRGDyK (SEQ ID NO:8), wherein y indicates D-Tyr;
(B) a linear RGD-containing peptide selected from the group consisting of:
(i) the hexapeptide GRGDSP (SEQ ID NO:3);
(ii) the heptapeptide GRGDSPK (SEQ ID NO:5), and
(iii) the peptide of sequence (GRGDSP)4K (SEQ ID NO:6);
(C) an RGD-peptidomimetic selected from the group consisting of $H_2N$—C(=NH)NH—$(CH_2)_5$—CO—NH—CH($CH_2$)—$(CH_2)_2$—COOH and $H_2N$—C(=NH)NH—$(CH_2)_2$—CO—piperidine-CONH—CH[$(CH_2)_4$]—$CH_2$—COOH, or
(D) an RGD-containing peptide or RGD-peptidomimetic residue selected from the group consisting of —NH-RGD-CO—NH—$(CH_2)_2$—NH— and —NH-RGD-CO—NH—$(CH_2)_3$piperazino-$(CH_2)_3$—NH— comprised within a ring formed by $R_1$ and $R_6$.
2. The conjugate according to claim 1, wherein:
(i) any of the $C_1$-$C_{25}$ hydrocarbyl groups is a $C_1$-$C_{25}$ alkyl, alkenyl or alkynyl;
(ii) said negatively charged group is selected from the group consisting of $COO^-$, $COS^-$, $SO_3^-$, and $PO_3^{2-}$;
(iii) said acidic group that is converted to a negatively charged group at the physiological pH is selected from the group consisting of COOH, COSH, $SO_3$H, and $PO_3H_2$, or a salt thereof;

(iv) said positively charged group is: (a) a cation derived from a N-containing group selected from the group consisting of —N$^+$(RR'R"), —(R)N—N$^+$(RR'R"), O←N$^+$(RR')—, >C=N$^+$(RR'), —C(=NR)—N$^+$RR'R" and —(R)N—C(=NR)—N$^+$RR'R"; (b) a cation derived from a heteroaromatic compound containing one or more N atoms and optionally O or S atoms, selected from the group consisting of pyrazolium, imidazolium, oxazolium, thiazolium, pyridinium, quinolinium, isoquinolinium, pyrimidinium, 1,2,4-triazinium, 1,3,5-triazinium and purinium, said cation being an end group or a group located within an alkyl chain; or (c) an onium group selected from the group consisting of —O$^+$(RR'), —S$^+$(RR'), —Se$^+$(RR'), —Te$^+$(RR'), —P$^+$(RR'R"), —As$^+$(RR'R"), —Sb$^+$(RR'R"), and —Bi$^+$(RR'R");

(v) said basic group that is converted to a positively charged group under physiological conditions is selected from the group consisting of —NRR', —C(=NR)—NR'R", —NR—NR'R", —(R)N—C(=NR)—NR'R", O←NR—, and >C=NR, or the basic group is a N-containing heteroaromatic radical selected from the group consisting of pyrazolyl, imidazolyl, oxazolyl, thiazolyl, pyridyl, quinolinyl, isoquinolinyl, pyrimidyl, 1,2,4-triazinyl, 1,3,5-triazinyl and purinyl, wherein said basic group is an end group or a group located within an alkyl chain;

wherein R, R' and R" each independently is H, optionally substituted hydrocarbyl or heterocyclyl, or two of R, R' and R" together with the N atom to which they are attached form a 3-7 membered saturated ring, optionally containing one or more heteroatoms selected from O, S or N, and optionally further substituted at the additional N atom, said 3-7 membered saturated ring being selected from the group consisting of aziridine, pyrrolidine, piperidine, morpholine, thiomorpholine, azepine and piperazine optionally substituted at the additional N atom by $C_1$-$C_6$ alkyl optionally substituted by halo, hydroxyl or amino.

3. The conjugate according to claim 1, wherein the photosensitizer is selected from the group consisting of: (i) a bacteriochlorophyll of the formula II, wherein M is 2H or a metal selected from the group consisting of Pd, Mn or Cu; and (ii) a chlorophyll of the formula II, wherein M is 2H or a metal selected from the group consisting of Pd, Mn or Cu.

4. The conjugate according to claim 1, wherein M is a radioisotope.

5. The conjugate according to claim 1, wherein M is $^{99m}$Tc, $^{67}$Ga, $^{195}$Pt, $^{111}$In, $^{51}$Cr, $^{60}$Co $^{103}$Pd, $^{195}$Pt, $^{105}$Rh, $^{106}$Rh, $^{188}$Re, $^{177}$Lu, $^{164}$Er, $^{117m}$Sn, $^{153}$Sm, $^{90}$Y, $^{64}$Cu, $^{67}$Cu, or $^{32}$P.

6. The conjugate according to claim 1, wherein the photosensitizer is a bacteriochlorophyll of formula II, wherein $R_4$ at position 3 is acetyl, $R_4$ at position 8 is ethyl, and $R'_4$ is methyl, or a chlorophyll of formula II, wherein $R_4$ at position 3 is vinyl, $R_4$ at position 8 is ethyl, and $R'_4$ is methyl.

7. The conjugate according to claim 6, wherein the photosensitizer is selected from the group consisting of:

(i) a chlorophyll or bacteriochlorophyll of the formula II, wherein $R_6$ is —NR$_9$R'$_9$, R$_9$ is H and R'$_9$ is $C_1$-$C_{10}$ alkyl substituted by (a) the acidic group $SO_3H$ or an alkaline salt thereof; (b) a basic group —NH—(CH$_2$)$_{2-6}$—NRR' wherein each of R and R' independently is H, $C_1$-$C_6$ alkyl optionally substituted by NH$_2$, or R and R' together with the N atom form a 5-6 membered saturated ring, optionally containing an O or N atom and optionally further substituted at the additional N atom by —(CH$_2$)$_{2-6}$—NH$_2$; (c) one or more OH; or (d) a polydentate ligand selected from the group consisting of EDTA, DTPA and DOTA, and their chelating complexes with metals; and (ii) a chlorophyll or bacteriochlorophyll of formula II, wherein $R_1$ and $R_6$ together form a cyclic ring comprising an RGD peptide or RGD peptidomimetic.

8. The conjugate according to claim 7, wherein (i) $R_6$ is —NH—(CH$_2$)$_2$—SO$_3$K, —NH—(CH$_2$)$_3$—SO$_3$K, —NH—(CH$_2$)$_3$—NH—(CH$_2$)$_3$—NH$_2$, —NH—(CH$_2$)$_2$-1-morpholino, —NH—(CH$_2$)$_3$-piperazino-(CH$_2$)$_3$—NH$_2$, —NH—CH$_2$—CH(OH)—CH$_2$(OH), or —NH—(CH$_2$)$_3$—NH-DTPA or its chelating complex with Gd; or (ii) $R_1$ and $R_6$ together form a cyclic ring comprising NH-RGD-CO—NH—(CH$_2$)$_2$—NH— or NH-RGD-CO—NH—(CH$_2$)$_2$-piperazino-(CH$_2$)$_2$—NH—.

9. The conjugate according to claim 1, wherein the photosensitizer is selected from the group consisting of:

(a) a bacteriochlorophyll of the formula II wherein m is 0; $R_1$ is NH—P, wherein P is the residue of an RGD-containing peptide or RGD peptidomimetic linked directly to the NH— or via a spacer; R'$_2$ is methoxy; $R_4$ at position 3 is acetyl and at position 8 is ethyl; R'$_4$ is methyl; and wherein
  (i) M is Pd, Mn, Cu or 2H and $R_6$ is —NH—(CH$_2$)$_2$—SO$_3^-$Me$^+$ or —NH—(CH$_2$)$_3$—SO$_3^-$Me$^+$, wherein Me$^+$ is Na$^+$ or K$^+$;
  (ii) M is Pd or 2H and $R_6$ is —NH—CH$_2$—CH(OH)—CH$_2$—OH;
  (iii) M is 2H and $R_6$ is —NH—(CH$_2$)$_3$—NH—(CH$_2$)$_3$—NH$_2$,
  (iv) M is 2H and $R_6$ is —NH—(CH$_2$)$_2$-morpholino; or
  (v) M is 2H and $R_6$ is —NH—(CH$_2$)$_3$-piperazino-(CH$_2$)$_3$—NH$_2$; and (b) a chlorophyll of the formula II wherein M is selected from the group consisting of Mn, Cu or 2H; $R_1$ is NH—P, wherein P is the residue of an RGD-containing peptide or RGD peptidomimetic linked directly to the NH— or via a spacer; $R_4$ at position 3 is vinyl and at position 8 is ethyl; R'$_4$ is methyl; and $R_6$ is –NH—(CH$_2$)$_2$—SO$_3^-$Me$^+$, wherein Me$^+$ is Na$^+$ or K$^+$.

10. The conjugate according to claim 1, selected from the group consisting of:

palladium 3$^1$-oxo-15-methoxycarbonylmethyl-rhodobacteriochlorin 13$^1$-(2-sulfoethyl)amide-17$^3$-[4-(methyl-5-(6-guanidino-hexanoylamino)-pentanoic acid)] amide potassium salt, palladium 3$^1$-oxo-15-methoxycarbonylmethyl-rhodobacteriochlorin 13$^1$-(2-sulfoethyl)amide-17$^3$-[7-amido-3-[[1-(4-guanidino-butyryl)-piperidine-3-carbonyl]-amino]-heptanoic acid] potassium salt, palladium 3$^1$-oxo-15-methoxycarbonylmethyl-rhodobacteriochlorin 13$^1$, 17$^3$-cyclo(2-RGD-amido-N-ethyl)diamide, 3$^1$-oxo-15-methoxycarbonylmethyl-rhodobacteriochlorin 13$^1$,17$^3$-cyclo(2-RGD-amido-N-ethyl)diamide, palladium 3$^1$-oxo-15-methoxycarbonylmethyl-rhodobacteriochlorin 13$^1$,17$^3$-cyclo{3-[4-(3-aminopropyl-DGR-amido)-piperazin-1-yl]-propyl}diamide, palladium 3$^1$-oxo-15-methoxycarbonylmethyl-rhodobacteriochlorin 13$^1$-(2-sulfoethyl)amide-17$^3$-(RGD-4C) amide potassium salt, 3$^1$-oxo-15-methoxycarbonylmethyl-rhodobacteriochlorin 13$^1$-(2-sulfoethyl) amide-17$^3$-(cycloRGDfK)amide potassium salt, manganese(III) $3^1$-oxo-15-methoxycarbonylmethyl-rhodobacteriochlorin $13^1$-(2-sulfoethyl)amide-$17^3$-(cyclo-RGDfK)amide potassium salt, copper(II) $3^1$-oxo-15-methoxycarbonylmethyl-rhodobacteriochlorin $13^1$-(2-sulfoethyl)amide-$17^3$-(cyclo-RGDfK)amide potassium salt, palladium $3^1$-oxo-15-methoxycarbonylmethyl-rhodobacteriochlorin $13^1$-(2-sulfoethyl)amide-$17^3$-(cyclo-RGDfK)amide potassium salt, $3^1$-oxo-15-methoxycarbonylmethyl-rhodobacteriochlorin $13^1$-(2-sulfoethyl)amide-$17^3$-(GRGDSP)amide potassium salt, palladium $3^1$-oxo-15-methoxycarbonylmethyl-rhodobacteriochlorin $13^1$-(2-sulfoethyl)amide-$17^3$-(GRGDSPK)amide potassium salt, palladium $3^1$-oxo-15-methoxycarbonylmethyl-rhodobacteriochlorin $13^1$-(2-sulfoethyl)amide-$17^3$-[(GRGDSP)$_4$K]amide potassium salt, palladium $3^1$-oxo-15-methoxycarbonylmethyl-rhodobacteriochlorin $13^1$-(2-sulfoethyl)amide-$17^3$-(cycloRGDf-N(Me)K)amide potassium salt, palladium $3^1$-oxo-15-methoxycarbonylmethyl-rhodobacteriochlorin $13^1$-(2-sulfoethyl)-$17^3$-N-[4-heptanedioic acid bis-(cycloRGDyK-amido)]amide potassium salt, palladium $3^1$-oxo-15-methoxycarbonylmethyl-rhodobacteriochlorin-$13^1$-(2,3-dihydroxypropyl)amide-$17^3$-(cycloRGDfK)amide, $3^1$-oxo-15-methoxycarbonylmethyl-rhodobacteriochlorin $13^1$-(3-DTPA-amido-N-propyl)amide-$17^3$-(cycloRGDfK)amide, $3^1$-oxo-15-methoxycarbonylmethyl-rhodobacteriochlorin $13^1$-(3-Gd-DTPA-amido-N-propyl)amide-$17^3$-(cycloRGDfK)amide, $3^1,3^2$-didehydrorhodochlorin $13^1$-(2-sulfoethyl)amide-$17^3$-(cycloRGDfK) amide potassium salt, manganese(III) $3^1,3^2$-didehydrorhodochlorin $13^1$-(2-sulfoethyl)amide-$17^3$-(cycloRGDfK)amide potassium salt, and copper(II) $3^1,3^2$-didehydrorhodochlorin $13^1$-(2-sulfoethyl)amide-$17^3$-(cycloRGDfK)amide potassium salt.

11. A pharmaceutical composition comprising a conjugate as defined in claim 1, and a pharmaceutically acceptable carrier.

12. The pharmaceutical composition according to claim 11, wherein the conjugate is palladium $3^1$-oxo-15-methoxycarbonylmethyl-rhodobacteriochlorin $13^1$-(2-sulfoethyl)amide-$17^3$-(cycloRGDfK)amide potassium salt.

13. The pharmaceutical composition according to claim 11, wherein the photosensitizer is bacteriochlorophyll of the formula II and the conjugate is $3^1$-oxo-15-methoxycarbonylmethyl-rhodobacteriochlorin 13'-(2-sulfoethyl) amide-$17^3$-(cycloRGDfK)amide potassium salt.

* * * * *